US011993571B2

(12) United States Patent
LaVoie et al.

(10) Patent No.: US 11,993,571 B2
(45) Date of Patent: *May 28, 2024

(54) INDOLE DERIVATIVES AS EFFLUX PUMP INHIBITORS

(71) Applicant: RUTGERS, THE STATE UNIVERSITY OF NEW JERSEY, New Brunswick, NJ (US)

(72) Inventors: Edmond J. LaVoie, New Brunswick, NJ (US); Ajit Parhi, New Brunswick, NJ (US); Yi Yuan, Monmouth Junction, NJ (US); Yongzheng Zhang, Monmouth Junction, NJ (US); Yangsheng Sun, Monmouth Junction, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/492,901

(22) PCT Filed: Mar. 9, 2018

(86) PCT No.: PCT/US2018/021848
§ 371 (c)(1),
(2) Date: Sep. 10, 2019

(87) PCT Pub. No.: WO2018/165611
PCT Pub. Date: Sep. 13, 2018

(65) Prior Publication Data
US 2021/0094912 A1 Apr. 1, 2021

Related U.S. Application Data

(60) Provisional application No. 62/523,154, filed on Jun. 21, 2017, provisional application No. 62/469,987, filed on Mar. 10, 2017.

(51) Int. Cl.
*C07D 209/42* (2006.01)
*C07D 401/12* (2006.01)
*C07D 401/14* (2006.01)
*C07D 403/12* (2006.01)
*C07D 405/04* (2006.01)

(52) U.S. Cl.
CPC ......... *C07D 209/42* (2013.01); *C07D 401/12* (2013.01); *C07D 401/14* (2013.01); *C07D 403/12* (2013.01); *C07D 405/04* (2013.01)

(58) Field of Classification Search
CPC .. C07D 209/42; C07D 401/12; C07D 401/14; C07D 403/12; C07D 405/04
See application file for complete search history.

(56) References Cited

U.S. PATENT DOCUMENTS

| | | | | |
|---|---|---|---|---|
| 3,238,215 A | * | 3/1966 | Zenitz | C07D 209/18 546/201 |
| 3,465,080 A | * | 9/1969 | Wright, Jr. | A61K 31/00 514/235.2 |
| 3,978,224 A | | 8/1976 | Steinman et al. | |
| 4,910,193 A | * | 3/1990 | Buchheit | A61K 31/00 514/183 |
| 4,938,949 A | | 7/1990 | Borch et al. | |
| 5,663,152 A | | 9/1997 | Hayano et al. | |
| 5,864,039 A | * | 1/1999 | Kawakita | C07D 401/12 546/214 |
| 6,204,279 B1 | | 3/2001 | Leger et al. | |
| 6,326,391 B1 | | 12/2001 | Markham et al. | |
| 6,506,339 B1 | * | 1/2003 | Girardot | A61L 2/18 435/1.1 |
| 6,555,569 B2 | | 4/2003 | Sutcliffe et al. | |
| 6,730,684 B1 | | 5/2004 | Miller et al. | |
| 7,855,228 B2 | | 12/2010 | Gitai et al. | |
| 7,893,020 B2 | | 2/2011 | Glinka et al. | |
| 8,642,076 B2 | | 2/2014 | Manoharan et al. | |
| 9,907,807 B2 | * | 3/2018 | Evers | A61P 29/00 |

(Continued)

FOREIGN PATENT DOCUMENTS

WO 1992004017 A1 3/1992
WO 2001026652 A1 4/2001
(Continued)

OTHER PUBLICATIONS

Olgen et al. Journal of Enzyme Inhibition and Medicinal Chemistry 2013, 28, 58-64 (Year: 2013).*
Bellemin et al. Eur J. Med. Chem. 1996, 31, 123-132 (Year: 1996).*
CAS Registry No. 2110778-37-3, which entered STN on Aug. 9, 2017 (Year: 2017).*
Woods et al. Am. Fam. Physician 1998, 57, 2731-2740 (Year: 1998).*
"Carbocyclic." Merriam-Webster.com Dictionary, Merriam-Webster, https://www.merriam-webster.com/dictionary/carbocyclic. Accessed Oct. 13, 2022. (Year: 2022).*
"Cycloalkyl." Merriam-Webster.com Dictionary, Merriam-Webster, https://www.merriam-webster.com/dictionary/cycloalkyl. Accessed Oct. 13, 2022. (Year: 2022).*

(Continued)

*Primary Examiner* — Matthew P Coughlin
(74) *Attorney, Agent, or Firm* — Viksnins Harris Padys Malen LLP

(57) ABSTRACT

Disclosed herein are compounds of formula (I): and salts thereof. Also disclosed are compositions comprising compounds of formula I and compounds of formula I for use in treating or preventing bacterial infections.

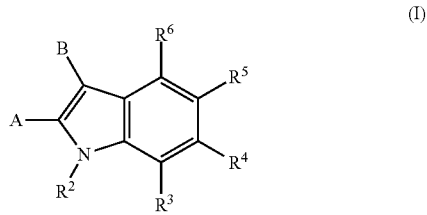

(I)

26 Claims, No Drawings

(56) References Cited

U.S. PATENT DOCUMENTS

| | | | |
|---|---|---|---|
| 9,926,261 | B2 | 3/2018 | Lavoie et al. |
| 9,950,993 | B2 | 4/2018 | Lavoie et al. |
| 11,458,121 | B2 * | 10/2022 | LaVoie .................. A61P 31/04 |
| 2003/0199689 | A1 * | 10/2003 | Nazare .................. A61P 43/00 540/602 |
| 2004/0204378 | A1 | 10/2004 | Nelson et al. |
| 2007/0155721 | A1 * | 7/2007 | Hersperger ............ A61P 43/00 546/187 |
| 2008/0132457 | A1 | 6/2008 | Bostian et al. |
| 2009/0042866 | A1 | 2/2009 | Lennox et al. |
| 2009/0215828 | A1 * | 8/2009 | Schunk ............... C07D 401/14 514/336 |
| 2010/0256112 | A1 | 10/2010 | Bradbury et al. |
| 2013/0296228 | A1 | 11/2013 | Patel et al. |
| 2014/0323532 | A1 | 10/2014 | Wei et al. |
| 2015/0175539 | A1 | 6/2015 | Jiricek et al. |
| 2015/0291565 | A1 | 10/2015 | Djaballah et al. |
| 2016/0271081 | A1 | 9/2016 | Lavoie et al. |
| 2016/0271082 | A1 | 9/2016 | Lavoie et al. |
| 2018/0179158 | A1 | 6/2018 | Dreier et al. |
| 2019/0031624 | A1 | 1/2019 | Lavoie et al. |
| 2019/0055188 | A1 | 2/2019 | Lavoie et al. |
| 2019/0084919 | A1 | 3/2019 | Lavoie et al. |
| 2020/0270211 | A1 * | 8/2020 | Burnett ................ C07C 233/79 |

FOREIGN PATENT DOCUMENTS

| | | | |
|---|---|---|---|
| WO | 2003000657 A1 | 3/2003 | |
| WO | WO-03028725 A1 * | 4/2003 | .......... A61K 31/445 |
| WO | 2005113579 A1 | 12/2005 | |
| WO | 2007115231 A2 | 10/2007 | |
| WO | 2008012782 A2 | 1/2008 | |
| WO | 2009103552 A1 | 8/2009 | |
| WO | 2009110002 A1 | 9/2009 | |
| WO | 2012084971 A1 | 6/2012 | |
| WO | 2014078294 A1 | 5/2014 | |
| WO | 2015164482 A1 | 10/2015 | |
| WO | 2016040505 A1 | 3/2016 | |
| WO | WO-2017023894 A1 * | 2/2017 | ............ A61P 35/00 |
| WO | 2018119395 A1 | 6/2018 | |
| WO | 2018165611 A1 | 9/2018 | |
| WO | 2018165612 A1 | 9/2018 | |
| WO | 2018165614 A1 | 9/2018 | |
| WO | 2018218192 A1 | 11/2018 | |
| WO | 2019005841 A1 | 1/2019 | |
| WO | WO-2019005841 A1 * | 1/2019 | .......... A61K 31/454 |
| WO | WO-2019099402 A1 * | 5/2019 | .......... C07D 409/12 |

OTHER PUBLICATIONS

Meyer et al. J. Pharm. Sci. 2007, 96, 3155-3167 (Year: 2007).*
Martos et al. European Journal of Microbiology and Immunology 2013, 3, 44-48 (Year: 2013).*
Astolfi, A., et al., "Pharmacophore-Based Repositioning of Approved Drugs as Novel *Staphylococcus aureus* NorA Efflux Pump Inhibitors", J Med Chem 60(4), 1598-1604 (2017).
Awuni, E., et al., "Effect of A22 on the Conformation of Bacterial Actin MreB", International Journal of Molecular Sciences 20, 1304 (2019).
Awuni, Y., et al., "Exploring the A22-Bacterial Actin MreB Interaction through Molecular Dynamics Simulations", J. Phys. Chem, B 120(37), 4867-4874 (2016).
Barker, C., et al., "Degradation of MAC13243 and studies of the interaction of resulting thiourea compounds with the lipoprotein targeting chaperone LoIA", Bioorganic & Medicinal Chemistry Letters 23, 2426-2431 (2013).
Bean, G., et al., "A22 disrupts the bacterial actin cytoskeleton by directly binding and inducing a low-affinity state in MreB", Biochemistry 48 (22), 4852-7 (2009).
Bohnert, J, et al., "Efflux inhibition by selective serotonin reuptake inhibitors in *Escherichia coli*", J Antimicrob Chemother 66, 2057-2060 (2011).
Bonez, P., et al., "Antibacterial, cyto and genotoxic activities of A22 compound ((S-3,4-dichlorobenzyl) Isothiourea hydrochloride)", Microbial Pathogenesis 99, 14-18 (2016).
Bonez, P, et al., "Anti-biofilm activity of A22 ((S-3,4-dichlorobenzyl) isothiourea hydrochloride) against Pseudomonas aeruginosa: Influence on biofilm formation, motility and bioadhesion", Microbial Pathogenesis 111, 6-13 (2017).
Buonerba, F, et al., "Improved Potency of Indole-Based NorA Efflux Pump Inhibitors: From Serendipity toward Rational Design and Development", J. Med. Chem DOI:10.1021/acs.jmedchem. 6b01281, 8 pages (Dec. 2, 2016).
Charles, E, "Inhibition of MreB and ftsZ proteins to minimize *E. coli* biofilms formation", doi: https://doi.org/10.1101/523167, 20 pages (2019).
Fleeman, R, et al., "Identification of a Novel Polyamine Scaffold With Potent Efflux Pump Inhibition Activity Toward Multi-Drug Resistant Bacterial Pathogens", Frontiers in Microbiology 9, 1301, 16 pages (2018).
Grossman, T., et al., "The Efflux Pump Inhibitor Timcodar Improves the Potency of Antimycobacterial Agents", Antimicrobial Agents and Chemotherapy 59(3), 1534-1541 (2015).
Gupta, S, et al., "Acceleration of Tuberculosis Treatment by Adjunctive Therapy with Verapamil as an Efflux Inhibitor", American Journal of respiratory and Critical Care Medicince 188, 600-607 (2013).
Handzlik, J, et al., "Recent Advances in Multi-Drug Resistance (MDR) Efflux Pump Inhibitors of Gram-Positive Bacteria *S. aureus*", Antibiotics 2, 28-45 (2013).
Iwai, N, et al., "Novel S-Benzylisothiourea Compound That Induces Spherical Cells in *Escherichia coli* Probably by Acting on a Rod-shape-determining Protein(s) Other Than Penicillin-binding Protein 2", Biosci Biotechnol Biochem 66 (12), 2658-2662 (2002).
Iwai, N, et al., "Structure-Activity Relationship of S-Benzylisothiourea Derivatives to Induce Spherical Cells in *Escherichia coli*", Biosci Biotechnol Biochem 68(11), 2265-2269 (2004).
Iwai, N, et al., "Structure-Activity Relationship Study of the Bacterial Actin-Like Protein MreB Inhibitors: Effects of Substitution of Benzyl Group in S-Benzylisothiourea", Biosci. Biotechnol. Biochem 71 (1), 246-248 (2007).
Lee, J, et al., "Roles of Indole as an Interspecies and Interkingdom Signaling Molecule", Trends in Microbiology 23 (11), 707-718 (2015).
Noguchi, N, et al., "Anti-infectious Effect of S-Benzylisothiourea Compound A22, Which Inhibits the Actin-Like Protein, MreB, in Shigella flexneri", Biol. Pharm. Bull 31 (7), 1327-1332 (2008).
Patent Cooperation Treaty, International Searching Authority, Search Report and Written Opinion for PCT/US2018/021848, 16 pages, dated Jun. 14, 2018.
Perry, J, et al., "In vitro activity of S-(3,4-dichlorobenzyl)isothiourea hydrochloride and novel structurally related compounds against multidrug-resistant bacteria, including Pseudomonas aeruginosa and Burkholderia cepacian complex", International Journal of Antimicrobial Agents, 39 (1), 27-32 (2012).
Pubchem, "101437777", CID 101437777, 9 pages, Create Date Dec. 18, 2015.
Pubchem, "10954401", CID 10954401, 14 pages, Create Date Oct. 26, 2006.
Pubchem, "67894517", CID 67894517, 10 pages, Create Date Nov. 30, 2012.
Pubchem, "6-Chloro-2,3,4,9-tetrahydro-1H-carbazol-1-amine", Compound Summary for CID 17743497, 15 pages (Create Date Nov. 13, 2007).
Pubchem, "LLVYCKNUAXLGFC-UHFFFAOYSA-N", Compound Summary for CID 67376113, 11 pages (create date Nov. 30, 2012).
Pubchem, "SCHEMBL9670581", Substance Record for SID 235049721, 7 pages, Feb. 13, 2015.
Pubchem Database, "Acetamide, N-cyclohexyl-2-phenyl-", Compound Summary for CID 82500, 16 pages (Create Date: Mar. 26, 2005).
Pubchem Database, "Cyclohexyloxybenzene", CID 137492, 17 pages (Create date: Mar. 27, 2005).

(56) References Cited

OTHER PUBLICATIONS

Pubchem Database, "N-Cyclohexyl-3-methylbenzamide", Compound Summary for CID 236099,14 pages (create date: Mar. 26, 2005).

Robertson, GT, et al., "A Novel Indole Compound That Inhibits Pseudomonas aeruginosa Growth by Targeting MreB is a Substrate for MexAB-OprM", Journal of Bacteriology 189 (19), 6870-6881 (2007).

Samosorn, S, et al., "Synthesis of functionalised 2-aryl-5-nitro-1H-indoles and their activity as bacterial NorA efflux pump inhibitors", Bioorganic & Medicinal Chemistry 14, 857-865 (2006).

Shi, H, et al., "Chiral twisting in a bacterial cytoskeletal polymer affects filament size and orientation", Nature Communications 11, 1408, 1-12 (2020).

STN CAS Registry No. Registry File No. 1026060-58-1, 1 page (2008).

STN CAS Registry No. Registry File No. 788216-67-0, 1 page (2004).

STN CAS Registry No. Registry File No. 860554-34-3, 1 page (2005).

Tambat, R, et al., "Microbe-Derived Indole Metabolite Demonstrates Potent Multidrug Efflux Pump Inhibition in *Staphylococcus aureus*", Frontiers in Microbiology 10, 2153, 13 pages (2019).

Taylor, P, et al., "A Forward Chemical Screen Identifies Antibiotic Adjuvants in *Escherichia coli*", ACS Chem Biol 7, 1547-1555 (2012).

Yamachika, S, et al., "Anti-Pseudomonas aeruginosa Compound, 1,2,3,4-Tetrahydro-1,3,5-triazine Derivative, Exerts Its Action by Primarily Targeting MreB", Biol Pharm Bull 35(10), 1740-1744 (2012).

Yang, X, et al., "A tobramycin vector enhances synergy and efficacy of efflux pump inhibitors against multidrug-resistant Gram-negative bacteria", J. Med. Chem 60, 3913-1932 (2017).

Yaqub, G, et al., "Conventional-Microwave Mediated Synthesis and In Vitro Antimicrobial Activity of Novel Carbazole-Efflux Pump Inhibitor Hybrid Antibacterials", Hindawi J. Chemistry, doi: 10.1155/2017/7243279, Article ID 724329, 5 pages (2017).

CAS Registry, RN 1566604-70-3, 1 page (Mar. 11, 2014).

CAS Registry, RN 1626576-60-0, 1 page (Sep. 26, 2014).

CAS Registry, RN 1788589-70-7, 1 page (Jun. 25, 2015).

CAS Registry, RN 1957085-66-3m 1 page (Jul. 21, 2016).

CAS Registry, RN 2058714-02-4, 1 page (Jan. 25, 2017).

Nagarajan, G, et al., "Effect of H4R antagonist N-(2-aminoethyl)-5-chloro-1H-indol-2-carboxamides and 5-chloro-2-(piperazin-1-ylmethyl)-1H-benzimidazole on histamine and 4-methylhistamine-induced mast cell response", Journal of Receptors and Signal Transduction 37(3), 304-313 (2017).

Wenzler, T, et al., "A new approach to chemotherapy: drug-induced differentiation kills African trypanosomes", Scientific Reports 6 (22451), 1-10 (2016).

Millson, D, et al., "Migraine pharmacotherapy with oral triptans: a rational approach to clinical management", Exp Opin Pharmacother I(3), 391-404 (2000).

CAS Registry, No. 1978423-07-2, 1 page (Aug. 24, 2016).

Almeida Da Silva PE, et al., "Molecular basis and mechanisms of drug resistance in *Mycobacterium tuberculosis*: classical and new drugs", J Antimicrob Chemother 66(7), 1417-1430 (2011).

Japanese Office Action, for JP Application No. 2019-549454, 7 pages, dated Sep. 29, 2022. [English Translation].

Louw, G, et al., "A balancing act: efflux/influx in mycobacterial drug resistance", Antimicrobial Agents and Chemotherapy 53(8), 3181-3189 (2009).

Rodrigues, L, et al., "Antituberculosis drugs: reducing efflux = increasing activity", Drug Discovery Today 22(3), 592-599 (2017).

Tsuyuguchi, K, "Diagnosis, treatment and prevention of infectious diseases. Topics: III. Various problems in antimicrobial agents; 3. Advances in antituberculosis drugs", Journal of Japanese Society of Internal Medicine 102(11); Nihon Naika Gakkai Zasshi. ;102(11):2922-2927, Japanese. doi: 10.2169/naika.102.2922 (2013).

\* cited by examiner

INDOLE DERIVATIVES AS EFFLUX PUMP INHIBITORS

PRIORITY OF INVENTION

This application claims priority from U.S. Provisional Patent Application No. 62/469,987 filed Mar. 10, 2017 and United States Provisional Patent Application No. 62/523,154 filed Jun. 21, 2017 both of which are hereby incorporated by reference in their entirety.

BACKGROUND OF THE INVENTION

Antibiotics have been effective tools in the treatment of infectious diseases. However, bacteria have developed several different mechanisms to overcome the action of antibiotics. These mechanisms of resistance can be specific such as for a molecule or a family of antibiotics, or the mechanisms can be non-specific. Several mechanisms of resistance can exist in a single bacterial strain, and those mechanisms may act independently or they may act synergistically to overcome the action of an antibiotic or a combination of antibiotics. Specific mechanisms include, for example, degradation of the drug, inactivation of the drug by enzymatic modification, and alteration of the drug target. Additional mechanisms of drug resistance include mechanisms in which access of the antibiotic to the target is prevented or reduced by decreasing the transport of the antibiotic into the cell or by increasing the efflux of the drug from the cell to the outside medium. Both of these mechanisms can lower the concentration of drug at the target site and allow bacterial survival in the presence of one or more antibiotics that would otherwise inhibit or kill the bacterial cells. Some bacteria utilize both mechanisms, combining low permeability of the cell wall (including membranes) with an active efflux of antibiotics. It has been shown that efflux of antibiotics can be mediated by more than one pump in a single organism and that almost all antibiotics are subject to resistance by this mechanism.

These multiple resistance mechanisms have become widespread and threaten the clinical utility of antibacterial therapy. The increase in antibiotic resistant strains has been particularly noted in major hospitals and care centers. The consequences of the increase in resistant strains include, for example higher morbidity and mortality, longer patient hospitalization, and an increase in treatment costs. Accordingly, there is a need for agents and methods for inhibiting one or more of these mechanisms of bacterial resistance.

SUMMARY OF THE INVENTION

Compounds disclose herein, when tested in combination with a known antibiotic, lower the minimum inhibitory concentration of the known antibiotic to inhibit bacterial cell growth. Not to be bound by theory the compounds are believed to exert this effect by the inhibition of a bacterial efflux pump(s).

Accordingly, one embodiment provides a compound of formula I:

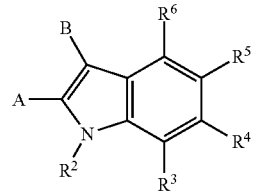

wherein:
one of A or B is —C(=O)N($R^{a1}$)—$R^1$, —($C_1$-$C_3$)alkyl-C(=O)N($R^{a1}$)$R^1$, —($C_1$-$C_3$)alkyl-O—$R^1$, —O—$R^1$, —($C_1$-$C_3$)alkyl-N($R^{a1}$)—$R^1$, —N($R^{a1}$)—$R^1$, or $R^1$ and the other of A or B is hydrogen, halogen, or ($C_1$-$C_4$)alkyl;
each $R^1$ is independently:
(a) ($C_1$-$C_{14}$)alkyl substituted with one or more groups selected from the group consisting of —$NR^{b2}R^{c2}$, —$NHNH_2$, —C(=$NR^{a2}$)($NR^{b2}R^{c2}$), —$NR^{a2}$C(=$NR^{a2}$)($R^{d2}$), and —$NR^{a2}$C(=$NR^{a2}$)($NR^{b2}R^{c2}$); and wherein ($C_1$-$C_{14}$)alkyl is optionally substituted independently with one or more halo, ($C_1$-$C_4$)alkyl or ($C_3$-$C_7$)carbocyclyl; or
(b) ($C_3$-$C_7$)carbocyclyl, ($C_3$-$C_7$)carbocyclyl-($C_1$-$C_4$)alkyl-, 4-7 membered monocyclic heterocyclyl, 4-7 membered monocyclic heterocyclyl-($C_1$-$C_4$)alkyl-, ($C_3$-$C_7$)carbocyclyl-$NR^e$—($C_1$-$C_4$)alkyl- or 4-7 membered monocyclic heterocyclyl-$NR^e$—($C_1$-$C_4$)alkyl- wherein each ($C_3$-$C_7$)carbocyclyl, ($C_3$-$C_7$)carbocyclyl-($C_1$-$C_4$)alkyl- or -, ($C_3$-$C_7$)carbocyclyl-$NR^e$—($C_1$-$C_4$)alkyl- is independently substituted with one or more $Z^1$ or $Z^2$, and wherein each 4-7 membered monocyclic heterocyclyl, 4-7 membered monocyclic heterocyclyl-($C_1$-$C_4$)alkyl- or 4-7 membered monocyclic heterocyclyl-$NR^e$—($C_1$-$C_4$)alkyl- is independently optionally substituted with one or more $Z^1$ or $Z^2$, and wherein any ($C_3$-$C_7$)carbocyclyl, ($C_3$-$C_7$)carbocyclyl-($C_1$-$C_4$)alkyl-, 4-7 membered monocyclic heterocyclyl, 4-7 membered monocyclic heterocyclyl-($C_1$-$C_4$)alkyl-, ($C_3$-$C_7$)carbocyclyl $NR^e$—($C_1$-$C_4$)alkyl- or 4-7 membered monocyclic heterocyclyl-$NR^e$—($C_1$-$C_4$)alkyl- of $R^1$ is independently optionally substituted with one or more halo, ($C_1$-$C_4$)alkyl, ($C_3$-$C_7$)carbocyclyl, —C(=O)$NH_2$, —C(=O)NH($C_1$-$C_4$)alkyl, —C(=O)N(($C_1$-$C_4$)alkyl)$_2$, —NHC(=O)($C_1$-$C_4$)alkyl-$NH_2$, or 3-7 membered monocyclic heterocyclyl wherein ($C_1$-$C_4$)alkyl, ($C_3$-$C_7$)carbocyclyl or 3-7 membered monocyclic heterocyclyl is optionally substituted with one or more halogen, ($C_1$-$C_4$)alkyl, —$NH_2$, —NH($C_1$-$C_4$)alkyl or —N(($C_1$-$C_4$)alkyl)$_2$;
$R^2$ is hydrogen, ($C_1$-$C_4$)alkyl or phenyl($C_1$-$C_3$)alkyl-, wherein the phenyl is optionally substituted with one or more ($C_1$-$C_4$)alkyl, —O($C_1$-$C_4$)alkyl, halogen, or —$NO_2$;
$R^3$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, aryl, or heteroaryl wherein the aryl or heteroaryl is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy;
$R^4$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, aryl, heteroaryl, aryl($C_1$-$C_4$)alkyl-, heteroaryl($C_1$-$C_4$)alkyl-, ($C_3$-$C_7$)carbocyclyl($C_1$-$C_4$)alkyl-, ($C_3$-$C_7$)carbocyclyl($C_2$-$C_4$)alkynyl-, phenoxy or heteroaryloxy, wherein the aryl, heteroaryl, aryl($C_1$-$C_4$)alkyl-, heteroaryl($C_1$-$C_4$)alkyl-, ($C_3$-$C_7$)carbocyclyl($C_1$-$C_4$)alkyl-, ($C_3$-$C_7$)carbocyclyl($C_2$-$C_4$)alkynyl-, phenoxy or heteroaryloxy, is optionally substituted with one or more groups independently selected from the group consisting of halo, —OH, —$NO_2$, —CN, ($C_1$-$C_4$)alkyl, ($C_1$-$C_4$)haloalkyl, ($C_1$-

$C_4$)alkoxy, $(C_1-C_4)$haloalkoxy, methylenedioxy (—OCH$_2$O—), and $(C_3-C_7)$carbocyclyl;

$R^5$ is hydrogen, halo, $(C_1-C_4)$alkyl, $(C_1-C_4)$haloalkyl, $(C_1-C_4)$alkoxy, $(C_1-C_4)$haloalkoxy, aryl, heteroaryl aryl$(C_1-C_4)$alkyl-, heteroaryl$(C_1-C_4)$alkyl-, $(C_3-C_7)$carbocyclyl$(C_1-C_4)$alkyl-, $(C_3-C_7)$carbocyclyl$(C_2-C_4)$alkynyl-, phenoxy or heteroaryloxy, wherein the aryl, heteroaryl, aryl$(C_1-C_4)$alkyl-, heteroaryl$(C_1-C_4)$alkyl-, $(C_3-C_7)$carbocyclyl$(C_1-C_4)$alkyl-, $(C_3-C_7)$carbocyclyl$(C_2-C_4)$alkynyl-, phenoxy or heteroaryloxy, is optionally substituted with one or more groups independently selected from the group consisting of halo, —OH, —NO$_2$, —CN, $(C_1-C_4)$alkyl, $(C_1-C_4)$haloalkyl, $(C_1-C_4)$alkoxy, $(C_1-C_4)$haloalkoxy, methylenedioxy (—OCH$_2$O—), and $(C_3-C_7)$carbocyclyl;

$R^6$ is hydrogen, halo, $(C_1-C_4)$alkyl, $(C_1-C_4)$haloalkyl, $(C_1-C_4)$alkoxy, $(C_1-C_4)$haloalkoxy, aryl, or heteroaryl wherein the aryl or heteroaryl is optionally substituted with one or more groups independently selected from the group consisting of halo, —OH, —NO$_2$, —CN, $(C_1-C_4)$alkyl, $(C_1-C_4)$haloalkyl, $(C_1-C_4)$alkoxy, and $(C_1-C_4)$haloalkoxy;

each $Z^1$ is independently selected from the group consisting of —NR$^{b3}$R$^{c3}$, —NHNH$_2$, —C(=NR$^{a3}$)(NR$^{b3}$R$^{c3}$), —NR$^{a3}$C(=NR$^{a3}$)(R$^{d3}$), and —NR$^{a3}$C(=NR$^{a3}$)(NR$^{b3}$R$^{c3}$);

each $Z^2$ is independently —$(C_1-C_6)$alkyl substituted with one or more $Z^1$ and optionally optionally substituted with one or more $Z^3$;

each $Z^3$ is independently halo or $(C_3-C_7)$carbocyclyl;

each $R^{a1}$ is independently hydrogen, $(C_1-C_4)$alkyl, $(C_3-C_7)$carbocyclyl or 3-7 membered monocyclic heterocycyl optionally substituted with one or more halogen or $(C_1-C_4)$alkyl;

each $R^{a2}$ is independently hydrogen, $(C_1-C_4)$alkyl or $(C_3-C_7)$carbocyclyl;

each $R^{b2}$ and $R^{c2}$ is independently hydrogen, $(C_1-C_4)$alkyl or $(C_3-C_7)$carbocyclyl;

$R^{d2}$ is $(C_1-C_4)$alkyl or $(C_3-C_7)$carbocyclyl;

each $R^{a3}$ is independently hydrogen $(C_1-C_4)$alkyl or $(C_3-C_7)$carbocyclyl;

each $R^{b3}$ and $R^{c3}$ is independently hydrogen $(C_1-C_4)$alkyl, or $(C_3-C_7)$carbocyclyl;

$R^{d3}$ is $(C_1-C_4)$alkyl or $(C_3-C_7)$carbocyclyl; and each $R^e$ is independently hydrogen, $(C_1-C_4)$alkyl or $(C_3-C_7)$carbocyclyl;

or a salt thereof.

One embodiment provides a compound of formula I:

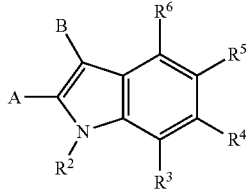

I wherein:
one of A or B is —C(=O)N(R$^{a1}$)—R$^1$, —$(C_1-C_3)$alkyl-C(=O)N(R$^{a1}$)R$^1$, —$(C_1-C_3)$alkyl-O—R$^1$, —$(C_1-C_3)$alkyl-N(R$^{a1}$)—R$^1$, —N(R$^{a1}$)—R$^1$, or R$^1$ and the other of A or B is H, halogen, or $(C_1-C_4)$alkyl;

each $R^1$ is independently:
(a) $(C_1-C_{14})$alkyl substituted with one or more groups selected from the group consisting of —NR$^{b2}$R$^{c2}$, —NHNH$_2$, —C(=NR$^{a2}$)(NR$^{b2}$R$^{c2}$), —NR$^{a2}$C(=NR$^{a2}$)(R$^{d2}$), and —NR$^{a2}$C(=NR$^{a2}$)(NR$^{b2}$R$^{c2}$); and wherein $(C_1-C_{14})$alkyl is optionally substituted independently with one or more halo, $(C_1-C_4)$alkyl or $(C_3-C_7)$carbocyclyl; or (b) $(C_3-C_7)$carbocyclyl, $(C_3-C_7)$carbocyclyl-$(C_1-C_4)$alkyl-, 4-7 membered monocyclic heterocyclyl, or 4-7 membered monocyclic heterocyclyl-$(C_1-C_4)$alkyl-, wherein each $(C_3-C_7)$carbocyclyl or $(C_3-C_7)$carbocyclyl-$(C_1-C_4)$alkyl- is independently substituted with one or more $Z^1$ or $Z^2$, and wherein each 4-7 membered monocyclic heterocyclyl or 4-7 membered monocyclic heterocyclyl-$(C_1-C_4)$alkyl- is independently optionally substituted with one or more $Z^1$ or $Z^2$, and wherein any $(C_3-C_7)$carbocyclyl, $(C_3-C_7)$carbocyclyl-$(C_1-C_4)$alkyl-, 4-7 membered monocyclic heterocyclyl, or 4-7 membered monocyclic heterocyclyl-$(C_1-C_4)$alkyl- of $R^1$ is independently optionally substituted independently with one or more halo, $(C_1-C_4)$alkyl or $(C_3-C_7)$carbocyclyl;

$R^2$ is hydrogen, $(C_1-C_4)$alkyl or phenyl$(C_1-C_3)$alkyl-, wherein the phenyl is optionally substituted with one or more $(C_1-C_4)$alkyl, —O$(C_1-C_4)$alkyl, halogen, or —NO$_2$;

$R^3$ is hydrogen, halo, $(C_1-C_4)$alkyl, $(C_1-C_4)$haloalkyl, $(C_1-C_4)$alkoxy, $(C_1-C_4)$haloalkoxy, aryl, or heteroaryl wherein the aryl or heteroaryl is optionally substituted with one or more groups independently selected from the group consisting of halo, —OH, —NO$_2$, —CN, $(C_1-C_4)$alkyl, $(C_1-C_4)$haloalkyl, $(C_1-C_4)$alkoxy, and $(C_1-C_4)$haloalkoxy;

$R^4$ is hydrogen, halo, $(C_1-C_4)$alkyl, $(C_1-C_4)$haloalkyl, $(C_1-C_4)$alkoxy, $(C_1-C_4)$haloalkoxy, aryl, or heteroaryl wherein the aryl or heteroaryl is optionally substituted with one or more groups independently selected from the group consisting of halo, —OH, —NO$_2$, —CN, $(C_1-C_4)$alkyl, $(C_1-C_4)$haloalkyl, $(C_1-C_4)$alkoxy, and $(C_1-C_4)$haloalkoxy;

$R^5$ is hydrogen, halo, $(C_1-C_4)$alkyl, $(C_1-C_4)$haloalkyl, $(C_1-C_4)$alkoxy, $(C_1-C_4)$haloalkoxy, aryl, or heteroaryl wherein the aryl or heteroaryl is optionally substituted with one or more groups independently selected from the group consisting of halo, —OH, —NO$_2$, —CN, $(C_1-C_4)$alkyl, $(C_1-C_4)$haloalkyl, $(C_1-C_4)$alkoxy, and $(C_1-C_4)$haloalkoxy;

$R^6$ is hydrogen, halo, $(C_1-C_4)$alkyl, $(C_1-C_4)$haloalkyl, $(C_1-C_4)$alkoxy, $(C_1-C_4)$haloalkoxy, aryl, or heteroaryl wherein the aryl or heteroaryl is optionally substituted with one or more groups independently selected from the group consisting of halo, —OH, —NO$_2$, —CN, $(C_1-C_4)$alkyl, $(C_1-C_4)$haloalkyl, $(C_1-C_4)$alkoxy, and $(C_1-C_4)$haloalkoxy;

each $Z^1$ is independently selected from the group consisting of —NR$^{b3}$R$^{c3}$, —NHNH$_2$, —C(=NR$^{a3}$)(NR$^{b3}$R$^{c3}$), —NR$^{a3}$C(=NR$^{a3}$)(R$^{d3}$), and —NR$^{a3}$C(=NR$^{a3}$)(NR$^{b3}$R$^{c3}$);

each $Z^2$ is independently —$(C_1-C_6)$alkyl substituted with one or more $Z^1$ and optionally substituted with one or more $Z^3$;

each $Z^3$ is independently halo or $(C_3-C_7)$carbocyclyl;

each $R^{a1}$ is independently hydrogen, $(C_1-C_4)$alkyl or $(C_3-C_7)$carbocyclyl;

each $R^{a2}$ is independently hydrogen, $(C_1-C_4)$alkyl or $(C_3-C_7)$carbocyclyl;

each $R^{b2}$ and $R^{c2}$ is independently hydrogen, $(C_1-C_4)$alkyl or $(C_3-C_7)$carbocyclyl;

$R^{d2}$ is $(C_1-C_4)$alkyl or $(C_3-C_7)$carbocyclyl;

each $R^{a3}$ is independently hydrogen $(C_1-C_4)$alkyl or $(C_3-C_7)$carbocyclyl;

each $R^{b3}$ and $R^{c3}$ is independently hydrogen $(C_1-C_4)$alkyl or $(C_3-C_7)$carbocyclyl; and $R^{d3}$ is $(C_1-C_4)$alkyl or $(C_3-C_7)$carbocyclyl;

or a salt thereof.

One embodiment provides a compound of formula I:

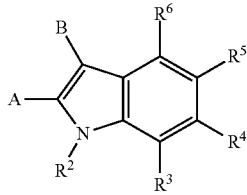

wherein:
one of A or B is —C(=O)N($R^{a1}$)—$R^1$, —($C_1$-$C_3$)alkyl-C(=O)N($R^{a1}$)$R^1$, —($C_1$-$C_3$)alkyl-O—$R^1$, —O—$R^1$, —($C_1$-$C_3$)alkyl-N($R^{a1}$)—$R^1$, —N($R^{a1}$)—$R^1$, or $R^1$ and the other of A or B is H, halogen, or ($C_1$-$C_4$)alkyl;

each $R^1$ is independently:
(a) ($C_1$-$C_{14}$)alkyl substituted with one or more groups selected from the group consisting of —$NR^{b2}R^{c2}$, —$NHNH_2$, —C(=$NR^{a2}$)($NR^{b2}R^{c2}$), —$NR^{a2}$C(=$NR^{a2}$)($R^{a2}$), and 13 $NR^{a2}$ ($NR^{a2}$)($NR^{b2}R^{c2}$), or
(b) ($C_3$-$C_7$)carbocyclyl, ($C_3$-$C_7$)carbocyclyl-($C_1$-$C_4$)alkyl-, 4-7 membered monocyclic heterocyclyl, or 4-7 membered monocyclic heterocyclyl-($C_1$-$C_4$)alkyl-, wherein each ($C_3$-$C_7$)carbocyclyl or ($C_3$-$C_7$)carbocyclyl-($C_1$-$C_4$)alkyl- is independently substituted with one or more groups selected from the group consisting of Z and —($C_1$-$C_6$)alkyl substituted with one or more Z, and wherein each 4-7 membered monocyclic heterocyclyl or 4-7 membered monocyclic heterocyclyl-($C_1$-$C_4$)alkyl- is independently optionally substituted with one or more groups selected from the group consisting of Z and —($C_1$-$C_6$)alkyl substituted with one or more Z, wherein each Z is independently selected from the group consisting of —$NR^{b3}R^{c3}$, —$NHNH_2$, —C(=$NR^{a3}$)($NR^{b3}R^{c3}$), —$NR^{a3}$C(=$NR^{a3}$)($R^{a3}$), and —$NR^{a3}$C(=$NR^{a3}$)($NR^{b3}R^{c3}$) and wherein each ($C_3$-$C_7$)carbocyclyl, ($C_3$-$C_7$)carbocyclyl-($C_1$-$C_4$)alkyl-, 4-7 membered monocyclic heterocyclyl, or 4-7 membered monocyclic heterocyclyl-($C_1$-$C_4$)alkyl-, is independently optionally substituted independently with one or more ($C_1$-$C_4$)alkyl;

$R^2$ is hydrogen, ($C_1$-$C_4$)alkyl or phenyl($C_1$-$C_3$)alkyl-, wherein the phenyl is optionally substituted with one or more ($C_1$-$C_4$)alkyl, —O($C_1$-$C_4$)alkyl, halogen, or —$NO_2$;

$R^3$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, aryl, or heteroaryl wherein the aryl or heteroaryl is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy;

$R^4$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, aryl, or heteroaryl wherein the aryl or heteroaryl is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy;

$R^5$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, aryl, or heteroaryl wherein the aryl or heteroaryl is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy;

$R^6$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, aryl, or heteroaryl wherein the aryl or heteroaryl is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy;

each $R^{a1}$ is independently hydrogen, ($C_1$-$C_4$)alkyl or ($C_3$-$C_7$)carbocyclyl;

each $R^{a2}$ is independently hydrogen, ($C_1$-$C_4$)alkyl or ($C_3$-$C_7$)carbocyclyl;

each $R^{b2}$ and $R^{c2}$ is independently hydrogen, ($C_1$-$C_4$)alkyl or ($C_3$-$C_7$)carbocyclyl;

$R^{a2}$ is ($C_1$-$C_4$)alkyl or ($C_3$-$C_7$)carbocyclyl;

each $R^{a3}$ is independently hydrogen ($C_1$-$C_4$)alkyl or ($C_3$-$C_7$)carbocyclyl;

each $R^{b3}$ and $R^{c3}$ is independently hydrogen ($C_1$-$C_4$)alkyl or ($C_3$-$C_7$)carbocyclyl; and $R^{a3}$ is ($C_1$-$C_4$)alkyl or ($C_3$-$C_7$)carbocyclyl;

or a salt thereof.

One embodiment provides a pharmaceutical composition comprising a compound of formula I or a pharmaceutically acceptable salt thereof as described herein, and a pharmaceutically acceptable vehicle.

One embodiment provides pharmaceutical composition comprising a compound of formula I or a pharmaceutically acceptable salt thereof as described herein, one or more antibacterial agents and a pharmaceutically acceptable vehicle.

One embodiment provides a method of inhibiting a bacterial efflux pump in an animal (e.g., a mammal such as a human) comprising administering to the animal a compound of formula I or a pharmaceutically acceptable salt thereof as described herein.

One embodiment provides a method of inhibiting a bacterial efflux pump in an animal (e.g., a mammal such as a human) comprising administering to the animal in need thereof a compound of formula I or a pharmaceutically acceptable salt thereof as described herein.

One embodiment provides a method of treating or preventing a bacterial infection in an animal (e.g., a mammal such as a human) comprising co-administering to the animal a compound of formula I or a pharmaceutically acceptable salt thereof as described herein and one or more antibacterial agents.

One embodiment provides a method of treating or preventing a bacterial infection in an animal (e.g., a mammal such as a human) comprising co-administering to the animal in need thereof a compound of formula I or a pharmaceutically acceptable salt thereof as described herein and one or more antibacterial agents.

One embodiment provides a method of inhibiting a bacterial efflux pump in an animal (e.g., a mammal such as a human) with a bacterial infection comprising administering to the animal a compound of formula I or a pharmaceutically acceptable salt thereof as described herein.

One embodiment provides a method of treating or preventing a bacterial infection in an animal (e.g., a mammal such as a human) infected with bacteria comprising co-administering to the animal a compound of formula I or a pharmaceutically acceptable salt thereof as described herein and one or more antibacterial agents.

One embodiment provides a compound of formula I or a pharmaceutically acceptable salt thereof as described herein for use in medical treatment.

One embodiment provides a compound of formula I or a pharmaceutically acceptable salt thereof as described herein for the prophylactic or therapeutic inhibition of a bacterial efflux pump for the treatment of a bacterial infection.

One embodiment provides a compound of formula I or a pharmaceutically acceptable salt thereof as described herein which is used in combination with one or more antibacterial agents for the prophylactic or therapeutic treatment of a bacterial infection.

One embodiment provides the use of a compound of formula I or a pharmaceutically acceptable salt thereof as described herein for the preparation of a medicament for inhibiting a bacterial efflux pump.

One embodiment provides the use of a compound of formula I or a pharmaceutically acceptable salt thereof as described herein for the preparation of a medicament for treating a bacterial infection in an animal (e.g., a mammal such as a human).

One embodiment provides the use of a compound of formula I or a pharmaceutically acceptable salt thereof as described herein for the preparation of a medicament which is used in combination with one or more antibacterial agents for treating a bacterial infection in an animal (e.g., a mammal such as a human).

One embodiment provides processes and intermediates disclosed herein that are useful for preparing compounds of formula I or salts thereof.

DETAILED DESCRIPTION

The following definitions are used, unless otherwise described: halo or halogen is fluoro, chloro, bromo, or iodo. Alkyl and alkoxy, etc. denote both straight and branched groups but reference to an individual radical such as propyl embraces only the straight chain radical (a branched chain isomer such as isopropyl being specifically referred to).

As used herein, the term "$(C_a$-$C_b)$alkyl" wherein a and b are integers refers to a straight or branched chain alkyl radical having from a to b carbon atoms. Thus when a is 1 and b is 6, for example, the term includes methyl, ethyl, n-propyl, isopropyl, n-butyl, isobutyl, sec-butyl, t-butyl, n-pentyl and n-hexyl.

The term "alkynyl" refers to an unsaturated alkyl radical having one or more triple bonds. Examples of such unsaturated alkyl groups ethynyl, 1- and 3-propynyl, 3-butynyl, and higher homologs and isomers.

The term "phenoxy" refers to a phenyl group attached to the remainder of the molecule via an oxygen atom ("oxy").

The term "heteroaryloxy" refers to a heteroaryl group attached to the remainder of the molecule via an oxygen atom ("oxy").

The term "aryl" as used herein refers to a single aromatic ring or a multiple condensed ring system wherein the ring atoms are carbon. For example, an aryl group can have 6 to 10 carbon atoms, or 6 to 12 carbon atoms. Aryl includes a phenyl radical. Aryl also includes multiple condensed ring systems (e.g., ring systems comprising 2 rings) having about 9 to 12 carbon atoms or 9 to 10 carbon atoms in which at least one ring is aromatic. Such multiple condensed ring systems may be optionally substituted with one or more (e.g., 1 or 2) oxo groups on any cycloalkyl portion of the multiple condensed ring system. It is to be understood that the point of attachment of a multiple condensed ring system, as defined above, can be at any position of the ring system including an aryl or a cycloalkyl portion of the ring. Typical aryl groups include, but are not limited to, phenyl, indenyl, naphthyl, 1,2,3,4-tetrahydronaphthyl, anthracenyl, and the like.

The term "heteroaryl" as used herein refers to a single aromatic ring or a multiple condensed ring system. The term includes single aromatic rings of from about 1 to 6 carbon atoms and about 1-4 heteroatoms selected from the group consisting of oxygen, nitrogen and sulfur in the rings. The sulfur and nitrogen atoms may also be present in an oxidized form provided the ring is aromatic. Such rings include but are not limited to pyridyl, pyrimidinyl, oxazolyl or furyl. The term also includes multiple condensed ring systems (e.g. ring systems comprising 2 rings) wherein a heteroaryl group, as defined above, can be condensed with one or more heteroaryls (e.g., naphthyridinyl), heterocycles, (e.g., 1,2,3, 4-tetrahydronaphthyridinyl), cycloalkyls (e.g., 5,6,7,8-tetrahydroquinolyl) or aryls (e.g. indazolyl) to form a multiple condensed ring system. Such multiple condensed ring systems may be optionally substituted with one or more (e.g., 1 or 2) oxo groups on the cycloalkyl or heterocycle portions of the condensed ring. In one embodiment a monocyclic or bicyclic heteroaryl has 5 to 10 ring atoms comprising 1 to 9 carbon atoms and 1 to 4 heteroatoms. It is to be understood that the point of attachment of a multiple condensed ring system (as defined above for a heteroaryl) can be at any position of the multiple condensed ring system including a heteroaryl, heterocycle, aryl or cycloalkyl portion of the multiple condensed ring system and at any suitable atom of the multiple condensed ring system including a carbon atom and heteroatom (e.g., a nitrogen). Exemplary heteroaryls include but are not limited to pyridyl, pyrrolyl, pyrazinyl, pyrimidinyl, pyridazinyl, pyrazolyl, thienyl, indolyl, imidazolyl, oxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl, benzofuranyl, benzimidazolyl and thianaphthenyl.

The term "heterocyclyl" or "heterocycle" as used herein refers to a single saturated or partially unsaturated ring or a multiple condensed ring system. The term includes single saturated or partially unsaturated rings (e.g., 3, 4, 5, 6 or 7-membered rings) from about 1 to 6 carbon atoms and from about 1 to 3 heteroatoms selected from the group consisting of oxygen, nitrogen and sulfur in the ring. The ring may be substituted with one or more (e.g., 1, 2 or 3) oxo groups and the sulfur and nitrogen atoms may also be present in their oxidized forms. Such rings include but are not limited to azetidinyl, tetrahydrofuranyl or piperidinyl. It is to be understood that the point of attachment for a heterocycle can be at any suitable atom of the heterocycle Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl and tetrahydrothiopyranyl.

The term "haloalkyl" includes an alkyl group as defined herein that is substituted with one or more (e.g., 1, 2, 3, or 4) halo groups. One specific halo alkyl is a "$(C_1$-$C_6)$ haloalkyl".

The term cycloalkyl, carbocycle, or carbocyclyl includes saturated and partially unsaturated carbocyclic ring systems. In one embodiment the cycloalkyl is a monocyclic carbocyclic ring. Such cycloalkyls include "$(C_3$-$C_7)$carbocyclyl" and "$(C_3$-$C_8)$cycloalkyl".

Specific values listed below for radicals, substituents, and ranges, are for illustration only; they do not exclude other defined values or other values within defined ranges for the radicals and substituents.

Specifically, $(C_1$-$C_6)$alkyl can be methyl, ethyl, propyl, isopropyl, butyl, iso-butyl, sec-butyl, pentyl, 3-pentyl, or hexyl; $(C_1$-$C_6)$alkoxy can be methoxy, ethoxy, propoxy, isopropoxy, butoxy, iso-butoxy, sec-butoxy, pentoxy, 3-pentoxy, or hexyloxy; $(C_3$-$C_8)$cycloalkyl can be cyclopropyl, cyclobutyl, cyclopentyl, or cyclohexyl; $(C_1$-$C_6)$haloalkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; aryl can be phenyl, indenyl, or naphthyl; and heteroaryl can be furyl, imidazolyl, triazolyl, triazinyl, oxazolyl, isoxazolyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

It is to be understood that the embodiments provided below are for compounds of formula I and all sub-formulas thereof (e.g., formulas Ia, Ib). It is to be understood the two or more embodiments may be combined.

In one embodiment one of A or B is —C(=O)N($R^{a1}$)—$R^1$ or —($C_1$-$C_3$)alkyl-C(=O)N($R^{a1}$)$R^1$, and the other of A or B is H, halogen, or ($C_1$-$C_6$)alkyl.

In one embodiment one of A or B is —C(=O)N($R^{a1}$)—$R^1$, and the other of A or B is H, halogen, or ($C_1$-$C_6$)alkyl.

In one embodiment one of A or B is —C(=O)N($R^{a1}$)—$R^1$, —($C_1$-$C_3$)alkyl-C(=O)N($R^{a1}$)$R^1$, —($C_1$-$C_3$)alkyl-O—$R^1$, —($C_1$-$C_3$)alkyl-N($R^{a1}$)—$R^1$, —N($R^{a1}$)—$R^1$, or $R^1$ and the other of A or B is hydrogen, bromo, fluoro, or methyl.

In one embodiment A is —C(=O)N($R^{a1}$)—$R^1$, and B is H.

In one embodiment A is —C(=O)N($R^{a1}$)—$R^1$, and B is hydrogen, bromo, fluoro, or methyl.

In one embodiment B is —C(=O)N($R^{a1}$)—$R^1$, and A is H.

In one embodiment one of A or B is —C(=O)N($R^{a1}$)—$R^1$ or —($C_1$-$C_3$)alkyl-C(=O)N($R^{a1}$)$R^1$, and the other of A or B is H.

In one embodiment one of A or B is —C(=O)N($R^{a1}$)—$R^1$ or —($C_1$-$C_3$)alkyl-C(=O)N($R^{a1}$)$R^1$, and the other of A or B is hydrogen, bromo, fluoro, or methyl.

In one embodiment one of A or B is —C(=O)N($R^{a1}$)—$R^1$, and the other of A or B is H.

In one embodiment $R^2$ is hydrogen, ($C_1$-$C_4$)alkyl or benzyl, wherein benzyl is optionally substituted with one or more ($C_1$-$C_4$)alkyl, —O($C_1$-$C_4$)alkyl, halogen or —$NO_2$.

In one embodiment $R^{a1}$ is hydrogen.

In one embodiment $R^2$ is hydrogen or ($C_1$-$C_4$)alkyl.

In one embodiment $R^2$ is hydrogen.

In one embodiment $R^2$ is hydrogen, methyl, or 4-fluorobenzyl.

In one embodiment a compound of formula I is a compound formula Ia or Ib:

Ia

Ib or a salt thereof.

In one embodiment a compound of formula I is a compound formula Ic or Id:

Ic

Id or a salt thereof.

In one embodiment a compound of formula I is a compound formula Ie or Ib:

Ie

If or a salt thereof.

In one embodiment a compound of formula I is a compound formula Ie or Ib:

Ig or a salt thereof.

In one embodiment $R^3$ is hydrogen or aryl wherein the aryl is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy and ($C_1$-$C_4$)haloalkoxy.

In one embodiment $R^3$ is hydrogen or phenyl wherein the phenyl is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy and ($C_1$-$C_4$)haloalkoxy.

In one embodiment $R^3$ is hydrogen or 4-fluorophenyl.

In one embodiment $R^4$ is hydrogen, aryl, or heteroaryl wherein the aryl or heteroaryl is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy.

In one embodiment $R^4$ is hydrogen, phenyl, or pyridinyl wherein the phenyl or pyridinyl is optionally substituted with one or more groups independently selected from the group consisting of halo, —OH, —NO$_2$, —CN, $(C_1-C_4)$alkyl, $(C_1-C_4)$haloalkyl, $(C_1-C_4)$alkoxy, and $(C_1-C_4)$haloalkoxy.

In one embodiment $R^4$ is hydrogen, 4-nitrophenyl, 4-fluorophenyl, 3,4-difluorophenyl, 4-t-butylphenyl, 4-methoxyphenyl, pyridin-4-yl, 4-hydroxyphenyl, 4-chlorophenyl, or 4-cyanophenyl.

In one embodiment $R^4$ is hydrogen, aryl, or heteroaryl wherein the aryl or heteroaryl is optionally substituted with one or more groups independently selected from the group consisting of halo, —OH, —NO$_2$, —CN, $(C_1-C_4)$alkyl, $(C_1-C_4)$haloalkyl, $(C_1-C_4)$alkoxy, methylenedioxy (—OCH$_2$O—), and $(C_1-C_4)$haloalkoxy.

In one embodiment $R^4$ is hydrogen, phenyl, or pyridinyl wherein the phenyl or pyridinyl is optionally substituted with one or more groups independently selected from the group consisting of halo, —OH, —NO$_2$, —CN, $(C_1-C_4)$alkyl, $(C_1-C_4)$haloalkyl, $(C_1-C_4)$alkoxy, methylenedioxy (—OCH$_2$O—), and $(C_1-C_4)$haloalkoxy.

In one embodiment $R^4$ is hydrogen, 4-nitrophenyl, 4-fluorophenyl, 3,4-difluorophenyl, 4-t-butylphenyl, 4-methoxyphenyl, pyridin-4-yl, 4-hydroxyphenyl, 4-chlorophenyl, 4-cyanophenyl, benzo[d][1,3]dioxolyl, 4-cyclopropylphenyl, benzyl, cyclopropylethyl, cyclopropylethynyl, 4-fluorophenoxy, 4-methylphenyl, 4-fluoro-3-methoxyphenyl, 2-chloro-4-fluorophenyl, 3-fluorophenyl, 2,4-difluorophenyl, 3-chloro-4-fluorophenyl, or bromo.

In one embodiment $R^4$ is aryl, or heteroaryl wherein the aryl or heteroaryl is optionally substituted with one or more groups independently selected from the group consisting of halo, —OH, —NO$_2$, —CN, $(C_1-C_4)$alkyl, $(C_1-C_4)$haloalkyl, $(C_1-C_4)$alkoxy, methylenedioxy (—OCH$_2$O—), and $(C_1-C_4)$haloalkoxy.

In one embodiment $R^4$ is phenyl, or pyridinyl wherein the phenyl or pyridinyl is optionally substituted with one or more groups independently selected from the group consisting of halo, —OH, —NO$_2$, —CN, $(C_1-C_4)$alkyl, $(C_1-C_4)$haloalkyl, $(C_1-C_4)$alkoxy, methylenedioxy (—OCH$_2$O—), and $(C_1-C_4)$haloalkoxy.

In one embodiment $R^4$ is 4-nitrophenyl, 4-fluorophenyl, 3,4-difluorophenyl, 4-t-butylphenyl, 4-methoxyphenyl, pyridin-4-yl, 4-hydroxyphenyl, 4-chlorophenyl, 4-cyanophenyl, benzo[d][1,3]dioxolyl, 4-cyclopropylphenyl, benzyl, cyclopropylethyl, cyclopropylethynyl, 4-fluorophenoxy, 4-methylphenyl, 4-fluoro-3-methoxyphenyl, 2-chloro-4-fluorophenyl, 3-fluorophenyl, 2,4-difluorophenyl, 3-chloro-4-fluorophenyl, or bromo.

In one embodiment $R^5$ is hydrogen or aryl wherein the aryl is optionally substituted with one or more groups independently selected from the group consisting of halo, —OH, —NO$_2$, —CN, $(C_1-C_4)$alkyl, $(C_1-C_4)$haloalkyl, $(C_1-C_4)$alkoxy and $(C_1-C_4)$haloalkoxy.

In one embodiment $R^5$ is hydrogen or phenyl wherein the phenyl is optionally substituted with one or more groups independently selected from the group consisting of halo, —OH, —NO$_2$, —CN, $(C_1-C_4)$alkyl, $(C_1-C_4)$haloalkyl, $(C_1-C_4)$alkoxy and $(C_1-C_4)$haloalkoxy.

In one embodiment $R^5$ is hydrogen or aryl wherein the aryl is optionally substituted with one or more groups independently selected from the group consisting of halo, —OH, —NO$_2$, —CN, $(C_1-C_4)$alkyl, $(C_1-C_4)$haloalkyl, $(C_1-C_4)$alkoxy, methylenedioxy (—OCH$_2$O—), and $(C_1-C_4)$haloalkoxy.

In one embodiment $R^5$ is hydrogen or phenyl wherein the phenyl is optionally substituted with one or more groups independently selected from the group consisting of halo, —OH, —NO$_2$, —CN, $(C_1-C_4)$alkyl, $(C_1-C_4)$haloalkyl, $(C_1-C_4)$alkoxy, methylenedioxy (—OCH$_2$O—), and $(C_1-C_4)$haloalkoxy.

In one embodiment $R^5$ is hydrogen or 4-fluorophenyl.

In one embodiment $R^4$ is halo, $(C_1-C_4)$alkyl, $(C_1-C_4)$haloalkyl, $(C_1-C_4)$alkoxy, $(C_1-C_4)$haloalkoxy, aryl, heteroaryl, aryl$(C_1-C_4)$alkyl-, heteroaryl$(C_1-C_4)$alkyl-, $(C_3-C_7)$carbocyclyl$(C_1-C_4)$alkyl-, $(C_3-C_7)$carbocyclyl$(C_2-C_4)$alkynyl-, phenoxy or heteroaryloxy, wherein the aryl, heteroaryl, aryl$(C_1-C_4)$alkyl-, heteroaryl$(C_1-C_4)$alkyl-, $(C_3-C_7)$carbocyclyl$(C_1-C_4)$alkyl-, $(C_3-C_7)$carbocyclyl$(C_2-C_4)$alkynyl-, phenoxy or heteroaryloxy, is optionally substituted with one or more groups independently selected from the group consisting of halo, —OH, —NO$_2$, —CN, $(C_1-C_4)$alkyl, $(C_1-C_4)$haloalkyl, $(C_1-C_4)$alkoxy, $(C_1-C_4)$haloalkoxy, methylenedioxy (—OCH$_2$O—), and $(C_3-C_7)$carbocyclyl; and $R^5$ is hydrogen, halo, $(C_1-C_4)$alkyl, $(C_1-C_4)$haloalkyl, $(C_1-C_4)$alkoxy, $(C_1-C_4)$haloalkoxy, aryl, heteroaryl aryl$(C_1-C_4)$alkyl-, heteroaryl$(C_1-C_4)$alkyl-, $(C_3-C_7)$carbocyclyl$(C_1-C_4)$alkyl-, $(C_3-C_7)$carbocyclyl$(C_2-C_4)$alkynyl-, phenoxy or heteroaryloxy, wherein the aryl, heteroaryl, aryl$(C_1-C_4)$alkyl-, heteroaryl$(C_1-C_4)$alkyl-, $(C_3-C_7)$carbocyclyl$(C_1-C_4)$alkyl-, $(C_3-C_7)$carbocyclyl$(C_2-C_4)$alkynyl-, phenoxy or heteroaryloxy, is optionally substituted with one or more groups independently selected from the group consisting of halo, —OH, —NO$_2$, —CN, $(C_1-C_4)$alkyl, $(C_1-C_4)$haloalkyl, $(C_1-C_4)$alkoxy, $(C_1-C_4)$haloalkoxy, methylenedioxy (—OCH$_2$O—), and $(C_3-C_7)$carbocyclyl;

In one embodiment $R^4$ is aryl, or heteroaryl, wherein the aryl, or heteroaryl, is optionally substituted with one or more groups independently selected from the group consisting of halo, —OH, —NO$_2$, —CN, $(C_1-C_4)$alkyl, $(C_1-C_4)$haloalkyl, $(C_1-C_4)$alkoxy, $(C_1-C_4)$haloalkoxy, methylenedioxy (—OCH$_2$O—), and $(C_3-C_7)$carbocyclyl; and $R^5$ is hydrogen, halo, $(C_1-C_4)$alkyl, $(C_1-C_4)$haloalkyl, $(C_1-C_4)$alkoxy, $(C_1-C_4)$haloalkoxy, aryl, heteroaryl aryl$(C_1-C_4)$alkyl-, heteroaryl $(C_1-C_4)$alkyl-, $(C_3-C_7)$carbocyclyl$(C_1-C_4)$alkyl-, $(C_3-C_7)$carbocyclyl$(C_2-C_4)$alkynyl-, phenoxy or heteroaryloxy, wherein the aryl, heteroaryl, aryl$(C_1-C_4)$alkyl-, heteroaryl $(C_1-C_4)$alkyl-, $(C_3-C_7)$carbocyclyl$(C_1-C_4)$alkyl-, $(C_3-C_7)$carbocyclyl$(C_2-C_4)$alkynyl-, phenoxy or heteroaryloxy, is optionally substituted with one or more groups independently selected from the group consisting of halo, —OH, —NO$_2$, —CN, $(C_1-C_4)$alkyl, $(C_1-C_4)$haloalkyl, $(C_1-C_4)$alkoxy, $(C_1-C_4)$haloalkoxy, methylenedioxy (—OCH$_2$O—), and $(C_3-C_7)$carbocyclyl.

In one embodiment $R^6$ is hydrogen or aryl wherein the aryl is optionally substituted with one or more groups independently selected from the group consisting of halo, —OH, —NO$_2$, —CN, $(C_1-C_4)$alkyl, $(C_1-C_4)$haloalkyl, $(C_1-C_4)$alkoxy and $(C_1-C_4)$haloalkoxy.

In one embodiment $R^6$ is hydrogen or phenyl wherein the phenyl is optionally substituted with one or more groups independently selected from the group consisting of halo, —OH, —NO$_2$, —CN, $(C_1-C_4)$alkyl, $(C_1-C_4)$haloalkyl, $(C_1-C_4)$alkoxy and $(C_1-C_4)$haloalkoxy.

In one embodiment $R^6$ is hydrogen or 4-fluorophenyl.

In one embodiment $R^6$ is hydrogen, 4-fluorophenyl, or methoxy

In one embodiment $R^1$ is $(C_1-C_{14})$alkyl substituted with one or more groups independently selected from —NR$^{b2}$R$^{c2}$.

In one embodiment $R^1$ is $(C_2-C_{10})$alkyl substituted with one or more groups independently selected from $-NR^{b2}R^{c2}$.

In one embodiment $R^1$ is $(C_1-C_{14})$alkyl substituted with one or more groups independently selected from $-NR^{b2}R^{c2}$.

In one embodiment $R^1$ is $(C_2-C_8)$alkyl substituted with two or more groups independently selected from $-NR^{b2}R^{c2}$.

In one embodiment $R^1$ is $(C_4-C_8)$alkyl substituted with two or more groups independently selected from $-NR^{b2}R^{c2}$.

In one embodiment $R^{b2}$ and $R^{c2}$ are each hydrogen.

In one embodiment $R^1$ is $(C_3-C_7)$carbocyclyl, -4-7 membered monocyclic heterocyclyl, 4-7 membered monocyclic heterocyclyl-$(C_1-C_4)$alkyl-, $(C_3-C_7)$carbocyclyl-$NR^e$—$(C_1-C_4)$alkyl- or 4-7 membered monocyclic heterocyclyl-$NR^e$—$(C_1-C_4)$alkyl- wherein each $(C_3-C_7)$carbocyclyl or $(C_3-C_7)$carbocyclyl-$NR^e$—$(C_1-C_4)$alkyl- is independently substituted with one or more $Z^1$ or $Z^2$, and wherein each 4-7 membered monocyclic heterocyclyl, 4-7 membered monocyclic heterocyclyl-$(C_1-C_4)$alkyl- or 4-7 membered monocyclic heterocyclyl-$NR^e$—$(C_1-C_4)$alkyl- is independently optionally substituted with one or more $Z^1$ or $Z^2$, and wherein any $(C_3-C_7)$carbocyclyl, $(C_3-C_7)$carbocyclyl-$(C_1-C_4)$alkyl-, 4-7 membered monocyclic heterocyclyl, 4-7 membered monocyclic heterocyclyl-$(C_1-C_4)$alkyl-, $(C_3-C_7)$carbocyclyl $NR^e$—$(C_1-C_4)$alkyl- or 4-7 membered monocyclic heterocyclyl-$NR^e$—$(C_1-C_4)$alkyl- of $R^1$ is independently optionally substituted independently with one or more halo, $(C_1-C_4)$alkyl, $(C_3-C_7)$carbocyclyl, $-C(=O)NH_2$, $-C(=O)NH(C_1-C_4)$alkyl, $-C(=O)N((C_1-C_4)$alkyl$)_2$, $-NHC(=O)(C_1-C_4)$alkyl-$NH_2$, or 3-7 membered monocyclic heterocyclyl wherein $(C_1-C_4)$alkyl, $(C_3-C_7)$carbocyclyl or 3-7 membered monocyclic heterocyclyl is optionally substituted with one or more halogen, $(C_1-C_4)$alkyl, $-NH_2$, $-NH(C_1-C_4)$alkyl or $-N((C_1-C_4)$alkyl$)_2$.

In one embodiment $R^1$ is -4-7 membered monocyclic heterocyclyl, 4-7 membered monocyclic heterocyclyl-$(C_1-C_4)$alkyl-, or 4-7 membered monocyclic heterocyclyl-$NR^e$—$(C_1-C_4)$alkyl- wherein each 4-7 membered monocyclic heterocyclyl, 4-7 membered monocyclic heterocyclyl-$(C_1-C_4)$alkyl- or 4-7 membered monocyclic heterocyclyl-$NR^e$—$(C_1-C_4)$alkyl- is independently optionally substituted with one or more $Z^1$ or $Z^2$, and wherein any $(C_3-C_7)$carbocyclyl, $(C_3-C_7)$carbocyclyl-$(C_1-C_4)$alkyl-, 4-7 membered monocyclic heterocyclyl, 4-7 membered monocyclic heterocyclyl-$(C_1-C_4)$alkyl-, $(C_3-C_7)$carbocyclyl $NR^e$—$(C_1-C_4)$alkyl- or 4-7 membered monocyclic heterocyclyl-$NR^e$—$(C_1-C_4)$alkyl- of $R^1$ is independently optionally substituted independently with one or more halo, $(C_1-C_4)$alkyl, $(C_3-C_7)$carbocyclyl, $-C(=O)NH_2$, $-C(=O)NH(C_1-C_4)$alkyl, $-C(=O)N((C_1-C_4)$alkyl$)_2$, $-NHC(=O)(C_1-C_4)$alkyl-$NH_2$, or 3-7 membered monocyclic heterocyclyl wherein $(C_1-C_4)$alkyl, $(C_3-C_7)$carbocyclyl or 3-7 membered monocyclic heterocyclyl is optionally substituted with one or more halogen, $(C_1-C_4)$alkyl, $-NH_2$, $-NH(C_1-C_4)$alkyl or $-N((C_1-C_4)$alkyl$)_2$.

In one embodiment $R^1$ is a 4-7 membered monocyclic heterocyclyl-$(C_1-C_4)$alkyl-, wherein the 4-7 membered monocyclic heterocyclyl-$(C_1-C_4)$alkyl- is substituted with one or more groups independently selected from the group consisting of Z and $-(C_1-C_6)$alkyl substituted with one or more Z, wherein each Z is independently selected from the group consisting of $-NR^{b3}R^{c3}$, $-NHNH_2$, $-C(=NR^{a3})(NR^{b3}R^{c3})$, $-NR^{a3}C(=NR^{a3})(R^{a3})$, and $-NR^{a3}C(=NR^{a3})(NR^{b3}R^{c3})$ and wherein the 4-7 membered monocyclic heterocyclyl-$(C_1-C_4)$alkyl- is optionally substituted with one or more $(C_1-C_6)$alkyl.\

In one embodiment $R^1$ is a 4-7 membered monocyclic heterocyclyl-$(C_1-C_4)$alkyl-, wherein the 4-7 membered monocyclic heterocyclyl-$(C_1-C_4)$alkyl- is substituted with one or more groups independently selected from the group consisting of Z and $(C_1-C_6)$alkyl substituted with one or more Z, wherein each Z is independently $-NR^{b3}R^{c3}$ and wherein the 4-7 membered monocyclic heterocyclyl-$(C_1-C_4)$alkyl- is optionally substituted with one or more $(C_1-C_6)$alkyl.

In one embodiment $R^1$ is pyrrolidinyl-$(C_1-C_4)$alkyl-, wherein the pyrrolidinyl-$(C_1-C_4)$alkyl- is substituted with one or more groups independently selected from the group consisting of Z and $-(C_1-C_6)$alkyl substituted with one or more Z, wherein each Z is independently $-NR^{b3}R^{c3}$ and wherein is pyrrolidinyl-$(C_1-C_4)$alkyl- is optionally substituted independently with one or more $(C_1-C_6)$alkyl In one embodiment $R^1$ is pyrrolidinyl-$(CH_2)$—, wherein the pyrrolidinyl-$(CH_2)$— is substituted with one or more groups independently selected from the group consisting of Z and $-(C_1-C_6)$alkyl substituted with one or more Z, wherein each Z is independently $-NR^{b3}R^{c3}$ and wherein the pyrrolidinyl-$(CH_2)$— is optionally substituted independently with one or more $(C_1-C_6)$alkyl.

In one embodiment $R^1$ is pyrrolidinyl-$(CH_2)$—, wherein the pyrrolidinyl-$(CH_2)$— is substituted on the pyrrolidinyl with an $-(C_1-C_6)$alkyl substituted with one or more $-NR^{b3}R^{c3}$.

In one embodiment $R^{b3}$ and $R^{c3}$ are each hydrogen.

In one embodiment $R^1$ is:

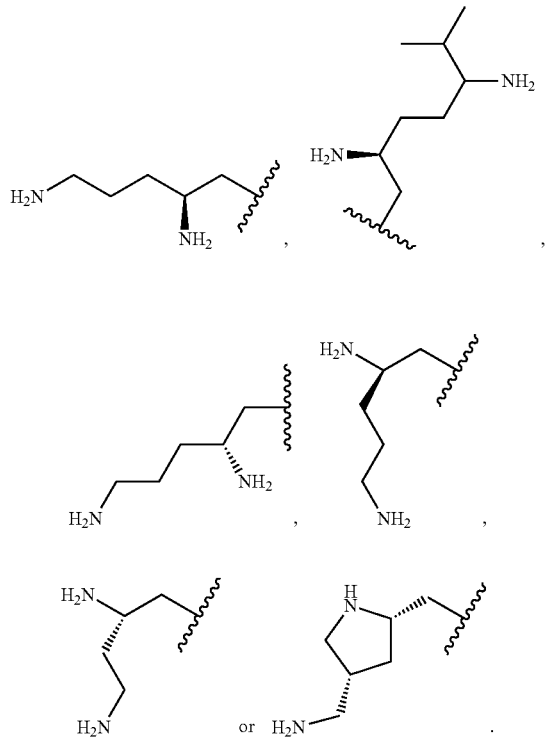

In one embodiment $R^1$ is:
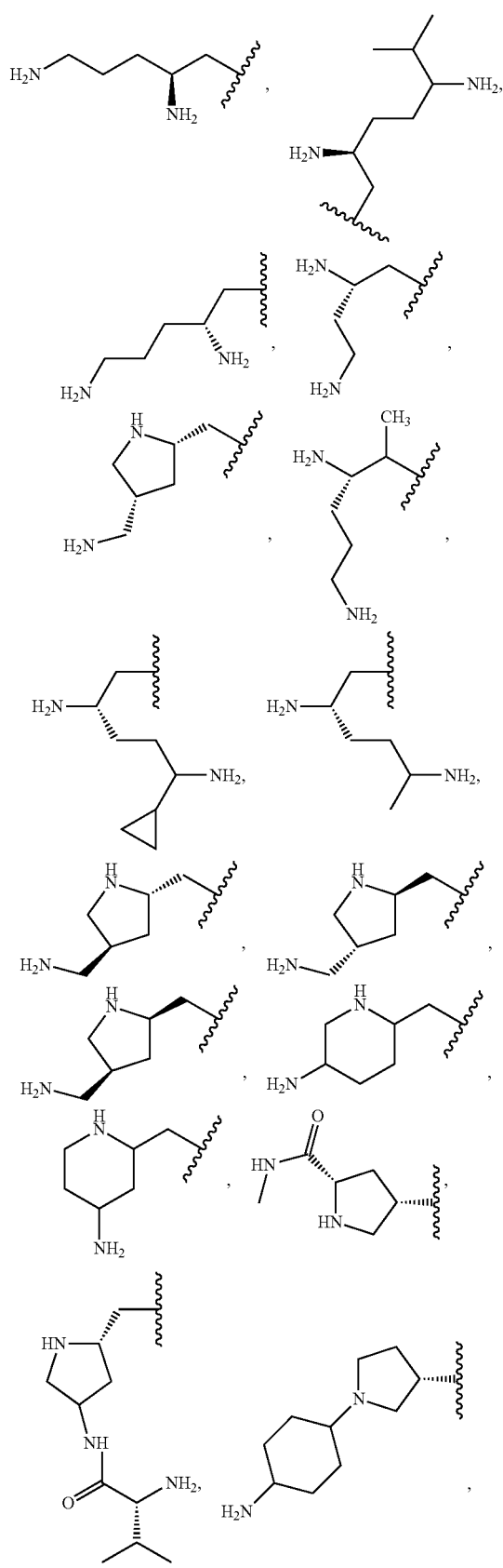
-continued
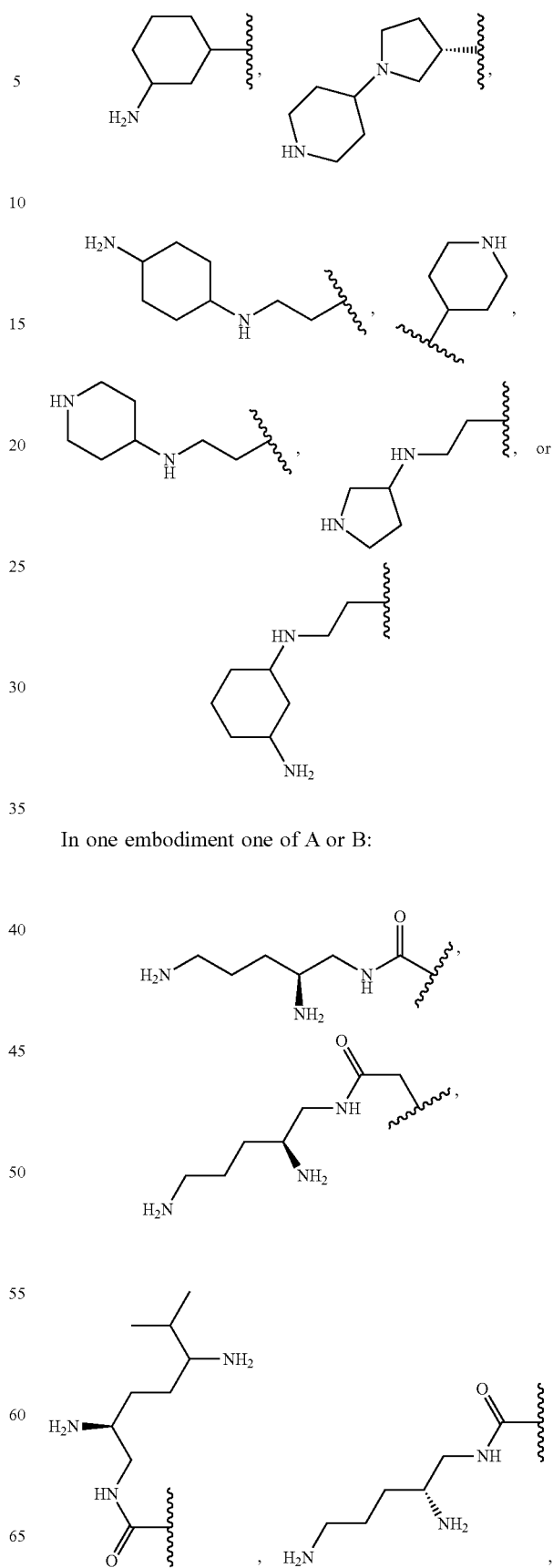
In one embodiment one of A or B:

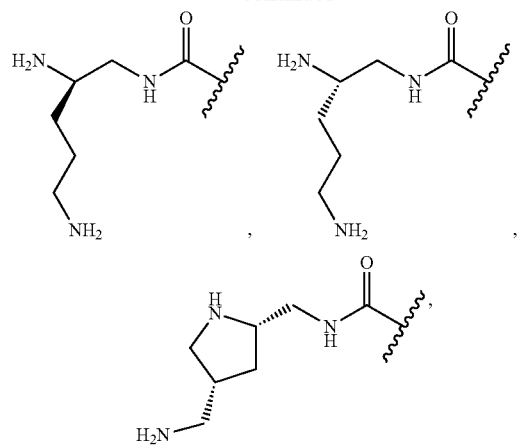
and the other of A or B is H.
In one embodiment one of A or B:
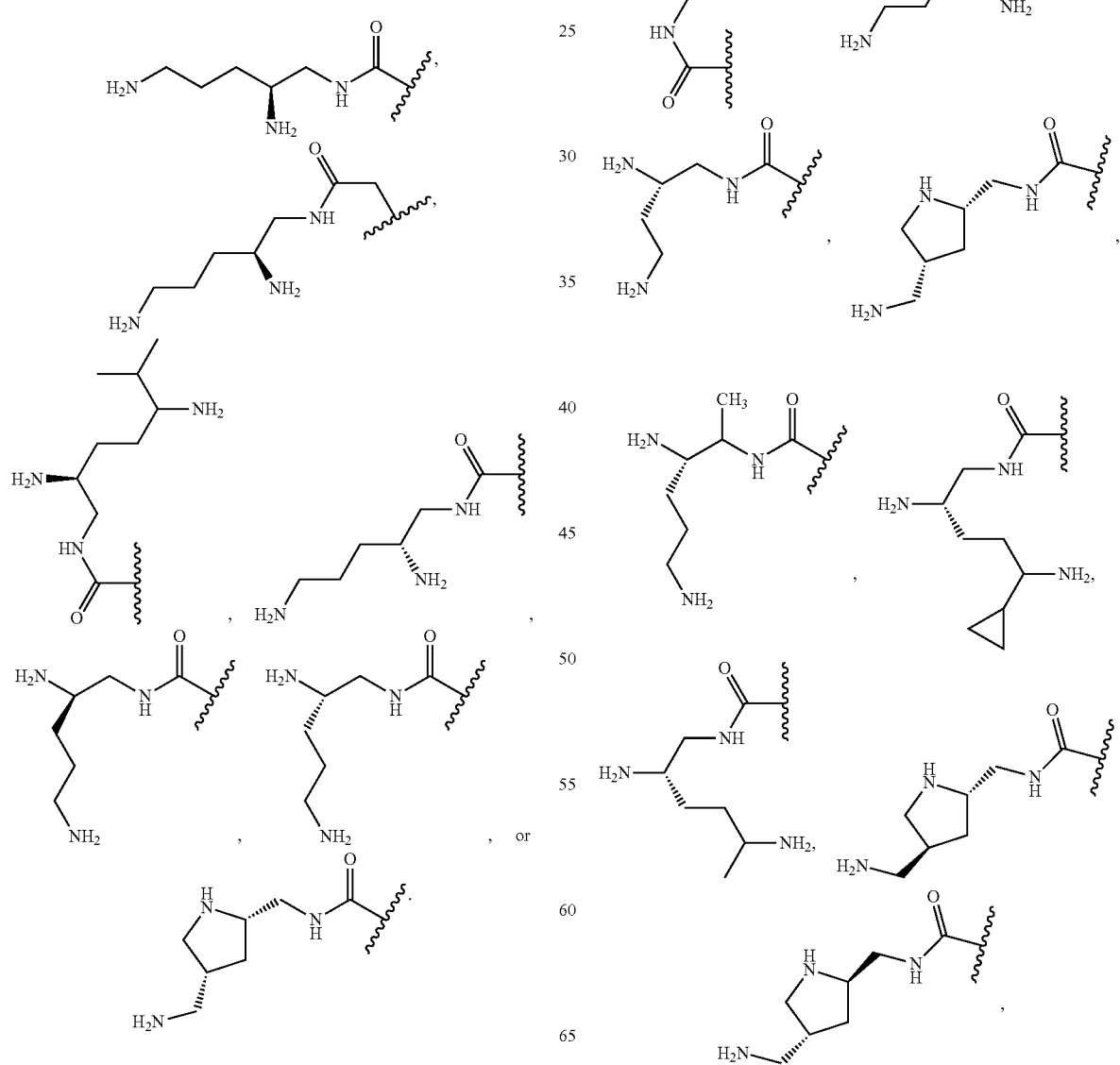
In one embodiment one of A or B:
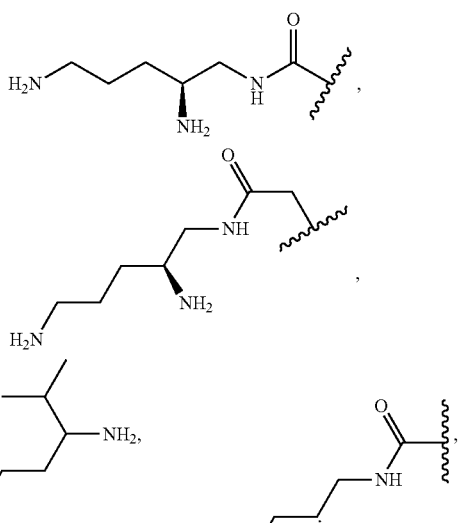

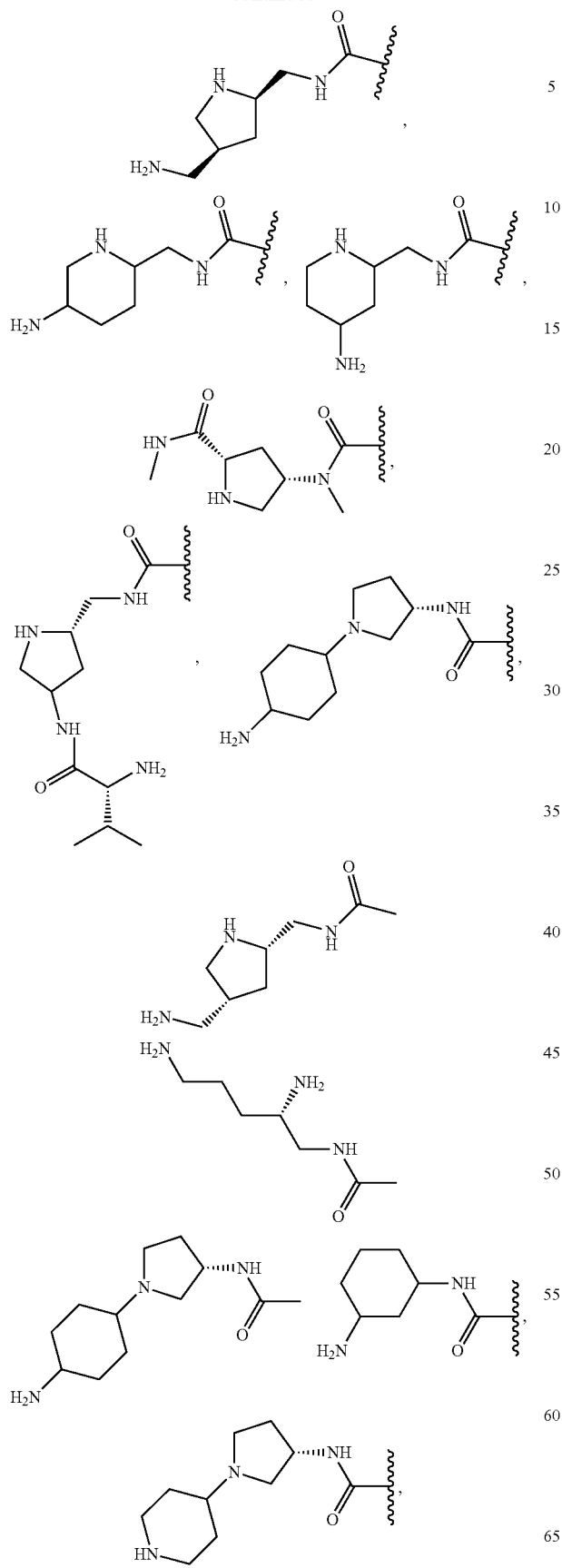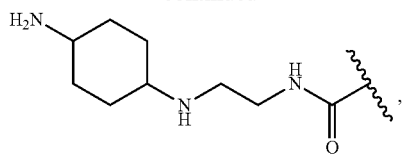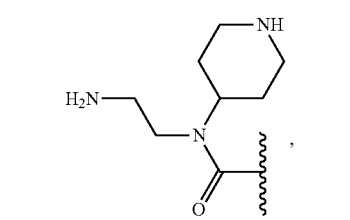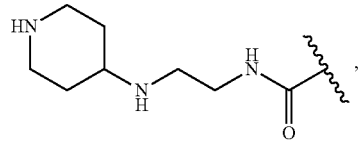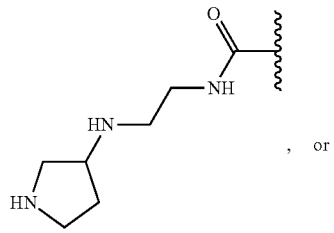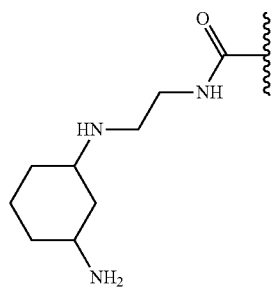
One embodiment provides a compound that is:
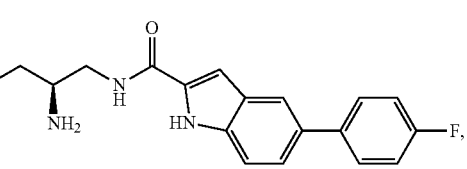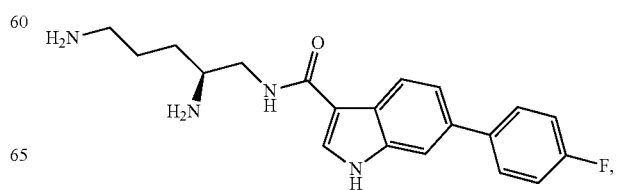

21
-continued
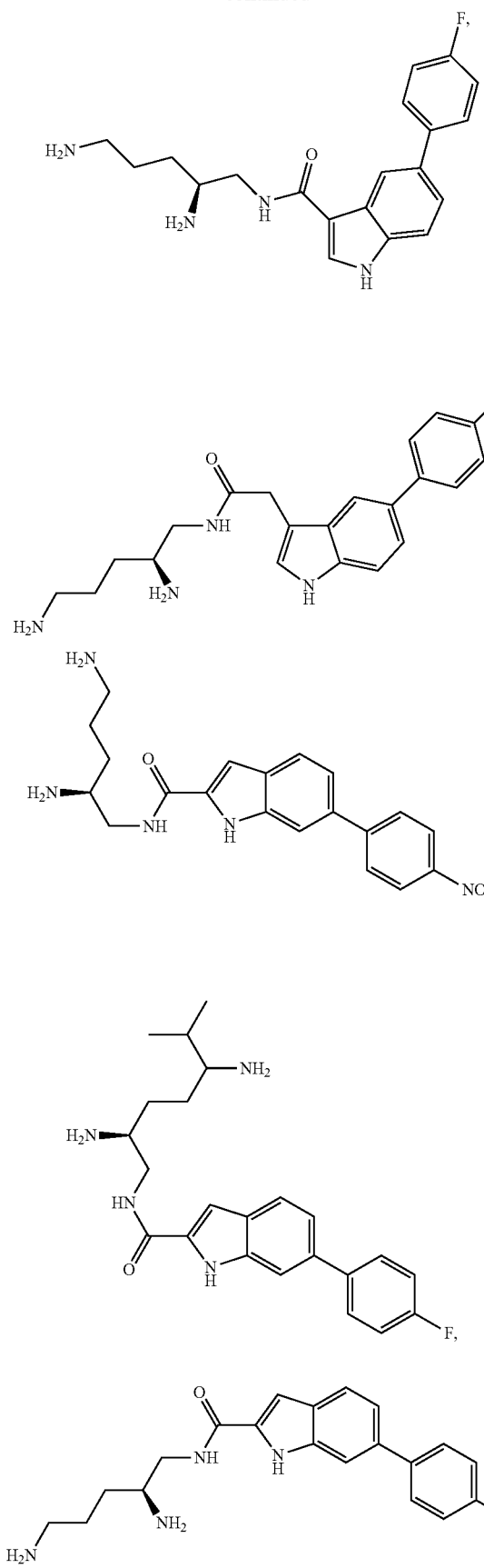
22
-continued
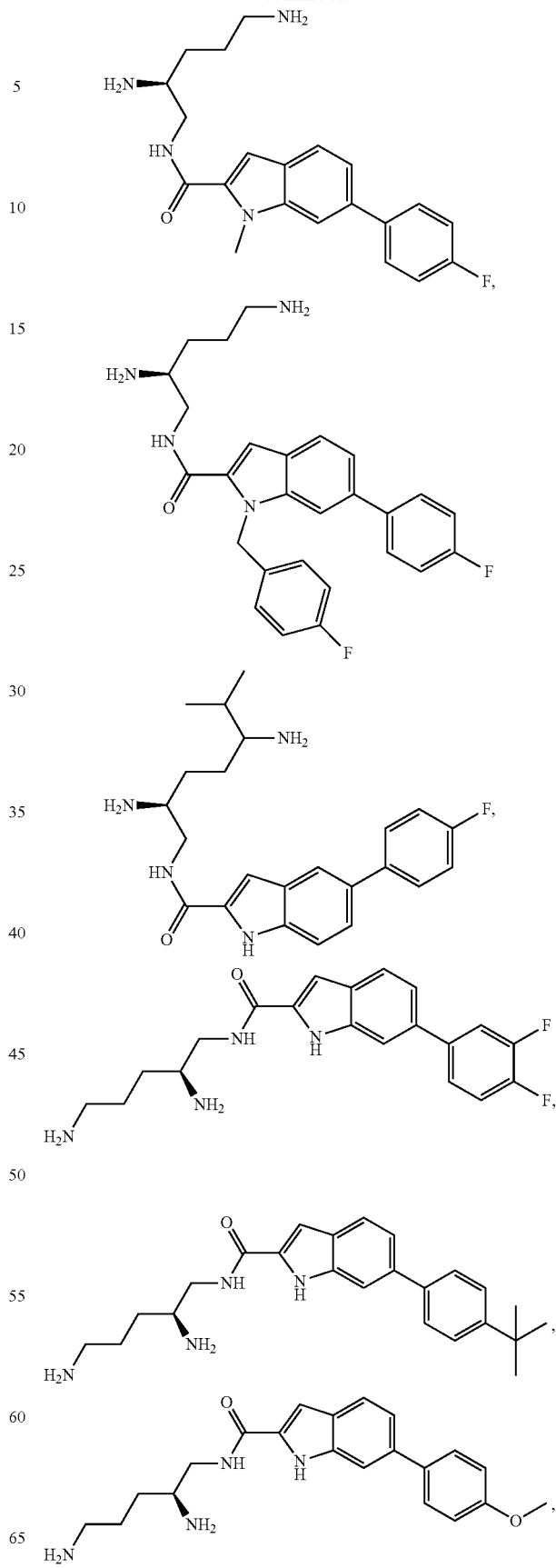

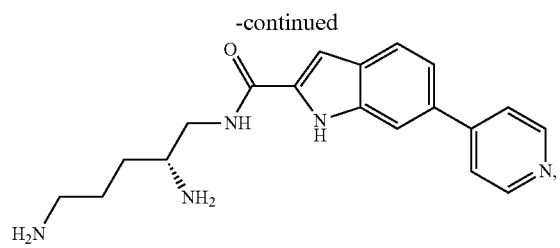
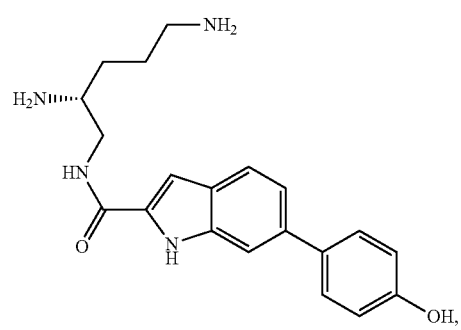
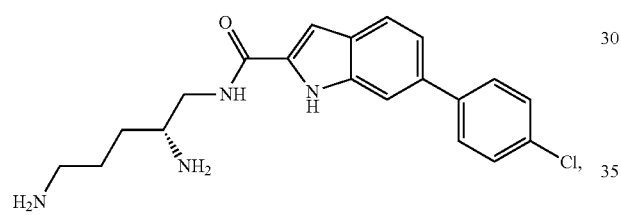
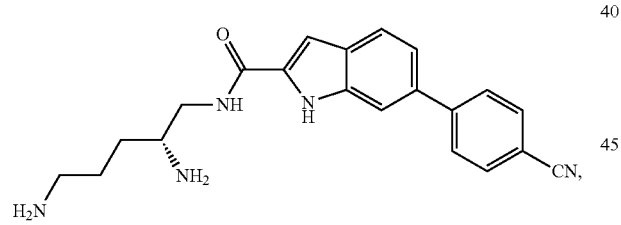
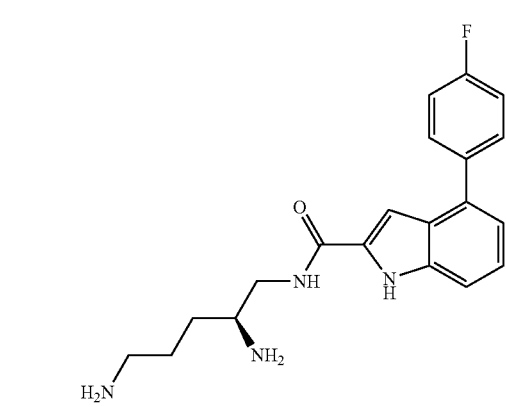
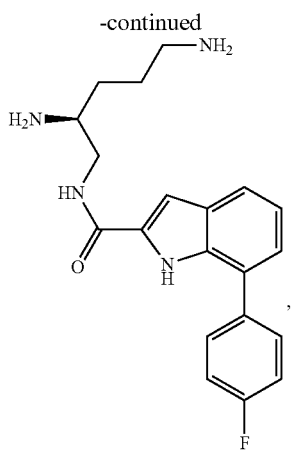
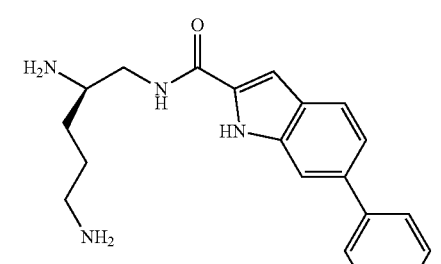
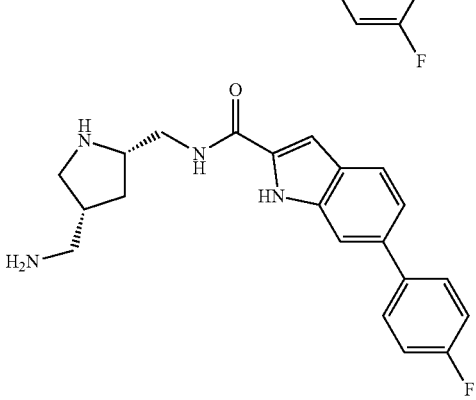
or a salt thereof.
One embodiment provides a compound that is:
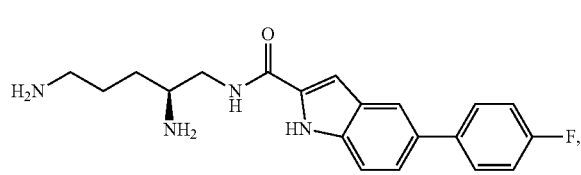

25
-continued
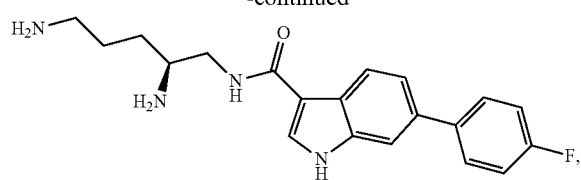
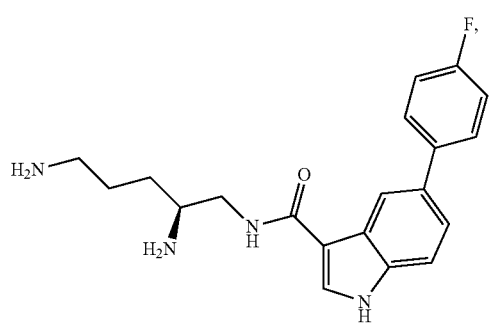
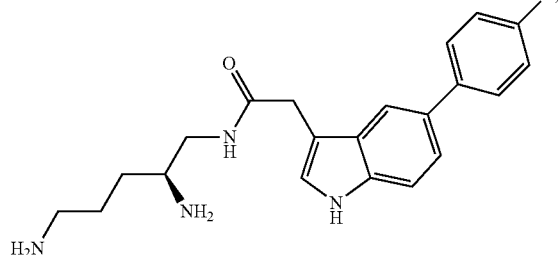
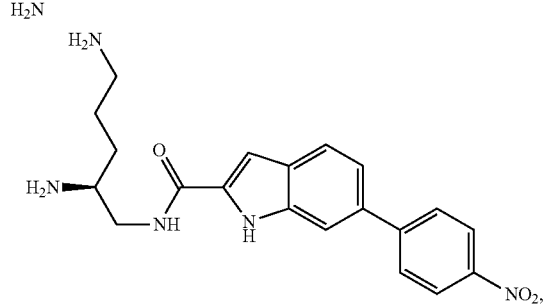
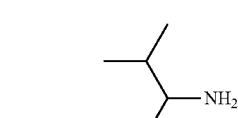
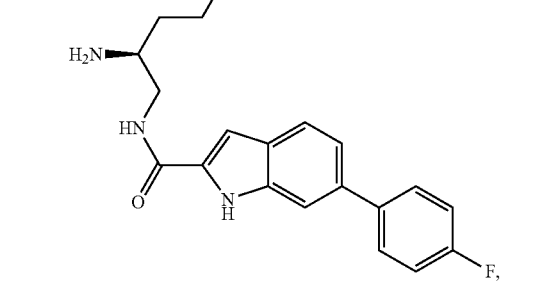
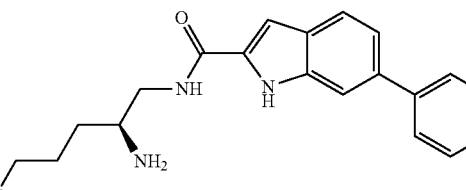
26
-continued
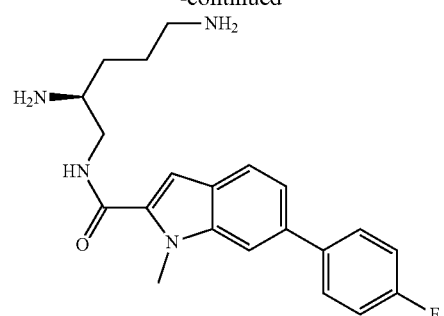
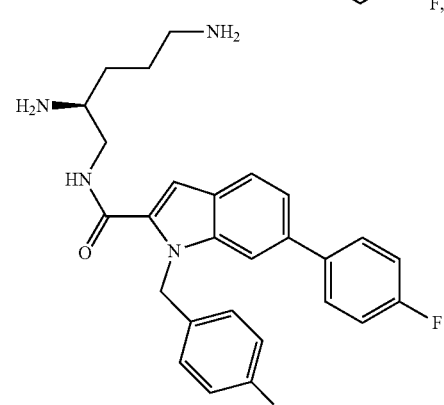
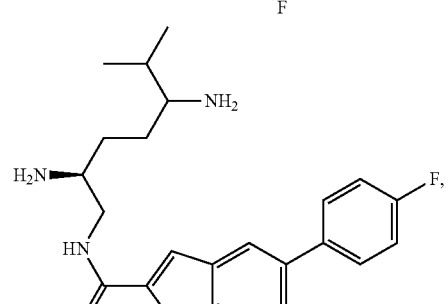
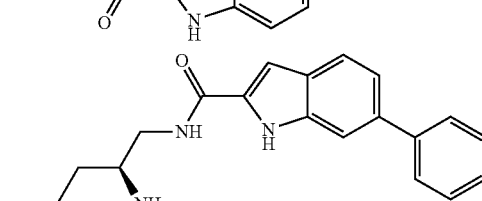
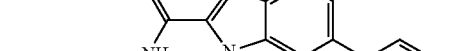

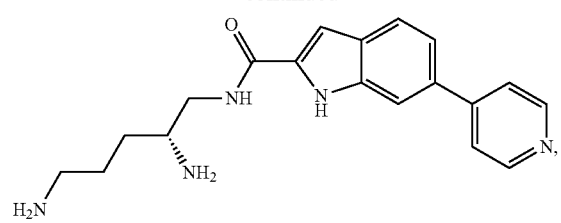
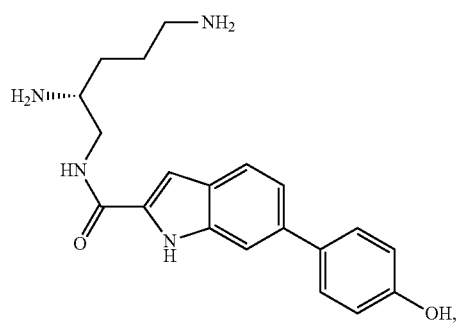
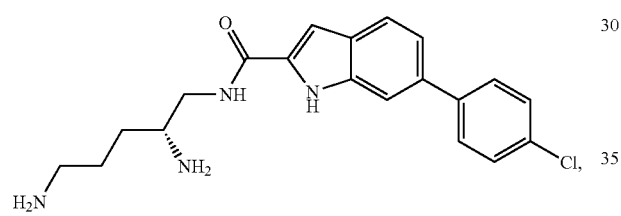
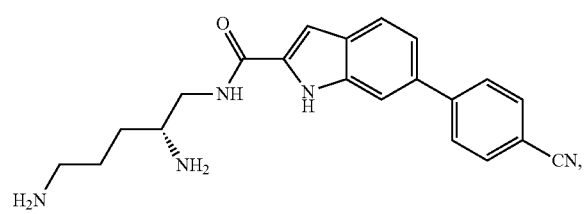
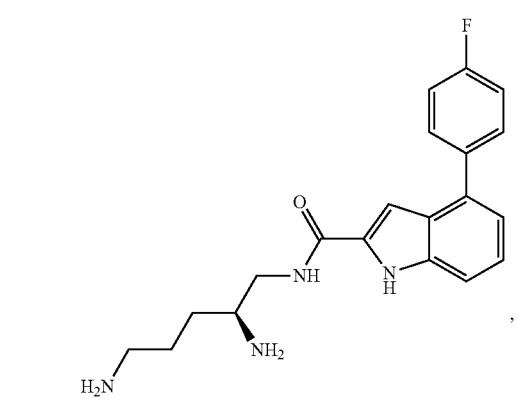
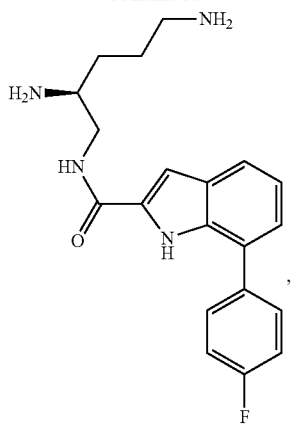
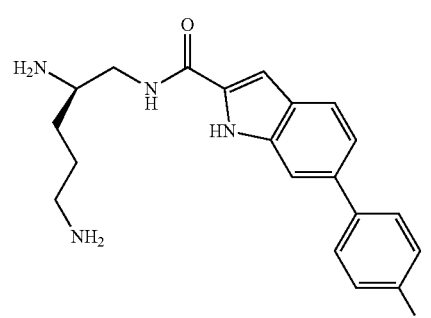
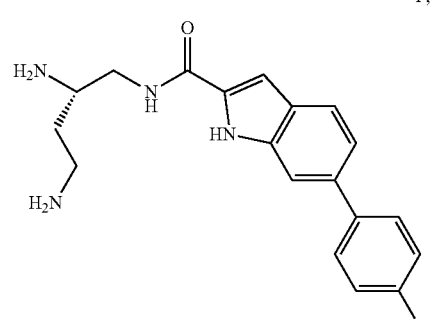
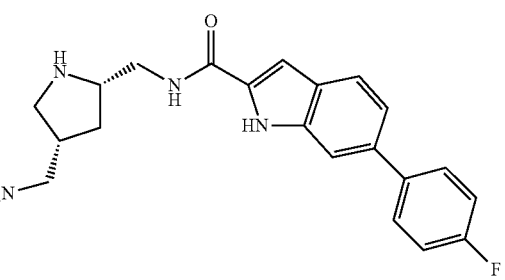
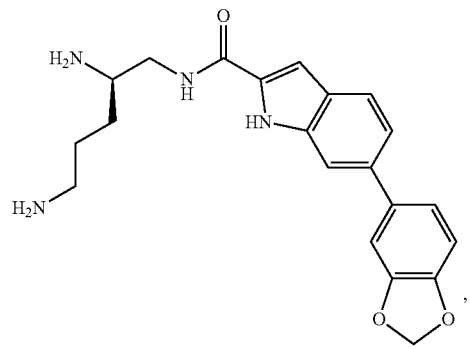

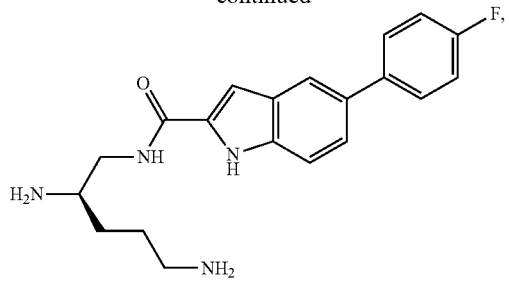
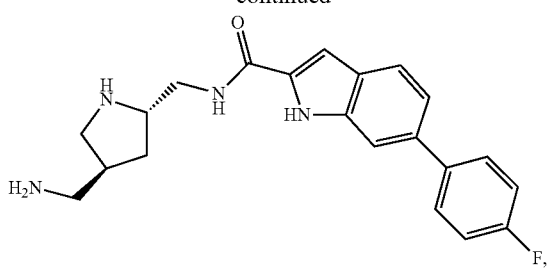
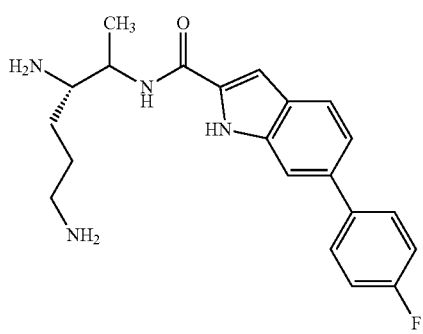
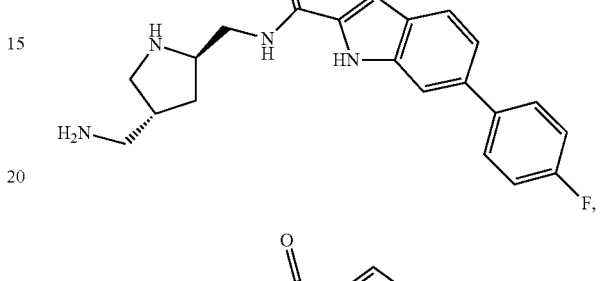
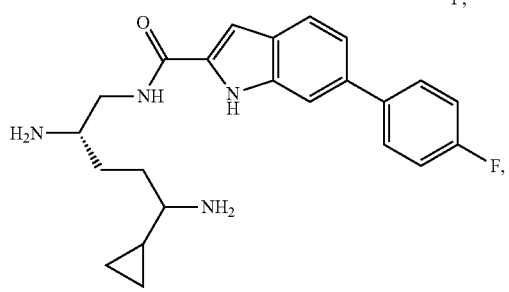
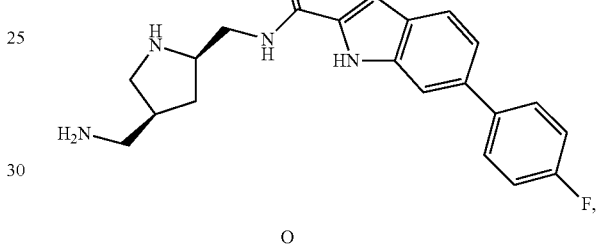
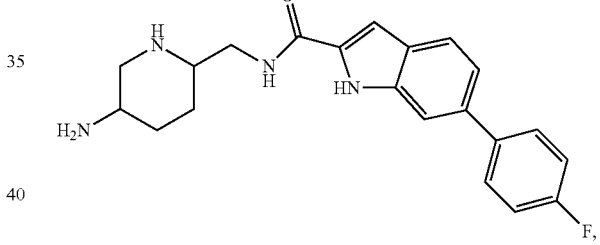
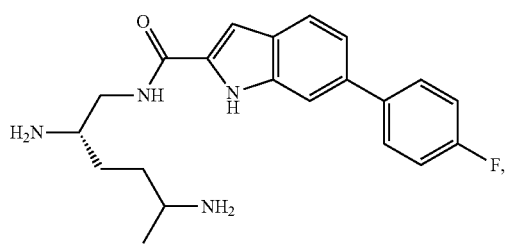
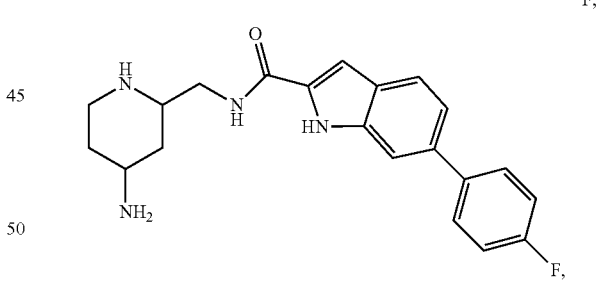
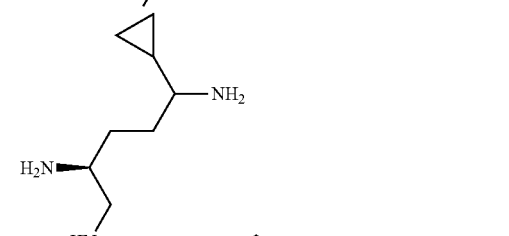
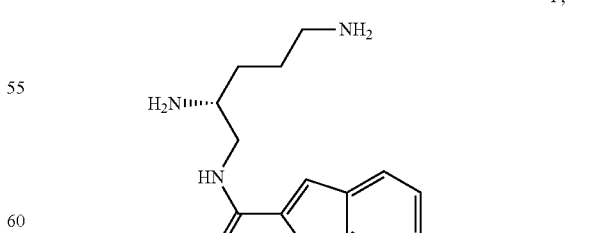
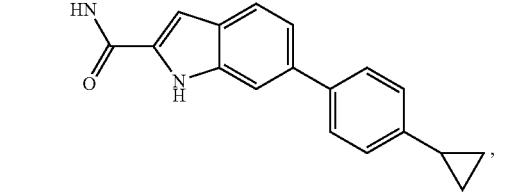
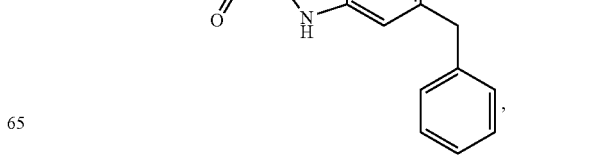

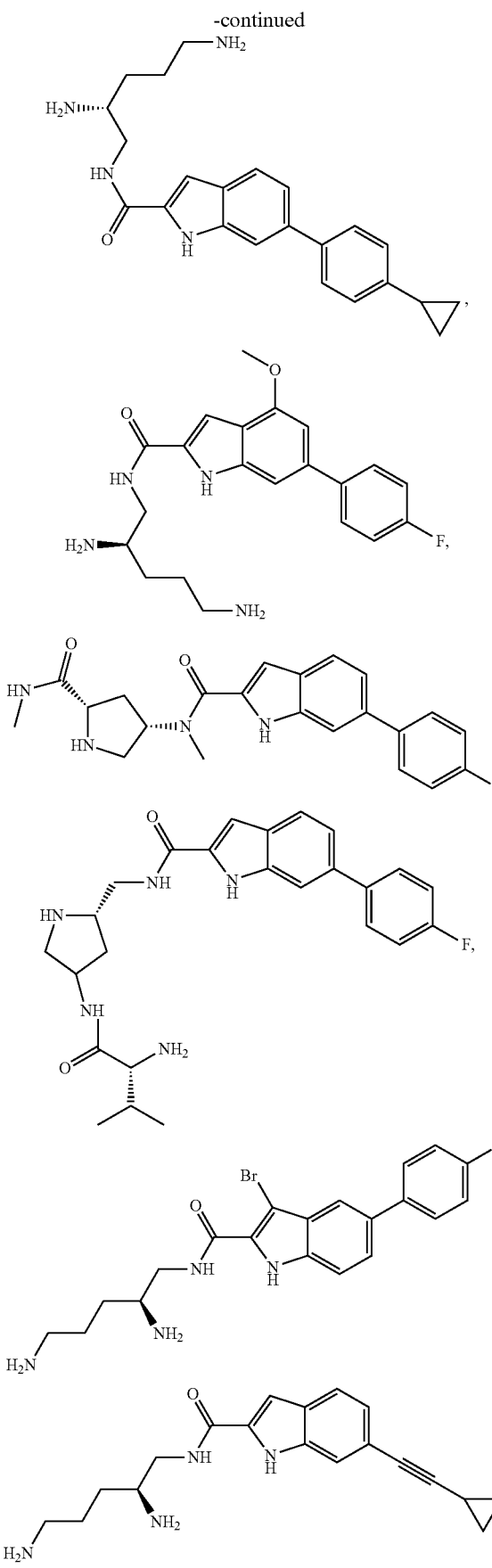
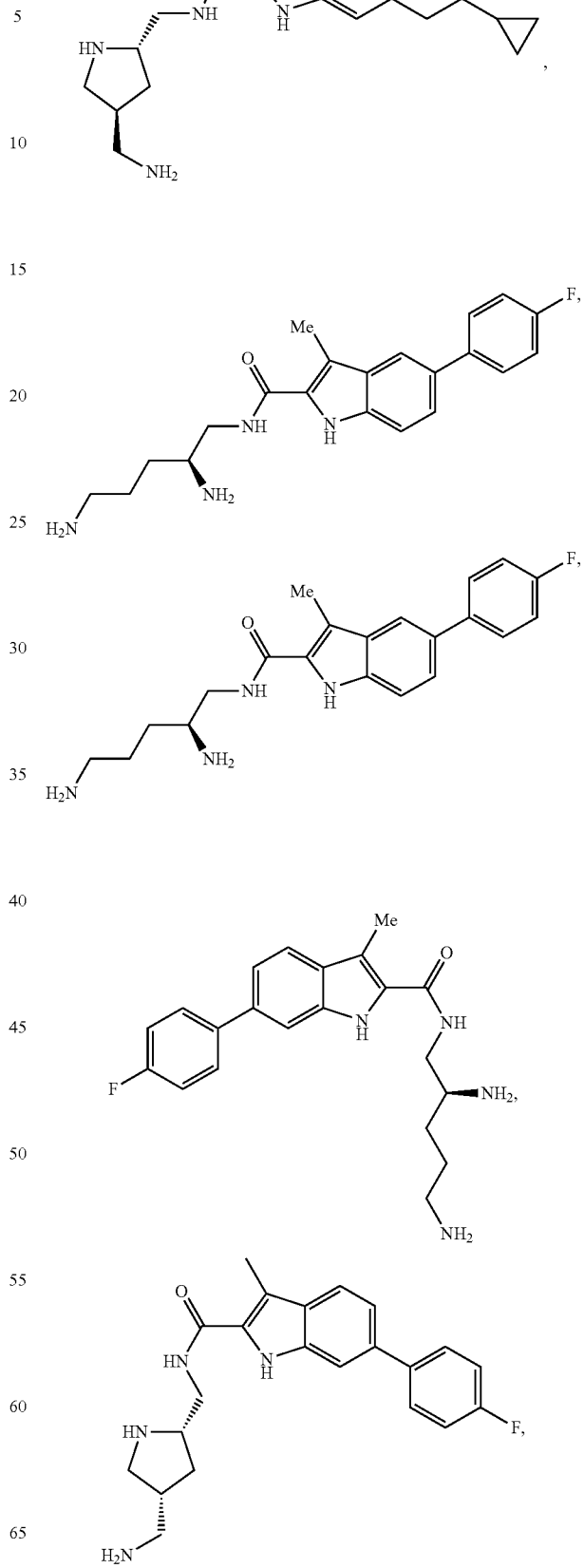

-continued
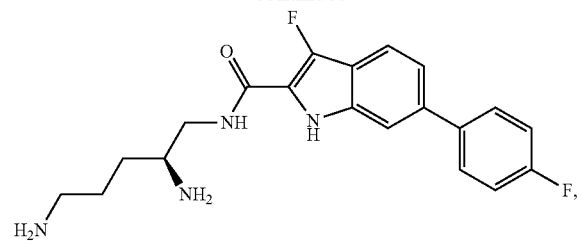
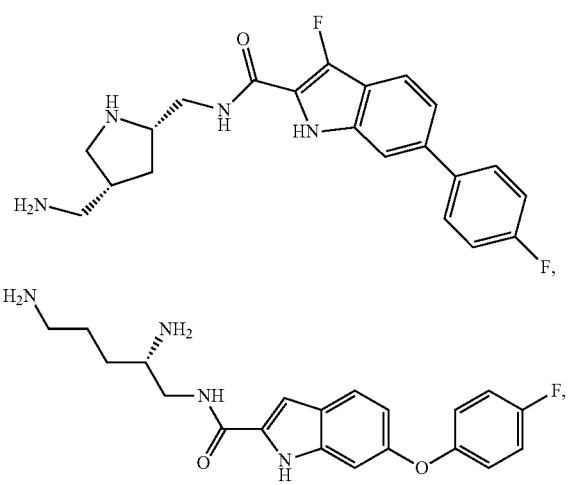
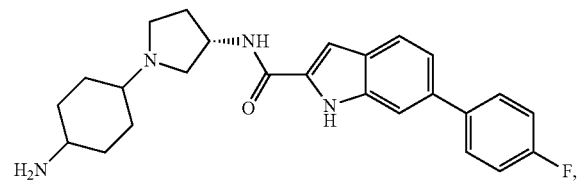
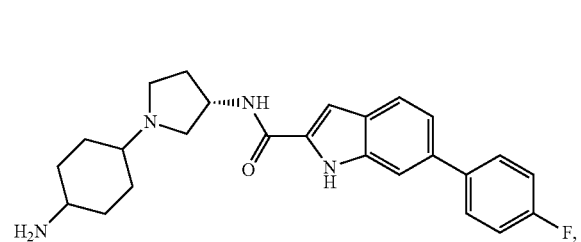
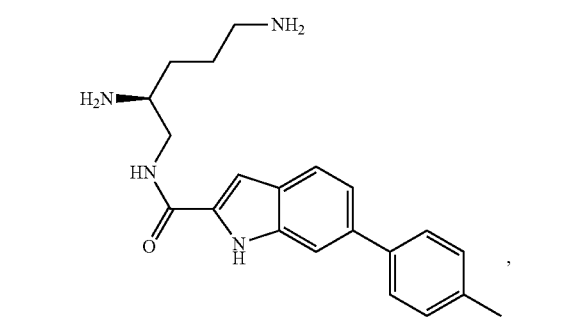
-continued
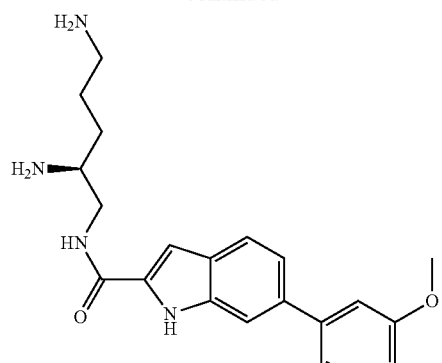
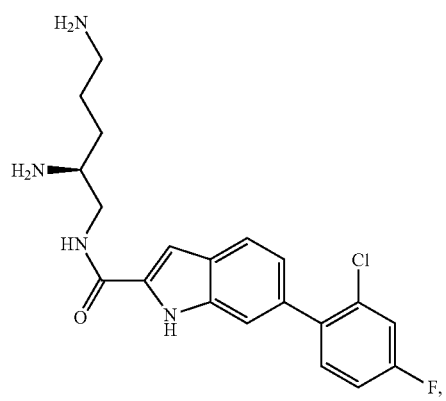
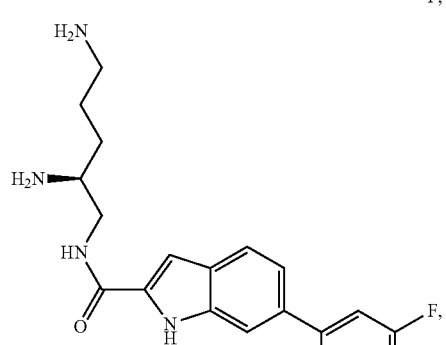
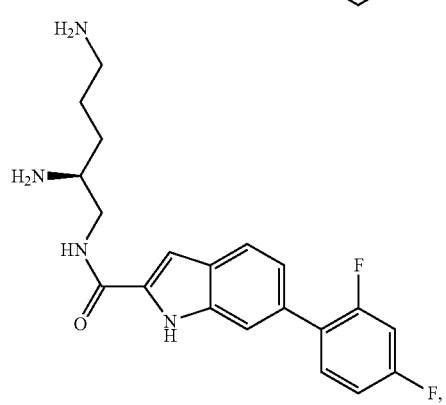

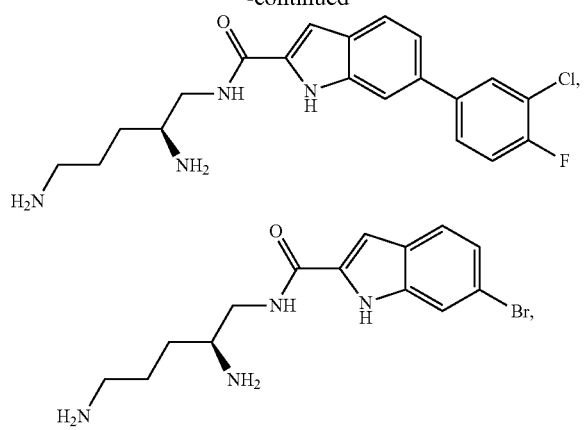
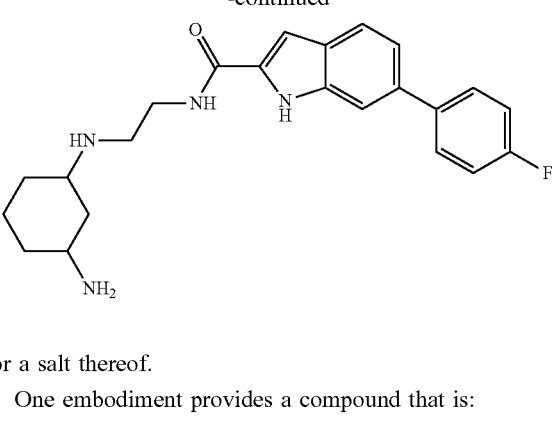
or a salt thereof.
One embodiment provides a compound that is:
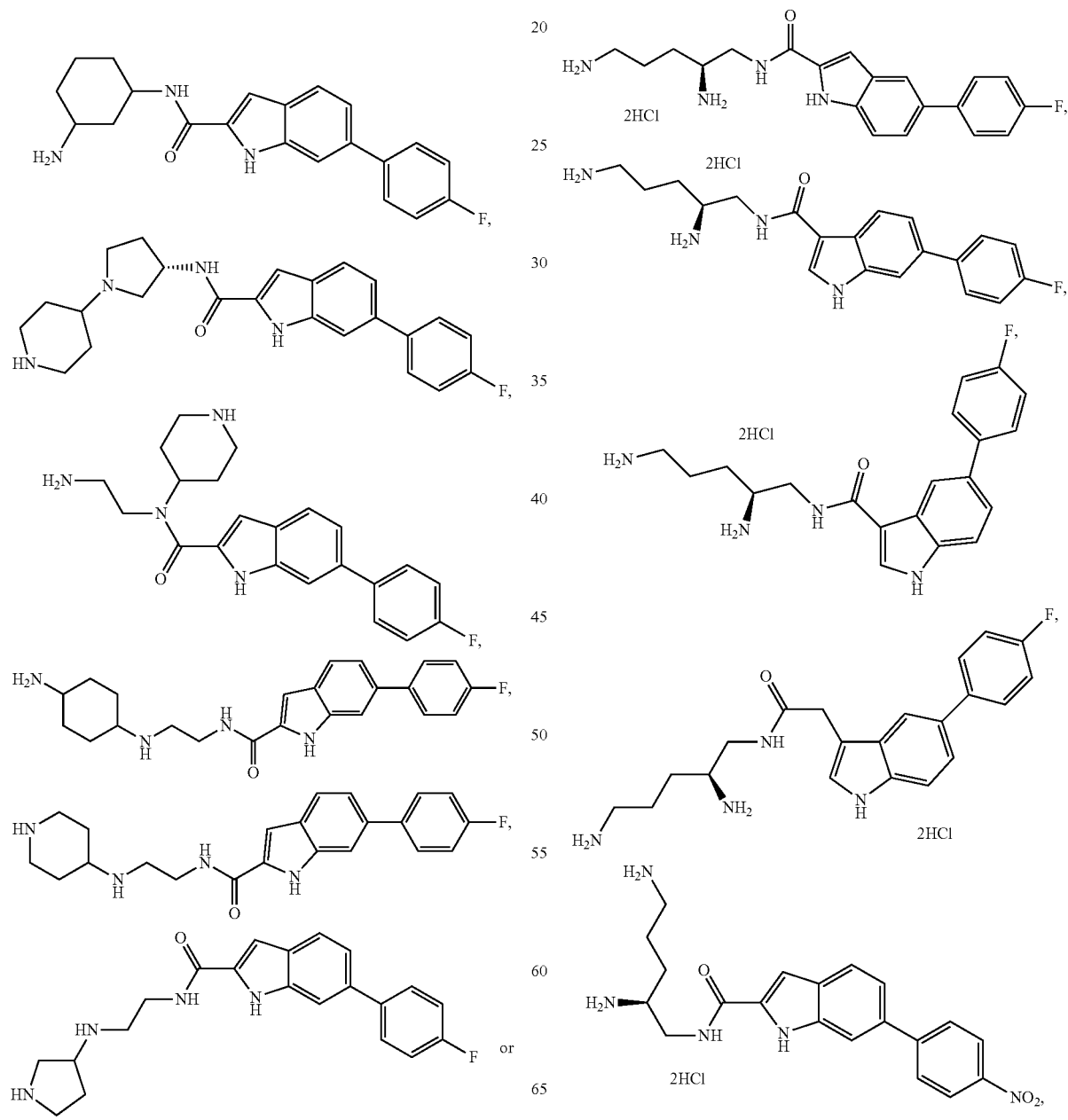

37 -continued
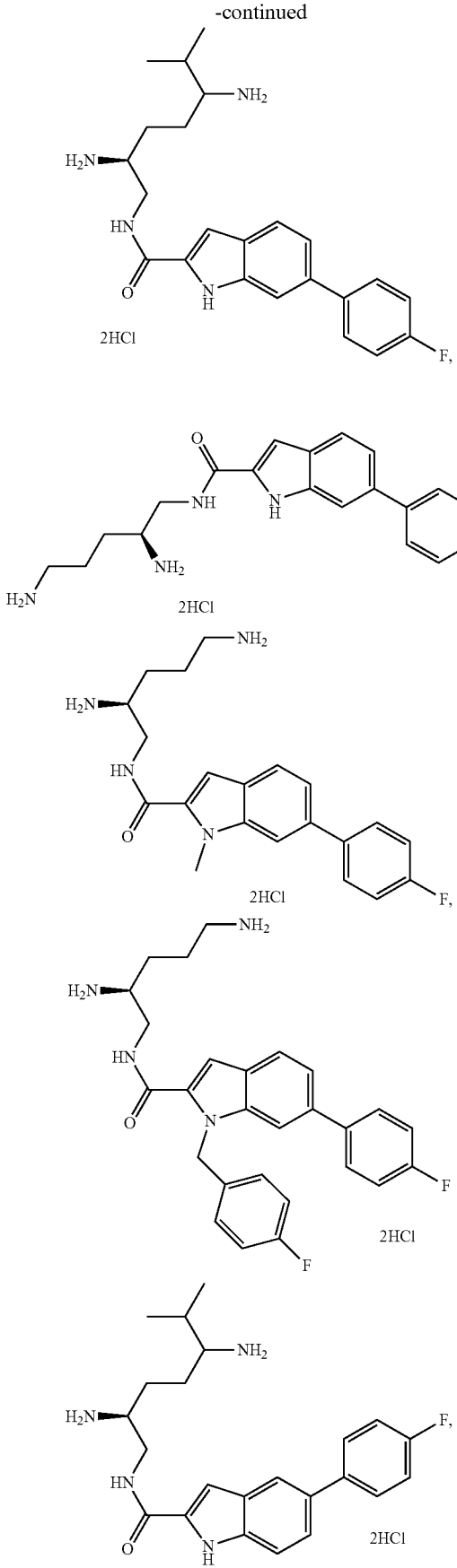
38 -continued
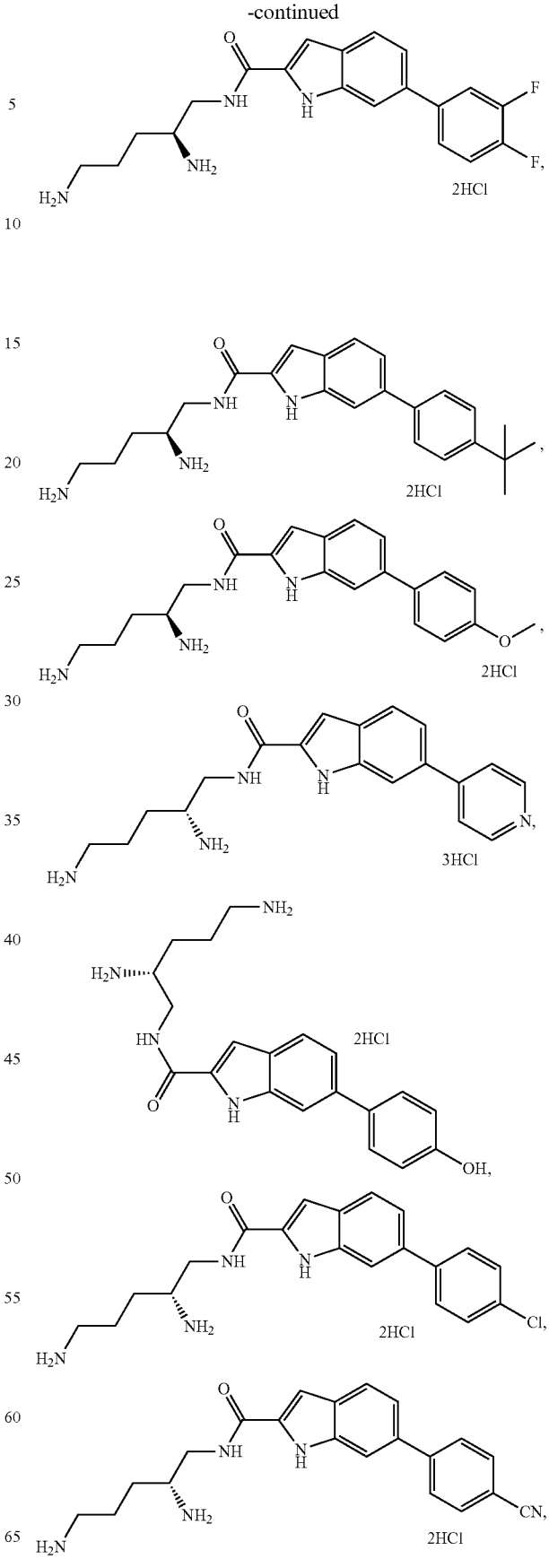

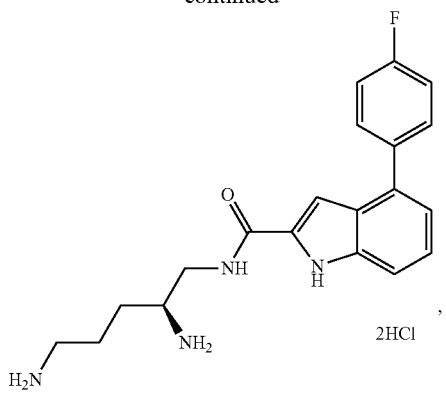
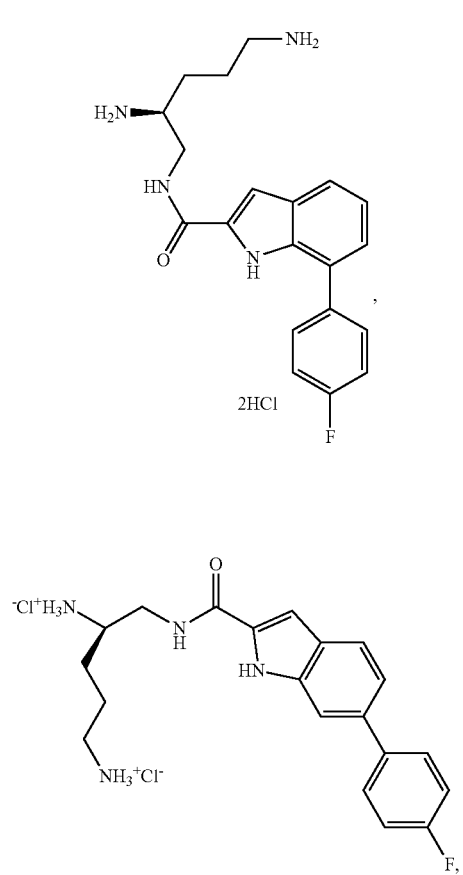
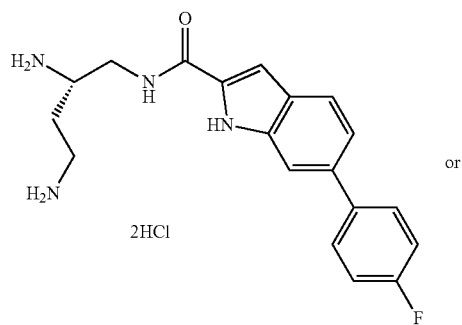
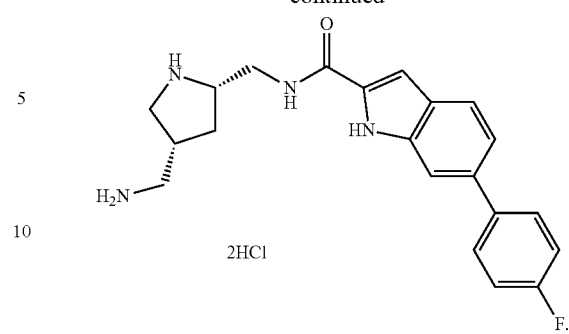
One embodiment provides a compound that is
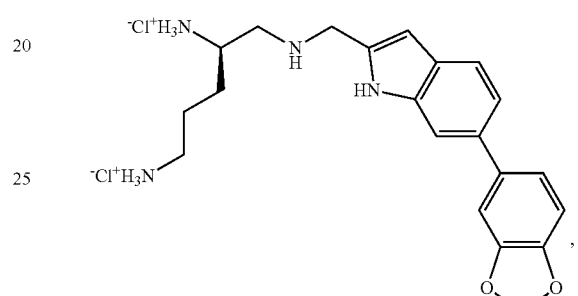
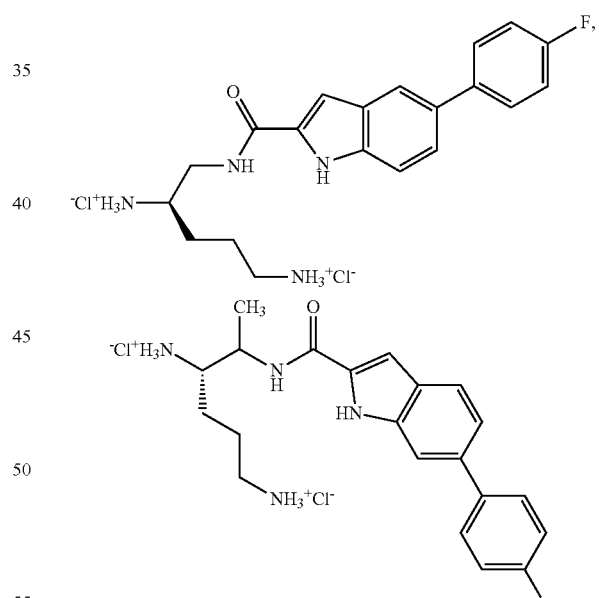
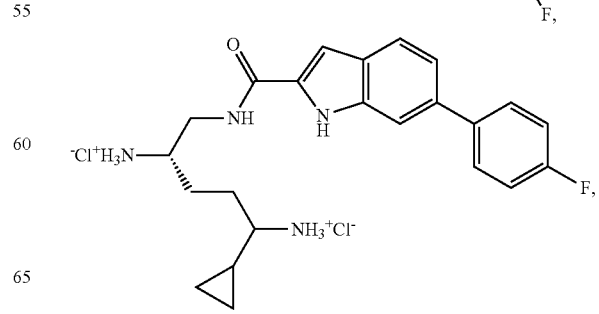

41
-continued
42
-continued
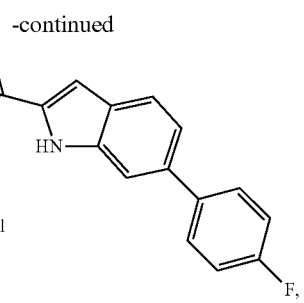
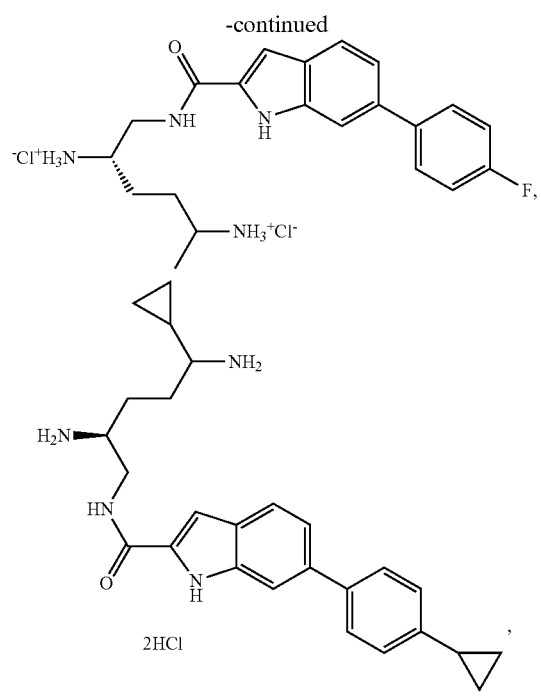
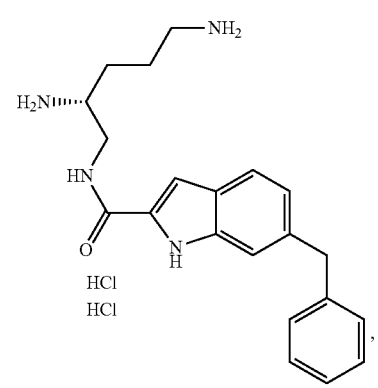
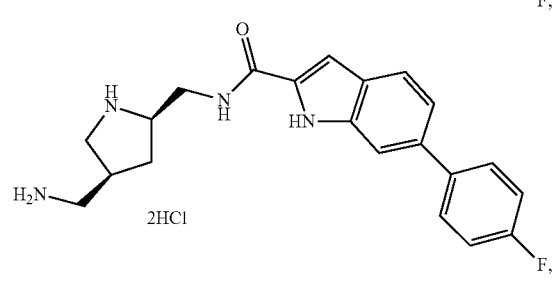
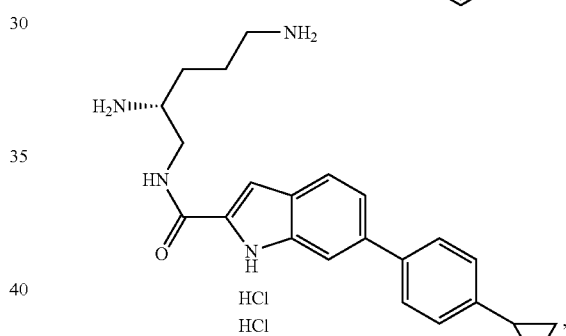
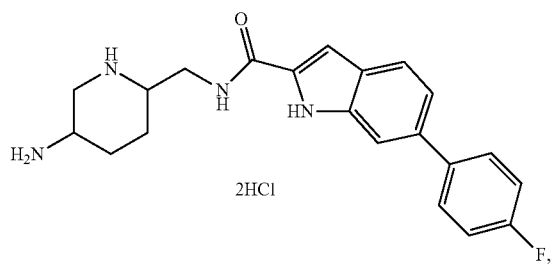
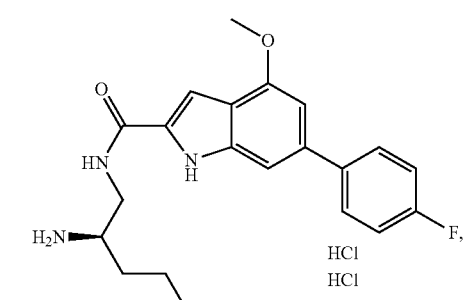

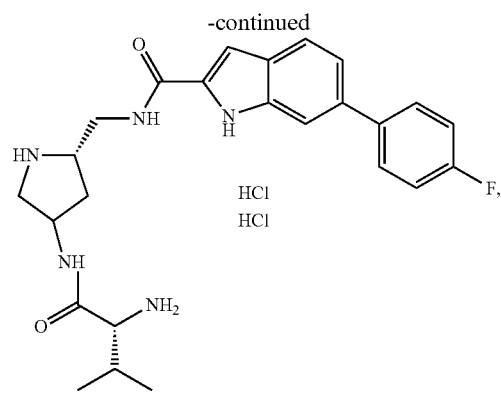
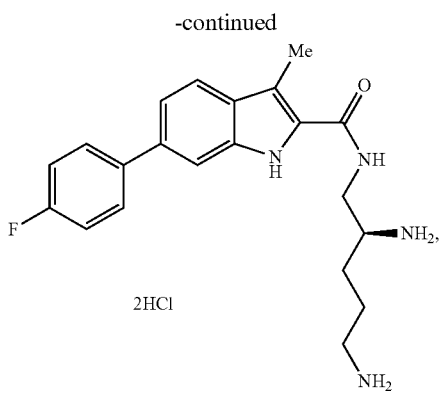
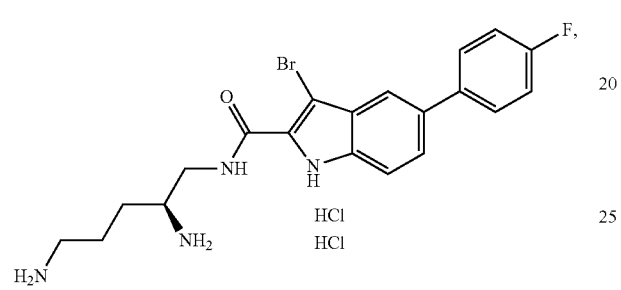
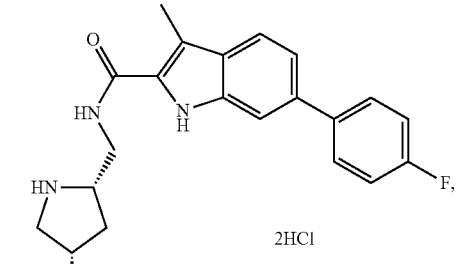
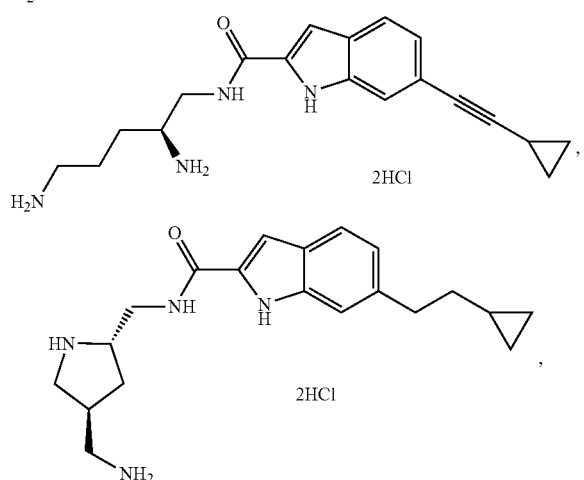
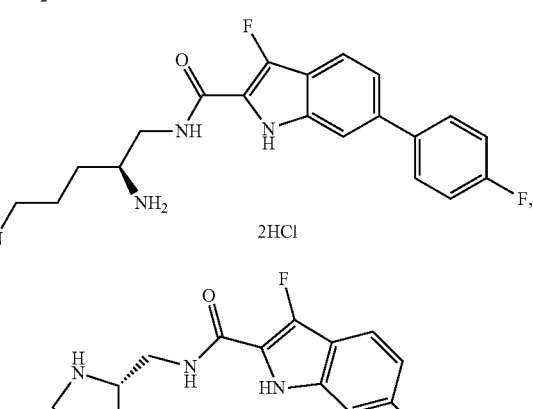
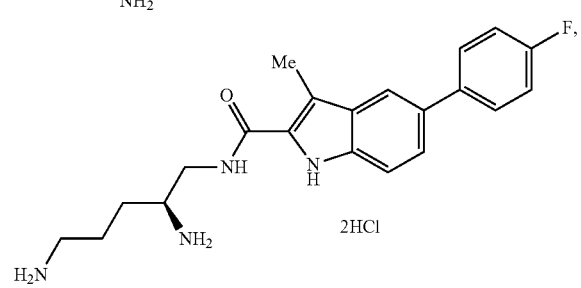
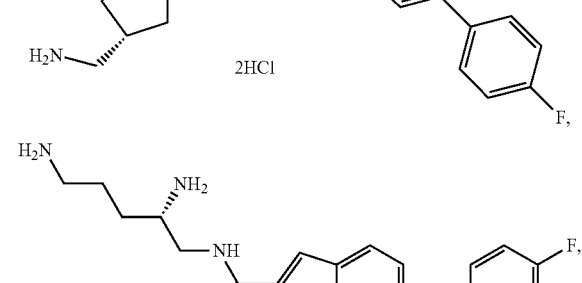
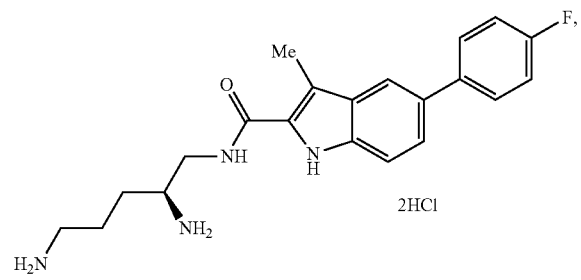
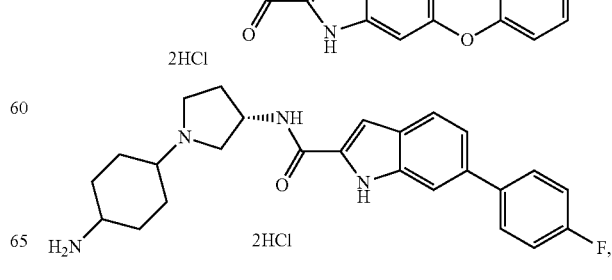

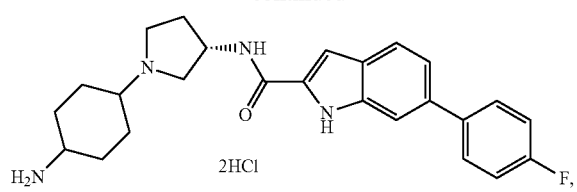
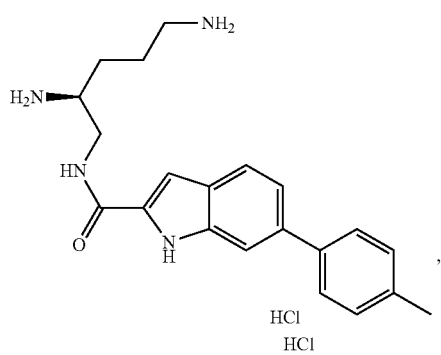
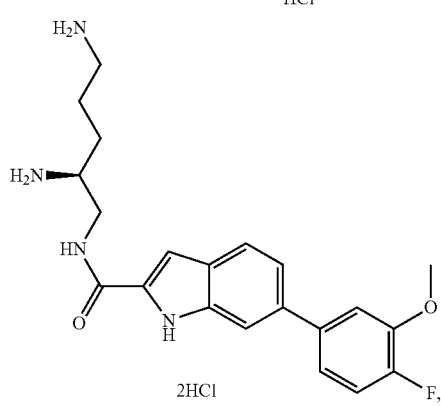
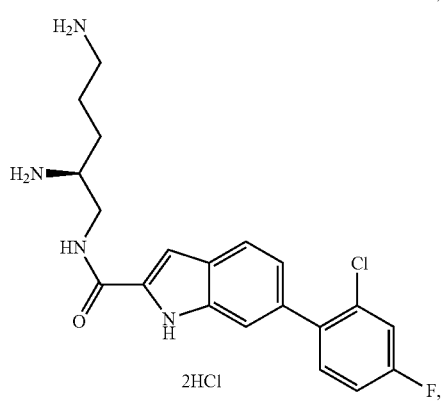
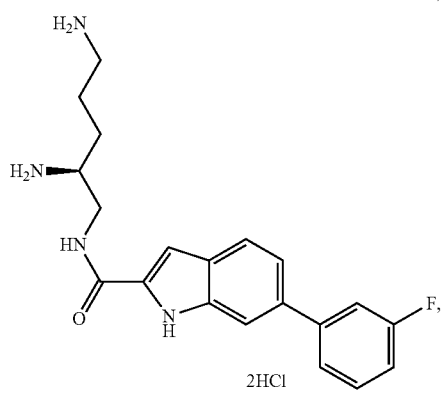
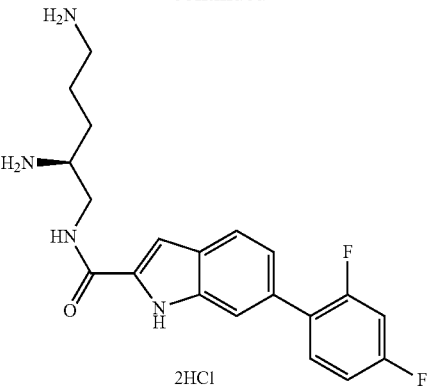
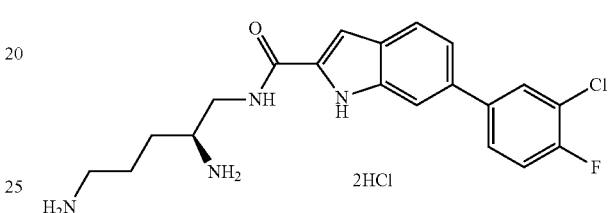
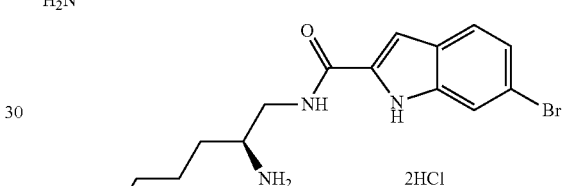
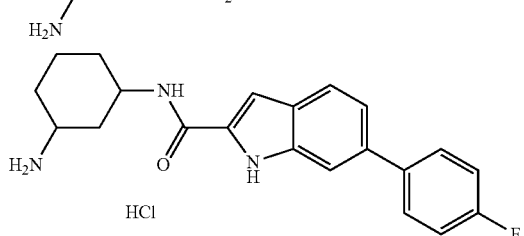
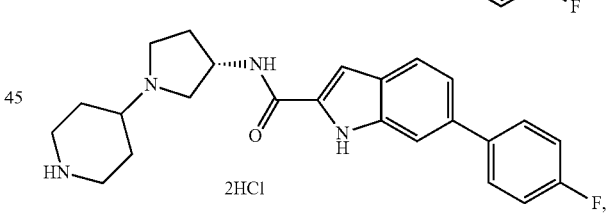
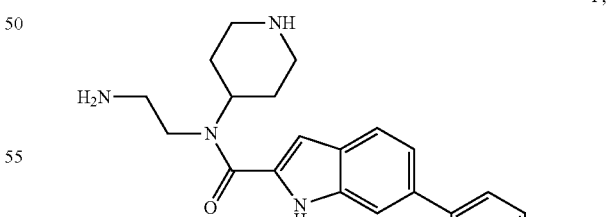
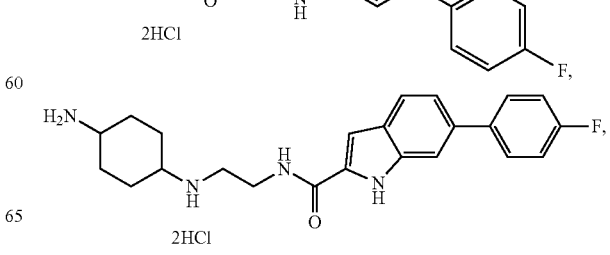

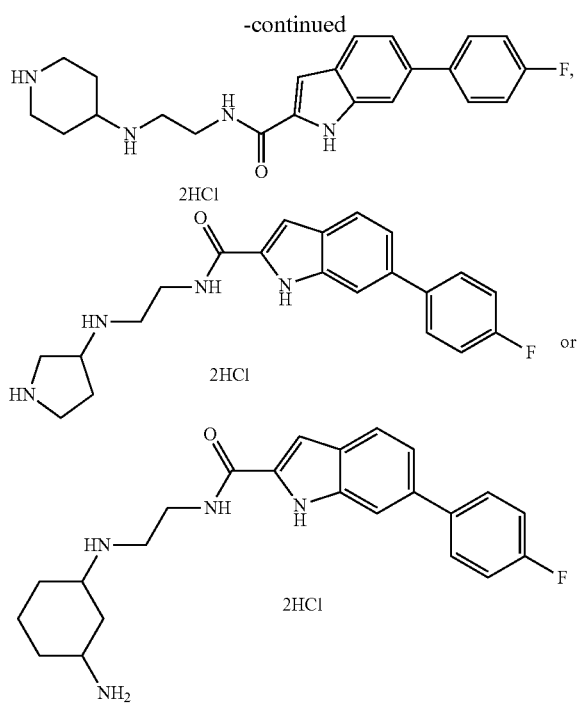

One embodiment provides a method for identifying a test compound capable of inhibiting a bacterial efflux inhibitor, comprising 1) contacting bacteria with a sub-inhibitory concentration of an antibiotic;

2) contacting the bacteria, either sequentially or simultaneously, with a) an inhibitory concentration of the antibiotic; and b) a test compound; and 3) quantifying the minimum inhibitory concentration (MIC) of the antibiotic, wherein a MIC that is lower than the intrinsic MIC of the antibiotic alone indicates the test compound is effective to inhibit a bacterial efflux pump inhibitor.

In certain embodiments, steps 1 and 2 are separated by about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 38, 39, 40, 41, 42, 43, 44, 45, 46, 47 or 48 hours. In certain embodiments, steps 1 and 2 are separated by about 12 hours. In certain embodiments, steps 1 and 2 are separated by about 24 hours.

One embodiment provides a method for identifying a test compound capable of inhibiting a bacterial efflux inhibitor, comprising 1) contacting bacteria with a sub-inhibitory concentration of an antibiotic;

2) contacting a first subset of the bacteria with an inhibitory concentration of the antibiotic;

3) contacting a second subset of the bacteria, either sequentially or simultaneously, with a) an inhibitory concentration of the antibiotic; and b) a test compound; and 4) quantifying the minimum inhibitory concentration (MIC) of the antibiotic for the first subset of bacteria and the second subset of bacteria, wherein a lower MIC in the second subset indicates the test compound is effective to inhibit a bacterial efflux pump inhibitor.

In certain embodiments, steps 1 and 2 and/or 1 and 3 are separated by about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 38, 39, 40, 41, 42, 43, 44, 45, 46, 47 or 48 hours. In certain embodiments, steps 1 and 2 are separated by about 12 hours. In certain embodiments, steps 1 and 2 are separated by about 24 hours. In certain embodiments, steps 1 and 3 are separated by about 12 hours. In certain embodiments, steps 1 and 3 are separated by about 24 hours. In certain embodiments, steps 2 and 3 are performed at substantially the same time (e.g., at about less than 10, 30, 60, 90 or 120 seconds apart, or about 3, 4 or 5 minutes apart).

One embodiment provides a method for identifying a test compound capable of lowering the minimum inhibitory concentration (MIC) of an antibiotic, comprising 1) contacting bacteria with a sub-inhibitory concentration of the antibiotic;

2) contacting the bacteria, either sequentially or simultaneously, with a) an inhibitory concentration of the antibiotic; and b) the test compound; and 3) quantifying the minimum inhibitory concentration (MIC) of the antibiotic, wherein a MIC that is lower than the intrinsic MIC of the antibiotic indicates the test compound is effective to lower the MIC of the antibiotic.

In certain embodiments, steps 1 and 2 are separated by about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 38, 39, 40, 41, 42, 43, 44, 45, 46, 47 or 48 hours. In certain embodiments, steps 1 and 2 are separated by about 12 hours. In certain embodiments, steps 1 and 2 are separated by about 24 hours.

One embodiment provides a method for identifying a test compound capable of lowering the minimum inhibitory concentration (MIC) of an antibiotic, comprising 1) contacting bacteria with a sub-inhibitory concentration of an antibiotic;

2) contacting a first subset of the bacteria with an inhibitory concentration of the antibiotic;

3) contacting a second subset of the bacteria, either sequentially or simultaneously, with a) an inhibitory concentration of the antibiotic; and b) a test compound; and 4) quantifying the minimum inhibitory concentration (MIC) of the antibiotic for the first subset of bacteria and the second subset of bacteria, wherein a lower MIC in the second subset indicates the test compound is effective to lower the MIC of the antibiotic.

In certain embodiments, steps 1 and 2 and/or 1 and 3 are separated by about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 38, 39, 40, 41, 42, 43, 44, 45, 46, 47 or 48 hours. In certain embodiments, steps 1 and 2 are separated by about 12 hours. In certain embodiments, steps 1 and 2 are separated by about 24 hours. In certain embodiments, steps 1 and 3 are separated by about 12 hours. In certain embodiments, steps 1 and 3 are separated by about 24 hours. In certain embodiments, steps 2 and 3 are performed at substantially the same time (e.g., at about less than 10, 30, 60, 90 or 120 seconds apart, or about 3, 4 or 5 minutes apart).

In one embodiment the invention provides a compound of formula I:

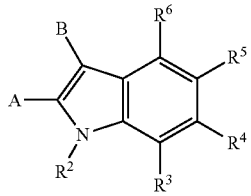

wherein:
one of A or B is —C(=O)N($R^{a1}$)—$R^1$, —($C_1$-$C_3$)alkyl-C(=O)N($R^{a1}$)$R^1$, —($C_1$-$C_3$)alkyl-O—$R^1$, —($C_1$-$C_3$)alkyl-N($R^{a1}$)—$R^1$, —N($R^{a1}$)—$R^1$, or $R^1$ and the other of A or B is H, halogen, or ($C_1$-$C_4$)alkyl;

each $R^1$ is independently:
(a) ($C_1$-$C_{14}$)alkyl substituted with one or more groups selected from the group consisting of —N$R^{b2}R^{c2}$, —NHNH$_2$, —C(=N$R^{a2}$)(N$R^{b2}R^{c2}$), —N$R^{a2}$C(=N$R^{a2}$)($R^{a2}$), and —N$R^{a2}$C(=N$R^{a2}$)(N$R^{b2}R^{c2}$); or (b) ($C_3$-$C_7$)carbocyclyl, ($C_3$-$C_7$)carbocyclyl-($C_1$-$C_4$)alkyl-, 4-7 membered monocyclic heterocyclyl, or 4-7 membered monocyclic heterocyclyl-($C_1$-$C_4$)alkyl-, wherein each ($C_3$-$C_7$)carbocyclyl or ($C_3$-$C_7$)carbocyclyl-($C_1$-$C_4$)alkyl- is independently substituted with one or more groups selected from the group consisting of Z and —($C_1$-$C_6$)alkyl substituted with one or more Z, and wherein each 4-7 membered monocyclic heterocyclyl or 4-7 membered monocyclic heterocyclyl-($C_1$-$C_4$)alkyl- is independently optionally substituted with one or more groups selected from the group consisting of Z and —($C_1$-$C_6$)alkyl substituted with one or more Z, wherein each Z is independently selected from the group consisting of —N$R^{b3}R^{c3}$, —NHNH$_2$, —C(=N$R^{a3}$)(N$R^{b3}R^{c3}$), —N$R^{a3}$C(=N$R^{a3}$)($R^{a3}$) and —N$R^{a3}$C(=N$R^{a3}$)(N$R^{b3}R^{c3}$) and wherein each ($C_3$-$C_7$)carbocyclyl, ($C_3$-$C_7$)carbocyclyl-($C_1$-$C_4$)alkyl-, 4-7 membered monocyclic heterocyclyl, or 4-7 membered monocyclic heterocyclyl-($C_1$-$C_4$)alkyl-, is independently optionally substituted independently with one or more ($C_1$-$C_4$)alkyl;

$R^2$ is hydrogen, ($C_1$-$C_4$)alkyl or phenyl($C_1$-$C_3$)alkyl-, wherein the phenyl is optionally substituted with one or more ($C_1$-$C_4$)alkyl, —O($C_1$-$C_4$)alkyl, halogen, or —NO$_2$;

$R^3$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, aryl, or heteroaryl wherein the aryl or heteroaryl is optionally substituted with one or more groups independently selected from the group consisting of halo, —OH, —NO$_2$, —CN, ($C_1$-$C_4$)alkyl, ($C_1$-$C_4$)haloalkyl, ($C_1$-$C_4$)alkoxy, and ($C_1$-$C_4$)haloalkoxy;

$R^4$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, aryl, or heteroaryl wherein the aryl or heteroaryl is optionally substituted with one or more groups independently selected from the group consisting of halo, —OH, —NO$_2$, —CN, ($C_1$-$C_4$)alkyl, ($C_1$-$C_4$)haloalkyl, ($C_1$-$C_4$)alkoxy, and ($C_1$-$C_4$)haloalkoxy;

$R^5$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, aryl, or heteroaryl wherein the aryl or heteroaryl is optionally substituted with one or more groups independently selected from the group consisting of halo, —OH, —NO$_2$, —CN, ($C_1$-$C_4$)alkyl, ($C_1$-$C_4$)haloalkyl, ($C_1$-$C_4$)alkoxy, and ($C_1$-$C_4$)haloalkoxy;

$R^6$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, aryl, or heteroaryl wherein the aryl or heteroaryl is optionally substituted with one or more groups independently selected from the group consisting of halo, —OH, —NO$_2$, —CN, ($C_1$-$C_4$)alkyl, ($C_1$-$C_4$)haloalkyl, ($C_1$-$C_4$)alkoxy, and ($C_1$-$C_4$)haloalkoxy;

each $R^{a1}$ is independently hydrogen, ($C_1$-$C_4$)alkyl or ($C_3$-$C_7$)carbocyclyl;

each $R^{a2}$ is independently hydrogen, ($C_1$-$C_4$)alkyl or ($C_3$-$C_7$)carbocyclyl;

each $R^{b2}$ and $R^{c2}$ is independently hydrogen, ($C_1$-$C_4$)alkyl or ($C_3$-$C_7$)carbocyclyl;

$R^{d2}$ is ($C_1$-$C_4$)alkyl or ($C_3$-$C_7$)carbocyclyl;

each $R^{a3}$ is independently hydrogen ($C_1$-$C_4$)alkyl or ($C_3$-$C_7$)carbocyclyl;

each $R^{b3}$ and $R^{c3}$ is independently hydrogen ($C_1$-$C_4$)alkyl or ($C_3$-$C_7$)carbocyclyl; and $R^{a3}$ is ($C_1$-$C_4$)alkyl or ($C_3$-$C_7$)carbocyclyl;

or a salt thereof.

Such methods may also be used to determine synergy between a test compound and an antibiotic.

As used herein, the term "minimum inhibitory concentration (MIC)" refers to the lowest concentration of a compound (e.g., an antibiotic) that prevents visible growth of a bacterium. Assays for measuring the MIC of a compound are known in the art, for example, as described herein. As used herein, the term "intrinsic MIC" refers to the MIC of a compound (e.g., an antibiotic) for the particular bacterial species that has not been pre-exposed to the compound.

As used herein, the term "sub-inhibitory concentration" refers to a concentration of the antibiotic that does not reduce the visible growth of the bacteria. In certain embodiments, the sub-inhibitory concentration is ½×MIC of the antibiotic. In certain embodiments, the sub-inhibitory concentration of the antibiotic is a concentration that is capable of inducing the expression of one or more efflux pumps in the bacteria.

As used herein, the term "inhibitory concentration" refers to a concentration of the antibiotic that reduces the visible growth of the bacteria. In certain embodiments, this concentration is the intrinsic MIC of the antibiotic.

In certain embodiments, the bacteria are a species of bacteria described herein. In certain embodiments, the bacteria are P. aeruginosa.

In certain embodiments, the antibiotic is an antibiotic described herein. In certain embodiments, the antibiotic is cefepime, clarithromycin, or levofloxacin.

In certain embodiments, the test compound is a compound described herein, such as a compound of formula I, an efflux pump inhibitor (EPI), etc.

One embodiment provides a method of identifying a combination of a test compound and an antibiotic that is capable of treating septicemia in an animal comprising:
1) administering the test compound to the animal intravenously;
2) administering the antibiotic to the animal either orally or intravenously;
3) administering the test compound to the animal subcutaneously;
4) administering the antibiotic to the animal either orally or intravenously; and
5) evaluating the animal for symptoms of septicemia, wherein a reduction in symptoms indicates the combination is effective to treat septicemia.

In certain embodiments, each administration is independently separated by approximately about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55 or 60 min. In certain embodiments, each administration is separated by about 5 minutes.

In certain embodiments, the method further comprises repeating steps 1-4. For example, in certain embodiments, steps 1-4 are repeated 24 hours after the antibiotic has been administered for the second time.

In certain embodiments, the combination of the test compound and antibiotic is a synergistic combination.

In certain embodiments, the animal is a non-human animal. For example, in certain embodiments, the animal is a mouse.

In certain embodiments, the antibiotic is an antibiotic described herein. In certain embodiments, the antibiotic is cefepime, clarithromycin, or levofloxacin.

In certain embodiments, the antibiotic is a cephalosporin.

In certain embodiments, the test compound is a compound described herein, such as a compound of formula I, an efflux pump inhibitor (EPI), etc.

One embodiment provides a method described herein for identifying a compound capable of inhibiting a bacterial efflux pump inhibitor (e.g., using an assay described in the Examples).

Generally, compounds of formula I as well as synthetic intermediates that can be used for preparing compounds of formula I can be prepared as illustrated in the following General Methods and Schemes. It is understood that variable groups shown below (e.g., $R^1$, $R^2$, $R^3$, $R^4$, $R^5$, $R^6$) can represent the final corresponding groups present in a compound of formula I or that these groups can represent groups that can be converted to the final corresponding groups present in a compound of formula I at a convenient point in a synthetic sequence. For example, the variable groups can contain one or more protecting groups that can be removed at a convenient point in a synthetic sequence to provide the final corresponding groups in the compound of formula I.

Schemes 1, 2 and 3 illustrate some general methods for the preparation of substituted 1[H]-indole carboxamides.

Scheme 1

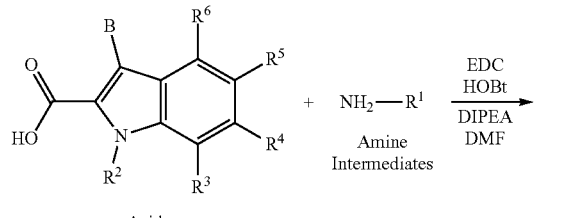

Acids

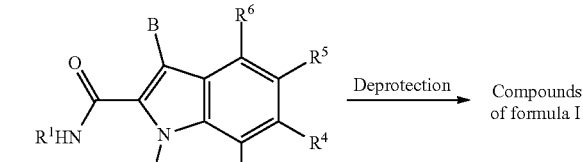

Scheme 2

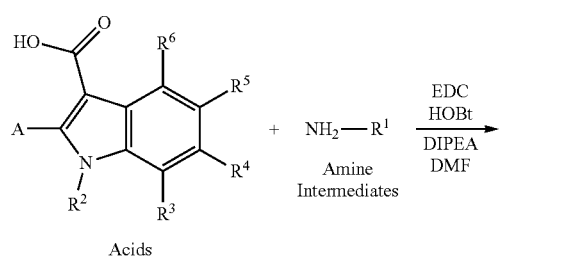

Acids

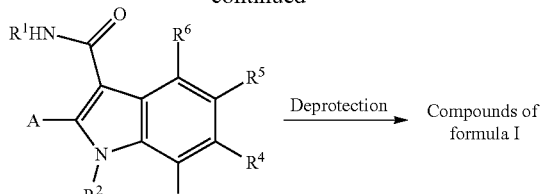

Scheme 3.

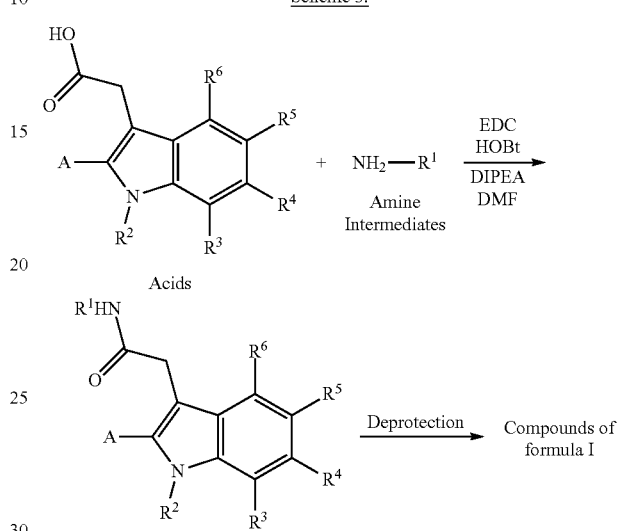

Acids

The compounds disclosed herein are bacterial efflux pump inhibitors. An efflux pump inhibitor is a compound that interferes with the ability of an efflux pump to export a substrate. The inhibitor may have intrinsic antibacterial properties of its own. The compounds disclosed herein may be useful for treating bacterial infections (e.g., gram negative and gram positive) when administered with an antibacterial agent.

In one embodiment the bacterial infection being treated is a Gram-negative bacterial strain infection. In one embodiment the Gram-negative bacterial strain is selected from the group consisting of *Acinetobacter baumannii, Acinetobacter calcoaceticus, Acinetobacter haemolyticus, Acinetobacter lwoffi, Actinobacillus actinomycetemcomitans, Aeromonas hydrophilia, Aggregatibacter actinomycetemcomitans, Agrobacterium tumefaciens, Bacteroides distasonis, Bacteroides eggerthii, Bacteroides forsythus, Bacteroides fragilis, Bacteroides ovalus, Bacteroides splanchnicus, Bacteroides thetaiotaomicron, Bacteroides uniformis, Bacteroides vulgatus, Bordetella bronchiseptica, Bordetella parapertussis, Bordetella pertussis, Borrelia burgdorferi, Branhamella catarrhalis, Burkholderia cepacia, Campylobacter coli, Campylobacter fetus, Campylobacter jejuni, Caulobacter crescentus, Chlamydia trachomatis, Citrobacter diversus, Citrobacter freundii, Enterobacter aerogenes, Enterobacter asburiae, Enterobacter cloacae, Enterobacter sakazakii, Escherchia coli, Francisella tularensis, Fusobacterium nucleatum, Gardnerella vaginalis, Haemophilus ducreyi, Haemophilus haemolyticus, Haemophilus influenzae, Haemophilus parahaemolyticus, Haemophilus parainfluenzae, Helicobacter pylori, Kingella denitrificans, Kingella indologenes, Kingella kingae, Kingella oralis, Klebsiella oxytoca, Klebsiella pneumoniae, Klebsiella rhinoscleromatis, Legionella pneumophila, Listeria monocytogenes, Moraxella bovis, Moraxella catarrhalis, Moraxella lacunata, Morgan-* ella morganii, Neisseria gonorrhoeae, Neisseria meningitidis, Pantoea agglomerans, Pasteurella canis, Pasteurella haemolytica, Pasteurella multocida, Pasteurella tularensis, Porphyromonas gingivalis, Proteus mirabilis, Proteus vulgaris, Providencia alcalifaciens, Providencia rettgeri, Providencia stuartii, Pseudomonas acidovorans, Pseudomonas aeruginosa, Pseudomonas alcaligenes, Pseudomonas fluorescens, Pseudomonas putida, Salmonella enteriditis, Salmonella paratyphi, Salmonella typhi, Salmonella typhimurium, Serratia marcescens, Shigella dysenteriae, Shigella jlexneri, Shigella sonnei, Stenotrophomonas maltophilla, Veillonella parvula, Vibrio cholerae, Vibrio parahaemolyticus, Yersinia enterocolitica, Yersinia intermedia, Yersinia pestis and Yersinia pseudotuberculosis.

In one embodiment the bacterial infection being treated is a Gram-positive bacterial strain infection. In one embodiment the Gram-positive bacterial strain is selected from the group consisting of Actinomyces naeslundii, Actinomyces viscosus, Bacillus anthracis, Bacillus cereus, Bacillus subtilis, Clostridium difficile, Corynebacterium diphtheriae, Corynebacterium ulcerans, Enterococcus faecalis, Enterococcus faecium, Micrococcus luteus, Mycobacterium avium, Mycobacterium intracellulare, Mycobacterium leprae, Mycobacterium tuberculosis, Propionibacterium acnes, Staphylococcus aureus, Staphylococcus epidermidis, Staphylococcus haemolyticus, Staphylococcus hominis, Staphylococcus hyicus, Staphylococcus intermedius, Staphylococcus saccharolyticus, Staphylococcus saprophyticus, Streptococcus agalactiae, Streptococcus mutans, Streptococcus pneumoniae, Streptococcus pyogenes, Streptococcus salivarius and Streptococcus sanguis.

The compositions can, if desired, also contain other active therapeutic agents, such as a narcotic, a non-steroid anti-inflammatory drug (NSAID), an analgesic, an anesthetic, a sedative, a local anesthetic, a neuromuscular blocker, an anti-cancer, an antimicrobial (for example, an aminoglycoside, an antifungal, an antiparasitic, an antiviral, a carbapenem, a cephalosporin (e.g., cefepime), a fluoroquinolone, a macrolide, a penicillin, a sulfonamide, a tetracycline, another antimicrobial), an anti-psoriatic, a corticosteriod, an anabolic steroid, a diabetes-related agent, a mineral, a nutritional, a thyroid agent, a vitamin, a calcium-related hormone, an antidiarrheal, an anti-tussive, an anti-emetic, an anti-ulcer, a laxative, an anticoagulant, an erythropoietin (for example, epoetin alpha), a filgrastim (for example, G-CSF, Neupogen), a sargramostim (GM-CSF, Leukine), an immunization, an immunoglobulin, an immunosuppressive (for example, basiliximab, cyclosporine, daclizumab), a growth hormone, a hormone replacement drug, an estrogen receptor modulator, a mydriatic, a cycloplegic, an alkylating agent, an anti-metabolite, a mitotic inhibitor, a radiopharmaceutical, an anti-depressant, an anti-manic agent, an anti-psychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog thereof, dornase alpha (Pulmozyme), a cytokine, or any combination thereof.

In one embodiment the antibacterial agent is selected from quinolones, tetracyclines, glycopeptides, aminoglycosides, β-lactams, cephalosporins, rifamycins, macrolides, ketolides, oxazolidinones, coumermycins, and chloramphenicol In certain embodiments, the antibacterial agent is a cephalosporin.

It will be appreciated that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

It will also be appreciated by those skilled in the art that certain compounds of the invention can exist in more than one tautomeric form. For example, a substituent of formula —NH—C($=$O)H in a compound of formula (I) could exist in tautomeric form as —N$=$C(OH)H. The present invention encompasses all tautomeric forms of a compound of formula I as well as mixtures thereof that can exist in equilibrium with non-charged and charged entities depending upon pH, which possess the useful properties described herein In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartrate, succinate, fumarate, benzoate, ascorbate, α-ketoglutarate, and α-glycerophosphate. Suitable inorganic salts may also be formed, including hydrochloride, sulfate, nitrate, bicarbonate, and carbonate salts. Salts may be obtained using standard procedures well known in the art, for example by reacting a sufficiently basic compound such as an amine with a suitable acid affording the corresponding anion. Alkali metal (for example, sodium, potassium or lithium) or alkaline earth metal (for example calcium) salts of carboxylic acids can also be made.

Pharmaceutically suitable counterions include pharmaceutically suitable cations and pharmaceutically suitable anions that are well known in the art. Examples of pharmaceutically suitable anions include, but are not limited to those described above (e.g. physiologically acceptable anions) including $Cl^-$, $Br^-$, $I^-$, $CH_3SO_3^-$, $H_2PO_4^-$, $CF_3SO_3^-$, p-$CH_3C_6H_4SO_3^-$, citrate, tartrate, phosphate, malate, fumarate, formate, or acetate.

It will be appreciated by those skilled in the art that a compound of the invention comprising a counterion can be converted to a compound of the invention comprising a different counterion. Such a conversion can be accomplished using a variety of well-known techniques and materials including but not limited to ion exchange resins, ion exchange chromatography and selective crystallization.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes. For oral administration the compounds can be formulated as a solid dosage form with or without an enteric coating.

Thus, the present compounds may be systemically administered, e.g., orally, in combination with a pharmaceutically acceptable vehicle such as an inert diluent, excipient or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 90% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations, particles, and devices.

The active compound may also be administered intravenously or intramuscularly by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina, nanoparticles, and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 1 to about 500 mg/kg, e.g., from about 5 to about 400 mg/kg of body weight per day, such as 1 to about 250 mg per kilogram body weight of the recipient per day.

The compound is conveniently formulated in unit dosage form; for example, containing 5 to 500 mg, 10 to 400 mg, or 5 to 100 mg of active ingredient per unit dosage form. In one embodiment, the invention provides a composition comprising a compound of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

Co-administration of a compound disclosed herein with one or more other active therapeutic agents (e.g., antibacterial agents) generally refers to simultaneous or sequential administration of a compound disclosed herein and one or more other active therapeutic agents, such that therapeutically effective amounts of disclosed herein and one or more other active therapeutic agents are both present in the body of the patient.

The ability of a compound disclosed herein to inhibit a bacterial efflux pump can be determined using a method like Test A or Test B as described in Example 67 and as shown in Table 1.

TABLE 1

| Example | Structure | Enhanced Activity in E. coli* | Enhanced Activity in P. aeruginosa** |
|---|---|---|---|
| 1 | 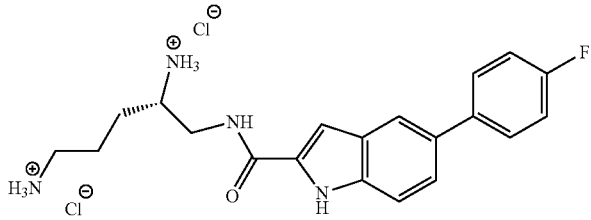 Chemical Formula: $C_{20}H_{25}Cl_2FN_4O$ Molecular Weight: 427.3454 | 2x/6.25 µg | 4x/6.25 µg |
| 2 | 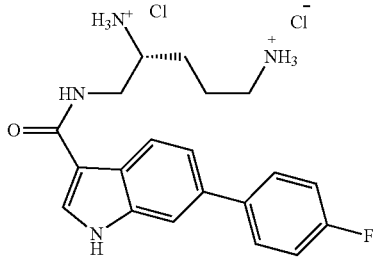 Chemical Formula: $C_{20}H_{25}Cl_2FN_4O$ Molecular Weight: 427.3454 | 128x/50 µg | 16x/25 µg |
| 3 | 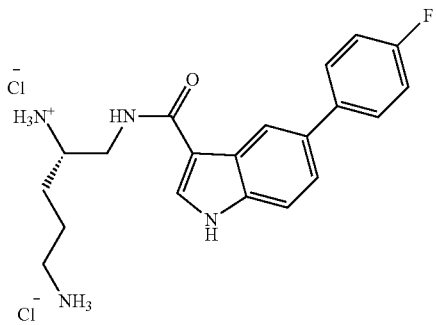 Chemical Formula: $C_{20}H_{25}Cl_2FN_4O$ Molecular Weight: 427.3454 | 512x/50 µg | 64x/50 µg |

TABLE 1-continued

| Example | Structure | Enhanced Activity in E. coli* | Enhanced Activity in P. aeruginosa** |
|---|---|---|---|
| 4 | Chemical Formula: $C_{21}H_{27}Cl_2FN_4O$<br>Molecular Weight: 441.3724 | 8x/25 µg | 2x/25 µg |
| 5 | Chemical Formula: $C_{20}H_{25}Cl_2N_5O_3$<br>Molecular Weight: 454.3520 I | 4x/6.25 µg | 4x/6.25 µg |
| 6 | Chemical Formula: $C_{23}H_{31}Cl_2FN_4O$<br>Molecular Weight: 469.4264 | 32x/3.13 µg | 16x/6.25 µg |
| 7 | Chemical Formula: $C_{20}H_{25}Cl_2FN_4O$<br>Molecular Weight: 427.3454 | 4x/6.25 µg | 32x/6.25 µg |

TABLE 1-continued
| Example | Structure | Enhanced Activity in E. coli* | Enhanced Activity in P. aeruginosa** |
|---|---|---|---|
| 8 | 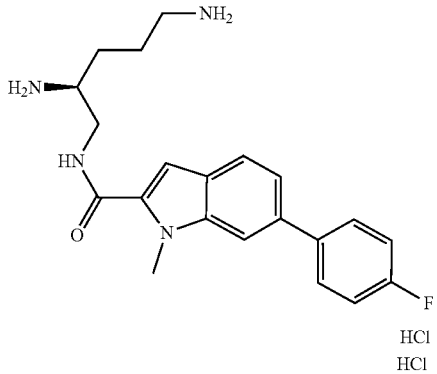<br>HCl HCl<br>Chemical Formula: $C_{21}H_{27}Cl_2FN_4O$<br>Molecular Weight: 441.3724 | 8x/6.25 µg | 4x/6.25 µg |
| 10 | 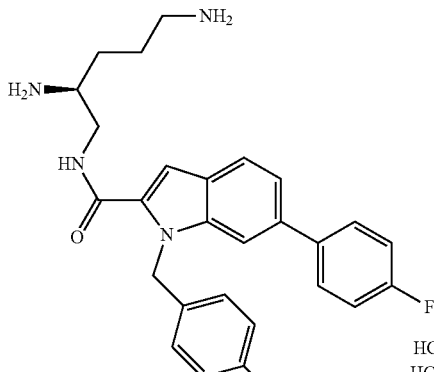<br>HCl HCl<br>Molecular Weight: 535.4608 | 1x/3.13 µg | 2x/6.25 µg |
| 10 | 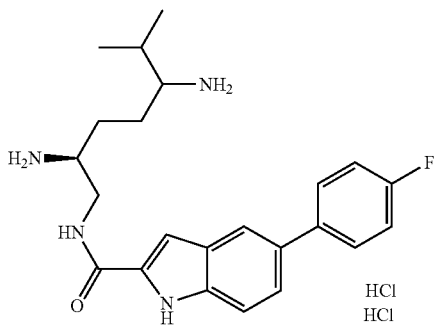<br>HCl HCl<br>Molecular Weight: 469.4264 | 4x/6.25 µg | 8x/6.25 µg |
| 11 | 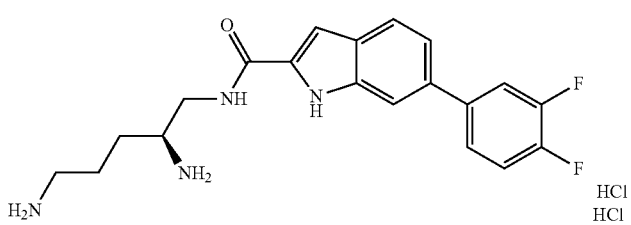<br>HCl HCl<br>Molecular Weight: 445.34 | 2x/6.25 µg | 4x/6.25 µg |

TABLE 1-continued
| Example | Structure | Enhanced Activity in *E. coli** | Enhanced Activity in *P. aeruginosa*** |
|---|---|---|---|
| 12 | 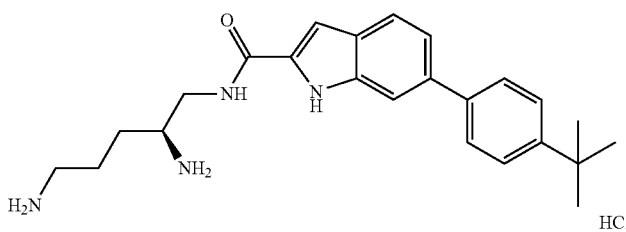 HCl HCl | 4x/3.13 μg | 1x/6.25 μg |
| 13 | 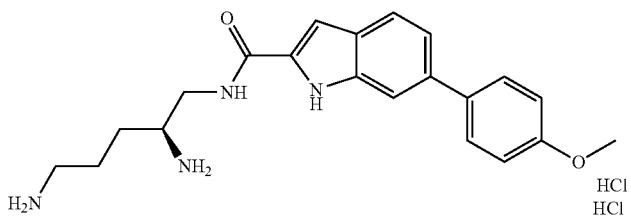 HCl HCl<br>Molecular Weight: 439.38 | 32x/50 μg | 4x/12.5 μg |
| 14 | 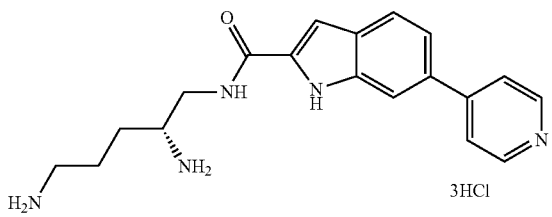 [SMILES: NCCC[C@@H](N)CNC(=O)c1cc2ccc(-c3ccncc3)cc2[nH]1 ; "3HCl"] 3HCl | 4x/50 μg | 4x/50 μg |
| 15 | 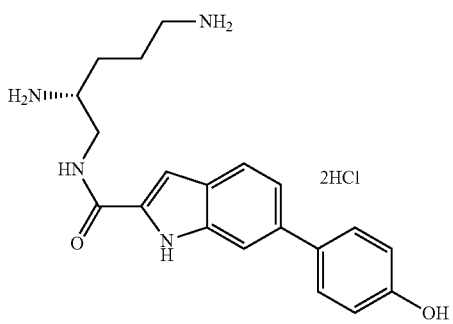 [SMILES: NCCC[C@@H](N)CNC(=O)c1cc2ccc(-c3ccc(O)cc3)cc2[nH]1] 2HCl | 4x/12.5 μg | 4x/50 μg |
| 16 | 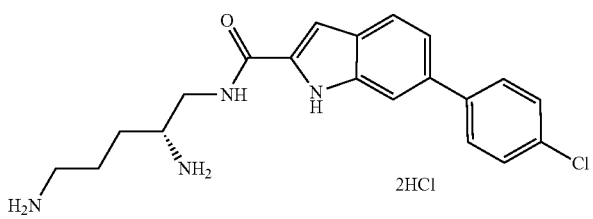 [SMILES: NCCC[C@@H](N)CNC(=O)c1cc2ccc(-c3ccc(Cl)cc3)cc2[nH]1] 2HCl | 2x/6.25 μg | 8x/6.25 μg |
| 17 | 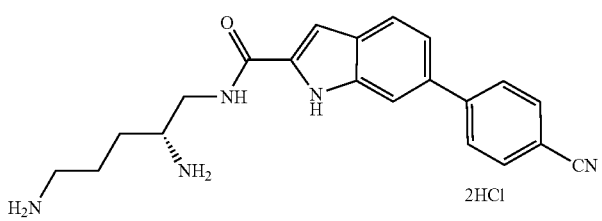 [SMILES: N#Cc1ccc(-c2ccc3cc(C(=O)NC[C@H](N)CCCN)[nH]c3c2)cc1] 2HCl | 2x/3.13 μg | 4x/3.13 μg |

TABLE 1-continued
| Example | Structure | Enhanced Activity in E. coli* | Enhanced Activity in P. aeruginosa** |
|---|---|---|---|
| 18 | 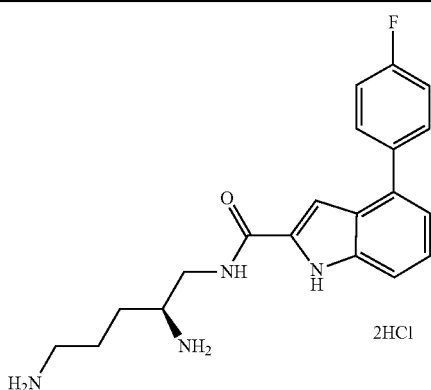 | 8x/6.25 µg | 4x/6.25 µg |
| 19 | 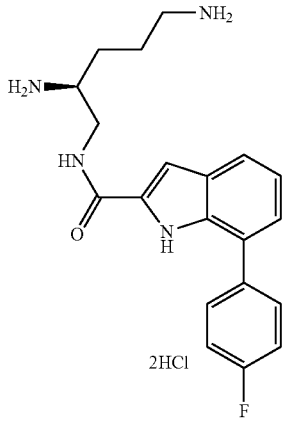 [SMILES: NCCC[C@H](N)CNC(=O)c1cc2cccc(-c3ccc(F)cc3)c2[nH]1] | 8x/6.25 µg | 2x/6.25 µg |
| 20 | 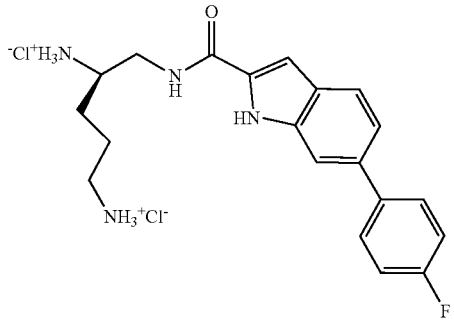 | 2x/50 µg | 8x/6.25 µg |
| 21 | 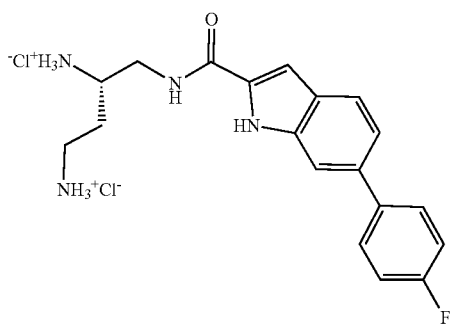 Molecular Weight: 413.3184 | 2x/6.25 µg | 4x/6.25 µg |

TABLE 1-continued
| Example | Structure | Enhanced Activity in E. coli* | Enhanced Activity in P. aeruginosa** |
|---|---|---|---|
| 22 | 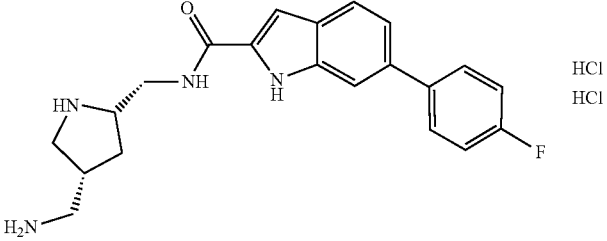 | 16x/25 µg | 32x/25 µg |
| 23 | 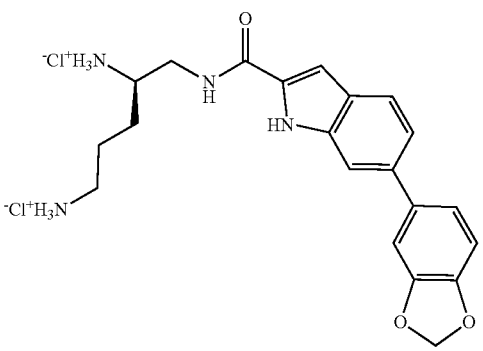 | 4x/12.5 µg | 8x/12.5 µg |
| 24 | 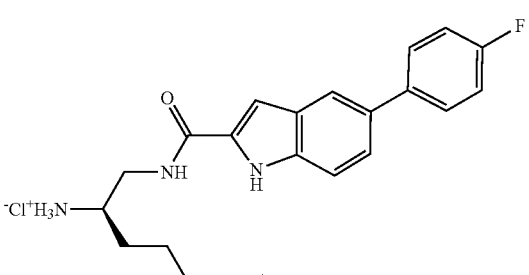 | 2x./6.25 µg | 2x./6.25 µg |
| 25 | 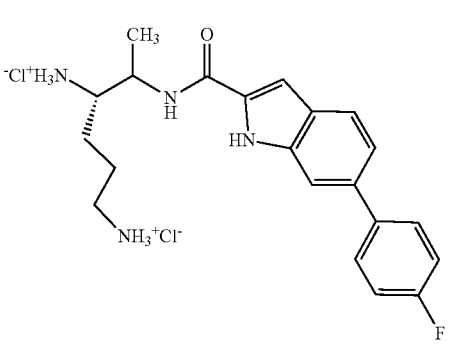 | 4x/12.5 µg | 8x/12.5 µg |
| 26 | 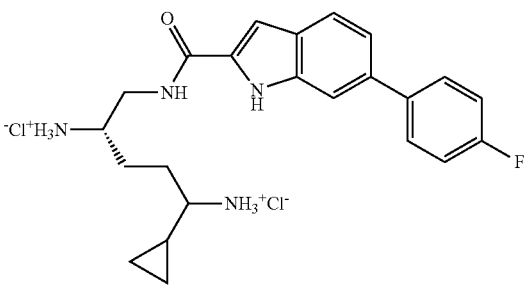 MW: 467.41 | 4x/12.5 µg | 16x/12.5 µg |

TABLE 1-continued
| Example | Structure | Enhanced Activity in E. coli* | Enhanced Activity in P. aeruginosa** |
|---|---|---|---|
| 27 | 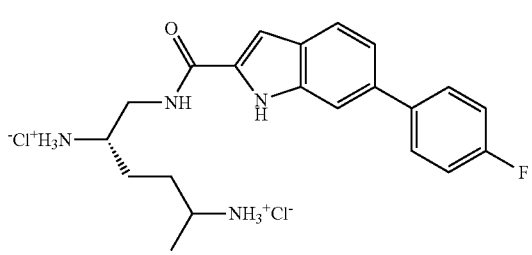 MW: 441.37 | 2x/12.5 µg | 8x/12.5 µg |
| 28 | 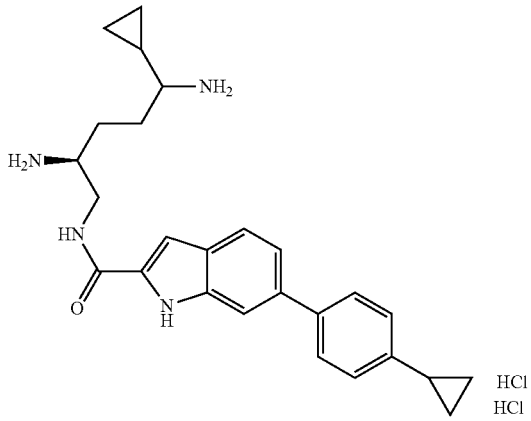 [SMILES: NC(CC[C@H](N)CNC(=O)c1cc2ccc(-c3ccc(C4CC4)cc3)cc2[nH]1)C1CC1 ; Cl ; Cl] | 4x/6.25 µg | 2x/6.25 µg |
| 29 (Example 22-re-synthesis | 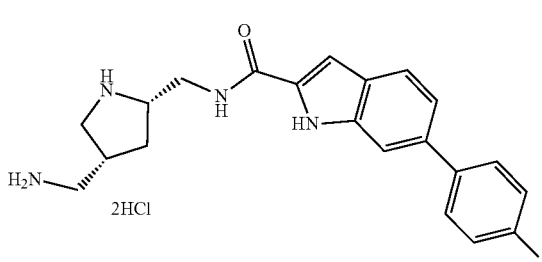 | — | 32x/6.25 µg |
| 30 | 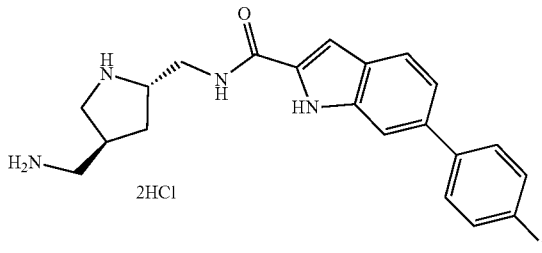 | — | 16x/6.25 µg |
| 31 | 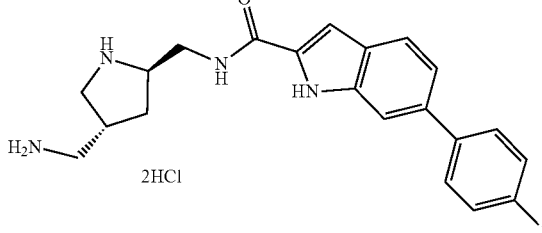 | — | 32x/6.25 µg |

TABLE 1-continued

| Example | Structure | Enhanced Activity in E. coli* | Enhanced Activity in P. aeruginosa** |
|---|---|---|---|
| 32 | 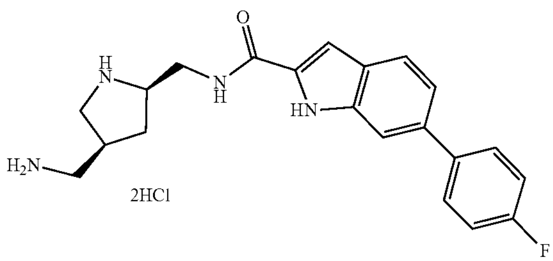 [SMILES: NC[C@H]1CN[C@@H](CNC(=O)c2cc3ccc(-c4ccc(F)cc4)cc3[nH]2)C1] | — | 32x/6.25 μg |
| 33 | 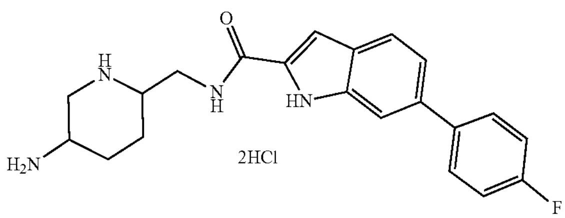 [SMILES: NC1CCC(CNC(=O)c2cc3ccc(-c4ccc(F)cc4)cc3[nH]2)NC1] | 2x/12.5 μg | |
| 34 | 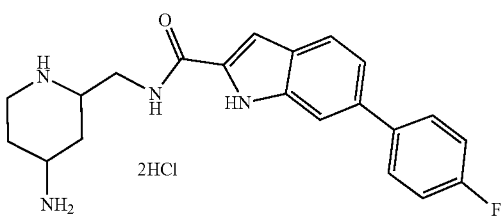 [SMILES: NC1CCNC(CNC(=O)c2cc3ccc(-c4ccc(F)cc4)cc3[nH]2)C1] | 2x/12.5 μg | 16x/12.5 μg |
| 35 | 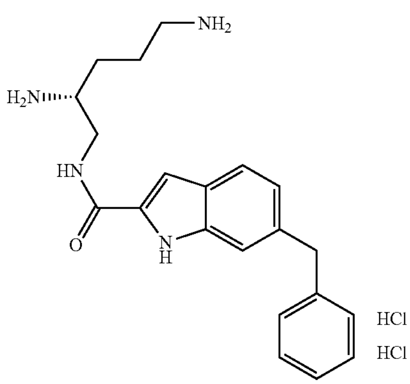 [SMILES: NCCC[C@@H](N)CNC(=O)c1cc2ccc(Cc3ccccc3)cc2[nH]1 ; Cl ; Cl] | 16x/6.25 μg | 16x/12.5 μg |
| 36 | 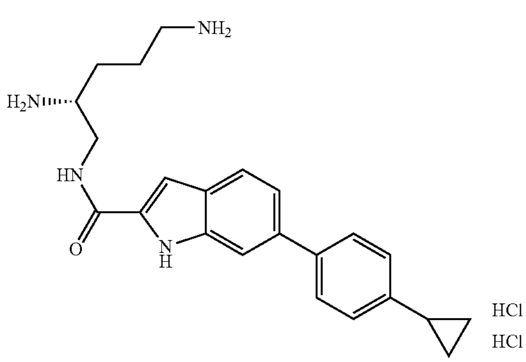 [SMILES: NCCC[C@@H](N)CNC(=O)c1cc2ccc(-c3ccc(C4CC4)cc3)cc2[nH]1 ; Cl ; Cl] | 2z/12.5 μg | — |

TABLE 1-continued

| Example | Structure | Enhanced Activity in *E. coli** | Enhanced Activity in *P. aeruginosa*** |
|---|---|---|---|
| 37 | 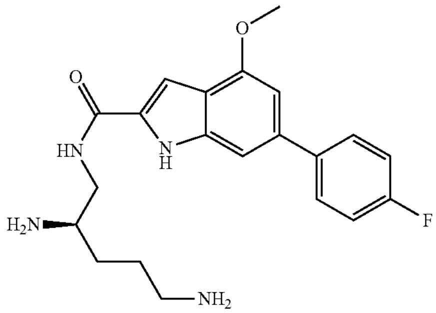 | 16x/12.5 µg | 2x/12.5 µg |
| 38 | 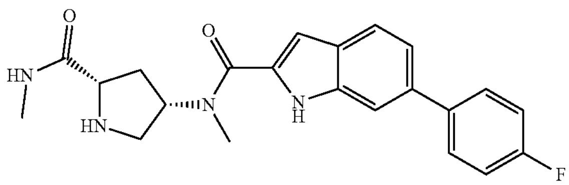 | 2x/50 µg | 2x/50 µg |
| 39 | MW: 524.46 | 2x/12.5 µg | 8x/50 µg |
| 40 | MW: 506.24 | 4x/6.25 µg | 8x/6.25 µg |
| 41 | MW: 397.34 | 16x/12.5 µg | 8x/12.5 µg |

TABLE 1-continued
| Example | Structure | Enhanced Activity in E. coli* | Enhanced Activity in P. aeruginosa** |
|---------|-----------|-------------------------------|---------------------------------------|
| 42 | 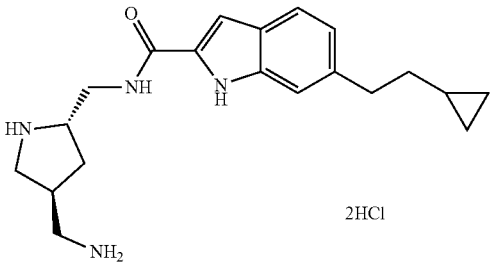 MW: 413.39 | 8x/25 µg | 16x/50 µg |
| 43 | 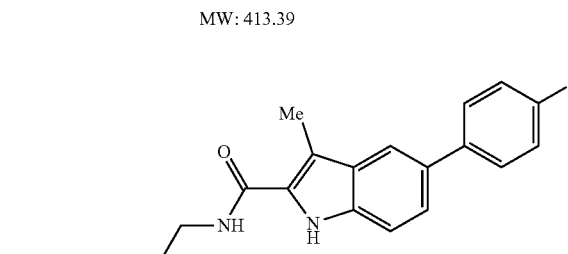 MW: 441.37 | — | — |
| 44 | 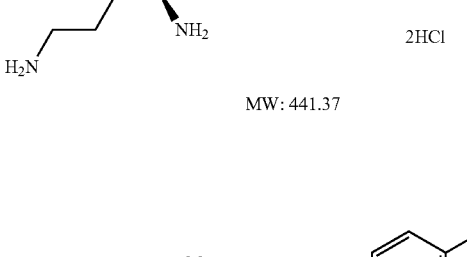 MW: 453.38 | 8x/12.5 µg | — |
| 45 | 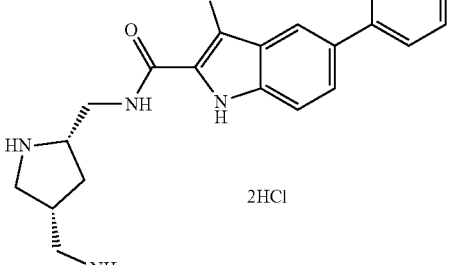 | 16x/6.25 µg | 32x/6.25 µg |

TABLE 1-continued
| Example | Structure | Enhanced Activity in E. coli* | Enhanced Activity in P. aeruginosa** |
|---------|-----------|-------------------------------|--------------------------------------|
| 46 | 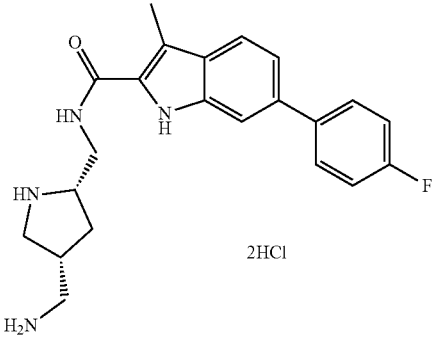 [SMILES: Cc1c(C(=O)NC[C@@H]2C[C@H](CN)CN2)[nH]c2cc(-c3ccc(F)cc3)ccc12] | 2x/12.5 µg | — |
| 47 | 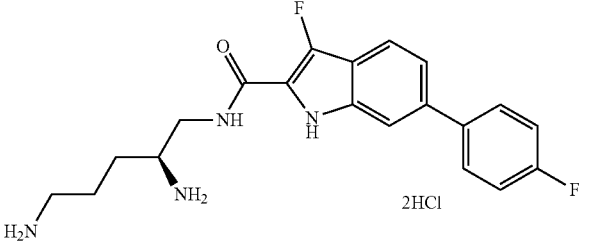 MW: 445.34 | 2x/12.5 µg | 16x/12.5 µg |
| 48 | 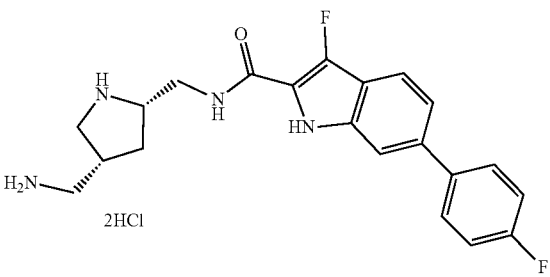 [SMILES: NC[C@@H]1CN[C@H](CNC(=O)c2[nH]c3cc(-c4ccc(F)cc4)ccc3c2F)C1] | — | — |
| 49 | 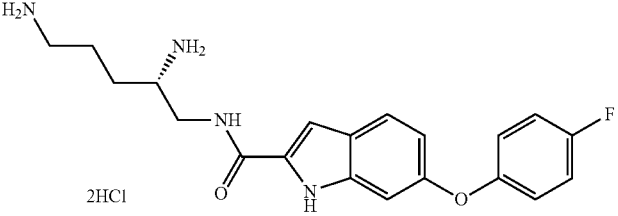 [SMILES: NCCC[C@H](N)CNC(=O)c1cc2ccc(Oc3ccc(F)cc3)cc2[nH]1] | — | — |
| 50 | 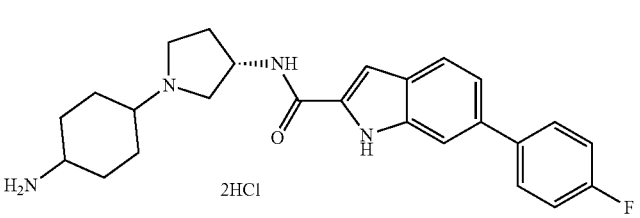 MW: 493.45 | — | — |

TABLE 1-continued
| Example | Structure | Enhanced Activity in *E. coli** | Enhanced Activity in *P. aeruginosa*** |
|---|---|---|---|
| 51 | 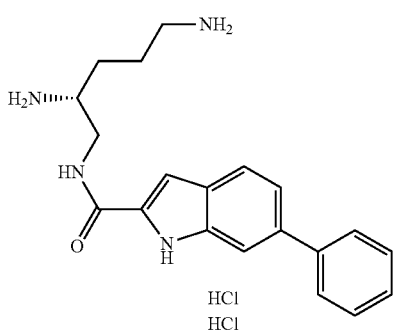 [SMILES: NCCC[C@@H](N)CNC(=O)c1cc2ccc(-c3ccccc3)cc2[nH]1 ; Cl ; Cl] | 4x/12.5 μg | 16x/12.5 μg |
| 52 | 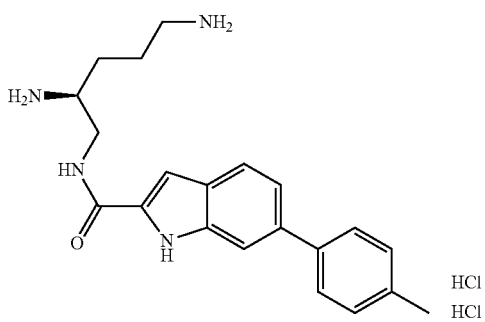 MW: 423.38 | 4x/6.25 μg | 4x/6.25 μg |
| 53 | 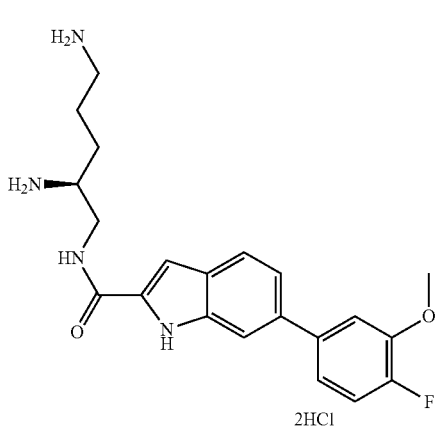 MW: 457.37 | 16x/12.5 μg | 16x/12.5 μg |

TABLE 1-continued
| Example | Structure | Enhanced Activity in *E. coli** | Enhanced Activity in *P. aeruginosa*** |
|---------|-----------|----------------------------------|----------------------------------------|
| 54 | 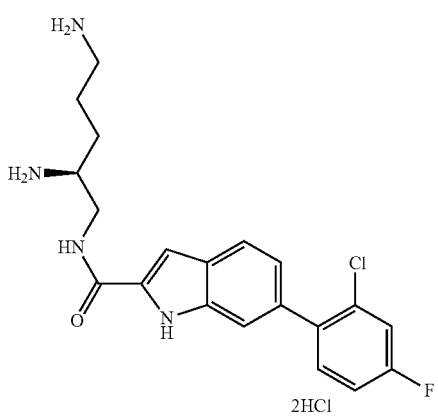 MW: 461.79 | 8x/6.25 µg | 16x/6.25 µg |
| 55 | 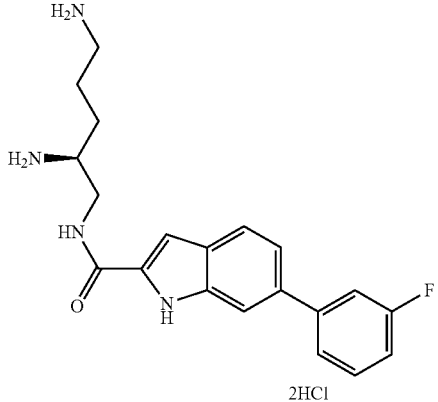 MW: 427.35 | 2x/6.25 µg | 4x/6.25 µg |
| 56 | 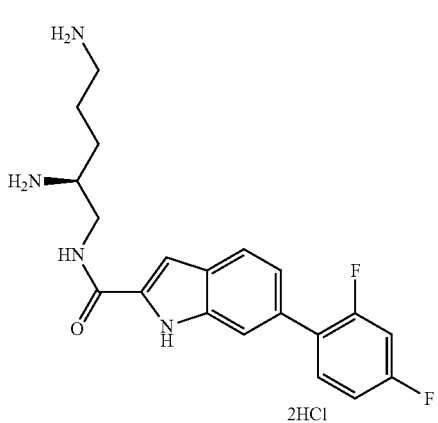 MW: 445.34 | 8x/6.25 µg | 2x/6.25 µg |

TABLE 1-continued
| Example | Structure | Enhanced Activity in *E. coli** | Enhanced Activity in *P. aeruginosa*** |
|---|---|---|---|
| 57 | 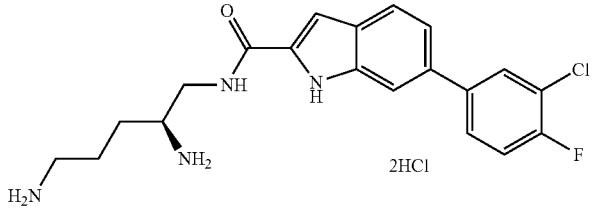 MW: 461.79 | 16x/6.25 µg | 16x/6.25 µg |
| 58 | 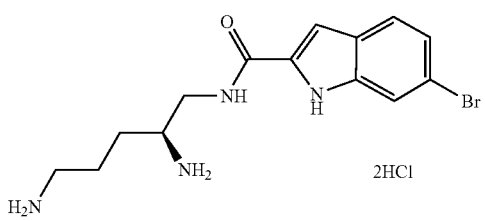 FW: 412.15 | — | — |
| 59 | 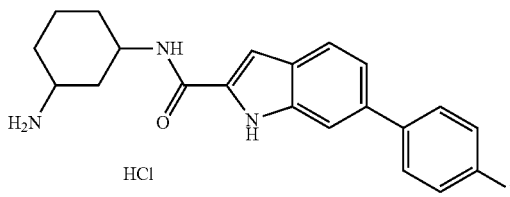 MW: 387.88 | — | — |
| 60 | 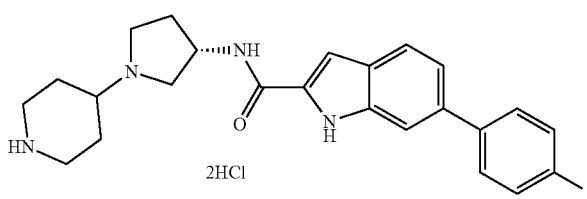 MW: 479.42 | — | — |
| 61 | 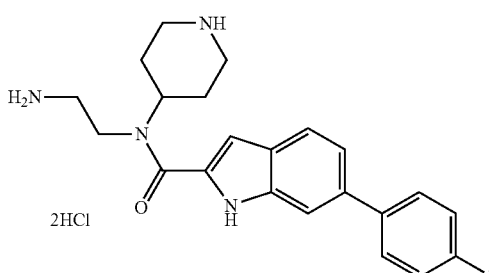 MW: 453.38 | — | 4x/12.5 µg |
| 62 | 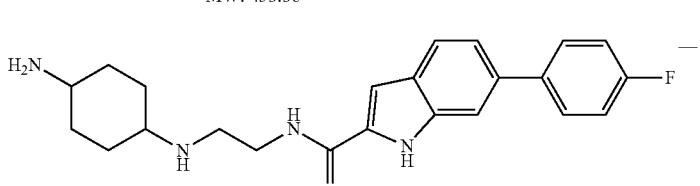 MW: 467.41 | — | 16x/12.5 µg |

TABLE 1-continued

| Example | Structure | Enhanced Activity in E. coli* | Enhanced Activity in P. aeruginosa** |
|---|---|---|---|
| 63 | 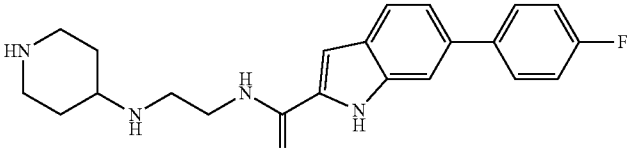 MW: 453.38 | — | 16x/12.5 |
| 64 | 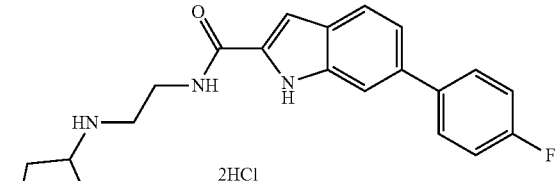 MW: 439.36 | — | — |
| 65 | 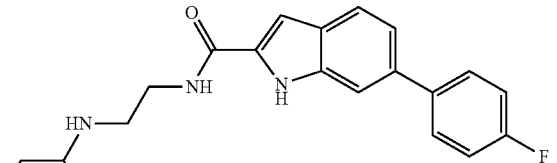 MW: 467.41 | 2x/12.5 µg | 4x/12.5 µg |

*These data were generated using clarithromycin as the antibiotic and the various EPIs against *Escherichia coli* ATCC 25922.
**These data were generated using levofloxacin as the antibiotic and the various EPIs against *Pseudomonas aeruginosa* ATCC 27853.

The invention will now be illustrated by the following non-limiting examples.

Preparation of Intermediates

Table 2 shows intermediates that were used or could be used to prepare compounds of described herein.

TABLE 2

Amine Intermediates

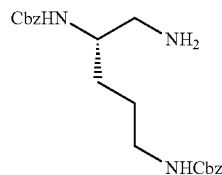

Intermediate A

TABLE 2-continued

Amine Intermediates

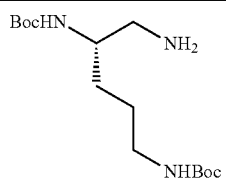

Intermediate B

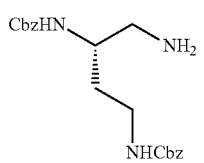

Intermediate C

TABLE 2-continued

Amine Intermediates

Intermediate D: CbzHN-CH(CH2NHBoc)-CH2-NH2

Intermediate E: BocHN-CH(CH2CH2CH2NHBoc)-CH2-NH2

Intermediate F: CbzHN-CH(CH2CH2NHBoc)-CH2-NH2

Intermediate G: BocHN-CH(CH2CH2NHBoc)-CH2-NH2

Intermediate H: BocHN-CH(CH2-NH2)-CH2CH2CH2-CH(NHBoc)-CH(CH3)2

Intermediate I: BocHN-CH(CH2-NH2)-CH2CH2CH2-CH(NHBoc)-Me

Intermediate J: BocHN-CH(CH2-NH2)-CH2CH2-CH(NHBoc)-cyclopropyl

Intermediate K: CbzHN-CH(CH(CH3)-NH2)-CH2CH2CH2-NHCbz

Intermediate L: 1-Bn-2-(CH2NH2)-4-(CH2NHBoc)-pyrrolidine

Intermediate M: 1-Bn-2-(CH2NH2)-4-(CH2NHBoc)-pyrrolidine (diastereomer)

Intermediate N: 1-Bn-2-(CH2NH2)-4-CN-pyrrolidine

Intermediate O: 1-Bn-2-(CH2NH2)-4-CN-pyrrolidine (diastereomer)

Intermediate P: 1-Bn-2-(CH2NH2)-4-CN-pyrrolidine (diastereomer)

Intermediate Q: 1-Bn-2-(CH2NH2)-4-CN-pyrrolidine (diastereomer)

TABLE 2-continued

Amine Intermediates

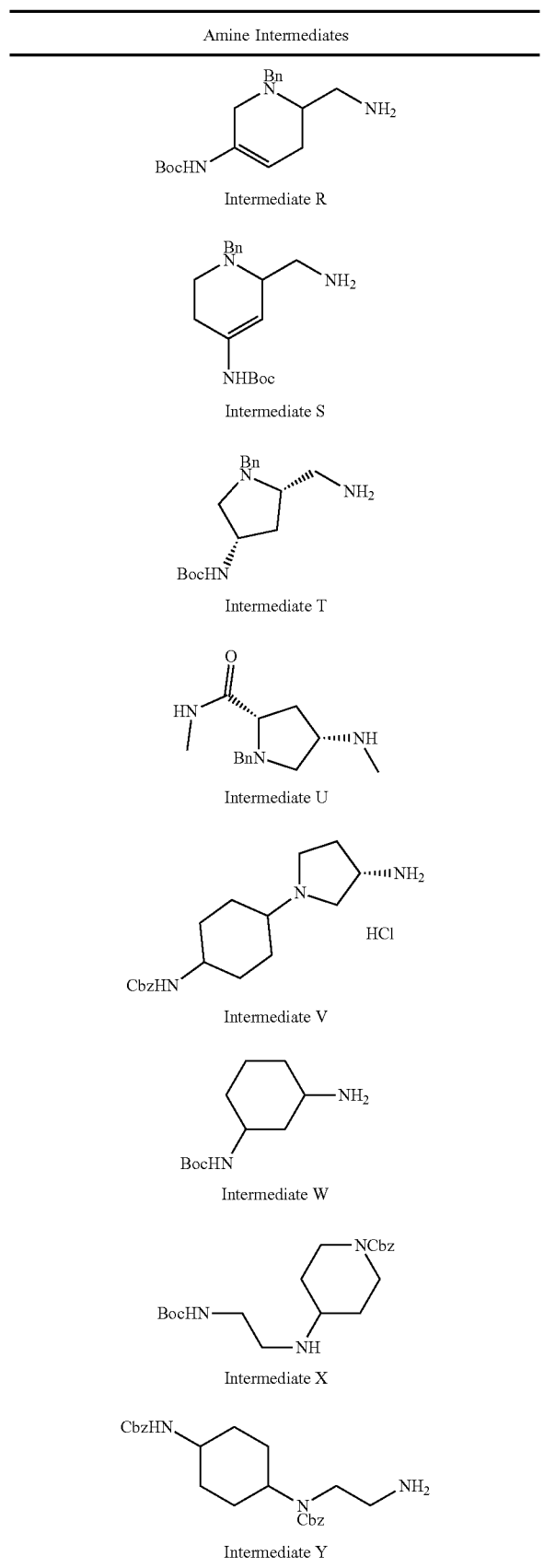

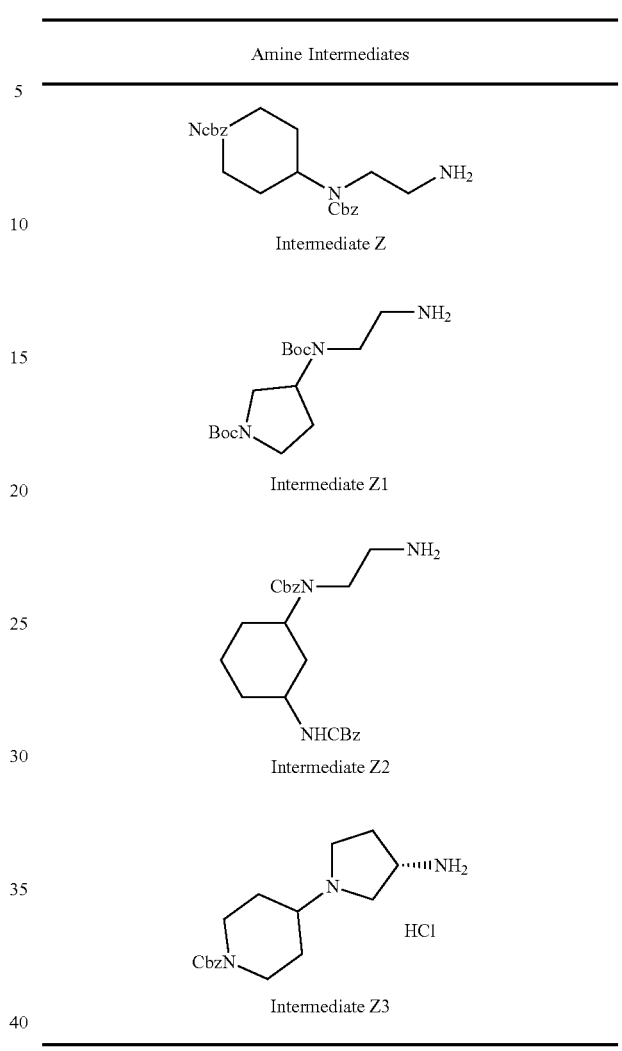

Schemes 4 illustrates a general method for the preparation of amine intermediates A-G.

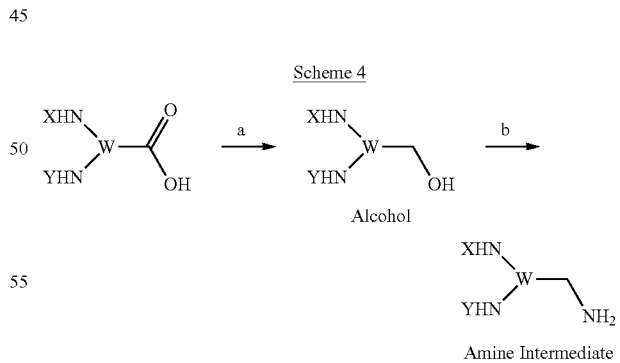

Reagents and Conditions: a) (i) N-methylmorpholine, isobutylchloroformate, DME, (ii) NaBH4, DME/H2O); b) (i) phthalimide, DIAD, PPh3, THF; (ii) hydrazine, Methanol.

The variables X and Y represent protecting groups as needed. The variable W represents a $(C_2-C_{13})$alkyl corresponding to the $R^1$ variable for compounds of formula I. It is to be understood that the two nitrogen atoms attached to W are attached on different carbon atoms of W.

Preparation of Amine Intermediate A (dibenzyl (5-aminopentane-1,4-diyl)(S)-dicarbamate)

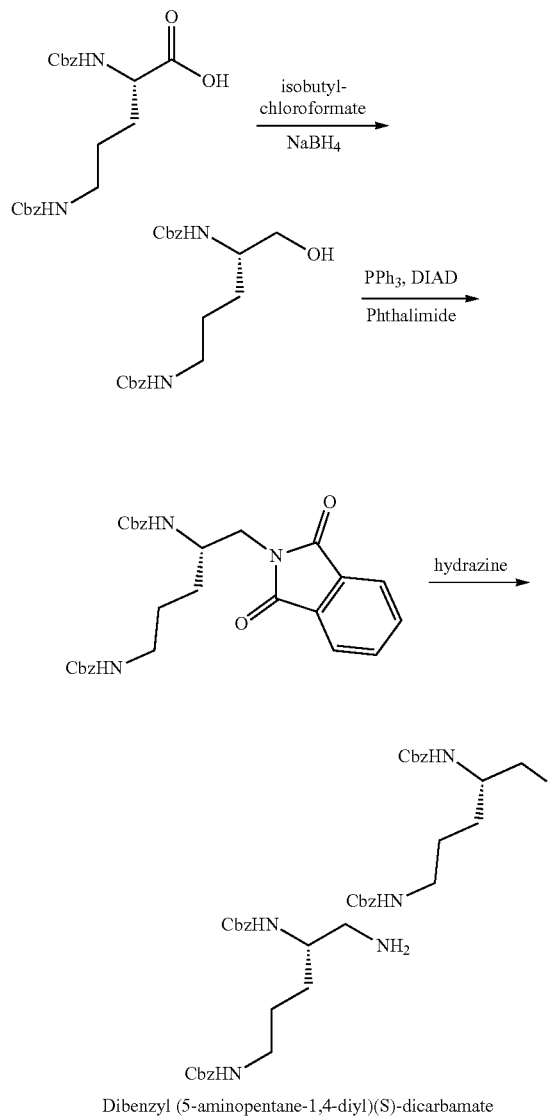

Dibenzyl (5-aminopentane-1,4-diyl)(S)-dicarbamate

Dibenzyl (5-(1,3-dioxoisoindolin-2-yl)pentane-1,4-diyl) (S)-dicarbamate (400 mg, 0.78 mmol) formed was dissolved in methanol (20 mL) and hydrazine monohydrate (80 µL, 1.55 mmol) was added. The reaction mixture was then refluxed for 2 hours and cooled to room temperature. The precipitate formed was filtered and methanol used to wash the filtrate. The filtrate was concentrated under reduced pressure and the remaining solid purified using an ISCO column chromatography on silica gel (0-10% methanol/methylene chloride with 1% $NH_3 \cdot H_2O$) to give product as a white powder. (206 mg, 68% yield); $^1H$ NMR ($CDCl_3$) (400 MHz) δ 7.36 (m, 10H), 5.18 (m, 6H), 3.60 (m, 1H), 3.19 (m, 2H), 2.70 (m, 2H), 1.70 (s, 2H), 1.46 (m, 4H); $^{13}C$ NMR (400 MHz, $CDCl_3$) δ 156.6, 136.6, 136.5, 128.53, 128.51, 128.1, 128.0, 66.6, 66.5, 53.0, 45.6, 40.7, 29.7. 26.5.

The requisite intermediates were prepared as shown in the following steps.

Step 1)

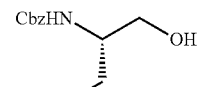

Dibenzyl (5-hydroxypentane-1,4-diyl)(S)-dicarbamate

To a solution of (S)-2,5-bis(((benzyloxy)carbonyl)amino) pentanoic acid (1.0 g, 2.5 mmol) in dimethoxyethane (20 mL) at −15° C. were successively added a solution of N-methyl morpholine (310 µL, 2.82 mmol) and isobutyl chloroformate (320 µL, 2.5 mmol). The reaction was stirred at −15° C. to −10° C. for 15 minutes. The precipitated N-methyl morpholine HCl was removed by filtration and washed with dimethoxyethane (10 mL), the combine filtrates were chilled to −15° C. in an ice-salt bath. Then a solution of sodium borohydride (283 mg, 7.5 mmol) in water (4 mL) was added in one portion at −15° C. This reaction mixture was stirred at this temperature for 10 minutes. The reaction was quenched by the addition of saturated aq. $NH_4Cl$ and the resulting mixture was extracted with ethyl acetate. The organic layer was washed with brine and dried over sodium sulfate. The solution was then filtered and concentrated under reduced pressure, purified by column chromatography on silica gel (0-70% ethyl acetate/hexanes) to give product as a white powder (508 mg, 52% yield); $^1H$ NMR ($CDCl_3$) (400 MHz) δ 7.34 (m, 10H), 5.07 (m, 6H), 3.69 (m, 3H), 3.22 (m, 2H), 1.54 (m, 4H); $^{13}C$ NMR (100 MHz, $CDCl_3$) δ 156.6, 156.5, 136.5, 136.3, 128.54, 128.52, 128.2, 128.1, 66.8, 66.7, 65.1, 52.8, 40.7, 28.5, 26.5.

Step 2)

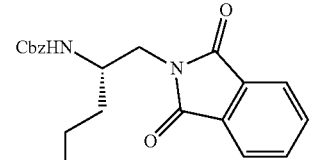

Dibenzyl (5-(1,3-dioxoisoindolin-2-yl)pentane-1,4-diyl)(S)-dicarbamate

Triphenylphosphine (325 mg, 1.24 mmol) and phthalimide (182 mg, 1.24 mmol) were added to a flask containing dry THF (5 mL). Dibenzyl (5-hydroxypentane-1,4-diyl)(S)-dicarbamate (400 mg, 1.03 mmol) was added and the flask was cooled to 0° C. DIAD (250 mg, 1.24 mmol) was added dropwise and reaction allowed to stir for 30 minutes at 0° C. and then overnight at room temperature. The mixture was concentrated under reduced pressure and residue was purified using an ISCO column chromatography on silica gel (0-70% ethyl acetate/hexanes) to give product as a white solid. (491 mg, 92% yield); $^1H$ NMR ($CDCl_3$) (400 MHz) δ 7.83 (m, 2H), 7.72 (m, 2H), 7.32 (m, 10H), 5.10 (m, 3H), 4.97 (m, 3H), 4.03 (m, 1H) 3.76 (m, 2H), 3.24 (m, 2H), 1.57 (m, 4H); $^{13}C$ NMR (100 MHz, $CDCl_3$) δ 168.5, 156.4, 156.2, 136.6, 136.5, 134.0, 132.1, 123.0, 131.9, 131.8, 128.6, 128.5, 128.4, 128.3, 128.0, 127.9, 127.8, 123.4, 66.6, 66.5, 50.7, 41.7, 40.6, 30.0, 26.3.

Preparation of Amine Intermediate B (di-tert-butyl (5-aminopentane-1,4-diyl)(S)-dicarbamate)

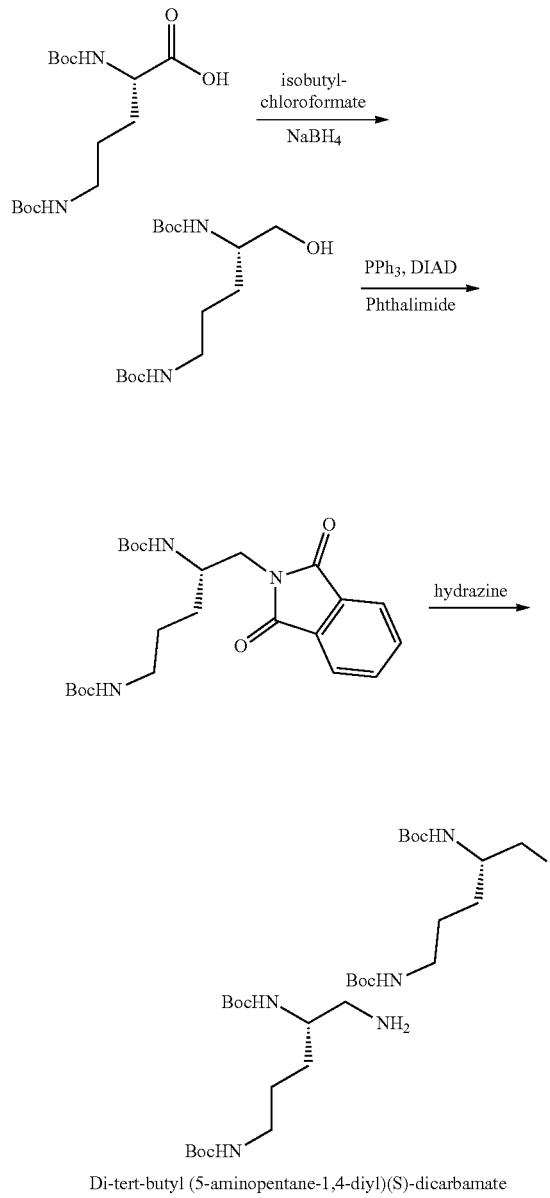

Di-tert-butyl (5-aminopentane-1,4-diyl)(S)-dicarbamate

Di-tert-butyl (5-(1,3-dioxoisoindolin-2-yl)pentane-1,4-diyl)(S)-dicarbamate (760 mg, 1.70 mmol) formed was dissolved in methanol (30 mL) and hydrazine monohydrate (177 μL, 3.40 mmol) was added. The reaction mixture was then refluxed for 2 hours and cooled to room temperature. The precipitate formed was filtered and methanol used to wash the filtrate. The filtrate was concentrated under reduced pressure and the remaining oil purified using an ISCO column chromatography on silica gel (0-10% methanol/methylene chloride with 1% NH$_3$·H$_2$O) to give product as a yellow oil. (450 mg, 83% yield); $^1$H NMR (CDCl$_3$) (300 MHz) δ 4.63 (m, 2H), 3.52-3.49 (m, 1H), 3.14-3.12 (m, 2H), 2.79-2.60 (m, 2H), 1.54-1.57 (m, 4H), 1.53-1.26 (m, 18H).

The requisite intermediates were prepared as shown in the following steps.

Step 1)

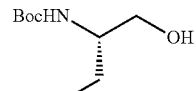

Di-tert-butyl (5-hydroxypentane-1,4-diyl)(S)-dicarbamate

To a solution of (S)-2,5-bis((tert-butoxycarbonyl)amino)pentanoic acid (1.0 g, 3.01 mmol) in THF 30 mL at −15° C. were successively added a solution of N-methyl morpholine (305 μL, 3.32 mmol) and isobutyl chloroformate (411 μL, 3.01 mmol). The reaction was stirred at −15° C. to −10° C. for 15 minutes. The precipitated N-methyl morpholine HCl was removed by filtration and washed with THF (10 mL), the combine filtrates were chilled to −15° C. in an ice-salt bath. Then a solution of sodium borohydride (342 mg, 9.03 mmol) in water (4 mL) was added in one portion at −15° C. This reaction mixture was stirred at this temperature for 10 minutes. The reaction was quenched by the addition of saturated aq. NH$_4$Cl and the resulting mixture was extracted with ethyl acetate. The organic layer was washed with brine and dried over sodium sulfate. The solution was then filtered and concentrated under reduced pressure, purified on column (0-100% ethyl acetate/hexanes) to give product as a white powder (750 mg, 78% yield); $^1$H NMR (CDCl$_3$) (300 MHz) δ 4.74-4.64 (m, 2H), 3.63-3.55 (m, 3H), 3.14-3.13 (m, 2H), 2.45 (m, 1H), 1.68-1.58 (m, 4H), 1.56-1.44 (m, 18H).

Step 2)

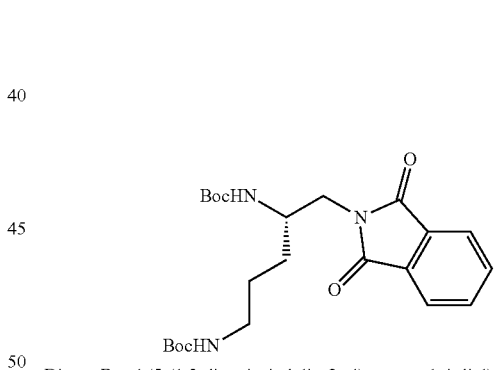

Di-tert-Butyl (5-(1,3-dioxoisoindolin-2-yl)pentane-1,4-diyl)(S)-dicarbamate

Triphenylphosphine (742 mg, 2.83 mmol) and phthalimide (417 mg, 2.83 mmol) were added to a flask containing dry THF (15 mL). Di-tert-butyl (5-hydroxypentane-1,4-diyl)(S)-dicarbamate (750 mg, 2.36 mmol) was added and the flask was cooled to 0° C. DIAD (573 mg, 2.83 mmol) was added dropwise and reaction allowed to stir for 30 minutes at 0° C. and overnight at room temperature. The mixture was concentrated under reduced pressure and residue was purified using an ISCO chromatography with silica gel (0-100% ethyl acetate/hexanes) to give product as a white solid. (760 mg, 72% yield). $^1$H NMR (CDCl$_3$) (300 MHz) δ 7.86-7.83 (m, 2H), 7.72-7.69 (m, 2H), 4.64-4.61 (m, 2H), 3.97-3.94 (m, 1H) 3.70-3.67 (m, 2H), 3.15-3.13 (m, 2H), 1.67-1.54 (m, 4H), 1.52-1.37 (m, 9H), 1.37-1.22 (m, 9H).

Preparation of Amine Intermediate C (dibenzyl (4-aminobutane-1,3-diyl)(S)-dicarbamate)

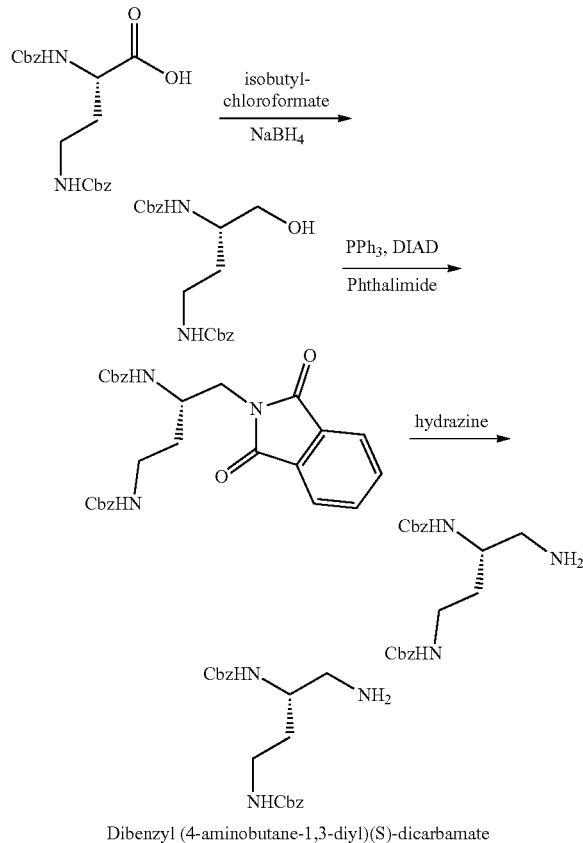

Dibenzyl (4-aminobutane-1,3-diyl)(S)-dicarbamate

Dibenzyl (4-(1,3-dioxoisoindolin-2-yl)butane-1,3-diyl) (S)-dicarbamate (170 mg, 0.34 mmol) was dissolved in methanol (5 mL) and hydrazine monohydrate (0.03 mL, 0.68 mmol) was added. The reaction mixture was then refluxed for 2 hours and cooled to room temperature. The precipitate formed was filtered and methanol used to wash the filtrate. The filtrate was concentrated under reduced pressure and the remaining solid was purified on an ISCO chromatography with silica gel (0-10% methanol/methylene chloride with 1% $NH_3·H_2O$) to give product as a white powder (77 mg, 61% yield). $^1H$ NMR ($CDCl_3$) (400 MHz) δ 7.34 (m, 10H), 5.77 (brs, 1H), 5.56 (d, 1H, J=8 Hz), 5.09 (m, 4H), 3.69 (m, 1H), 3.44 (m, 1H), 3.02 (m, 1H), 2.74 (m, 2H), 2.26 (s, 2H), 1.68 (m, 1H), 1.47 (m, 1H); $^{13}C$ NMR (100 MHz, $CDCl_3$) δ 157.0, 156.5, 136.7, 136.4, 128.5, 128.4, 128.1, 128.0, 66.8, 66.5, 50.5, 45.5, 37.6, 33.0.

The requisite intermediates were prepared as shown in the following steps:
Step 1)

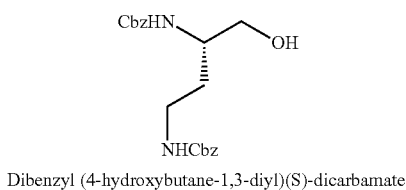 [SMILES: O=C(NCC[C@@H](CO)NC(=O)OCc1ccccc1)OCc1ccccc1]

Dibenzyl (4-hydroxybutane-1,3-diyl)(S)-dicarbamate

To a solution of (S)-2,4-bis(((benzyloxy)carbonyl)amino) butanoic acid (1.0 g, 2.77 mmol) in dimethoxymethane (10 mL) at −15° C. were successively added N-methyl morpholine (340 μL, 3.13 mmol) and isobutyl chloroformate (360 μL, 2.77 mmol). The reaction was stirred at −15° C. to −10° C. for 15 minutes. The precipitated N-methyl morpholine HCl was removed by filtration and washed with dimethoxyethane (10 mL) and the combine filtrates were chilled to −15° C. in an ice-salt bath. Then a solution of sodium borohydride (378 mg, 8.31 mmol) in water (5 mL) was added in one portion at −15° C. This reaction mixture was stirred at this temperature for 10 minutes. The reaction was quenched by the addition of saturated aq. $NH_4Cl$ and the resulting mixture was extracted with ethyl acetate. The organic layer was washed with brine and dried over sodium sulfate. The solution was then filtered and concentrated under reduced pressure, purified by column chromatography on silica gel (0-70% ethyl acetate/hexanes) to give product as a white powder (491 mg, 48% yield); $^1H$ NMR ($CDCl_3$) (400 MHz) 7.33 (m, 10H), 5.72 (s, 1H), 5.63 (d, 1H, J=8 Hz), 5.08 (s, 4H), 3.48 (m, 5H), 3.02 (m, 1H), 1.71 (m, 1H), 1.57 (m, 1H); $^{13}C$ NMR (100 MHz, $CDCl_3$) δ 157.0, 156.7, 136.5, 136.3, 128.55, 128.50, 128.1, 128.07, 128.02, 66.8, 66.6, 64.6, 50.4, 37.7, 31.7.
Step 2)

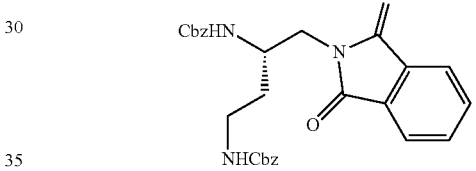

Dibenzyl (4-(1,3-dioxoisoindolin-2-yl)butane-1,3-diyl)(S)-dicarbamate

Triphenylphosphine (365 mg, 1.39 mmol) and phthalimide (204 mg, 1.39 mmol) were added to a flask containing dry THF (6 mL). Dibenzyl (4-hydroxybutane-1,3-diyl)(S)-dicarbamate (432 mg, 1.39 mmol) was added and the flask was cooled to 0° C. DIAD (281 mg, 1.39 mmol) was added dropwise and reaction allowed to stir for 30 minutes at 0° C. and overnight at room temperature. The mixture was concentrated under reduced pressure and residue was purified on an ISCO chromatography with silica gel (0-70% ethyl acetate/hexanes) to give product as a white solid (237 mg, 41% yield). $^1H$ NMR ($CDCl_3$) (400 MHz) δ 7.83 (m, 2H), 7.70 (m, 2H), 7.36 (m, 10H), 5.61 (brs, 1H), 5.46 (d, 1H, J=8 Hz), 5.10 (m, 4H), 4.12 (m, 1H), 3.78 (m, 2H), 3.51 (m, 1H), 3.08 (m, 1H), 1.83 (m, 1H), 1.54 (m, 1H); $^{13}C$ NMR (100 MHz, $CDCl_3$) δ 168.5, 156.7, 156.5, 136.7, 136.4, 134.1, 131.7, 128.5, 128.4, 128.0, 127.9, 127.7, 123.4, 66.6, 66.5, 53.4, 48.8, 41.8, 37.4, 33.2.

Preparation of Amine Intermediate D (benzyl t-butyl (3-aminopropane-1,2-diyl)(R)-dicarbamate)

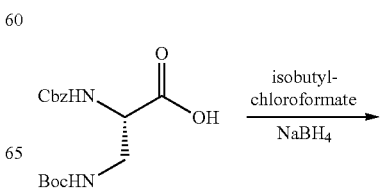

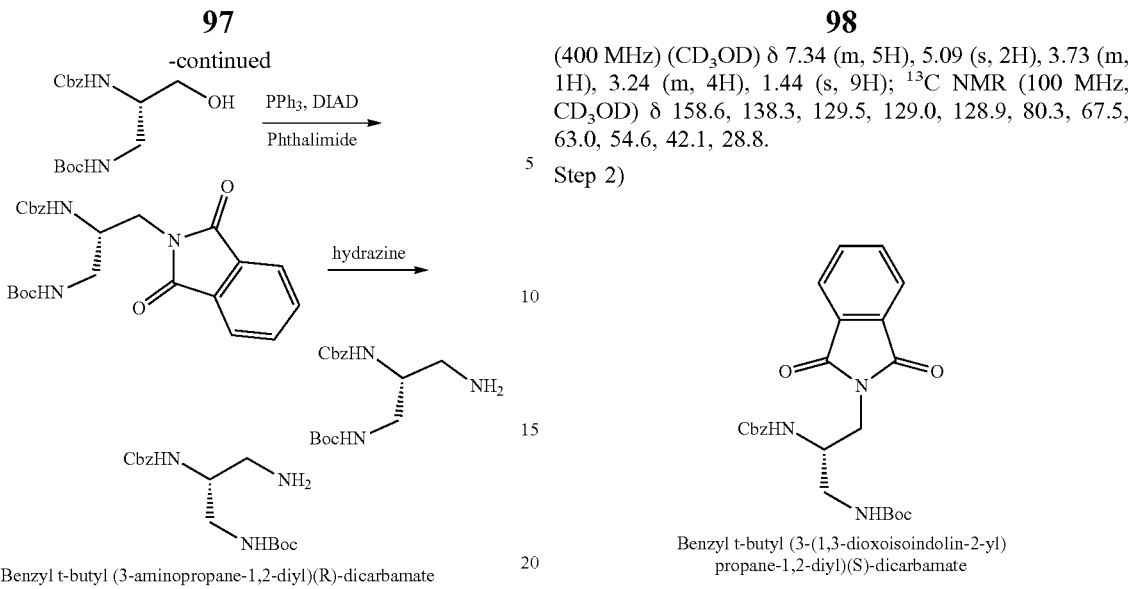

Benzyl t-butyl (3-(1,3-dioxoisoindolin-2-yl)propane-1,2-diyl)(S)-dicarbamate (450 mg, 0.99 mmol) was dissolved in methanol (10 mL) and hydrazine monohydrate (0.1 mL, 1.98 mmol) was added. The reaction mixture was then refluxed for 2 hours and cooled to room temperature. The precipitate formed was filtered and methanol used to wash the filtrate. The filtrate was concentrated under reduced pressure and the remaining solid purified on an ISCO column chromatography with silica gel (0-10% Methanol/methylene chloride with 1% $NH_3 \cdot H_2O$) to give product as a colorless oil. (140 mg, 44% yield); $^1H$ NMR (CDCl$_3$, 400 MHz) δ 7.27 (m, 5H), 6.37 (s, 1H), 5.87 (s, 1H), 5.02 (s, 2H), 3.94 (s, 4H), 3.60 (m, 1H), 3.12 (m, 2H), 2.70 (m, 2H), 1.36 (s, 9H).

The requisite intermediates were prepared were prepared as shown in the following steps
Step 1)

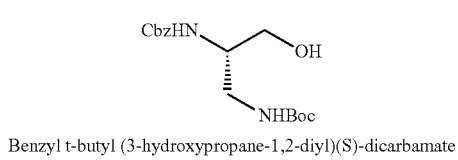 [SMILES: CC(C)(C)OC(=O)NC[C@@H](CO)NC(=O)OCc1ccccc1]

Benzyl t-butyl (3-hydroxypropane-1,2-diyl)(S)-dicarbamate

To a solution of (S)-2-(((benzyloxy)carbonyl)amino)-3-((t-butoxycarbonyl)amino)propanoic acid (900 mg, 2.66 mmol) in DME (10 mL) at −15° C. were successively added a solution of N-methyl morpholine (0.33 mL, 3 mmol) and isobutyl chloroformate (0.35 mL, 2.66 mmol). The reaction was stirred at −15 to −10° C. for 15 minutes. The precipitated N-methyl morpholine HCl was removed by filtration and washed with DME (10 mL), the combine filtrates were chilled to −15° C. in an ice-salt bath. Then a solution of sodium borohydride (301 mg, 7.98 mmol) in water (5 mL) was added in one portion at −15° C. This reaction mixture was stirred at this temperature for 10 minutes. The reaction was quenched by the addition of saturated aqueous NH$_4$Cl and the resulting mixture was extracted with ethyl acetate. The organic layer was washed with brine and dried over sodium sulfate. The solution was then filtered. concentrated under reduced pressure and purified by column chromatography on silica gel (0-70% ethyl acetate/hexanes) to give product as a white powder (675 mg, 78% yield); $^1H$ NMR (400 MHz) (CD$_3$OD) δ 7.34 (m, 5H), 5.09 (s, 2H), 3.73 (m, 1H), 3.24 (m, 4H), 1.44 (s, 9H); $^{13}C$ NMR (100 MHz, CD$_3$OD) δ 158.6, 138.3, 129.5, 129.0, 128.9, 80.3, 67.5, 63.0, 54.6, 42.1, 28.8.

Step 2)

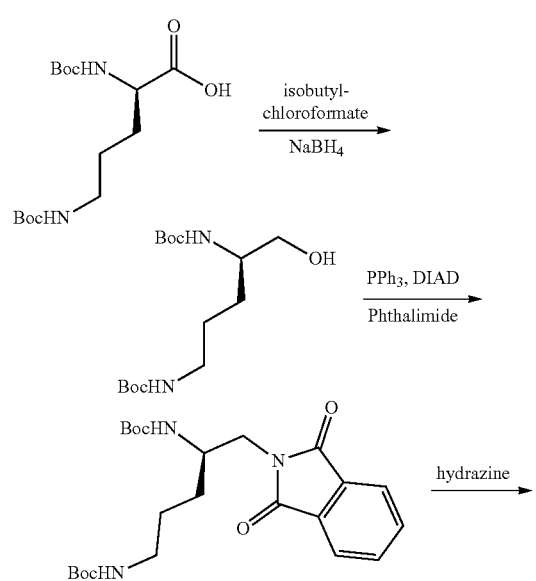

Benzyl t-butyl (3-(1,3-dioxoisoindolin-2-yl) propane-1,2-diyl)(S)-dicarbamate

Triphenylphosphine (709 mg, 2.71 mmol) and phthalimide (398 mg, 2.71 mmol) were added to a flask containing dry THF (6 mL). Benzyl t-butyl (3-hydroxypropane-1,2-diyl)(S)-dicarbamate (730 mg, 2.26 mmol) was added and the flask was cooled to 0° C. DIAD (548 mg, 2.71 mmol) was added dropwise and reaction allowed to stir for 30 minutes at 0° C. and then overnight at room temperature. The mixture was concentrated under reduced pressure and residue purified on an ISCO chromatography with silica gel (0-70% ethyl acetate/hexanes) to give the product as a white solid (556 mg, 55% yield). $^1H$ NMR (CDCl$_3$) (400 MHz) δ 7.83 (m, 2H), 7.71 (m, 2H), 7.28 (m, 5H), 5.70 (m, 1H), 5.26 (m, 1H), 5.02 (s, 2H), 4.06 (m, 1H), 3.84 (m, 2H), 3.31 (m, 2H), 1.44 (s, 9H), $^{13}C$ NMR (100 MHz, CDCl$_3$) δ 168.5, 156.6, 156.3, 136.4, 134.1, 131.8, 128.3, 127.9, 123.4, 79.7, 66.6, 51.6, 41.9, 39.2, 28.3, 21.9.

Preparation of Amine Intermediate E (di-tert-butyl (5-aminopentane-1,4-diyl)(R)-dicarbamate)

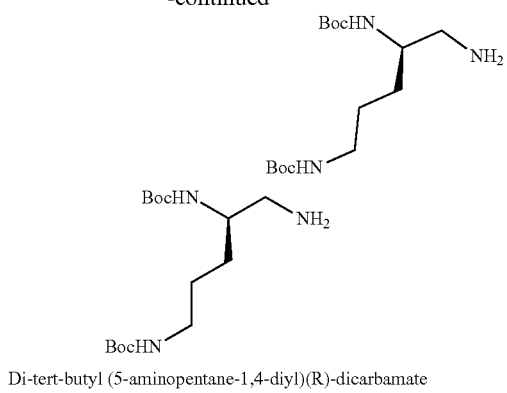

Di-tert-butyl (5-aminopentane-1,4-diyl)(R)-dicarbamate

Di-tert-butyl (5-(1,3-dioxoisoindolin-2-yl)pentane-1,4-diyl)(R)-dicarbamate (1.71 g, 2.24 mmol) was dissolved in methanol (20 mL) and hydrazine monohydrate (220 µL, 4.47 mmol) was added. The reaction mixture was then refluxed for 2 hours and cooled to room temperature. The precipitate formed was filtered and methanol was used to wash the solid. The filtrate was concentrated under reduced pressure and the residual oil purified using an ISCO chromatograph with silica (0-10% methanol/methylene chloride+1% NH$_4$OH) to give product as a yellow oil. (560 mg, 79%); $^1$H NMR (CDCl$_3$) (300 MHz) δ 4.62 (m, 2H), 3.52 (m, 1H), 3.14-3.09 (m, 2H), 2.79-2.60 (m, 2H), 1.64-1.57 (m, 4H), 1.48-1.23 (m, 18H).

The requisite intermediates were prepared as shown in the following steps.

Step 1)

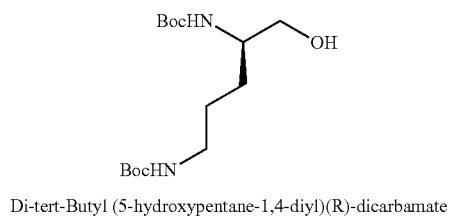 [SMILES: CC(C)(C)OC(=O)NCCC[C@H](CO)NC(=O)OC(C)(C)C]

Di-tert-Butyl (5-hydroxypentane-1,4-diyl)(R)-dicarbamate

To a solution of (R)-2,5-bis((tert-butoxycarbonyl)amino)pentanoic acid (1.70 g, 5.11 mmol) in THF 30 ml at −15° C. were successively added a solution of N-methyl morpholine (620 µL, 5.70 mmol) and isobutyl chloroformate (668 µL, 5.11 mmol). The reaction was stirred at −15° C. to −10° C. for 15 minutes. The precipitated N-methyl morpholine HCl was removed by filtration and the solid washed with THF (10 mL), the combine filtrates were chilled to −15° C. in an ice-salt bath. Then a solution of sodium borohydride (580 mg, 15.33 mmol) in water (4 mL) was added in one portion at −15° C. This reaction mixture was stirred at this temperature for 10 minutes. The reaction was quenched by the addition of saturated aq. NH$_4$Cl and the resulting mixture was extracted with ethyl acetate. The organic layer was washed with brine and dried over sodium sulfate. The solution was then filtered and the filtrate concentrated under reduced pressure. The crude product was used directly for next step without further purification.

Step 2)

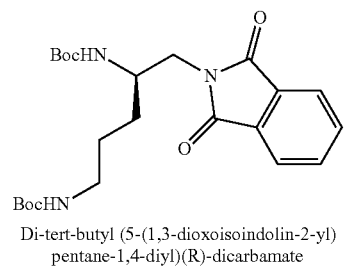 [SMILES: CC(C)(C)OC(=O)NCCC[C@H](CN1C(=O)c2ccccc2C1=O)NC(=O)OC(C)(C)C]

Di-tert-butyl (5-(1,3-dioxoisoindolin-2-yl)pentane-1,4-diyl)(R)-dicarbamate

Triphenylphosphine (1.61 g, 6.13 mmol) and phthalimide (902 mg, 6.13 mmol) were added to a flask containing dry THF (40 mL). Di-tert-butyl (5-hydroxypentane-1,4-diyl)(R)-dicarbamate (1.63 g, 5.11 mmol) was added and the flask was cooled to 0° C. DIAD (1.24 g, 6.13 mmol) was added dropwise and reaction allowed to stir for 30 minutes at 0° C. and overnight at room temperature. The mixture was concentrated under reduced pressure and residue purified using an ISCO chromatograph with silica (0-100% ethyl acetate/hexanes) to give product as a white solid. (1.71 g, 74%); $^1$H NMR (CDCl$_3$) (300 MHz) δ 7.89-7.82 (m, 2H), 7.76-7.69 (m, 2H), 4.64-4.62 (m, 2H), 3.97-3.94 (m, 1H) 3.74-3.67 (m, 2H), 3.15-3.13 (m, 2H), 1.66-1.52 (m, 4H), 1.52-1.43 (m, 9H), 1.27-1.23 (m, 9H).

Preparation of Amine Intermediate F (Benzyl t-butyl (5-aminopentane-1,4-diyl)(S)-dicarbamate)

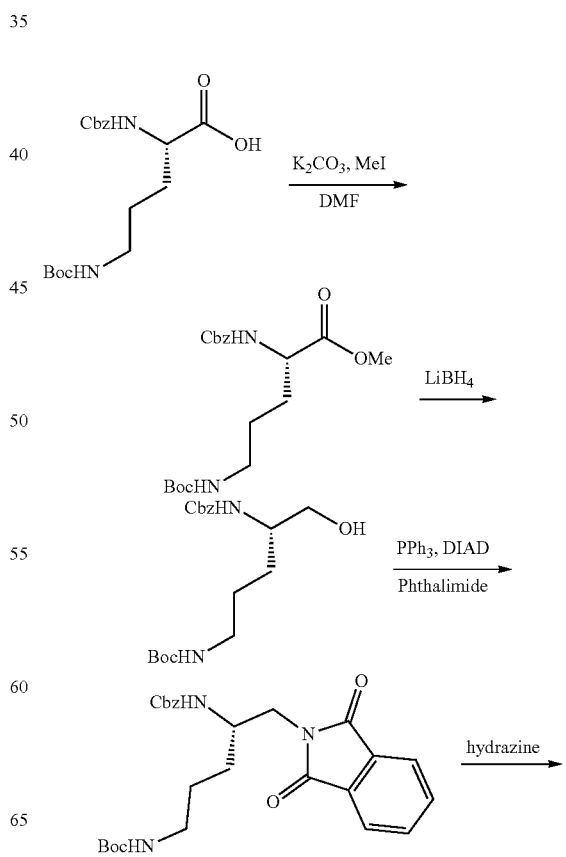

-continued

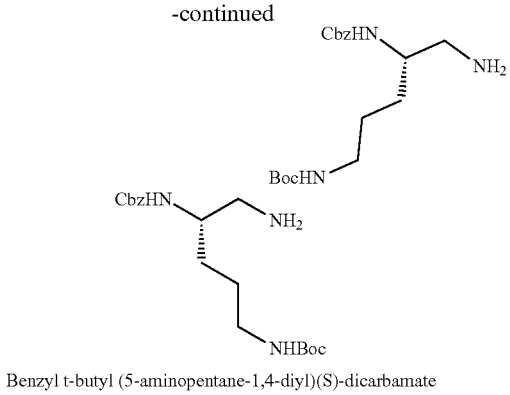

Benzyl t-butyl (5-aminopentane-1,4-diyl)(S)-dicarbamate

The phthalimide (340 mg, 0.71 mmol) formed was dissolved in methanol (20 mL) and hydrazine monohydrate (0.07 mL, 1.41 mmol) was added. The reaction mixture was then refluxed for 2 hours and cooled to room temperature. The precipitate formed was filtered and methanol was used to wash the filtrate. The filtrate was concentrated under reduced pressure and the remaining solid was purified by an ISCO column chromatography on silica gel using (0-10% Methanol/DCM with 1% $NH_3 \cdot H_2O$) to give product as a white powder. (164 mg, 66% yield); $^1$H NMR (CDCl$_3$) (400 MHz) δ 7.25 (m, 5H), 5.41 (d, 1H, J=8 Hz), 5.00 (s, 1H), 4.84 (brs, 1H); 3.50 (m, 1H), 3.01 (m, 2H), 2.61 (m, 2H), 1.40 (m, 4H), 1.36 (s, 9H); $^{13}$C NMR (100 MHz, CDCl$_3$) δ 156.6, 156.0, 136.6, 128.4, 128.1, 128.0, 78.9, 66.6, 53.2, 45.7, 40.2, 29.7, 28.4, 26.6, 25.0, 24.9.

The requisite intermediates were prepared as follows:

Step 1)

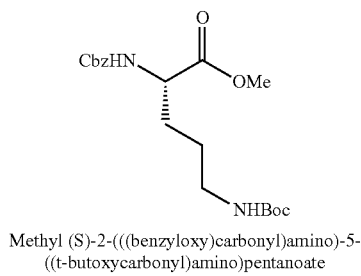 [SMILES: COC(=O)[C@H](CCCNC(=O)OC(C)(C)C)NC(=O)OCc1ccccc1]

Methyl (S)-2-(((benzyloxy)carbonyl)amino)-5-((t-butoxycarbonyl)amino)pentanoate (S)-2-(((Benzyloxy)carbonyl)amino)-5-((t-butoxycarbonyl)amino)pentanoic acid (1.0 g, 2.73 mmol) was dissolved in DMF (5 mL) and $K_2CO_3$ (453 mg, 3.26 mmol). The reaction was cooled to 0° C. and methyl iodide (775 mg, 5.46 mmol) was added. The reaction was allowed to warm to room temperature and stirred at the temperature overnight. Then the reaction mixture was washed with saturated sodium bicarbonate solution and extracted with ethyl acetate. The combined organic layers were washed with brine, dried over sodium sulfate, concentrated under reduced pressure and purified by ISCO column chromatography on silica gel (0-60% ethyl acetate/hexanes) to give product as a colorless oil. (761 mg, 73% yield); $^1$H NMR (400 Hz, CDCl$_3$) δ 7.19 (s, 5H), 6.06 (d, 1H, J=8 Hz), 5.12 (brs, 1H), 4.94 (s, 2H), 4.17 (m, 1H), 3.55 (s, 3H), 2.94 (m, 2H), 1.69 (m, 1H), 1.55 (m, 1H), 1.40 (m, 2H), 1.27 (s, 9H); $^{13}$C NMR (100 MHz, CDCl$_3$) δ 172.7, 156.0, 155.9, 136.3, 128.2, 128.1, 127.9, 127.8, 78.6, 67.2, 66.5, 53.7, 39.8, 29.2, 28.2, 25.9.

Step 2)

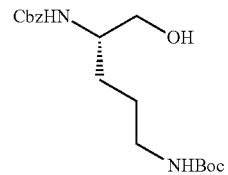

Benzyl t-butyl (5-hydroxypentane-1,4-diyl)(S)-dicarbamate

To a solution of methyl (S)-2-(((benzyloxy)carbonyl)amino)-5-((t-butoxycarbonyl)amino)pentanoate (431 mg, 1.13 mmol) in THF (5 mL)/ethanol (1 mL) was added LiBH$_4$ (32 mg, 1.47 mmol) at 0° C. The mixture was stirred at that temperature for 30 minutes and warmed to room temperature and stirred overnight. The reaction mixture was poured into water and extracted with ethyl acetate. The combine organic layers were washed with brine and dried over sodium sulfate and concentrated under reduced pressure. It was purified on ISCO chromatograph on silica gel (0-70% ethyl acetate/hexanes to give product as a colorless oil (385 mg, 97% yield). $^1$H NMR (CDCl$_3$) (400 MHz) δ 7.28 (m, 5H), 5.02 (s, 3H), 3.60 (m, 4H), 3.04 (m, 2H), 1.47 (m, 4H), 1.36 (m, 9H); $^{13}$C NMR (100 MHz, CDCl$_3$) δ 156.6, 156.1, 136.4, 128.5, 128.1, 128.0, 79.3, 66.8, 65.0, 62.7, 52.9, 52.4, 40.3, 29.8, 28.4, 26.7, 26.0.

Step 3)

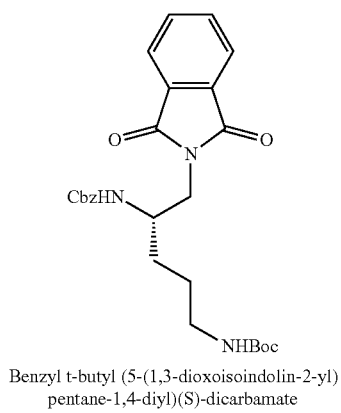 [SMILES: CC(C)(C)OC(=O)NCCC[C@@H](CN1C(=O)c2ccccc2C1=O)NC(=O)OCc1ccccc1]

Benzyl t-butyl (5-(1,3-dioxoisoindolin-2-yl)pentane-1,4-diyl)(S)-dicarbamate

Triphenylphosphine (325 mg, 1.24 mmol) and phthalimide (182 mg, 1.24 mmol) were added to a flask containing dry THF (5 mL). Dibenzyl (5-hydroxypentane-1,4-diyl)(S)-dicarbamate (400 mg, 1.03 mmol) was added and the flask was cooled to 0° C. DIAD (250 mg, 1.24 mmol) was added dropwise and reaction allowed to stir for 30 minutes at 0° C. and then overnight at room temperature. The mixture was concentrated under reduced pressure and the residue purified using an ISCO chromatograph on silica gel (0-70% ethyl acetate/hexanes) to give product as a white solid. (340 mg, 69% yield); $^1$H NMR (CDCl$_3$) (400 MHz) δ 7.82 (m, 2H), 7.71 (m, 2H), 7.27 (m, 5H), 5.18 (brs, 1H), 4.96 (m, 2H), 4.67 (brs, 1H), 4.02 (m, 1H) 3.75 (m, 2H), 3.14 (m, 2H), 1.55 (m, 4H), 1.44 (s, 9H); $^{13}$C NMR (100 MHz, CDCl$_3$) δ 168.4, 156.3, 156.0, 136.6, 133.9, 131.8, 128.4, 128.3, 127.8, 127.7, 123.3, 78.9, 66.3, 60.3, 50.7, 41.9, 40.2, 29.9, 28.4, 26.4.

Preparation of Amine Intermediate G (di-tert-butyl (4-aminobutane-1,3-diyl)(S)-dicarbamate)

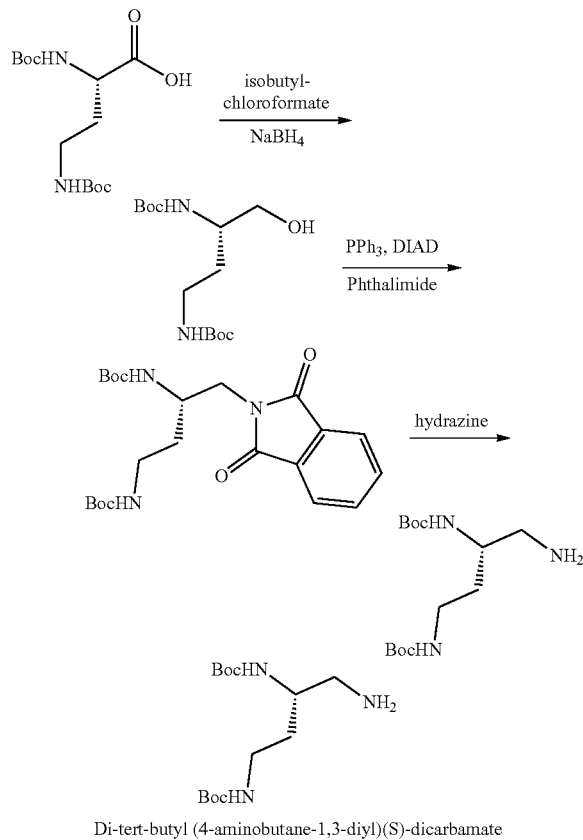

Di-tert-butyl (4-aminobutane-1,3-diyl)(S)-dicarbamate

Di-tert-butyl (4-(1,3-dioxoisoindolin-2-yl)butane-1,3-diyl)(S)-dicarbamate (900 mg, 2.08 mmol) formed was dissolved in methanol (10 mL) and hydrazine monohydrate (203 μL, 4.16 mmol) was added. The reaction mixture was then refluxed for 2 hours and cooled to room temperature. The precipitate formed was filtered and methanol used to wash the solid. The filtrate was concentrated under reduced pressure and the remaining oil purified using an ISCO chromatograph on silica gel (0-10% methanol/methylene chloride with 1% NH$_3$·H$_2$O) to give product as a colorless oil (436 mg, 70% yield). $^1$H NMR (CDCl$_3$) (300 MHz) δ 5.30-5.24 (m, 1H), 4.75 (m, 1H), 3.62-3.60 (m, 1H), 3.40 (m, 1H), 2.95-2.94 (m, 1H), 1.73-1.62 (m, 2H), 1.45-1.37 (m, 18H).

The requisite intermediates were prepared as shown in the following steps.

Step 1)

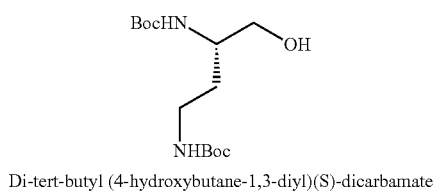 [SMILES: CC(C)(C)OC(=O)NCC[C@@H](CO)NC(=O)OC(C)(C)C]

Di-tert-butyl (4-hydroxybutane-1,3-diyl)(S)-dicarbamate

To a solution of (S)-2,4-bis((tert-butoxycarbonyl)amino)butanoic acid (1.17 g, 3.67 mmol) in THF 40 mL) at −15° C. were successively added a solution of N-methyl morpholine (451 μL, 4.10 mmol) and isobutyl chloroformate (481 μL, 3.67 mmol). The reaction was stirred at −15° C. to −10° C. for 15 minutes. The precipitated N-methyl morpholine HCl was removed by filtration and washed with THF (10 mL), the combine filtrates were chilled to −15° C. in an ice-salt bath. Then a solution of sodium borohydride (417 mg, 11.01 mmol) in water (4 mL) was added in one portion at −15° C. This reaction mixture was stirred at this temperature for 10 minutes. The reaction was quenched by the addition of saturated aq. NH$_4$Cl and the resulting mixture was extracted with ethyl acetate. The organic layer was washed with brine and dried over sodium sulfate. The solution was then filtered and concentrated under reduced pressure. The crude product was used directly for next step without further purification.

Step 2)

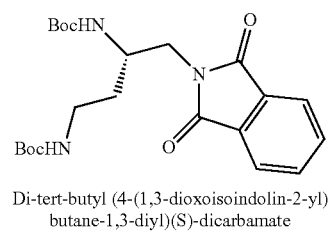 [SMILES: CC(C)(C)OC(=O)NCC[C@@H](CN1C(=O)c2ccccc2C1=O)NC(=O)OC(C)(C)C]

Di-tert-butyl (4-(1,3-dioxoisoindolin-2-yl)butane-1,3-diyl)(S)-dicarbamate

Triphenylphosphine (1.16 g, 4.41 mmol) and phthalimide (649 mg, 4.41 mmol) were added to a flask containing dry THF (40 mL). Di-tert-butyl (4-hydroxybutane-1,3-diyl)(S)-dicarbamate (1.12 g, 3.67 mmol) was added and the flask was cooled to 0° C. DIAD (892 mg, 4.41 mmol) was added dropwise and reaction allowed to stir for 30 minutes at 0° C. and then overnight at room temperature. The mixture was concentrated under reduced pressure and residue purified on an ISCO chromatograph using silica gel (0-100% ethyl acetate/hexanes) to give product as a white solid. (901 mg, 57% yield); $^1$H NMR (CDCl$_3$) (300 MHz) δ 7.87-7.83 (m, 2H), 7.75-7.71 (m, 2H), 5.08 (m, 1H), 4.79-4.76 (m, 1H), 4.02 (m, 1H), 3.75-3.73 (m, 2H) 3.42 (m, 1H), 3.02-3.00 (m, 1H), 1.79-1.73 (m, 2H), 1.57-1.45 (m, 9H), 1.27-1.24 (m, 9H).

Preparation of Amine Intermediate H (di-tert-butyl ((2S)-1-amino-6-methylheptane-2,5-diyl)dicarbamate)

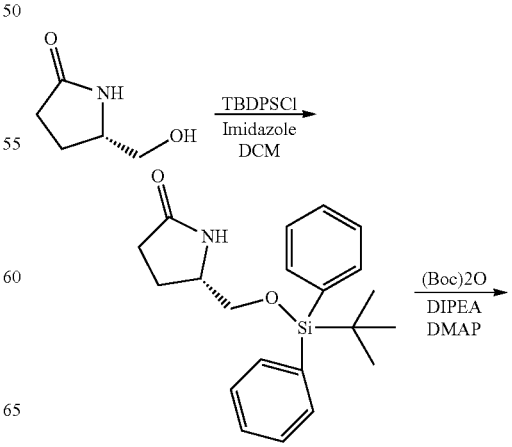

-continued

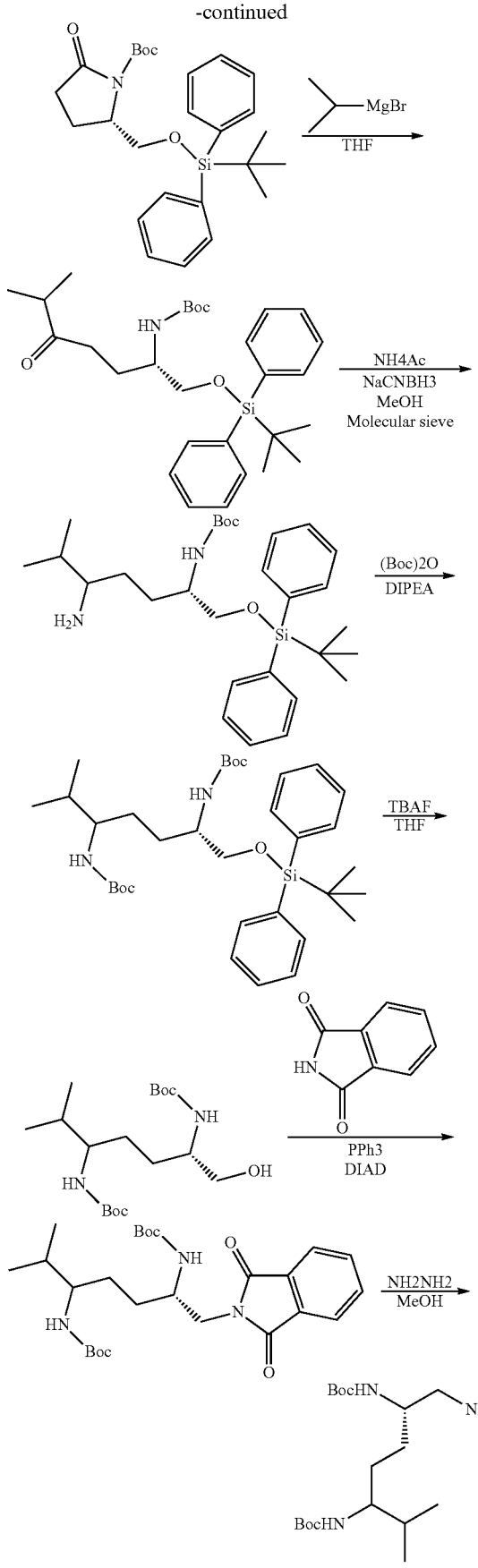

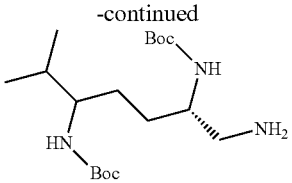

Di-tert-butyl ((2S)-1-amino-6-methylheptane-2,5-diyl)dicarbamate

Di-tert-butyl ((2S)-1-(1,3-dioxoisoindolin-2-yl)-6-methylheptane-2,5-diyl)dicarbamate (3.0 g, 6.13 mmol) was dissolved in methanol (50 mL), and hydrazine monohydrate (1.2 mL, 24.5 mmol) was added to this solution. After the reaction mixture was refluxed for 2 hours, it was cooled to room temperature. The precipitate formed was filtered and methanol was used to wash the solid. The filtrate was concentrated under reduced pressure. The reaction mixture was diluted with EtOAc, washed with saturated NaHCO$_3$, saturated ammonium chloride and brine sequentially. The organic layer was dried over sodium sulfate and concentrated under reduced pressure. The crude product (2.4 g, 100% yield) was used directly without further purification. $^1$H NMR (CDCl3) (300 MHz) δ 4.99 (m, 1H), 4.60 (m, 1H), 3.50 (m, 1H), 2.70 (m, 1H), 1.67 (m, 4H), 1.31 (s, 9H), 1.27 (s, 9H), 0.85 (m, 6H).

The requisite intermediates were prepared as shown in the following steps.

Step 1)

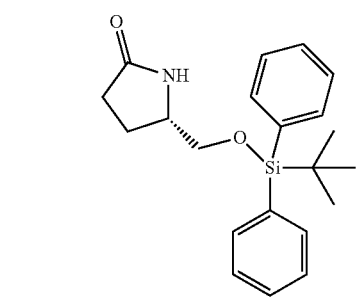

(S)-5-(((tert-Butyldiphenylsilyl)oxy)methyl)pyrrolidin-2-one

To a solution of (S)-5-(hydroxymethyl)pyrrolidin-2-one (5.0 g, 43.5 mmol) in methylene chloride (100 mL) at 0° C. was added imidazole (4.44 g, 65.2 mmol) and tert-butylchlorodiphenylsiane (13.2 g, 47.8 mmol). The reaction was stirred at 0° C. for 30 min, then warmed up to room temperature and stirred at room temperature overnight. The reaction was diluted with DCM, washed with saturated NaHCO$_3$, saturated ammonium chloride and brine sequentially. The organic layer was dried over sodium sulfate and concentrated under reduced pressure. The crude product (15.4 g, yield: 100% yield) was used in the next step directly without further purification.

Step 2)

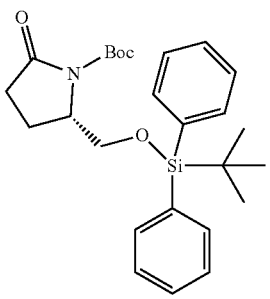

(S)-tert-Butyl 2-(((tert-butyldiphenylsilyl)oxy)methyl)-5-oxopyrrolidine-1-carboxylate To a solution (S)-5-(((tert-butyldiphenylsilyl)oxy)methyl)pyrrolidin-2-one (15.4 g, 43.5 mmol) in DCM (150 mL) at 0° C. was added DIPEA (15.2 mL, 87 mmol), 4-dimethylaminopyridine (0.532 g, 4.35 mmol) and (Boc)$_2$O (19.0 g, 87 mmol). After the mixture was stirred at 0° C. for 30 minutes, the reaction was warmed up to room temperature and stirred at room temperature overnight. The reaction mixture was diluted with methylene chloride, washed with saturated NaHCO$_3$ and brine, dried over sodium sulfate and concentrated under reduced pressure. The residue was purified by ISCO column chromatography on silica gel (0-50% ethyl acetate/hexanes) to give product as a white solid (5.5 g, 84% yield). $^1$H NMR (300 MHz, CDCl$_3$) δ 7.55-7.52 (m, 4H), 7.37-7.19 (m, 6H), 4.15 (m, 1H), 3.81 (m, 1H), 3.63 (m, 1H), 2.72 (m, 1H), 2.37 (m, 1H), 2.05 (m, 2H), 1.36 (s, 9H), 0.97 (s, 9H).

Step 3)

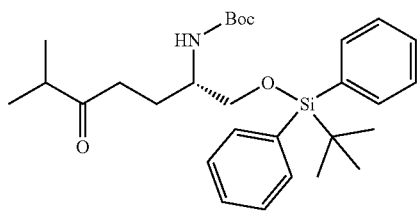

(S)-tert-Butyl (1-((tert-butyldiphenylsilyl)oxy)-6-methyl-5-oxoheptan-2-yl)carbamate To a solution (S)-tert-butyl 2-(((tert-butyldiphenylsilyl)oxy)methyl)-5-oxopyrrolidine-1-carboxylate (5.0 g, 11.0 mmol) in THF (150 mL) at −78° C. was added 1.0 M isopropyl magnesium chloride (13.2 mL, 13.2 mmol) dropwise. After the mixture was stirred at −78° C. for 2 hours, the reaction was warmed to 0° C. and stirred at room temperature for another 2 hours. The reaction mixture was quenched with saturated ammonium chloride, and extracted with EtOAc three times. The combined organic layers were washed with brine, dried over sodium sulfate and concentrated under reduced pressure. The residue was purified on ISCO chromatograph on silica gel (0-40% ethyl acetate/hexanes to give the desired product as a white solid. (4.8 g, 87.7% yield); $^1$H NMR (300 MHz, CDCl$_3$) 7.65 (m, 4H), 7.40 (m, 6H), 4.64 (br, 1H), 3.66-3.60 (m, 2H), 2.60-2.48 (m, 2H), 1.82 (m, 2H), 1.64 (s, 1H), 1.44-0.86 (m, 24H).

Step 4)

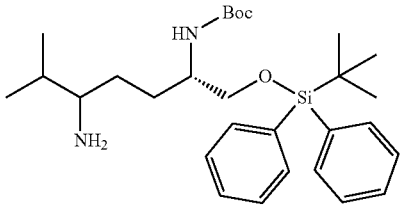

tert-Butyl ((2S)-5-amino-1-((tert-butyldiphenylsilyl)oxy)-6-methylheptan-2-yl)carbamate To a solution (S)-tert-butyl (1-((tert-butyldiphenylsilyl)oxy)-6-methyl-5-oxoheptan-2-yl)carbamate (4.5 g, 9.03 mmol) and ammonium acetate (6.97 g, 90.3 mmol) in MeOH (100 mL) was added molecular sieves and sodium cyanoborohydride (5.68 g, 90.3 mmol). The reaction mixture was stirred at room temperature overnight after which the molecular sieves were filtered off and washed with EtOAc. The combined organic layers were washed with sodium bicarbonate and brine, dried over sodium sulfate and concentrated under reduced pressure. The crude product was used directly in the next step without further purification.

Step 5)

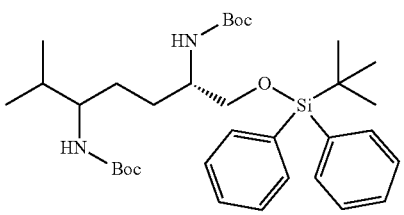

Di-tert-butyl ((2S)-1-((tert-butyldiphenylsilyl)oxy)-6-methylheptane-2,5-diyl)dicarbamate To a solution tert-butyl ((2S)-5-amino-1-((tert-butyldiphenylsilyl)oxy)-6-methylheptan-2-yl)carbamate (4.5 g, 9.03 mmol) in methylene chloride (100 mL) at room temperature was added DIPEA (1.88 mL, 10.8 mmol) and (Boc)$_2$O (2.37 g, 10.8 mmol). The reaction was stirred at room temperature overnight. The reaction mixture was diluted with methylene chloride, washed with saturated NaHCO$_3$ and brine, dried over sodium sulfate and concentrated under reduced pressure. The residue was purified by ISCO column chromatography on silica gel (0-30% ethyl acetate/hexanes) to give product as a white solid. (4.5 g, 83% yield); $^1$H NMR (300 MHz, CDCl$_3$) δ 7.61 (m, 4H), 7.60-7.34 (m, 6H), 4.68 (m, 1H), 4.25 (m, 1H), 3.66-3.55 (m, 3H), 3.38 (m, 1H), 1.63-1.05 (m, 31H), 0.88 (m, 6H).

Step 6)

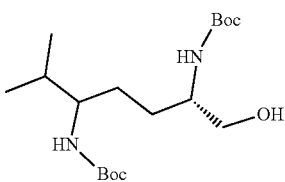

Di-tert-butyl ((2S)-1-hydroxy 6-methylheptan-2,5-diyl)dicarbamate

To a solution di-tert-butyl ((2S)-1-((tert-butyldiphenylsilyl)oxy)-6-methylheptane-2,5-diyl)dicarbamate (4.5 g, 7.51 mmol) in THF (100 mL) at 0° C. was added 1 M TBAF (30.0 mL, 30 mmol). The reaction was stirred at room temperature overnight. The reaction mixture was quenched with saturated ammonium chloride and extracted with EtOAc three times. The combined organic layer was washed with brine, dried over sodium sulfate and concentrated under reduced pressure. The residue was purified by ISCO column chromatography on silica gel (0-100% ethyl acetate/hexanes) to give product as a white solid. (2.4 g, 89% yield). $^1$H NMR (300 MHz, CDCl$_3$) δ 4.75 (m, 1H), 4.41-4.29 (m, 1H), 3.62-3.38 (m, 4H), 1.71-1.33 (m, 23H), 0.88 (m, 6H).

Step 7)

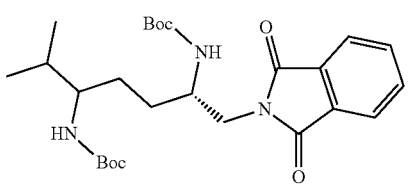

Di-tert-butyl ((2S)-1-(1,3-dioxoisoindolin-2-yl)-6-methylheptane-2,5-diyl)dicarbamate Triphenylphosphine (1.57 g, 6.0 mmol) and phthalimide (0.882 g, 6.0 mmol) were added to a flask containing dry THF (50 mL). Di-tert-butyl ((2S)-1-hydroxy-6-methylheptane-2,5-diyl)dicarbamate (1.81 g, 1.03 mmol) was added and the flask was cooled to 0° C. DIAD (1.21 g, 6.0 mmol) was added drop wise and reaction allowed to stir for 30 minutes at 0° C. and overnight at room temperature. The mixture was concentrated under reduced pressure and residue was purified using ISCO column chromatography on silica gel (0-70% ethyl acetate/hexanes) to give product as a white solid. $^1$H NMR (300 MHz, CDCl$_3$) δ 7.97-7.70 (m, 4H), 6.39 (bs, 2H), 4.97 (m, 2H), 4.34 (m, 1H), 3.94 (m, 1H), 3.69 (m, 1H), 1.67-0.85 (m, 29H).

Amine intermediates I and J were prepared according to the preparation of amine intermediate H, using the appropriate Grignard reagent.

Preparation of Amine Intermediates L and M (tert-butyl (((3S,5R)-5-(aminomethyl)-1-benzylpyrrolidin-3-yl)methyl)carbamate and tert-butyl (((3R,5S)-5-(aminomethyl)-1-benzylpyrrolidin-3-yl)methyl)carbamate)

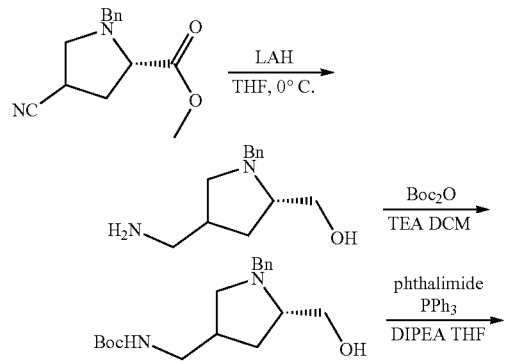

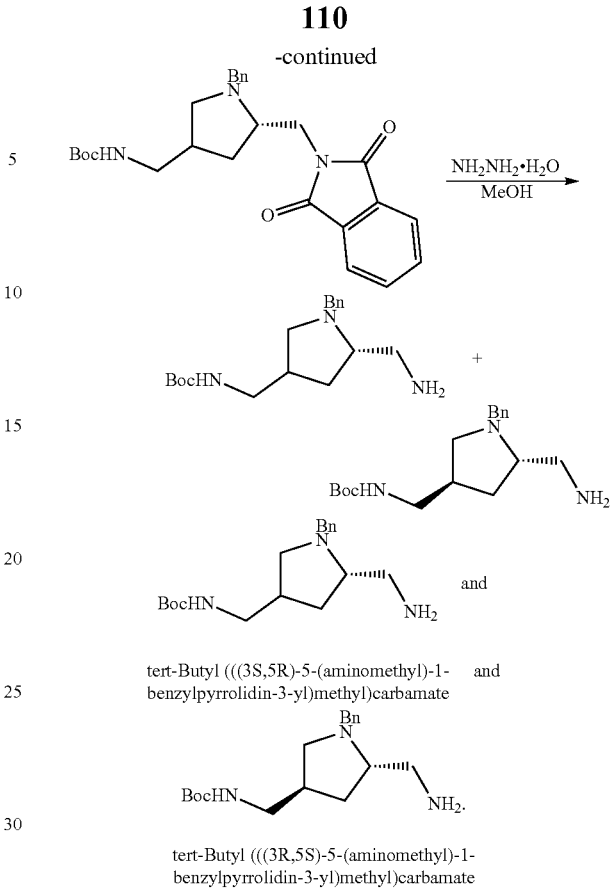

tert-Butyl (((3S,5R)-5-(aminomethyl)-1-benzylpyrrolidin-3-yl)methyl)carbamate and tert-Butyl (((3R,5S)-5-(aminomethyl)-1-benzylpyrrolidin-3-yl)methyl)carbamate To a solution of tert-butyl (((5S)-1-benzyl-5-(hydroxymethyl)pyrrolidin-3-yl)methyl)carbamate (1.58 g, 5.23 mmol), triphenylphosphine (1.51 g, 5.75 mmol) and phthalimide (846 mg, 5.75 mmol) in THF (20 mL) was added DIAD (1.16 mL, 5.75 mmol) at 0° C. It was stirred at 0° C.-room temperature and monitored by TLC. After finishing the reaction it was concentrated under reduced pressure and purified on column chromatography with silica gel using 50-90% ethyl acetate in hexanes to give crude product as an off-white solid (2.8 g, ~80% purity).

To the solution of the above crude product (2.8 g, ~80% purity, ~5.2 mmol) in MeOH (30 mL) was added hydrazine monohydrate (1.8 mL, 36.0 mmol). The mixture was stirred at 80° C. for 1 hour then cooled to room temperature. The solvent was removed under reduce pressure and the residue was triturated with CH$_2$Cl$_2$. The white solid was removed by filtration and the filtrate was concentrated under reduced pressure and purified by column chromatography on silica gel. Elution with EtOAc then 1% NH$_3$·H$_2$O in 10% MeOH/CH$_2$Cl$_2$ afforded the top Rf spot (386 mg, yellow oil, 25% yield in 2 steps) as tert-butyl (((3S,5R)-5-(aminomethyl)-1-benzylpyrrolidin-3-yl)methyl)carbamate. $^1$H NMR (300 MHz, CDCl$_3$) δ 7.30 (m, 5H), 5.28 (br. S, 1H), 3.99 (d, J=13.5 Hz, 1H), 3.15 (d, J=12.9 Hz, 1H), 3.09 (m, 2H), 2.70-2.90 (m, 3H), 2.51 (m, 1H), 2.04-2.34 (m, 3H), 1.36-1.50 (m, 10H), and the bottom Rf spot (498 mg, white solid, 32% yield in 2 steps) as tert-butyl (((3S,5R)-5-(aminomethyl)-1-benzylpyrrolidin-3-yl)methyl)carbamate. $^1$H NMR (300 MHz, CDCl$_3$) δ 7.30 (m, 5H), 4.52 (br. S, 1H), 3.57 (d, J=12.9 Hz, 1H), 3.47 (d, J=12.9 Hz, 1H), 2.81-3.02 (m, 5H), 1.80-1.95 (m, 2H), 1.59 (m, 1H), 1.43 (s, 9H), 0.70 (m, 1H)

The requisite intermediates were prepared as shown in the following steps.

Step 1)

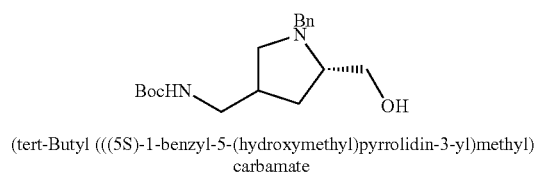 [SMILES: CC(C)(C)OC(=O)NCC1C[C@@H](CO)N(Cc2ccccc2)C1]

(tert-Butyl (((5S)-1-benzyl-5-(hydroxymethyl)pyrrolidin-3-yl)methyl) carbamate

To a solution of (2S)-methyl 1-benzyl-4-cyanopyrrolidine-2-carboxylate (2.37 g mg, 9.72 mmol) in dry THF (50 mL) at 0° C. under $N_2$ was added LAH (730 mg, 19.4 mmol) in several portions. The reaction mixture was stirred at 0° C. for 30 minutes then room temperature for 1 hour. Then the reaction mixture was cooled to 0° C. and slowly added $H_2O$ (0.7 mL), 15% NaOH solution (0.7 mL), EtOAc, and $H_2O$ (2.8 mL). After stirring at room temperature for 30 min $Na_2SO_4$ was added. The reaction mixture was stirred for 30 minutes then the solid was removed by passing a Celite pad. The filtrate was concentrated under reduced pressure to give a crude intermediate ((2S)-4-(aminomethyl)-1-benzylpyrrolidin-2-yl)methanol. The crude intermediate was not further purified and identified. It was directly used in next step. The above intermediate was dissolved in methylene chloride (30 mL) then it was added $Boc_2O$ (2.54 g, 11.7 mmol) and TEA (2.02 mL, 14.6 mmol). The reaction mixture was stirred at room temperature overnight. The reaction mixture was diluted with methylene chloride and washed with water, brine then dried over anhydrous sodium sulfate. The solvent was removed and the residue was purified by column chromatography on silica gel using EtOAc. The desired product was collected (1.58 g, 54% yield) as light yellow oil. $^1$H NMR (300 MHz, $CDCl_3$) δ 7.30 (m, 5H), 4.84 (br. S, 1H), 3.98 (d, J=13.5 Hz, 1H), 3.72 (m, 1H), 3.48 (d, J=11.1 Hz, 1H), 3.26 (d, J=12.9 Hz, 1H), 3.07 (m, 2H), 2.73 (m, 2H), 2.43 (m, 1H), 2.26 (m, 1H), 2.10 (m, 1H), 1.60 (m, 2H), 1.42 (s, 9H).

Preparation of Amine Intermediate N (tert-butyl (2S,4S)-2-(aminomethyl)-4-cyanopyrrolidine-1-carboxylate)

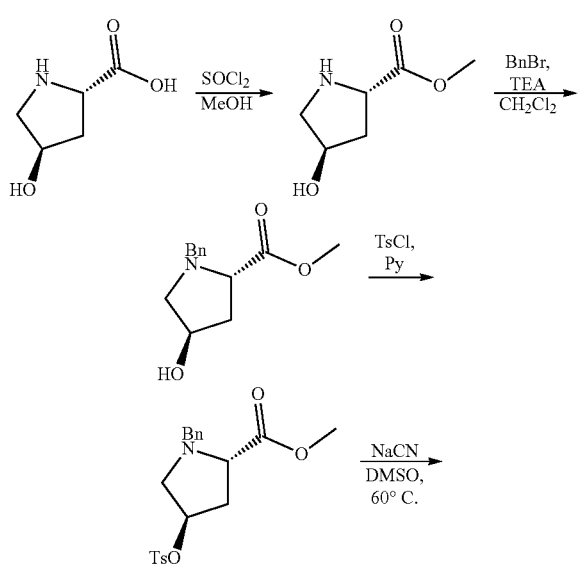

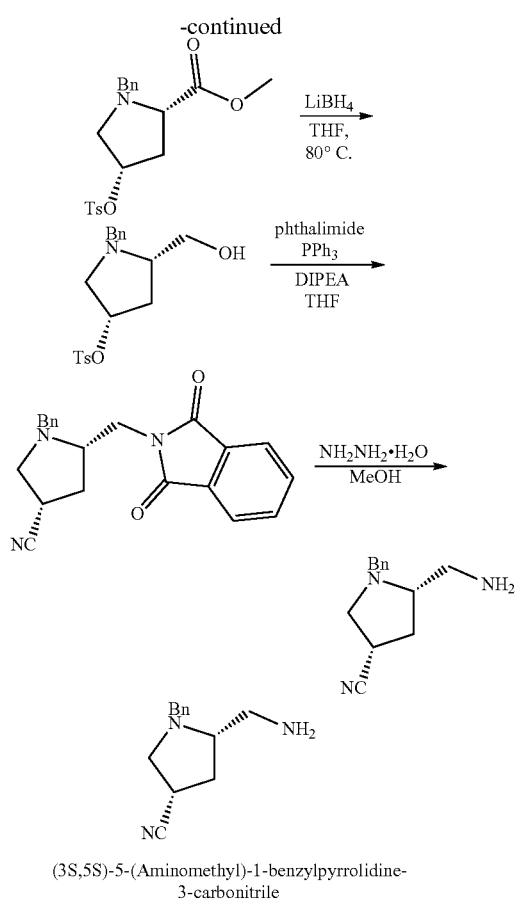

(3S,5S)-5-(Aminomethyl)-1-benzylpyrrolidine-3-carbonitrile

The crude (3S,5S)-1-benzyl-5-((1,3-dioxoisoindolin-2-yl)methyl)pyrrolidine-3-carbonitrile from the previous step (2.0 g, ~90% pure) in MeOH (30 mL) was added $NH_2NH_2·H_2O$ (1.5 mL). The reaction mixture was stirred at 50° C. for 2 hours. The solvent was removed under reduced pressure and the residue was triturated with $CH_2Cl_2$. The white solid was removed by filtration and the filtrate was washed with brine, dried over $Na_2SO_4$, concentrated under reduced pressure and purified on silica gel column. Elution with 1% ammonia in 10% $MeOH/CH_2Cl_2$ afforded the desired product (0.96 g, 87% yield in two steps) as a light-yellow liquid. $^1$H NMR (300 MHz, $CDCl_3$) 7.33-7.26 (m, 5H), 4.02 (d, J=14 Hz, 1H), 3.32 (d, J=14 Hz, 1H), 3.18 (dd, J=10 Hz, J=2 Hz, 1H), 2.99-2.91 (m, 2H), 2.77-2.64 (m, 2H), 2.49 (dd, J=9 Hz, J=8 Hz, 1H), 2.34-2.22 (m, 1H), 2.13-2.05 (m, 1H).

The amine was prepared from the following steps:

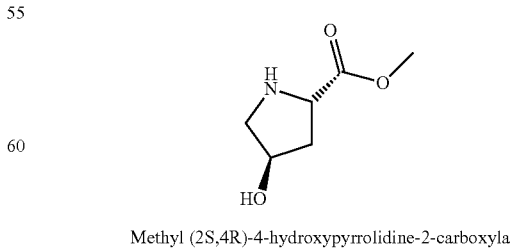

Methyl (2S,4R)-4-hydroxypyrrolidine-2-carboxylate (2S,4R)-4-Hydroxypyrrolidine-2-carboxylic acid (30 g, 0.23 mol) in MeOH (300 mL) was cooled to 0° C., $SOCl_2$ (33 mL) was added portion wise over 10 min. The resulting mixture was stirred at room temperature overnight. The methanol was removed and the residue triturated with CH$_2$Cl$_2$ (200 mL) to give the desired product as a white solid, which was used in the next step without further purification.

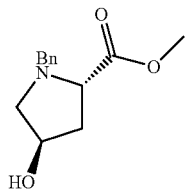

Methyl (2S,4R)-1-benzyl-4-hydroxypyrrolidine-2-carboxylate

The crude methyl (2S,4R)-4-hydroxypyrrolidine-2-carboxylate (~0.23 mol) in CH$_2$Cl$_2$ (300 mL), was added TEA (96 mL, 0.69 mol), then BnBr (32.6 mL, 0.27 mol) portion wise. The reaction temperature was increased to boiling and was cooled down by water bath. After stirring at room temperature overnight, the reaction mixture was washed with water, 1N NaOH solution, brine, dried over Na$_2$SO$_4$, and concentrated under reduced pressure to give a crude product, which was purified by silica gel plug. Elution with 50% EtOAc/hexanes afforded the desired product (50 g, 86% yield) as light-yellow liquid. $^1$H NMR (300 MHz, CDCl$_3$) 7.32-7.30 (m, 5H), 4.48-4.41 (m, 1H), 3.89 (d, J=13 Hz, 1H), 3.72-3.60 (m, 5H), 3.32 (dd, J=10 Hz, J=5 Hz, 1H), 2.46 (dd, J=10 Hz, J=4 Hz, 1H), 2.29-2.20 (m, 1H), 2.11-2.04 (m, 1H), 1.91 (br. s, 1H).

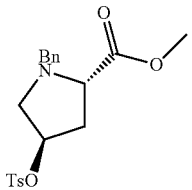

Methyl (2S,4R)-1-benzyl-4-(tosyloxy)pyrrolidine-2-carboxylate

Methyl (2S,4R)-1-benzyl-4-hydroxypyrrolidine-2-carboxylate (3.25 g, 13.8 mmol) in dry pyridine (7.0 mL) was cooled to 0° C., TsCl (2.75 g, 14.5 mmol) was added. The resulting mixture was stirred at room temperature overnight. The reaction mixture was diluted with CH$_2$Cl$_2$ and washed with 10% citric acid (2×50 ml), brine, and dried over Na$_2$SO$_4$. The organic solution was concentrated under reduced pressure to give the desired crude product (2.0 g, 70% yield) as light brown oil, which was used in next step without further purification. $^1$H NMR (300 MHz, CDCl$_3$) 7.77-7.73 (m, 2H), 7.33-7.22 (m, 7H), 4.98-4.95 (m, 1H), 3.84 (d, J=13 Hz, 1H), 3.64 (s, 3H), 3.61-3.53 (m, 2H), 3.27-3.24 (m, 1H), 2.63 (dd, J=11 Hz, J=4 Hz, 1H), 2.44 (s, 3H), 2.77-2.25 (m, 2H).

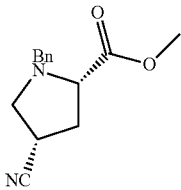

Methyl (2S,4R)-1-benzyl-4-cyanopyrrolidine-2-carboxylate

Methyl (2S,4R)-1-benzyl-4-(tosyloxy)pyrrolidine-2-carboxylate (3.79 g, 9.7 mmol) in dry DMSO (10 mL) was added NaCN (0.96 g, 19.5 mmol). The reaction mixture as stirred at 60° C. overnight. The reaction mixture was diluted with CH$_2$Cl$_2$, washed with water, brine, and dried over Na$_2$SO$_4$. The organic solution was concentrated under reduced pressure to give the desired crude product (3.79 g, 84% yield) as light brown oil, which was used in next step without further purification. $^1$H NMR (300 MHz, CDCl$_3$) 7.31 (m, 5H), 3.95 (d, J=14 Hz, 1H), 3.74 (s, 3H), 3.63-3.61 (m, 1H), 3.48 (dd, J=9 Hz, J=6 Hz, 1H), 3.24 (dd, J=9 Hz, J=5 Hz, 1H), 3.08-3.05 (m, 1H), 2.85 (dd, J=9 Hz, J=8 Hz, 1H), 2.56-2.31 (m, 2H).

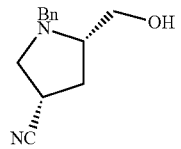

(3S,5S)-1-Benzyl-5-(hydroxymethyl)pyrrolidine-3-carbonitrile

Methyl (2S,4S)-1-benzyl-4-cyanopyrrolidine-2-carboxylate (2.0 g, 8.2 mmol) in dry THF (30 mL) was added LiBH$_4$ (0.36 g, 16.4 mmol). The reaction mixture as stirred at 80° C. for 1 hour. The reaction mixture was cooled to room temperature and acetone (1 mL) was added to quench the excess LiBH$_4$. After stirring for 30 minutes, the solvent was removed under reduced pressure, and the residue was partitioned between EtOAc and saturated NaHCO$_3$ solution. The organic layer was washed with brine, dried over Na$_2$SO$_4$, concentrated under reduced pressure and purified on silica gel column. Elution with 50% EtOAc/hexanes afforded the desired product (1.1 g, 62% yield) as light-yellow oil. $^1$H NMR (300 MHz, CDCl$_3$) 7.33-7.26 (m, 5H), 4.03 (d, J=14 Hz, 1H), 3.77 (dd, J=11 Hz, J=3 Hz, 1H), 3.53-3.47 (m, 1H), 3.39 (d, J=14 Hz, 1H), 3.22 (d, J=Hz, 1H), 2.99-2.94 (m, 1H), 2.85-2.79 (m, 1H), 2.61-2.56 (m, 1H), 2.40-2.23 (m, 2H).

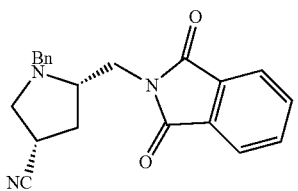

(3S,5S)-1-Benzyl-5-((1,3-dioxoisoindolin-2-yl)methyl)pyrrolidine-3-carbonitrile

A solution of (3S,5S)-1-benzyl-5-(hydroxymethyl)pyrrolidine-3-carbonitrile (1.1 g, 5.1 mmol) in THF (15 mL) was added phthalimide (823 mg, 5.6 mmol), Ph₃P (1.46 g, 5.6 mmol), then cooled to 0° C., DIAD (1.13 mL, 5.6 mmol) was added portion wise over 5 minutes. The resulting mixture was stirred at room temperature overnight. The solvent was removed under reduced pressure and the residue was purified on silica gel column. Elution with 10-30% EtOAc/hexanes afforded the crude product (2 g, ~90% pure), which was used directly in next step. ¹H NMR (300 MHz, CDCl₃) 7.87-7.84 (m, 2H), 7.76-7.71 (m, 2H), 7.32-7.19 (m, 5H), 4.23 (d, J=13 Hz, 1H), 3.87 (d, J=5 Hz, 2H), 3.44 (d, J=14 Hz, 1H), 3.18 (dd, J=10 Hz, J=4 Hz, 1H), 3.03-2.96 (m, 1H), 2.94-2.85 (m, 1H), 2.56 (dd, J=10 Hz, J=7 Hz, 1H), 2.38-2.16 (m, 2H).

Amine intermediates O, P and Q were prepared according the preparation of amine intermediate M using the appropriate 4-hydroxypyrrolidine-2-carboxylic acid.

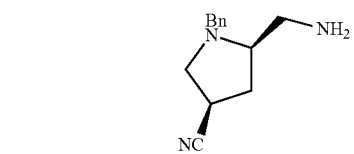

(3S,5S)-5-(Aminomethyl)-1-benzylpyrrolidine-3-carbonitrile (amine intermediate O)

¹H NMR (300 MHz, CDCl₃) 7.33-7.26 (m, 5H), 4.02 (d, J=14 Hz, 1H), 3.32 (d, J=13 Hz, 1H), 3.18 (d, J=10 Hz, 1H), 3.00-2.64 (m, 4H), 2.50 (dd, J=10 Hz, J=7 Hz, 1H), 2.34-2.05 (m, 2H).

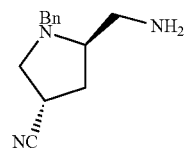

(3S,5S)-5-(Aminomethyl)-1-benzylpyrrolidine-3-carbonitrile (amine intermediate P)

¹H NMR (300 MHz, CDCl₃) 7.32-7.26 (m, 5H), 4.00 (d, J=13 Hz, 1H), 3.36 (d, J=13 Hz, 1H), 3.23 (dd, J=9 Hz, J=8 Hz, 1H), 2.95-2.80 (m, 3H), 2.69 (d, J=10 Hz, 1H), 2.50 (t, J=10 Hz, 1H), 2.26-2.20 (m, 2H).

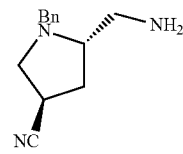

(3R,5S)-5-(Aminomethyl)-1-benzylpyrrolidine-3-carbonitrile (amine intermediate Q)

¹H NMR (300 MHz, CDCl₃) 7.30-7.26 (m, 5H), 3.99 (d, J=14 Hz, 1H), 3.56 (d, J=13 Hz, 1H), 3.23 (dd, J=9 Hz, J=7 Hz, 1H), 2.99-2.78 (m, 3H), 2.69 (dd, J=13 Hz, J=2 Hz, 1H), 2.50 (t, J=10 Hz, 1H), 2.34-2.15 (m, 2H).

Preparation of Amine Intermediate R (tert-butyl (6-(aminomethyl)-1-benzyl-1,2,5,6-tetrahydropyridin-3-yl)carbamate)

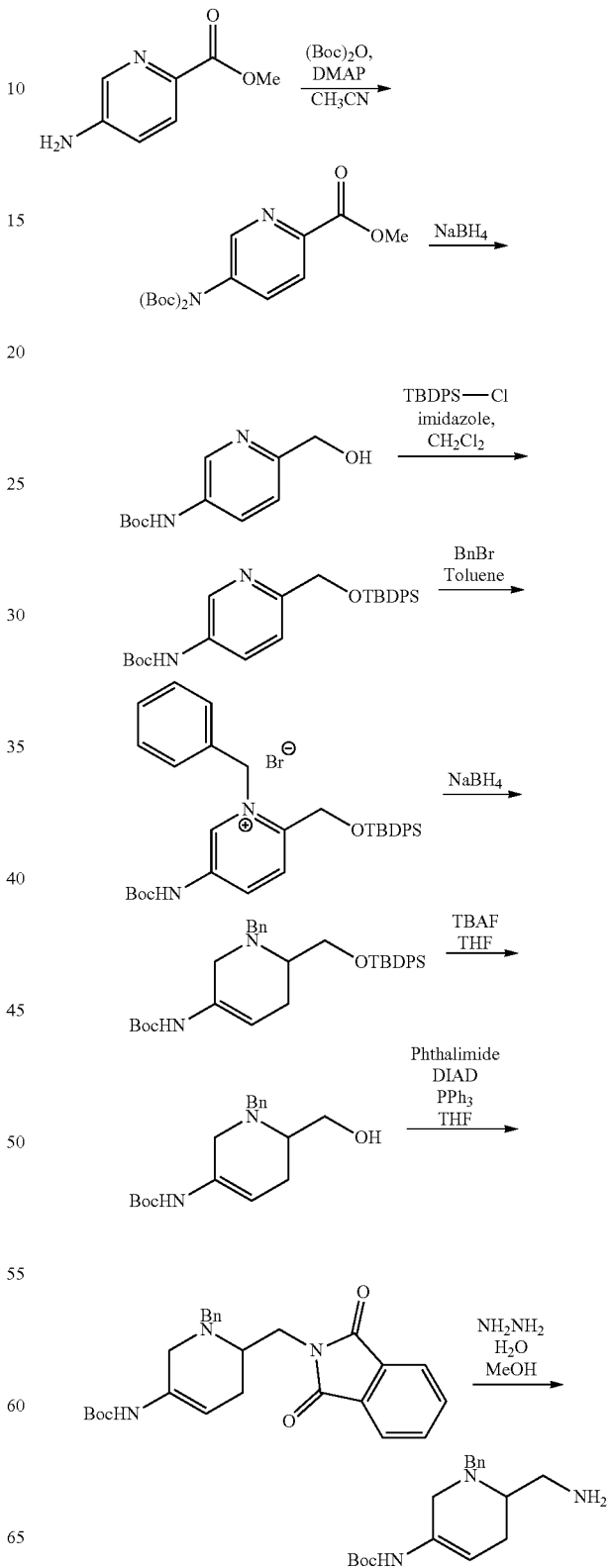

-continued

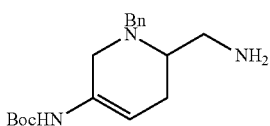

tert-Butyl (6-(aminomethyl)-1-
benzyl-1,2,5,6-
tetrahydropyridin-3-
yl)carbamate To a solution of crude tert-butyl (1-benzyl-6-((1,3-dioxoisoindolin-2-yl)methyl)-1,2,5,6-tetrahydropyridin-3-yl)carbamate (100 mg, 0.22 mmol) in MeOH (5 mL) was added hydrazine hydrate (21 μL, 0.44 mmol). The reaction mixture was stirred at room temperature overnight. The reaction mixture was concentrated under reduced pressure, and the resulting residue was suspended in dichloromethane. The suspension was filtered through Celite. The filtrate was then washed with water and brine. The organic layer was dried over sodium sulfate, and it was concentrated under reduced pressure to give product (15 mg, 35%) as a yellow oil. $^1$H NMR (300 MHz, CDCl$_3$). 7.40-7.22 (m, 5H), 5.83 (s, 1H), 5.50 (s, 1H), 3.77-3.63 (m, 2H), 3.17-2.82 (m, 4H), 2.67-2.64 (m, 1H), 2.34-2.29 (m, 1H), 2.04-1.92 (m, 1H), 1.43 (s, 9H).

The requisite intermediates were prepared as follows:

Step 1)

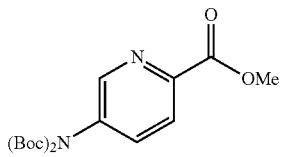

Methyl 5-(N,N-di-tert-butyloxycarbonyl)amino-2-pyridinecarboxylate

To a solution of methyl 5-aminopicolinate (1.78 g, 11.70 mmol) in acetonitrile (50 mL), Boc anhydride (5.20 g, 23.58 mmol) and DMAP (300 mg, 2.46 mmol) were added. The reaction mixture was stirred overnight at room temperature. The reaction mixture was then diluted with dichloromethane and washed with water, then with brine. The organic layer was dried over sodium sulfate, and it was concentrated under reduced pressure. The resulting residue was purified using silica gel chromatography eluting with 0 to 50% ethyl acetate/hexanes to give product (2.92 g, 83%) as a yellow solid. $^1$H NMR (300 MHz, CDCl$_3$). 8.52 (d, J=2 Hz, 1H), 8.16 (d, J=8 Hz, 1H), 7.65-7.61 (m, 1H), 4.02 (s, 3H), 1.40 (s, 18H).

Step 2)

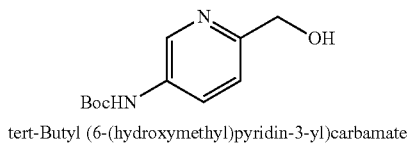 [SMILES: CC(C)(C)OC(=O)Nc1ccc(CO)nc1]

tert-Butyl (6-(hydroxymethyl)pyridin-3-yl)carbamate

To a solution of methyl 5-(N,N-di-tert-butyloxycarbonyl)amino-2-pyridinecarboxylate (2.00 g, 5.70 mmol) in methanol (100 mL), sodium borohydride (650 mg, 17.00 mmol) was added. The reaction mixture was refluxed for overnight. The reaction mixture was concentrated under reduced pressure, and the resulting residue was diluted with ethyl acetate. It was then washed with 1N NaOH and brine. The organic layer was dried over sodium sulfate, and it was concentrated under reduced pressure to give the desired product (920 mg, 72%) as a white solid. $^1$H NMR (300 MHz, CDCl$_3$). 8.40 (d, J=2 Hz, 1H), 7.97-7.95 (m, 1H), 7.20 (d, J=9 Hz, 1H), 6.52 (br. s, 1H), 4.71 (s, 2H), 3.41 (br. s, 1H), 1.53 (s, 9H).

Step 3)

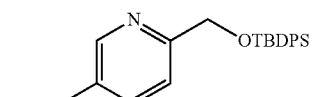

tert-Butyl (6-(((tert-butyldiphenylsilyl)oxy)methyl)pyridin-3-yl)carbamate

To a solution of tert-butyl (6-(hydroxymethyl)pyridin-3-yl)carbamate (920 mg, 4.11 mmol) in dichloromethane (10 mL), tert-butyldiphenylsilyl chloride (1.24 mL, 4.52 mmol) and imidazole (560 mg, 8.24 mmol) were added. The reaction mixture was stirred for overnight. The reaction mixture was diluted with dichloromethane, and it was then washed with water and then brine. The organic layer was dried over sodium sulfate and was concentrated under reduced pressure. The resulting residue was purified using silica column chromatography eluting with 0 to 50% ethyl acetate/hexanes to give product (1.90 g, 100%) as a white solid. $^1$H NMR (300 MHz, CDCl$_3$) 8.33 (s, 1H), 7.95 (s, 1H), 7.69-7.66 (m, 4H), 7.59 (d, J=Hz, 1H), 7.44-7.33 (m, 6H), 6.48 (br. s, 1H), 4.82 (s, 2H), 1.53 (s, 9H), 1.11 (s, 9H).

Step 4)

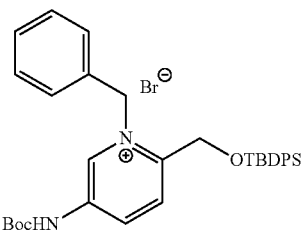

1-Benzyl-5-(((tert-butoxycarbonyl)amino)-2-(((tert-butyldiphenylsilyl)oxy)methyl)pyridin-1-ium
bromide To a solution of tert-butyl (6-(((tert-butyldiphenylsilyl)oxy)methyl)pyridin-3-yl)carbamate (1.90 g, 4.10 mmol) in toluene (20 mL), benzyl bromide (1.45 mL, 12.30 mmol) was added. The reaction mixture was refluxed for 10 hours. The reaction mixture was then cooled to room temperature, and hexanes was added to form a white suspension. The suspension was filtered to give product as a white solid (2.0 g, 77%). $^1$H NMR (300 MHz, CDCl$_3$) 10.44 (br. s, 1H), 10.21 (s, 1H), 9.22 (d, J=9 Hz, 1H), 7.65-7.30 (m, 14H), 7.05 (d, J=8 Hz, 2H), 5.64 (s, 2H), 4.75 (s, 2H), 1.53 (s, 9H), 1.08 (s, 9H).

Step 5)

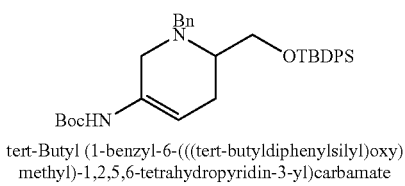

tert-Butyl (1-benzyl-6-(((tert-butyldiphenylsilyl)oxy)methyl)-1,2,5,6-tetrahydropyridin-3-yl)carbamate To a solution of 1-benzyl-5-((tert-butoxycarbonyl)amino)-2-(((tert-butyldiphenylsilyl)oxy)methyl)pyridin-1-ium bromide (2.0 g, 3.16 mmol) in MeOH (20 mL) was added sodium borohydride (240 mg, 6.31 mmol). The reaction mixture was stirred at room temperature overnight. The reaction mixture was concentrated under reduced pressure, and the resulting residue was diluted with ethyl acetate. The organic layer was washed with 1N NaOH and brine. The organic layer was then dried over sodium sulfate and concentrated under reduced pressure to give the desired product as a brown oil (1.76 g, 100%). $^1$H NMR (300 MHz, CDCl$_3$) 7.72-7.70 (m, 14H), 7.02 (d, J=6 Hz, 1H), 5.77 (s, 1H), 5.42 (s, 1H), 3.92-3.85 (m, 3H), 3.72-3.62 (m, 2H), 3.03-2.97 (m, 3H), 2.37-2.18 (m, 1H), 1.42 (s, 9H), 1.07 (s, 9H).

Step 6)

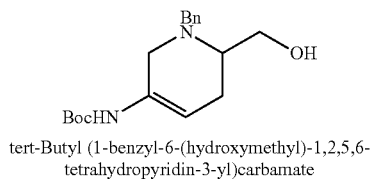 [SMILES: CC(C)(C)OC(=O)NC1=CCC(CO)N(Cc2ccccc2)C1]

tert-Butyl (1-benzyl-6-(hydroxymethyl)-1,2,5,6-tetrahydropyridin-3-yl)carbamate

To a solution of tert-butyl (1-benzyl-6-(((tert-butyldiphenylsilyl)oxy)methyl)-1,2,5,6-tetrahydropyridin-3-yl)carbamate (1.76 g, 3.16 mmol) in tetrahydrofuran (20 mL) was added 1M TBAF in tetrahydrofuran (6.40 mL, 6.40 mmol). The reaction mixture was stirred at room temperature overnight. The reaction mixture was concentrated under reduced pressure, and the resulting residue was purified on a silica gel column eluting with 0 to 100% ethyl acetate/hexanes. The product was obtained as a brown oil (413 mg, 45%). $^1$H NMR (300 MHz, CDCl$_3$) 7.33-7.24 (m, 5H), 5.82 (s, 1H), 5.52 (s, 1H), 3.82-3.62 (m, 2H), 3.53-3.47 (m, 1H), 3.30-3.24 (m, 1H), 3.12-2.96 (m, 2H), 2.41-2.34 (m, 2H), 1.90-1.82 (m, 1H), 1.43 (s, 9H).

Step 7)

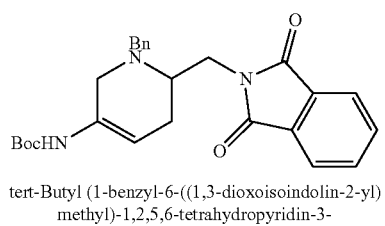

tert-Butyl (1-benzyl-6-((1,3-dioxoisoindolin-2-yl)methyl)-1,2,5,6-tetrahydropyridin-3-yl)carbamate To a solution of tert-butyl (1-benzyl-6-(hydroxymethyl)-1,2,5,6-tetrahydropyridin-3-yl)carbamate (413 mg, 1.30 mmol) in tetrahydrofuran (10 mL), were added triphenylphosphine (374 mg, 1.43 mmol) and phthalimide (210 mg, 1.43 mmol). Then, DIAD (0.29 mL, 1.43 mmol) was added slowly to the mixture at 0° C. The reaction mixture was then stirred at room temperature overnight. The reaction mixture was diluted with dichloromethane washed with water and then brine. The organic layer was dried over sodium sulfate and was concentrated under reduced pressure to give the crude product (314 mg, 54%) as a yellow oil.

Preparation of Amine S (tert-butyl (6-(aminomethyl)-1-benzyl-1,2,3,6-tetrahydropyridin-4-yl)carbamate)

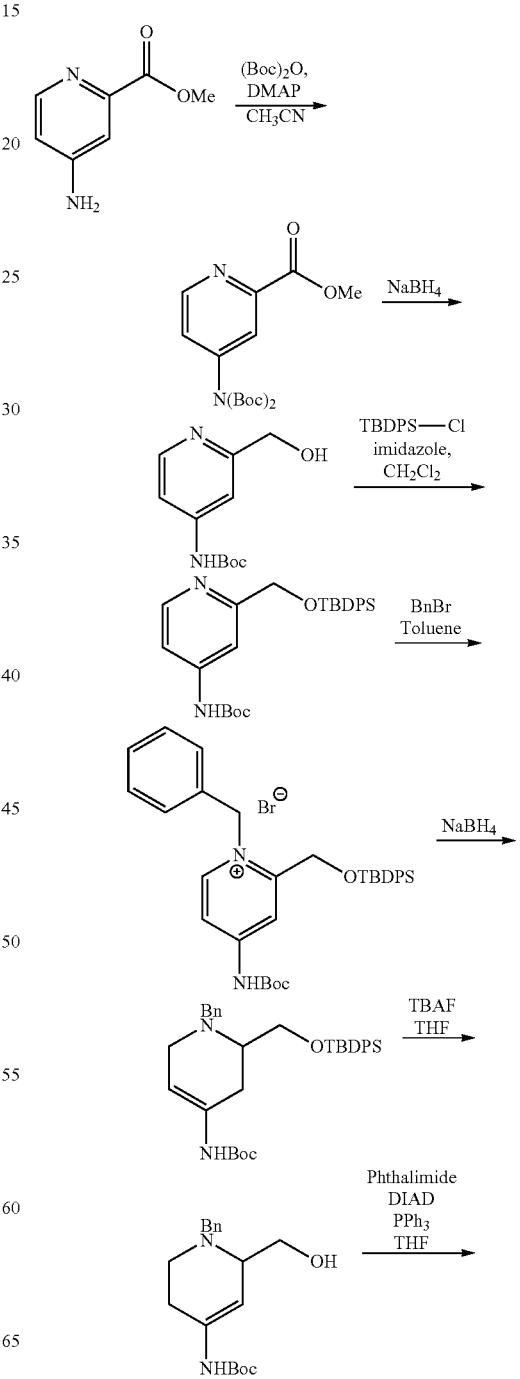

121

-continued

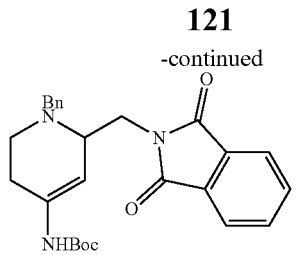

→ NH₂NH₂
H₂O
MeOH

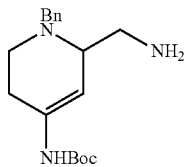

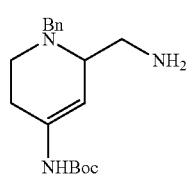

tert-Butyl (6-(aminomethyl)-1-benzyl-1,2,3,6-
tetrahydropyridin-4-yl)carbamate

To a solution of crude tert-butyl (1-benzyl-6-((1,3-dioxoisoindolin-2-yl)methyl)-1,2,3,6-tetrahydropyridin-4-yl)carbamate (100 mg, 0.22 mmol) in MeOH (5 mL) was added hydrazine hydrate (21 μL, 0.44 mmol). The reaction mixture was stirred at room temperature overnight. The reaction mixture was concentrated under reduced pressure and the resulting residue suspended in dichloromethane. The suspension was filtered through Celite. The filtrate was then washed with water and then brine. The organic layer was dried over sodium sulfate, and it was concentrated under reduced pressure to give the desired product (30 mg, 43%) as a yellow oil. ¹H NMR (300 MHz, CDCl₃) 7.36-7.23 (m, 5H), 5.67-5.65 (m, 2H), 3.75-3.48 (m, 2H), 3.28-3.21 (m, 1H), 3.10-3.04 (m, 1H), 2.95-2.86 (m, 2H), 2.73-2.65 (m, 1H), 2.38-2.33 (m, 1H), 1.99-1.93 (m, 1H), 1.46 (s, 9H).

The requisite intermediates were prepared as follows:
Step 1)

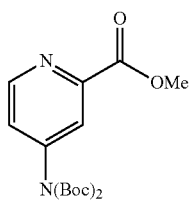

Methyl 4-(N,N-di-tert-butyloxycarbonyl)amino-2-pyridinecarboxylate

To a solution of methyl 4-aminopicolinate (1.80 g, 11.79 mmol) in acetonitrile (50 mL), Boc anhydride (5.20 g, 23.58 mmol) and DMAP (288 mg, 2.36 mmol) were added. The reaction mixture was stirred overnight at room temperature. The reaction mixture was then diluted with dichloromethane and washed with water, and then brine. The organic layer was dried over sodium sulfate and concentrated under reduced pressure. The resulting residue was purified on column eluting with 0 to 50% ethyl acetate/hexanes to give product (1.98 g, 48%) as a yellow solid. ¹H NMR (300 MHz, CDCl₃) 8.73 (d, J=5 Hz, 1 Hz), 7.95 (d, J=2 Hz, 1H), 7.32-7.29 (m, 1H), 4.10 (s, 3H), 1.45 (s, 18H).

122

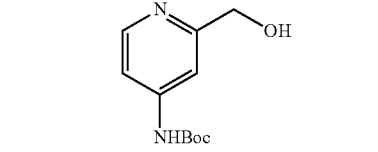

tert-Butyl (2-(hydroxymethyl)pyridin-4-yl)carbamate

Step 2)

To a solution of methyl 4-(N,N-di-tert-butyloxycarbonyl)amino-2-pyridinecarboxylate (1.10 g, 3.10 mmol) in methanol (30 mL), was added sodium borohydride (360 mg, 9.52 mmol). The reaction mixture was refluxed overnight. The reaction mixture was concentrated under reduced pressure and the resulting residue was diluted with ethyl acetate. It was then washed with 1N NaOH and then brine. The organic layer was dried over sodium sulfate and concentrated under reduced pressure to give the desired product (600 mg, 86%) as a white solid. ¹H NMR (300 MHz, CDCl₃) 8.36 (d, J=5 Hz, 1H), 7.36 (s, 1H), 7.14-7.12 (m, 1H), 6.77 (br. s, 1H), 4.70 (s, 2H), 1.52 (s, 9H).

Step 3)

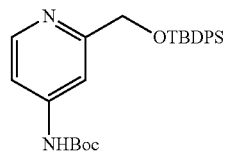

tert-Butyl (2-(((tert-butyldiphenylsilyl)oxy)methyl)
pyridin-4-yl)carbamate

To a solution of tert-butyl (2-(hydroxymethyl)pyridin-4-yl)carbamate (600 mg, 2.68 mmol) in dichloromethane (10 mL), were added tert-butyldiphenylsilyl chloride (0.77 mL, 2.95 mmol) and imidazole (365 mg, 5.36 mmol). The reaction mixture was stirred overnight. The reaction mixture was diluted with dichloromethane and washed with water and then brine. The organic layer was dried over sodium sulfate and concentrated under reduced pressure. The resulting residue was purified on the column eluting with 0 to 50% ethyl acetate/hexanes to give product (1.20 g, 97%) as a white solid. ¹H NMR (300 MHz, CDCl₃) 8.31 (d, J=5 Hz, 1H), 7.69-7.67 (m, 4H), 7.50-7.33 (m, 8H), 6.71 (br. s, 1H), 4.82 (s, 2H), 1.54 (s, 9H), 1.13 (s, 9H).

Step 4)

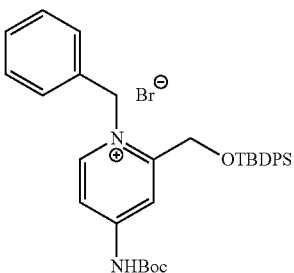

1-Benzyl-4-((tert-butoxycarbonyl)amino)-2-
(((tert-butyldiphenylsilyl)oxy)methyl)pyridin-1-ium
bromide To a solution of tert-butyl (2-(((tert-butyldiphenylsilyl)oxy)methyl)pyridin-4-yl)carbamate (1.00 g, 2.16 mmol) in toluene (30 mL), was added benzyl bromide (0.77 mL, 6.48 mmol). The reaction mixture was refluxed for 10 hours. The reaction mixture was then cooled to room temperature, and hexanes was added to form white suspension. The suspension was filtered to give product as a white solid (1.20 g, 88%). $^1$H NMR (300 MHz, CDCl$_3$) 11.16 (br. s, 1H), 8.65-8.58 (m, 3H), 7.58-7.15 (m, 13H), 6.94 (d, J=7 Hz, 2H), 5.59 (s, 2H), 4.73 (s, 2H), 1.54 (s, 9H), 1.09 (s, 9H).

Step 5)

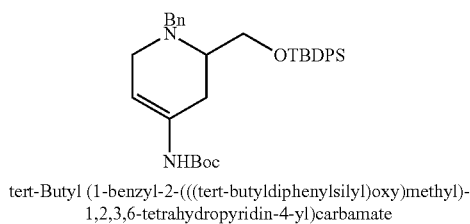

tert-Butyl (1-benzyl-2-(((tert-butyldiphenylsilyl)oxy)methyl)-1,2,3,6-tetrahydropyridin-4-yl)carbamate To a solution of 1-benzyl-4-((tert-butoxycarbonyl)amino)-2-(((tert-butyldiphenylsilyl)oxy)methyl)pyridin-1-ium bromide (235 mg, 0.37 mmol) in MeOH (2 mL) was added sodium borohydride (38 mg, 0.73 mmol) The reaction mixture was stirred at room temperature overnight. The reaction mixture was concentrated under reduced pressure, and the resulting residue was diluted with ethyl acetate. The organic layer was washed with 1N NaOH and then brine. The organic layer was dried over sodium sulfate and concentrated under reduced pressure to give the desired product as a colorless oil (200 mg, 97%). $^1$H NMR (300 MHz, CDCl$_3$) 7.77-7.65 (m, 4H), 7.44-7.22 (m, 11H), 5.78-5.71 (m, 2H), 3.99-3.51 (m, 4H), 3.30 (m, 1H), 3.07-3.06 (m, 1H), 2.91-2.85 (m, 1H). 2.53-2.47 (m, 1H), 2.20-2.13 (m, 1H), 1.47 (s, 9H), 1.07 (s, 9H).

Step 6)

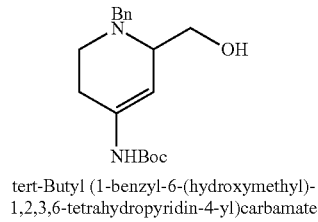 [SMILES: CC(C)(C)OC(=O)NC1=CC(CO)N(Cc2ccccc2)CC1]

tert-Butyl (1-benzyl-6-(hydroxymethyl)-1,2,3,6-tetrahydropyridin-4-yl)carbamate

To a solution of tert-butyl (1-benzyl-2-(((tert-butyldiphenylsilyl)oxy)methyl)-1,2,3,6-tetrahydropyridin-4-yl)carbamate (200 mg, 0.36 mmol) in tetrahydrofuran (5 mL) was added 1M TBAF in tetrahydrofuran (1.00 mL, 1.00 mmol). The reaction mixture was stirred at room temperature overnight. The reaction mixture was concentrated under reduced pressure and the resulting residue was purified using silica gel column chromatography eluting with 0 to 100% ethyl acetate/hexanes. The product was obtained as a colorless oil (30 mg, 26%). $^1$H NMR (300 MHz, CDCl$_3$) 7.31 (m, 5H), 5.73-5.71 (m, 2H), 3.87-3.82 (m, 1H), 3.64-3.54 (m, 2H), 3.42-3.36 (m, 1H), 3.24-3.25 (m, 1H), 3.03-2.94 (m, 1H), 2.69-2.61 (m, 1H), 2.34-2.24 (m, 1H), 1.97-1.88 (m, 1H), 1.46 (s, 9H).

Step 7)

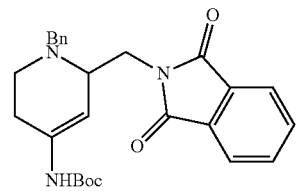

tert-Butyl (1-benzyl-6-((1,3-dioxoisoindolin-2-yl)methyl)-1,2,3,6-tetrahydropyridin-4-yl)carbamate To a solution of tert-butyl (1-benzyl-6-(hydroxymethyl)-1,2,3,6-tetrahydropyridin-4-yl)carbamate (318 mg, 1.00 mmol) in tetrahydrofuran (2 mL), triphenylphosphine (286 mg, 1.10 mmol) and phthalimide (159 mg, 1.10 mmol) were added. Then, DIAD (0.22 mL, 1.10 mmol) was added slowly to the mixture at 0° C. The reaction mixture was stirred at room temperature overnight. The reaction mixture was diluted with dichloromethane washed with water and then brine. The organic layer was dried over sodium sulfate and concentrated under reduced pressure to give the crude product (251 mg, 56%) as a yellow oil.

Preparation of Amine Intermediate T: tert-butyl ((3S,5S)-5-(aminomethyl)-1-benzylpyrrolidin-3-yl)carbamate

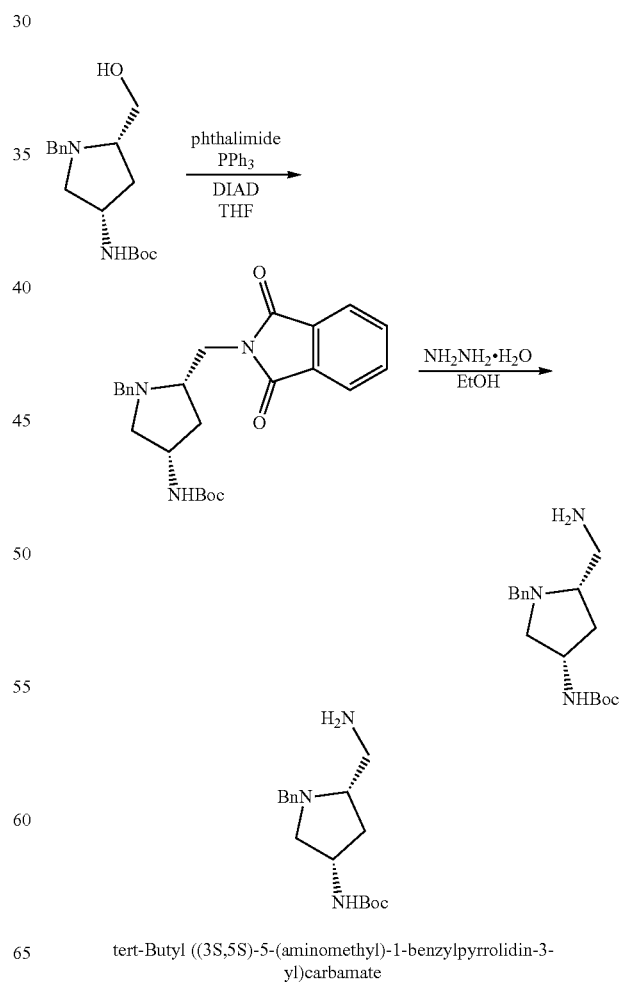

tert-Butyl ((3S,5S)-5-(aminomethyl)-1-benzylpyrrolidin-3-yl)carbamate

To a flask containing triphenylphosphine (1.08 g, 4.12 mmol) and phthalimide (0.605 g, 4.12 mmol) in THF (15 mL) was added tert-butyl ((3S,5S)-1-benzyl-5-(hydroxymethyl)pyrrolidin-3-yl)carbamate (1.05 g, 3.43 mmol) followed by DIAD (677 mL, 4.29 mmol) at 0° C. The reaction mixture was stirred at 0° C. and allowed to warm to room temperature and was stirred overnight. The mixture was concentrated under reduced pressure and residue purified using column chromatography on silica gel to give phthalimide product (1.0 g, 67%) as a white solid. Then it was dissolved in ethanol (20 mL) and hydrazine monohydrate (0.22 mL, 4.57 mmol) was added. The reaction mixture was heated at 60° C. until no starting material left. The precipitate formed was filtered off and the filtrate was concentrated under reduced pressure to give the amine product (0.53 g, 76% yield) as a gel. MS: Calcd for $C_{17}H_{27}N_3O_2$ 306.21 [M+H$^+$], found 306.25 [M+H]$^+$.

Preparation of Amine Intermediate U: (2S,4S)-1-benzyl-N-methyl-4-(methylamino)pyrrolidine-2-carboxamide

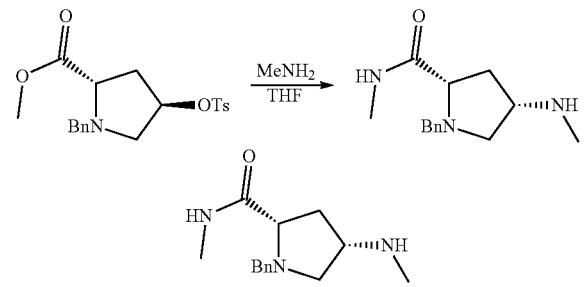

(2S,4S)-1-benzyl-N-methyl-4-(methylamino)pyrrolidine-2-carboxamide

To a solution of methylamine in THF (2.0 M, 20 mL) was added (2S,4R)-methyl 1-benzyl-4-(tosyloxy)pyrrolidine-2-carboxylate (0.63 g, 1.62 mmol). The reaction mixture was heated at 100° C. in a sealed tube. To the reaction mixture was added methylene chloride then concentrated under reduced pressure. The residue was purified by column chromatography on silica gel (0-15% methanol in ethyl acetate) to give the product as a white powder (0.095 g, 25% yield). $^1$H NMR (300 MHz, D$_2$O) δ 7.32 (m, 5H), 3.85 (d, J=12.9 Hz, 1H), 3.45 (d, J=12.9 Hz, 1H), 3.20 (t, J=7.2 Hz, 1H), 3.13 (m, 1H), 2.95 (d, J=9.9 Hz, 1H), 2.75 (s, 3H), 2.49 (m, 2H), 2.32 (s, 3H), 1.73 (m, 1H). MS: Calcd for $C_{14}H_{21}N_3O$ 248.17 [M+H$^+$], found 248.15 [M+H]$^+$.

Preparation of Amine Intermediate V: (S)-benzyl (4-(3-aminopyrrolidin-1-yl)cyclohexyl)carbamate

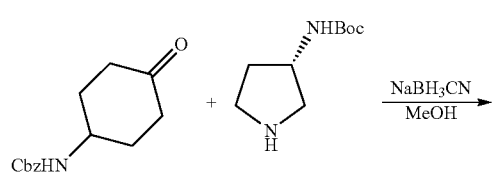

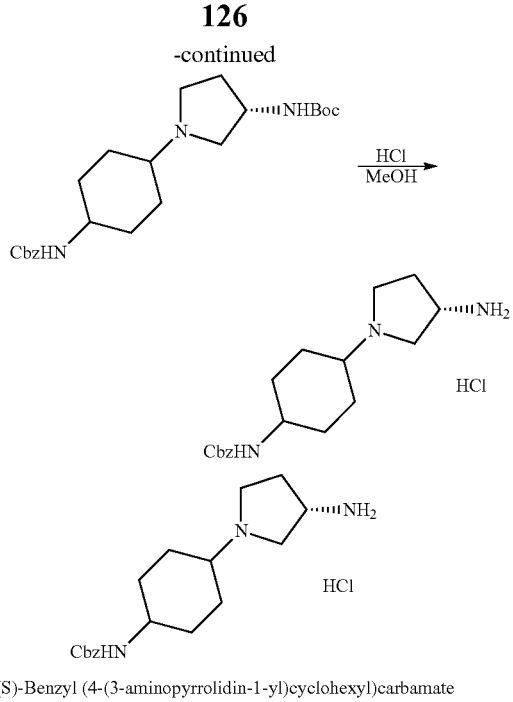

(S)-Benzyl (4-(3-aminopyrrolidin-1-yl)cyclohexyl)carbamate

To a solution of (S)-benzyl (4-(3-N-Boc-aminopyrrolidin-1-yl)cyclohexyl)carbamate (350 mg, 0.84 mmol) in MeOH (8 mL) HCl solution (4 M in dioxane, 1 mL, 4 mmol) was added. The reaction mixture was stirred at room temperature until no starting material left, then solvent was removed under reduced pressure. The residue was triturated with EtOAc and the precipitate was collected as an off-white powder (280 mg, 60% yield). MS: Calcd for $C_{18}H_{27}N_3O_2$ 318.21 [M+H$^+$], found 318.25 [M+H]$^+$.

The requisite intermediates were prepared as follows:

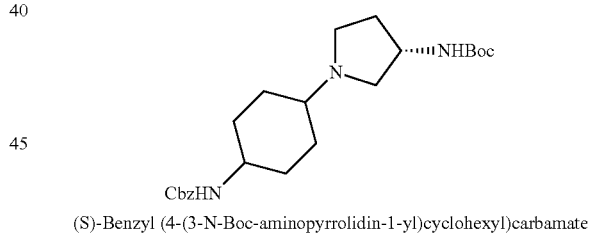

(S)-Benzyl (4-(3-N-Boc-aminopyrrolidin-1-yl)cyclohexyl)carbamate

To the mixture of benzyl (4-oxocyclohexyl)carbamate (0.50 g, 2 mmol) and (S)-tert-butyl pyrrolidin-3-ylcarbamate (0.37 g, 2 mmol) in MeOH (20 mL) was added 4 Å molecular sieves and NaBH$_3$CN (0.15 g, 2.4 mmol). The reaction mixture was stirred at room temperature and checked by TLC. After finishing the reaction, it was concentrated under reduced pressure and purified by column chromatography on silica using 0-10% MeOH in EtOAc to provide the product as a colorless solid (0.35 g, 42% yield). $^1$H NMR (300 MHz, CDCl$_3$) δ 7.35 (m, 5H), 5.08 (s, 2H), 4.85 (br, 1H), 4.56 (br, 1H), 4.15 (m, 1H), 3.50 (m, 1H), 2.92 (m, 1H), 2.69 (m, 2H), 2.39 (m, 1H), 2.23 (m, 1H), 2.04 (m, 1H), 1.95 (m, 1H), 1.68 (m, 2H), 1.43 (m, 9H), 1.36 (m, 2H), 1.21 (m, 2H). MS: Calcd for $C_{23}H_{35}N_3O_4$ 418.26 [M+H]$^+$, found 418.30 [M+H]$^+$.

Amine intermediate W

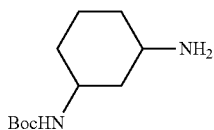

This compound was commercially available.

Amine intermediate X

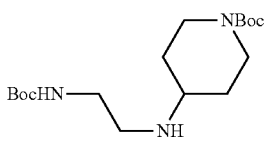

This compound was commercially available.

Preparation of Amine Intermediate Y: benzyl (2-aminoethyl)(4-(((benzyloxy)carbonyl)amino)cyclohexyl)carbamate hydrogen chloride salt

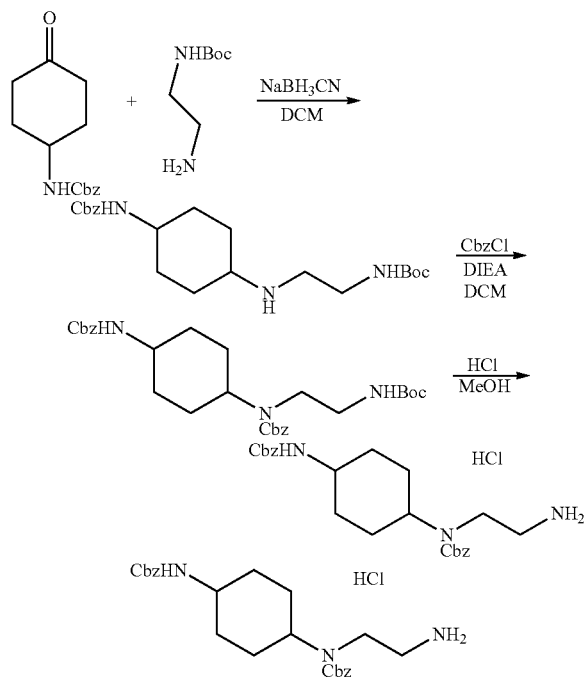

Benzyl (2-aminoethyl)(4-(((benzyloxy)carbonyl)amino)cyclohexyl)carbamate hydrogen chloride salt To a solution of benzyl (2-(tert-butoxycarbonyl)amino)ethyl)(4-(((benzyloxy)carbonyl)amino)cyclohexyl)carbamate (370 mg, 0.84 mmol) in MeOH (10 mL) was added a solution of HCl in dioxane (4 M in dioxane, 2 mL, 8 mmol) was added. It was stirred at room temperature until no starting material left. The solvent was removed under reduced pressure. The residue was triturated with Et₂O and the precipitate was collected as an off-white powder (250 mg, 77% yield). MS: Calcd for $C_{24}H_{31}N_3O_4$ 426.23 [M+H]⁺, found 426.30 [M+H]⁺.

The requisite intermediates were prepared as follows:
Step 1):

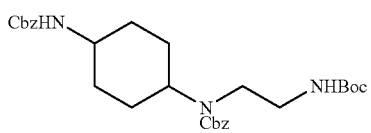

Benzyl (2-(tert-butoxycarbonyl)amino)ethyl)(4-(((benzyloxy)carbonyl)amino)cyclohexyl)carbamate To a solution of benzyl (4-((2-N-Boc-aminoethyl)amino)cyclohexyl)carbamate (420 mg, 1.07 mmol) in MeOH (10 mL) CbzCl (0.245 mL, 1.6 mmol) and DIEA (0.56 mL, 3.2 mmol) were added at 0° C. The reaction mixture was stirred at 0° C.-room temperature. until no starting material left. The reaction mixture was diluted with EtOAc and washed with water and then brine and the organic layer concentrated under reduced pressure. The residue was purified by silica gel column chromatography using 20-30% EtOAc in hexanes to provide the product as a white powder (460 mg, 82% yield). MS: Calcd for $C_{29}H_{39}N_3O_6$ 526.28 [M+H]⁺, found 526.40 [M+H]⁺.

Step 2):

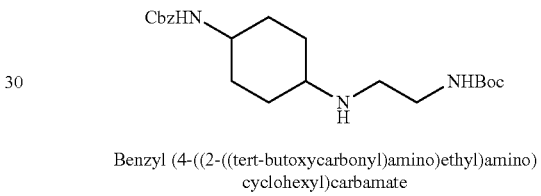

Benzyl (4-((2-((tert-butoxycarbonyl)amino)ethyl)amino)cyclohexyl)carbamate

To the mixture of benzyl (4-oxocyclohexyl)carbamate (0.50 g, 2 mmol) and tert-butyl (2-aminoethyl)carbamate (0.40 g, 2.5 mmol) in DCM (20 mL) was added 4 Å molecular sieves and NaBH₃CN (0.19 g, 3.0 mmol). The reaction mixture was stirred at room temperature and checked by TLC. After the reaction was complete, it was concentrated under reduced pressure and the residue purified by column chromatography provide the product as a colorless solid (0.42 g, 54% yield). MS: Calcd for $C_{21}H_{33}N_3O_4$ 392.25 [M+H]⁺, found 392.25 [M+H]⁺.

Preparation of Amine Intermediate Z: benzyl 4-((2-aminoethyl)((benzyloxy)carbonyl)amino)piperidine-1-carboxylate hydrogen chloride salt

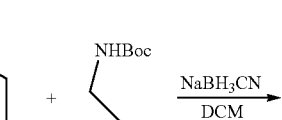

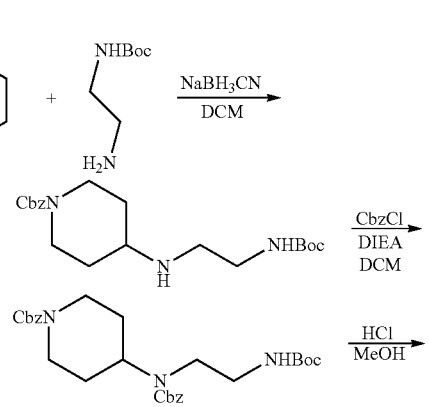

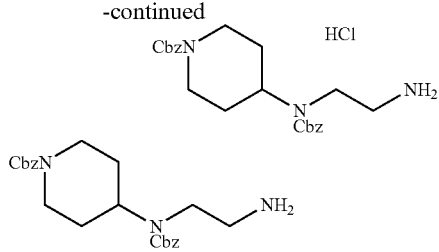

Benzyl 4-((2-aminoethyl)((benzyloxy)carbonyl)amino)piperidine-1-carboxylate hydrogen chloride salt To a solution of benzyl 4-(((benzyloxy)carbonyl)(2-((tert-butoxycarbonyl)amino)ethyl)amino)piperidine-1-carboxylate (280 mg, 0.55 mmol) in MeOH (10 mL) was added HCl in solution (4 M in dioxane, 1 mL, 4 mmol). The reaction mixture was stirred at room temperature until no starting material left. The solvent was removed under reduced pressure. The residue was triturated with Et$_2$O and the precipitate was collected as an off-white powder (195 mg, 79% yield). MS: Calcd for C$_{23}$H$_{29}$N$_3$O$_4$ 412.22 [M+H]$^+$, found 412.25 [M+H]$^+$.

The requisite intermediates were prepared as follows:

Step 1):

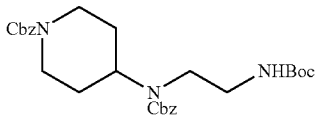

Benzyl 4-(((benzyloxy)carbonyl)(2-((tert-butoxycarbonyl)amino)ethyl)amino)piperidine-1-carboxylate To a solution of benzyl 4-((2-((tert-butoxycarbonyl)amino)ethyl)amino)piperidine-1-carboxylate (450 mg, 1.2 mmol) in MeOH (10 mL) were added CbzCl (0.25 mL, 1.75 mmol) and DIEA (0.62 mL, 3.6 mmol) at 0° C. The reaction mixture was stirred at 0° C.-room temperature until no starting material left based upon TLC analysis. The reaction mixture was diluted with EtOAc and washed with water and then brine. The residue was purified by column chromatography using 20-35% EtOAc in hexanes to provide the product as a white powder (290 mg, 47% yield). MS: Calcd for C$_{28}$H$_{37}$N$_3$O$_6$ 512.27 [M+H]$^+$, found 512.35 [M+H]$^+$.

Step 2):

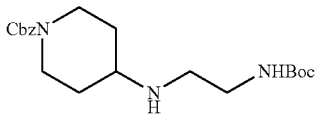

Benzyl 4-((2-((tert-butoxycarbonyl)amino)ethyl)amino)piperidine-1-carboxylate

To the mixture of benzyl (4-oxocyclohexyl)carbamate (0.467 g, 2 mmol) and tert-butyl (2-aminoethyl)carbamate (0.40 g, 2.5 mmol) in DCM (20 mL) was added 4 Å molecular sieves and NaBH$_3$CN (0.19 g, 3.0 mmol). The reaction mixture was stirred at room temperature and checked by TLC. After the reaction was complete, it was concentrated and purified by silica gel column chromatography to provide the product as a colorless solid (0.46 g, 61% yield). MS: Calcd for C$_{20}$H$_{31}$N$_3$O$_4$ 378.23 [M+H]$^+$, found 378.20 [M+H]$^+$.

Preparation of Amine Intermediate Z1: tert-butyl 3-((2-aminoethyl)(tert-butoxycarbonyl)amino)pyrrolidine-1-carboxylate

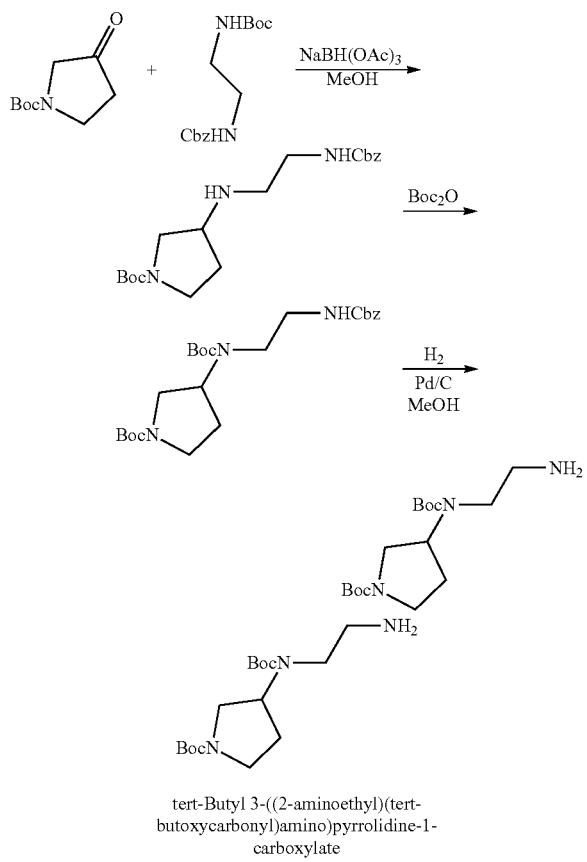

tert-Butyl 3-((2-aminoethyl)(tert-butoxycarbonyl)amino)pyrrolidine-1-carboxylate To a solution of tert-butyl 3-((2-(((benzyloxy)carbonyl)amino)ethyl)(tert-butoxycarbonyl)amino)pyrrolidine-1-carboxylate (50 mg, 0.11 mmol) in MeOH (5 mL) was added Pd/C (10%, 20 mg). The reaction mixture was stirred under H$_2$ overnight. The reaction mixture was filtered through a Celite pad and washed with methanol and the solvent removed under reduced pressure. The residue was collected as an off-white powder (33 mg, 91%) which was used for reaction without purification.

The requisite intermediates were prepared as follows:

Step 1):

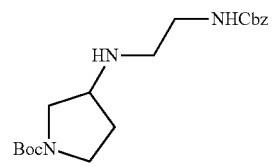

tert-Butyl 3-((2-(((benzyloxy)carbonyl)amino)ethyl)amino)pyrrolidine-1-carboxylate To the mixture of tert-butyl 3-oxopyrrolidine-1-carboxylate (0.388 g, 2 mmol) and benzyl (2-aminoethyl)carbamate (0.185 g, 1 mmol) in MeOH (10 mL) was added 4 Å molecular sieves and NaBH(OAc)₃ (0.64 g, 3.0 mmol). It was stirred at room temperature and checked by TLC. After the reaction was complete, it was concentrated under reduced pressure and extracted with EtOAc and the organic layer concentrated under reduced pressure. The residue was purified by column chromatography on silica gel to provide the product as a colorless oil (0.15 g, 41% yield).

Step 2):

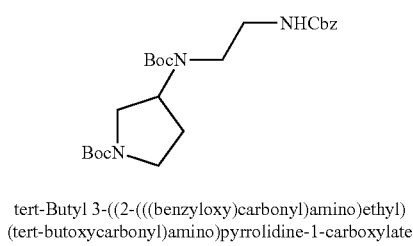 [SMILES: CC(C)(C)OC(=O)N1CCC(N(CCNC(=O)OCc2ccccc2)C(=O)OC(C)(C)C)C1]

tert-Butyl 3-((2-(((benzyloxy)carbonyl)amino)ethyl)
(tert-butoxycarbonyl)amino)pyrrolidine-1-carboxylate To a solution of tert-butyl 3-((2-(((benzyloxy)carbonyl)amino)ethyl)amino)pyrrolidine-1-carboxylate (0.14 g, 0.38 mmol) in DCM (20 mL) was added Boc₂O (0.125 g, 0.57 mmol). The reaction mixture was stirred at room temperature until TLC analysis showed no starting material left. The reaction mixture was concentrated and purified by column chromatography on silica gel to provide the product as a white powder (0.13 g, 74%).

Preparation of Amine Intermediate Z2: benzyl (2-aminoethyl)(3-(((benzyloxy)carbonyl)amino)cyclohexyl)carbamate

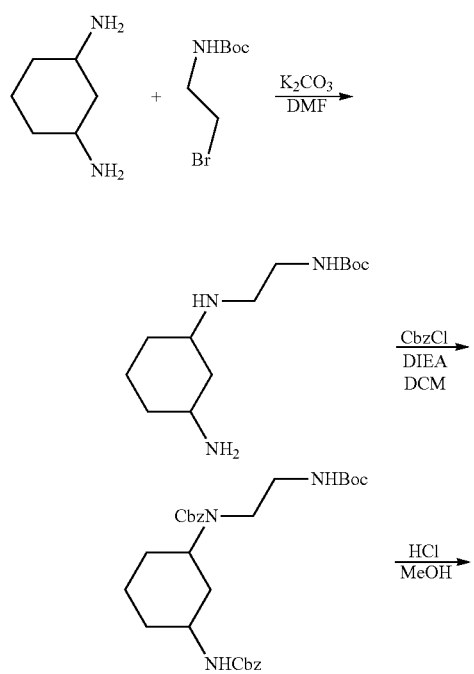

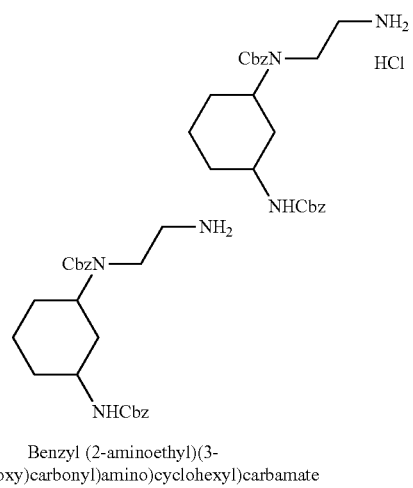

Benzyl (2-aminoethyl)(3-(((benzyloxy)carbonyl)amino)cyclohexyl)carbamate

To a solution of benzyl (3-((2-((tert-butoxycarbonyl)amino)ethyl)amino)cyclohexyl)-carbamate (460 mg, 0.87 mmol) in THF (10 mL) was added HCl in dioxane (4 M in dioxane, 1 mL, 4 mmol). The reaction mixture was stirred at room temperature until no starting material was left. The solvent was removed under reduced pressure. The residue was purified on column chromatography on silica gel with MeOH (with 5% ammonia) in EtOAc to give an off-white powder (250 mg, 62% yield). MS: Calcd for $C_{24}H_{31}N_3O_4$ 426.23 [M+H]⁺, found 426.25 [M+H]⁺.

The requisite intermediates were prepared as follows:

Step 1):

tert-butyl (2-((3-aminocyclohexyl)amino)ethyl)
carbamate

To a solution of cyclohexane-1,3-diamine (0.23 g, 2 mmol) and tert-butyl (2-bromoethyl)carbamate (0.45 g, 2 mmol) in DMF was added K₂CO₃ (0.83 g, 6 mmol) at room temperature. The mixture was stirred at room temperature overnight. The reaction mixture was diluted with EtOAc. The organic layer was washed with water and then brine. The organic layer was concentrated under reduced pressure. The crude mixture was used for next step without purification. MS: Calcd for $C_{13}H_{27}N_3O_2$ 258.21 [M+H]⁺, found 258.25 [M+H]⁺.

Step 2):

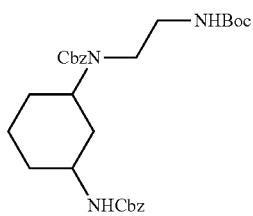

Benzyl (2-((tert-butoxycarbonyl)amino)ethyl)(3-(((benzyloxy)carbonyl)amino)cyclohexyl)carbamate To a solution of crude tert-butyl (2-((3-aminocyclohexyl)amino)ethyl)carbamate (515 mg, 2 mmol) in DMF (6 mL) were added CbzCl (0.72 mL, 5 mmol) and DIEA (1.0 mL, 6 mmol) at 0° C. The reaction mixture was stirred at 0° C.-room temperature until no starting material was left. The reaction mixture diluted with EtOAc and the organic layer washed with water and then brine. The organic layer was concentrated under reduced pressure. The residue was purified by column chromatography on silica gel using 0-30% EtOAc in hexanes to provide the product as a white powder (470 mg, 42% yield in two steps). MS: Calcd for $C_{29}H_{39}N_3O_6$ 526.28 $[M+H]^+$, found 526.35 $[M+H]^+$.

Preparation of Amine Intermediate Z3: (S)-benzyl 4-(3-aminopyrrolidin-1-yl)piperidine-1-carboxylate hydrogen chloride salt

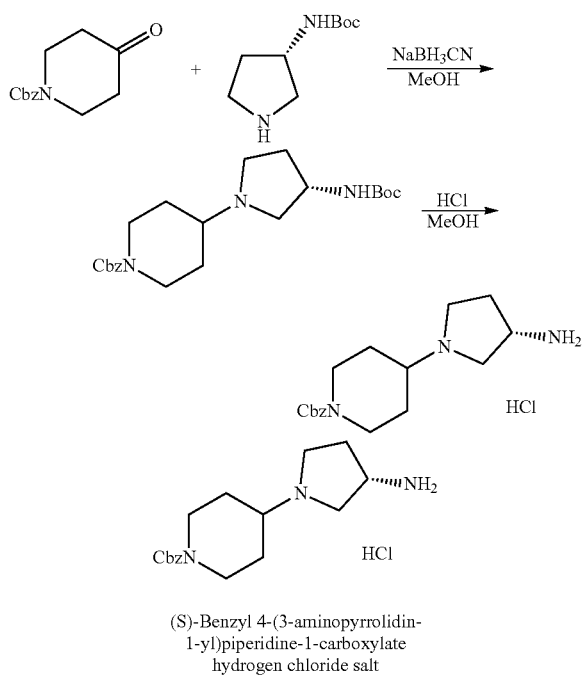

(S)-Benzyl 4-(3-aminopyrrolidin-1-yl)piperidine-1-carboxylate hydrogen chloride salt To a solution of (S)-benzyl 4-(3-((tert-butoxycarbonyl)amino)pyrrolidin-1-yl)piperidine-1-carboxylate (420 mg, 1.04 mmol) in MeOH (10 mL) was added HCl in dioxane (4 M in dioxane, 1.5 mL, 6 mmol). The reaction mixture was stirred at room temperature until no starting material left. Solvent was removed from the reaction mixture under reduced pressure. The residue was triturated with $Et_2O$ and the precipitate was collected as an off-white powder (260 mg, 67% yield). MS: Calcd for $C_{17}H_{25}N_3O_2$ 304.19 $[M+H]^+$, found 304.20 $[M+H]^+$.

The requisite intermediates were prepared as follows:

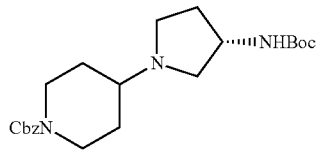

(S)-Benzyl 4-(3-((tert-butoxycarbonyl)amino) pyrrolidin-1-yl)piperidine-1-carboxylate To the mixture of benzyl 4-oxopiperidine-1-carboxylate (0.467 g, 2 mmol) and (S)-tert-butyl pyrrolidin-3-ylcarbamate (0.37 g, 2 mmol) in MeOH (20 mL) was added 4 Å molecular sieves and $NaBH_3CN$ (0.15 g, 2.4 mmol). The reaction mixture was stirred at room temperature and monitored by TLC analysis. After the reaction was complete, the reaction mixture was concentrated under reduced pressure and the residue purified by column chromatography on silica gel with 0-15% MeOH in EtOAc to provide the desired product as a colorless solid (0.43 g, 53% yield). MS: Calcd for $C_{22}H_{33}N_3O_4$ 404.25 $[M+H]^+$, found 404.25 $[M+H]^+$.

EXAMPLES

Example 1. Preparation of (S)—N-(2,5-diaminopentyl)-5-(4 fluorophenyl)-1H-indole-2-carboxamide dihydrochloride

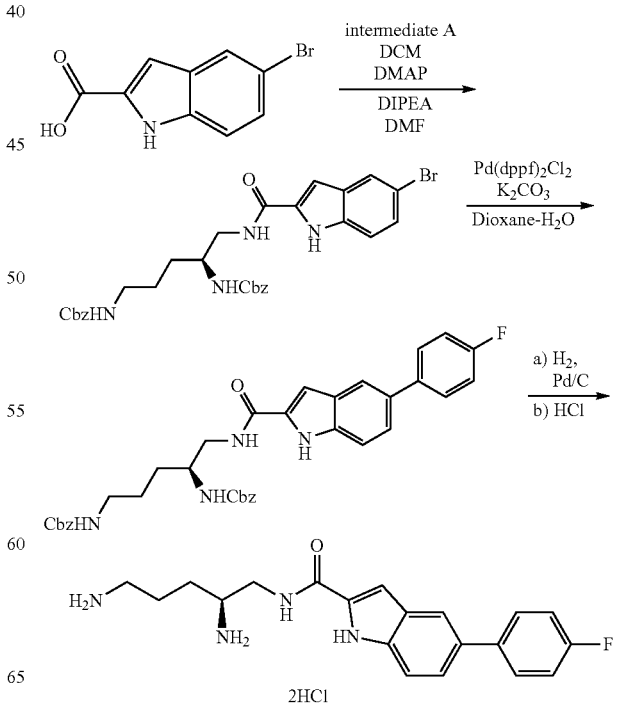

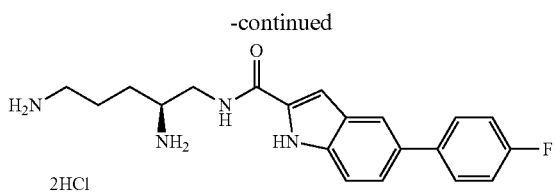

2HCl (S)-N-(2,5-Diaminopentyl)-5-(4-fluorophenyl)-1H-indole-2-carboxamide dihydrochloride To a solution of dibenzyl (5-(5-(4-fluorophenyl)-1H-indole-2-carboxamido)pentane-1,4-diyl)(S)-dicarbamate (16 mg, 0.03 mmol) in MeOH (10 mL) was added Pd/C (10%, 50 mg). The reaction mixture was stirred under $H_2$ overnight. It was filtered through a pad of Celite and concentrated under reduced pressure. It was dissolved in MeOH (2 mL) and HCl solution (4 M in dioxane, 0.05 mL) was added. It was stirred at room temperature overnight and solvent was removed under reduced pressure. The residue was triturated with EtOAc and the precipitate was collected as an off-white powder (8 mg, 62% yield). $^1$H NMR (300 MHz, $D_2O$) δ 8.00 (s, 1H), 7.78 (s, 1H), 7.71 (m, 2H), 7.68 (m, 2H), 7.51 (m, 1H), 7.25 (m, 2H), 3.79 (m, 1H), 3.69 (m, 1H), 3.45 (m, 1H), 3.07 (m, 2H), 1.87 (m, 4H). MS (ESI+): 355.20 [M+H]$^+$ for $C_{20}H_{23}FN_4O$.

The requisite intermediates were prepared as shown in the following steps.

Step 1)

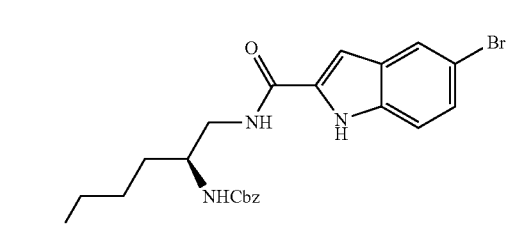

Dibenzyl (5-(5-bromo-1H-indole-2-carboxamido)pentane-1,4-diyl)(S)-dicarbamate

To a solution of 5-bromo-1H-indole-2-carboxylic acid (72 mg, 0.3 mmol) in dry methylene chloride (5 mL) was added DIPEA (0.15 mL, 1.2 mmol), DMAP (37 mg, 0.3 mmol) and EDC (69 mg, 0.36 mmol). The reaction mixture was stirred at room temperature and dibenzyl (5-aminopentane-1,4-diyl)-(S)-dicarbamate (intermediate A) (116 mg, 0.3 mmol) was added. The reaction mixture was stirred at room temperature overnight. Then it was concentrated under reduced pressure and purified by column chromatography on silica gel (60-80% ethyl acetate/hexanes) to give the product (75 mg, 41% yield) as a white solid. $^1$H NMR (300 MHz, CDCl$_3$) δ 9.22 (br, 1H), 7.75 (s, 1H), 7.63 (m, 1H), 7.48 (m, 1H), 7.35 (m, 1H), 5.08 (m, 4H), 3.87 (m, 1H), 3.52 (m, 2H), 3.22 (m, 2H), 1.56 (m, 4H).

Step 2)

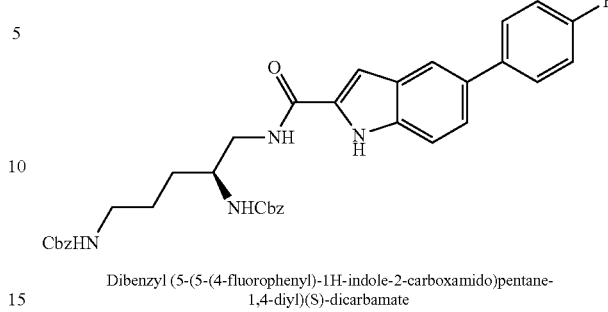

Dibenzyl (5-(5-(4-fluorophenyl)-1H-indole-2-carboxamido)pentane-1,4-diyl)(S)-dicarbamate The mixture of dibenzyl (5-(5-bromo-1H-indole-2-carboxamido)pentane-1,4-diyl)(S)-dicarbamate (70 mg, 0.11 mmol), (4-fluorophenyl)boronic acid (30 mg, 0.22 mmol), $K_2CO_3$ solution in water (2 M, 0.165 mL) in dioxane (4 mL) was degassed and Pd(dppf)$_2$Cl$_2$ (8 mg, 0.01 mmol) was added. The mixture was heated at 95° C. overnight and it was extracted with EtOAc. The organic phases were combined, washed with brine and concentrated under reduced pressure. The residue was purified by column chromatography on silica gel (50-70% ethyl acetate/hexanes) to give the product (17 mg, 25% yield) as a white solid. $^1$H NMR (300 MHz, CD$_3$COCD$_3$) δ 7.91 (m, 2H), 7.86 (s, 1H), 7.70 (m, 1H), 7.55 (m, 1H), 7.33 (m, 1H), 7.28 (m, 10H), 7.11 (m, 2H), 6.45 (br, 1H), 6.37 (br, 1H), 5.05 (m, 4H), 3.88 (m, 1H), 3.50 (m, 2H), 3.17 (m, 2H), 1.63 (m, 4H).

Example 2. Preparation of (S)—N-(2,5-diaminopentyl)-6-(4-fluorophenyl)-1H-indole-3-carboxamide dihydrochloride

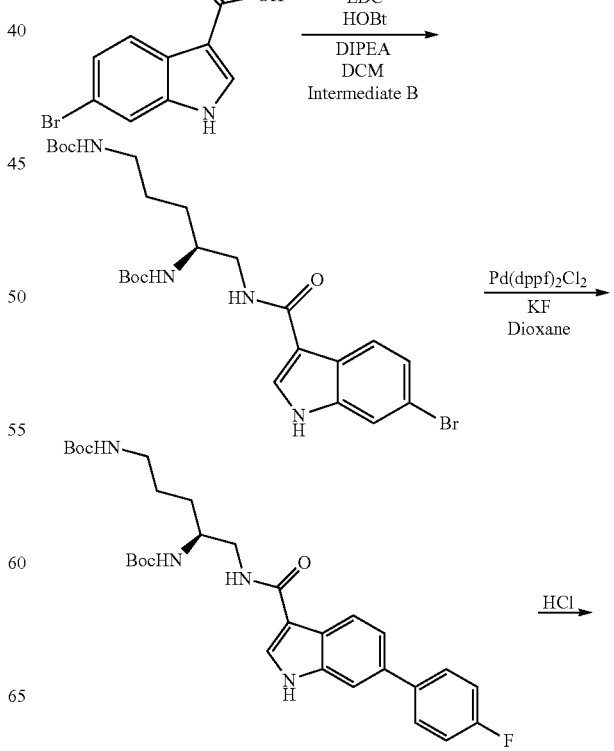

-continued

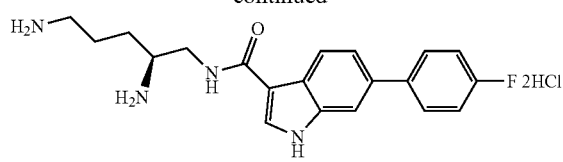

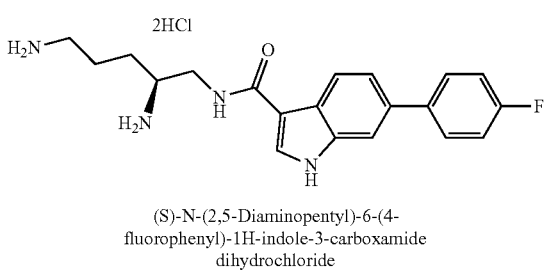

(S)-N-(2,5-Diaminopentyl)-6-(4-fluorophenyl)-1H-indole-3-carboxamide dihydrochloride To a solution of di-tert-butyl (5-(6-(4-fluorophenyl)-1H-indole-3-carboxamido)pentane-1,4-diyl)(S)-dicarbamate (50 mg, 0.09 mmol) in MeOH (5 mL) was added HCl in solution (4 M in dioxane, 0.1 mL). It was stirred at room temperature overnight and solvent was removed. The residue was triturated with EtOAc and the precipitate was collected as a pale brown powder (28 mg, 73% yield). $^1$H NMR (300 MHz, CD$_3$OD) δ 8.19 (d, J=8.1 Hz, 1H), 8.07 (m, 2H), 7.65 (m, 2H), 7.43 (s, 1H), 7.25 (m, 1H), 7.18 (m, 1H), 3.69 (m, 1H), 3.60 (m, 1H), 3.49 (m, 1H), 3.05 (m, 2H), 1.88 (m, 4H).

The requisite intermediates were prepared as shown in the following steps.

Step 1)

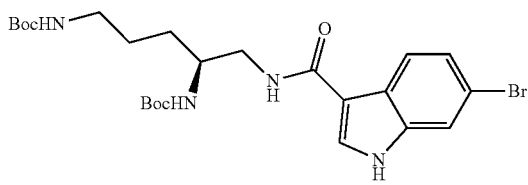

di-tert-Butyl (5-(6-bromo-1H-indole-3-carboxamido)pentane-1,4,-diyl)(S)-dicarbamate To a solution of 6-bromo-1H-indole-3-carboxylic acid (72 mg, 0.3 mmol) in dry methylene chloride (5 mL) was added DIPEA (0.15 mL, 1.2 mmol), HOBt (28 mg, 0.18 mmol) and EDC (69 mg, 0.36 mmol). The reaction mixture was stirred at room temperature for 5 minutes and di-tert-butyl (5-aminopentane-1,4-diyl)(S)-dicarbamate (intermediate B)(95 mg, 0.3 mmol) was added. The reaction mixture was stirred at room temperature overnight. Then it was concentrated under reduced pressure and purified by column chromatography on silica gel (60-80% ethyl acetate/hexanes) to give the product (72 mg, 45% yield) as a white solid. 1H NMR (300 MHz, CDCl$_3$) δ 9.72 (br, 1H), 8.00 (d, J=9 Hz, 1H), 7.69 (s, 1H), 7.52 (s, 1H), 7.28 (m, 1H), 6.98 (br, 1H), 5.01 (br, 1H), 4.76 (br, 1H), 3.76 (m, 1H), 3.46 (m, 2H), 3.11 (m, 2H), 1.55 (m, 4H), 1.42 (s, 9H), 1.33 (s, 9H).

Step 2)

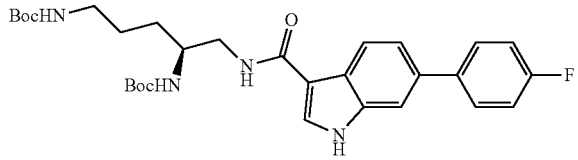

Di-tert-butyl (5-(6-(4-fluorophenyl)-1H-indole-3-carboxamido)pentane-1,4-diyl)(S)-dicarbamate The mixture of di-tert-butyl (5-(6-bromo-1H-indole-3-carboxamido)pentane-1,4-diyl)(S)-dicarbamate (70 mg, 0.13 mmol), (4-fluorophenyl)boronic acid (36 mg, 0.26 mmol), KF (38 mg, 0.65 mmol) in dioxane (5 mL) was degassed and Pd(dppf)$_2$Cl$_2$ (21 mg, 0.026 mmol) was added. The reaction mixture was heated at 100° C. overnight and it was concentrated under reduced pressure and purified by column chromatography on silica gel (50-80% ethyl acetate/hexanes) to give the product (29 mg, 40% yield) as a white solid. $^1$H NMR (300 MHz, CDCl$_3$) δ 9.00 (br, 1H), 7.78 (m, 1H), 7.67 (s, 1H), 7.53 (m, 2H), 7.43 (m, 1H), 7.32 (m, 1H), 7.07 (m, 2H), 6.84 (br, 1H), 4.92 (br, 1H), 4.68 (br, 1H), 3.80 (m, 1H), 3.52 (m, 2H), 3.13 (m, 2H), 1.60 (m, 4H), 1.43 (s, 9H), 1.36 (s, 9H).

Example 3. Preparation of (S)—N-(2,5-diaminopentyl)-5-(4-fluorophenyl)-1H-indole-3-carboxamide dihydrochloride

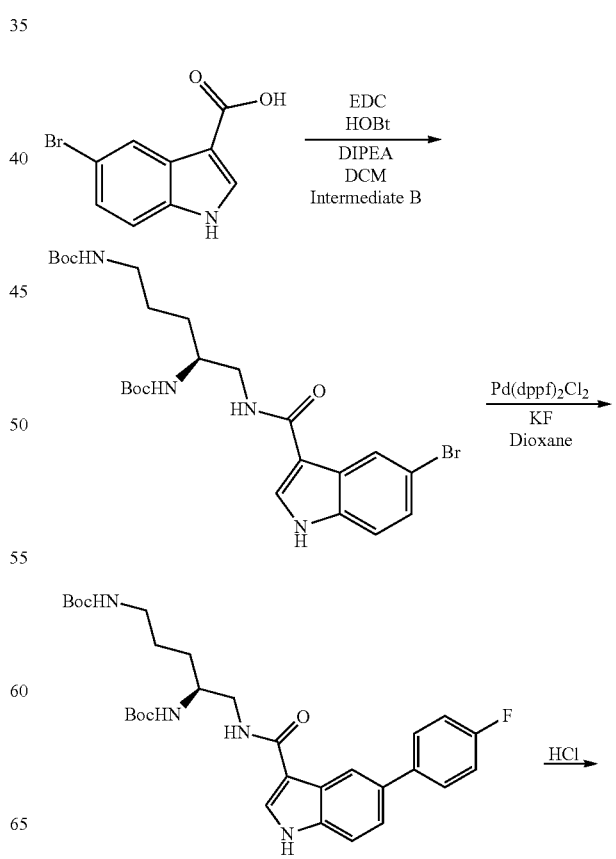

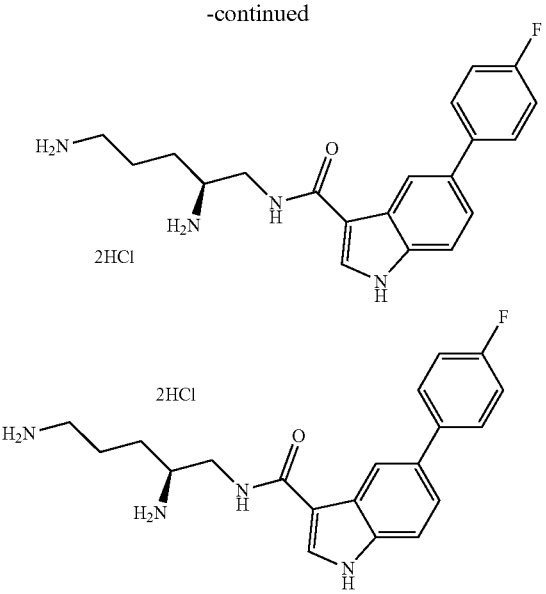

(S)-N-(2,5-Diaminopentyl)-5-(4-fluorophenyl)-1H-indole-3-carboxamide hihydrochloride To a solution of di-tert-butyl (5-(5-(4-fluorophenyl)-1H-indole-3-carboxamido)pentane-1,4-diyl)(S)-dicarbamate (35 mg, 0.06 mmol) in MeOH (5 mL) was added HCl solution (4 M in dioxane, 0.1 mL). It was stirred at room temperature overnight and solvent was removed under reduced pressure. The residue was triturated with EtOAc and the precipitate was collected as an off-white powder (18 mg, 67% yield). $^1$H NMR (300 MHz, D$_2$O) δ 8.23 (s, 1H), 7.98 (s, 1H), 7.77 (m, 2H), 7.65 (m, 1H), 7.63 (m, 1H), 7.24 (t, J=8.4 Hz, 2H), 3.73 (m, 1H), 3.62 (m, 1H), 3.57 (m, 1H), 3.04 (m, 2H), 1.84 (m, 4H).

The requisite intermediates were prepared as shown in the following steps.

Step 1)

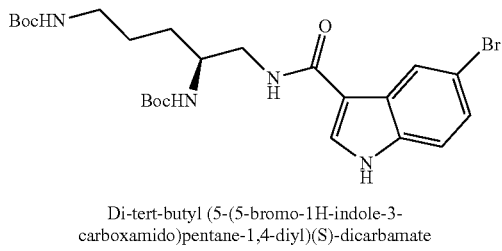 [SMILES: CC(C)(C)OC(=O)NCCC[C@@H](CNC(=O)c1c[nH]c2ccc(Br)cc12)NC(=O)OC(C)(C)C]

Di-tert-butyl (5-(5-bromo-1H-indole-3-carboxamido)pentane-1,4-diyl)(S)-dicarbamate To a solution of 5-bromo-1H-indole-3-carboxylic acid (72 mg, 0.3 mmol) in dry methylene chloride (5 mL) was added DIPEA (0.15 mL, 1.2 mmol), HOBt (28 mg, 0.18 mmol) and EDC (69 mg, 0.36 mmol). The reaction mixture was stirred at room temperature and di-tert-butyl (5-aminopentane-1,4-diyl)(S)-dicarbamate (intermediate B) (95 mg, 0.3 mmol) was added. The reaction mixture was stirred at room temperature overnight. Then it was diluted with EtOAc and washed with water and brine. The organic layer was dried over anhydrous sodium sulfate and filtered. The filtrate was concentrated under reduced pressure and purified by column chromatography on silica gel (60-80% ethyl acetate/hexanes) to give the product (90 mg, 56% yield) as a white solid. $^1$H NMR (300 MHz, CDCl$_3$) δ 9.62 (br, 1H), 8.31 (s, 1H), 7.72 (s, 1H), 7.28 (m, 2H), 7.01 (br, 1H), 5.03 (br, 1H), 4.75 (br, 1H), 3.76 (m, 1H), 3.48 (m, 2H), 3.11 (m, 2H), 1.56 (m, 4H), 1.42 (s, 9H), 1.34 (s, 9H).

Step 2)

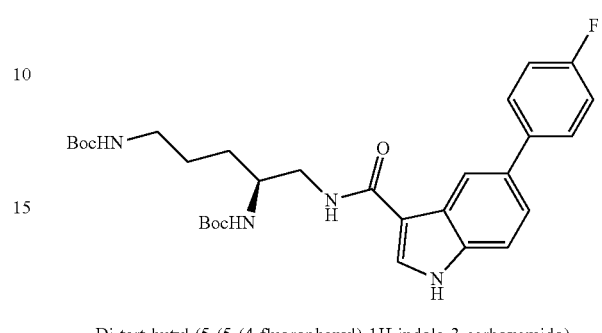

Di-tert-butyl (5-(5-(4-fluorophenyl)-1H-indole-3-carboxamido)pentane-1,4-diyl)(S)-dicarbamate The mixture of di-tert-butyl (5-(5-bromo-1H-indole-3-carboxamido)pentane-1,4-diyl)(S)-dicarbamate (70 mg, 0.13 mmol), (4-fluorophenyl)boronic acid (36 mg, 0.26 mmol), KF (38 mg, 0.65 mmol) in dioxane (5 mL) was degassed and Pd(dppf)$_2$Cl$_2$ (21 mg, 0.026 mmol) was added. The mixture was heated at 100° C. overnight and it was concentrated under reduced pressure and purified by column chromatography on silica gel (50-80% ethyl acetate/hexanes) to give the product (35 mg, 48% yield) as a white solid. $^1$H NMR (300 MHz, CDCl$_3$) δ 9.10 (br, 1H), 8.32 (s, 1H), 7.78 (s, 1H), 7.65 (m, 2H), 7.44 (m, 2H), 7.07 (m, 2H), 6.94 (br, 1H), 4.95 (br, 1H), 4.69 (br, 1H), 3.80 (m, 1H), 3.52 (m, 2H), 3.13 (m, 2H), 1.60 (m, 4H), 1.42 (s, 9H), 1.30 (s, 9H).

Example 4. Preparation of (S)—N-(2,5-diaminopentyl)-2-(5-(4-fluorophenyl)-1H-indol-3-yl)acetamide dihydrochloride

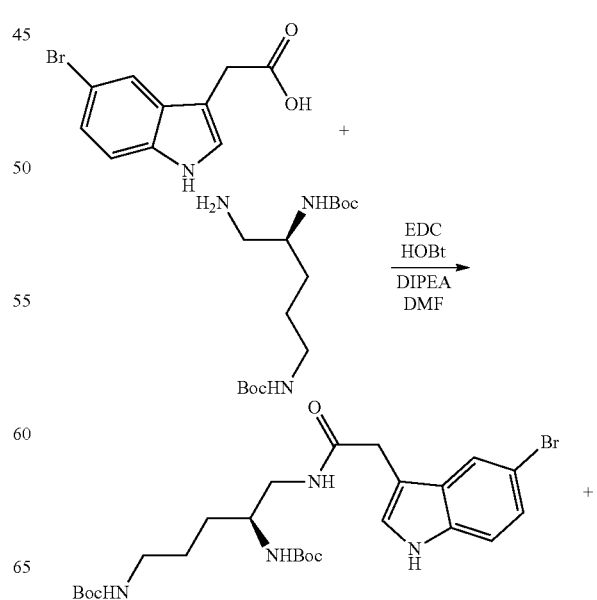

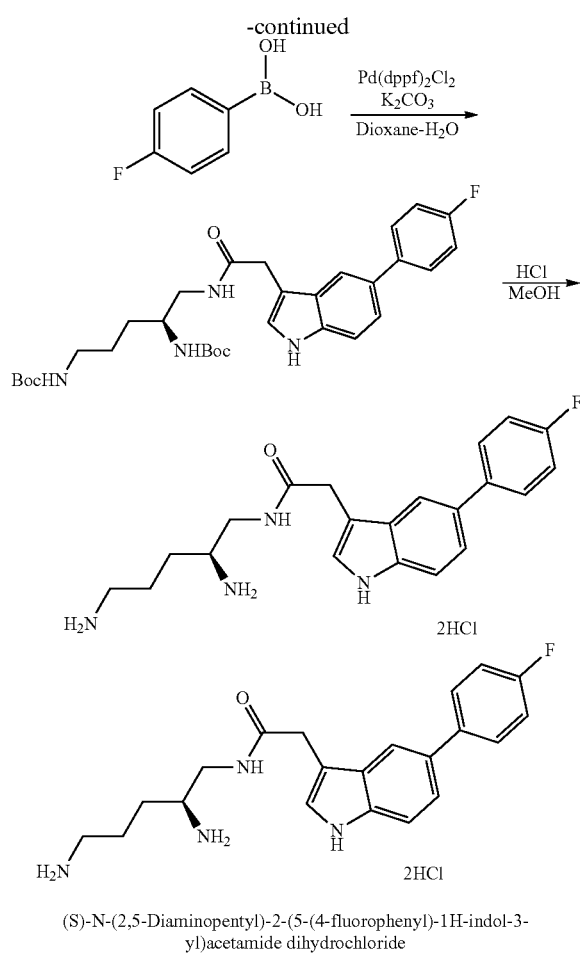

(S)-N-(2,5-Diaminopentyl)-2-(5-(4-fluorophenyl)-1H-indol-3-yl)acetamide dihydrochloride To a solution of di-tert-butyl (5-(2-(5-(4-fluorophenyl)-1H-indol-3-yl)acetamido)pentane-1,4-diyl)(S)-dicarbamate (30 mg, 0.05 mmol) in MeOH (5 mL) was added HCl solution (4 M in dioxane, 0.15 mL). The reaction mixture was stirred at room temperature overnight and solvent was removed under reduced pressure. The residue was triturated with EtOAc and the precipitate was collected as an off-white powder (16 mg, 69% yield). $^1$H NMR (300 MHz, D$_2$O) δ 7.85 (m, 1H), 7.74 (m, 2H), 7.59 (m, 1H), 7.50 (m, 1H), 7.33 (m, 2H), 7.24 (m, 1H), 3.76 (s, 2H), 3.42 (m, 1H), 3.33 (m, 1), 3.29 (m, 21H), 2.89 (m, 2H), 1.62-1.43 (m, 4H).

The requisite intermediates were prepared as shown in the following steps.

Step 1)

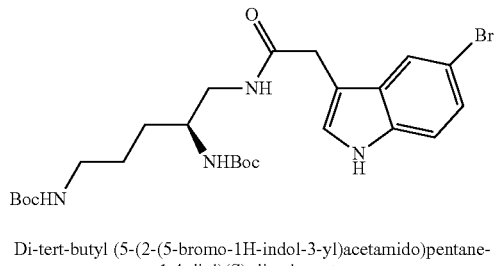

Di-tert-butyl (5-(2-(5-bromo-1H-indol-3-yl)acetamido)pentane-1,4-diyl)(S)-dicarbamate To a solution of 2-(5-bromo-1H-indol-3-yl)acetic acid (76 mg, 0.3 mmol) in dry methylene chloride (5 mL) was added DIPEA (0.11 mL, 0.6 mmol), HOBt (28 mg, 0.18 mmol) and EDC (69 mg, 0.36 mmol). The reaction mixture was stirred at room temperature and di-tert-butyl (5-aminopentane-1,4-diyl)(S)-dicarbamate (Intermediate B) (95 mg, 0.3 mmol) was added. The reaction mixture was stirred at room temperature overnight. Then it was diluted with EtOAc and washed with water and brine. The organic layer was dried over anhydrous sodium sulfate and filtered. The filtrate was concentrated under reduced pressure and purified by chromatography on silica gel (50-70% ethyl acetate/hexanes) to give the product (100 mg, 60% yield) as a white solid. $^1$H NMR (300 MHz, CDCl$_3$) δ 8.31 (br, 1H), 7.68 (s, 1H), 7.28 (m, 2H), 7.17 (s, 1H), 6.14 (br, 1H), 4.62 (br, 2H), 3.77 (s, 2H), 3.50 (m, 1H), 3.26 (m, 2H), 3.07 (m, 2H), 1.63 (m, 4H), 1.42 (s, 9H), 1.38 (s, 9H).

Step 2)

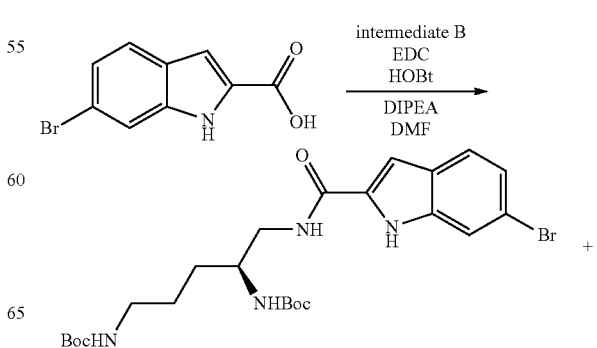

di-tert-butyl (5-(2-(5-(4-fluorophenyl)-1H-indol-3-yl)acetamido)pentane-1,4-diyl)(S)-dicarbamate The mixture of di-tert-butyl (5-(2-(5-bromo-1H-indol-3-yl)acetamido)pentane-1,4-diyl)(S)-dicarbamate (95 mg, 0.17 mmol), (4-fluorophenyl)boronic acid (48 mg, 0.34 mmol), KF (41 mg, 0.68 mmol) in dioxane (8 mL) was degassed and Pd(dppf)$_2$Cl$_2$ (26 mg, 0.03 mmol) was added. The mixture was heated at 100° C. overnight and it was concentrated under reduced pressure and purified by column chromatography on silica gel (50-70% ethyl acetate/hexanes) to give the product (32 mg, 33% yield) as a white solid. $^1$H NMR (300 MHz, CDCl$_3$) δ 8.61 (br, 1H), 7.67 (m, 1H), 7.56 (m, 1H), 7.41 (s, 1H), 7.21 (m, 2H), 7.10 (m, 3H), 6.24 (br, 1H), 4.72 (br, 1H), 4.65 (br, 1H), 3.73 (s, 2H), 3.48 (m, 1H), 3.22 (m, 2H), 3.04 (m, 2H), 1.83-1.63 (m, 4H), 1.42 (s, 9H), 1.36 (s, 9H).

Example 5. Preparation of (S)—N-(2,5-diaminopentyl)-6-(4-nitrophenyl)-1H-indole-2-carboxamide dihydrochloride

143

-continued

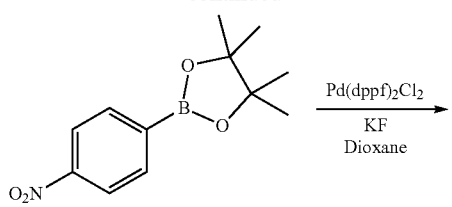

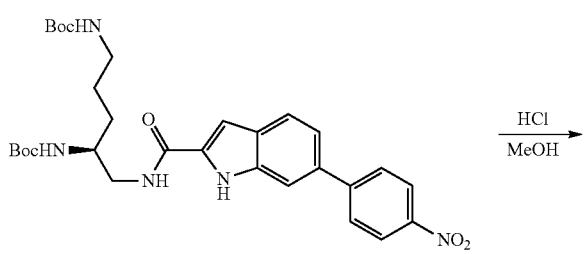

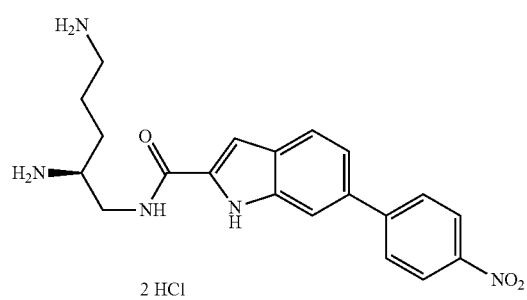

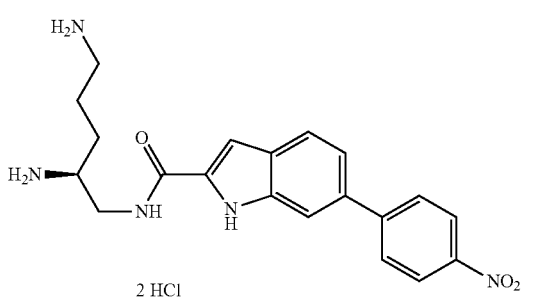

(S)-N-(2,5-Diaminopentyl)-6-(4-nitrophenyl)-1H-indole-2-carboxamide dihydrochloride To a solution of di-tert-butyl (5-(6-(4-nitrophenyl)-1H-indole-2-carboxamido)pentane-1,4-diyl)(S)-dicarbamate (10 mg, 0.017 mmol) in MeOH (1 mL) was added HCl in dioxane (4M, 0.05 mL, 0.2 mmol). The reaction mixture was stirred at room temperature overnight. The residue was concentrated under reduced pressure and triturated with EtOAc to afford product (7 mg, 96% yield) as a brown solid. $^1$H NMR (300 MHz, D$_2$O) δ 8.17 (m, 2H), 7.76 (m, 4H), 7.48 (m, 1H), 7.27 (m, 1H), 3.70 (m, 1H), 3.60 (m, 2H), 3.06 (m, 2H), 1.86 (m, 4H).

The requisite intermediates were prepared as shown in the following steps.

144

Step 1)

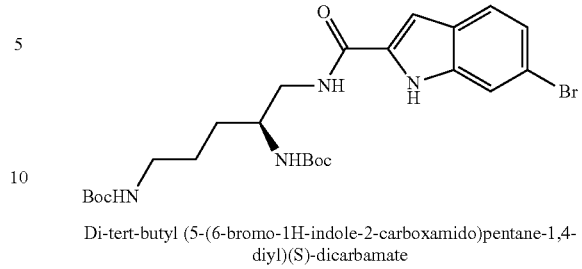

Di-tert-butyl (5-(6-bromo-1H-indole-2-carboxamido)pentane-1,4-diyl)(S)-dicarbamate To a solution of 6-bromo-1H-indole-2-carboxylic acid (240 mg, 1 mmol) in dry DMF (5 mL) was added DIPEA (0.35 mL, 2 mmol), HOBt (157 mg, 1 mmol) and EDC (230 mg, 2.4 mmol). The reaction mixture was stirred at room temperature and di-tert-butyl (5-aminopentane-1,4-diyl)(S)-dicarbamate (intermediate B) (317 mg, 1 mmol) was added. The reaction mixture was stir at room temperature overnight. Then it was diluted with EtOAc and washed with water and brine. The organic layer was dried over anhydrous sodium sulfate and filtered. The filtrate was concentrated under reduced pressure and purified by column chromatography on silica gel with 40-60% ethyl acetate in hexanes to give the desired product (340 mg, 57% yield) as a yellow solid.

Step 2)

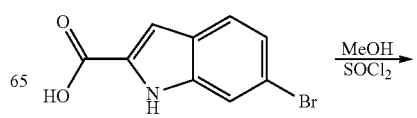

Di-tert-butyl (5-(6-(4-nitrophenyl)-1H-indole-2-carboxamido)pentane-1,4-diyl)(S)-dicarbamate The mixture of di-tert-butyl (5-(6-bromo-1H-indole-2-carboxamido)pentane-1,4-diyl)(S)-dicarbamate (108 mg, 0.2 mmol), 4,4,5,5-tetramethyl-2-(4-nitrophenyl)-1,3,2-dioxaborolane (100 mg, 0.4 mmol), KF (47 mg, 0.8 mmol) in dioxane (10 mL) was degassed and Pd(dppf)$_2$Cl$_2$ (50 mg, 0.06 mmol) was added. The mixture was heated at 100° C. overnight and it was concentrated under reduced pressure and purified by column chromatography on silica gel (50-80% ethyl acetate/hexanes) to give the desired product (36 mg, 31% yield) as a brown powder.

Example 6. Preparation of N-((2S)-2,5-diamino-6-methylheptyl)-6-(4-fluorophenyl)-1H-indole-2-carboxamide dihydrochloride

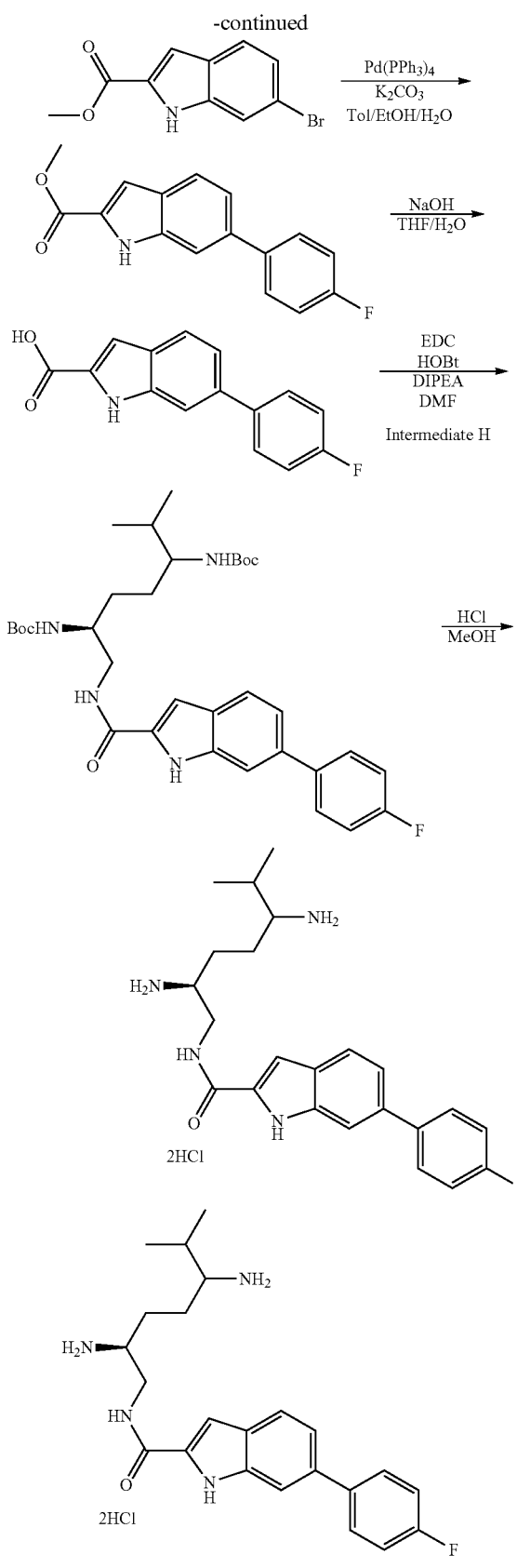

N-((2S)-2,5-Diamino-6-methylheptyl)-6-(4-fluorophenyl)-1H-indole-2-carboxamide dihydrochloride To a solution of di-tert-butyl ((2S)-1-(6-(4-fluorophenyl)-1H-indole-2-carboxamido)-6-methylheptane-2,5-diyl)dicarbamate (32 mg, 0.05 mmol) in MeOH (3 mL) was added HCl in dioxane (4M, 0.15 mL, 0.6 mmol). The reaction mixture was stirred at room temperature overnight. TLC showed no starting material left. The reaction mixture was concentrated under reduced pressure and triturated with EtOAc to afford the desired product (23 mg, 86% yield) as an off-white solid. $^1$H NMR (300 MHz, CD$_3$OD) δ 7.74 (m, 1H), 7.72 (m, 2H), 7.54 (m, 1H), 7.51 (m, 1H), 7.22 (m, 3H), 3.61 (m, 2H), 3.47 (m, 1H), 3.06 (m, 1H), 2.05-1.70 (m, 4H), 0.99 (t, J=5.1 Hz, 6H). MS (ESI+): 397.25 [M+H]$^+$ for C$_{23}$H$_{29}$FN$_4$O.

The requisite intermediates were prepared as shown in the following steps.

Step 1)

Methyl 6-bromo-1H-indole-2-carboxylate

To a suspension of 6-bromo-1H-indole-2-carboxylic acid (5.0 g, 20.8 mmol) in MeOH (100 mL) was added SOCl$_2$ (2.26 mL, 31 mmol) very slowly. The mixture was heated under reflux until TLC showed no starting material left. Solvent was removed under reduced pressure and the crude product was collected as a brown powder (5.2 g, 98% yield) after drying. It was used for next step reaction without purification. $^1$H NMR (300 MHz, CDCl$_3$) δ 8.88 (br, 1H), 7.59 (s, 1H), 7.55 (d, J=6 Hz, 1H), 7.25 (m, 1H), 7.19 (s, 1H), 3.96 (s, 3H).

Step 2)

Methyl 6-(4-fluorophenyl)-1H-indole-2-carboxylate

The mixture of methyl 6-bromo-1H-indole-2-carboxylate (510 mg, 2 mmol), (4-fluorophenyl)boronic acid (520 mg, 4 mmol) in a mixture of toluene, ethanol and sat. NaHCO$_3$ solution (18/2/2 mL) was degassed and Pd(PPh$_3$)$_4$ (90 mg, 0.08 mmol) was added. The reaction mixture was heated at 100° C. overnight and it was extracted with EtOAc and washed with brine and concentrated under reduced pressure. The residue was purified by column chromatography on silica gel (10-30% ethyl acetate/hexanes) to give the desired product (390 mg, 72% yield) as an off-white powder. $^1$H NMR (300 MHz, CDCl$_3$) δ 8.94 (br, 1H), 7.74 (d, J=8.4 Hz, 1H), 7.62 (m, 3H), 7.36 (d, J=8.4 Hz, 1H), 7.24 (m, 1H), 7.15 (m, 2H), 3.96 (s 3H).

Step 3)

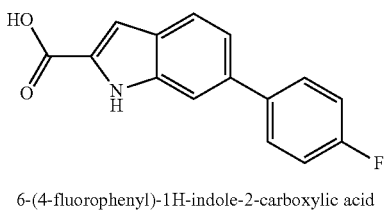 [SMILES: O=C(O)c1cc2ccc(-c3ccc(F)cc3)cc2[nH]1]

6-(4-fluorophenyl)-1H-indole-2-carboxylic acid

To a solution of methyl 6-(4-fluorophenyl)-1H-indole-2-carboxylate (0.35 g, 1.3 mmol) in THF was added NaOH solution (2 M, 5 mL). It was stirred at room temperature until no starting material left. THF was removed under reduced pressure and the residue was acidified with HCl solution. The precipitate was filtered and washed with water. It was dried to provide the product as an off-white powder (290 mg, 88% yield) which was used for next step reaction without further purification. $^1$H NMR (300 MHz, CDCl$_3$) δ 11.48 (br, 1H), 7.68 (s, 1H), 7.65 (m, 1H), 7.64 (m, 1H), 7.60 (m, 1H), 7.55 (d, J=8.4 Hz, 1H), 7.26 (m, 1H), 7.19 (m, 1H), 6.66 (s, 1H). MS (ESI−): 254.05 [M−H]$^-$ for C$_{15}$H$_{10}$FNO$_2$.

Step 4)

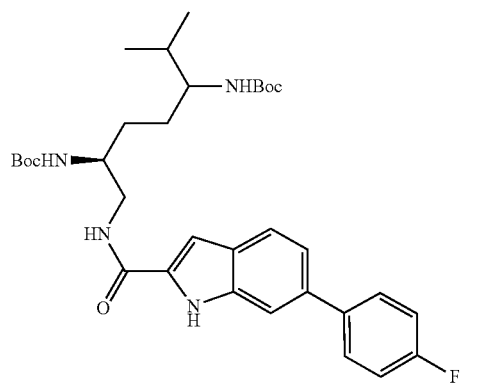

Di-tert-butyl ((2S)-1-(6-(4-fluorophenyl)-1H-indole-2-carboxamido)-6-methylheptane-2,5-diyl)dicarbamate To a solution of 6-(4-fluorophenyl)-1H-indole-2-carboxylic acid (26 mg, 0.1 mmol) in dry DMF (1 mL) was added DIPEA (0.018 mL, 0.1 mmol), HOBt (16 mg, 0.1 mmol) and EDC (23 mg, 0.12 mmol). The reaction mixture was stirred at room temperature and di-tert-butyl ((2S)-1-amino-6-methylheptane-2,5-diyl)dicarbamate (Intermediate H) (36 mg, 0.1 mmol) was added. The reaction mixture was stirred at room temperature overnight. Then it was diluted with EtOAc and washed with water and brine. The organic layer was dried over anhydrous sodium sulfate and filtered. The filtrate was concentrated under reduced pressure and purified by column chromatography on silica gel with 30-40% ethyl acetate in hexanes to give the desired product (32 mg, 54% yield) as a white solid. $^1$H NMR (300 MHz, CDCl$_3$) δ 9.17 (br, 1H), 7.69 (m, 1H), 7.60 (m, 3H), 7.34 (m, 1H), 7.15 (m, 2H), 6.92 (m, 1H), 4.93 (br, 1H), 4.73 (br, 1H), 4.35 (m, 1H), 3.84 (m, 1H), 3.49 (m, 2H), 1.66 (m, 5H), 1.58 (s, 9H), 1.42 (s, 9H), 0.90 (t, J=4.5 Hz, 6H).

Example 7. Preparation of (S)—N-(2,5-diaminopentyl)-6-(4-fluorophenyl)-1H-indole-2-carboxamide dihydrochloride

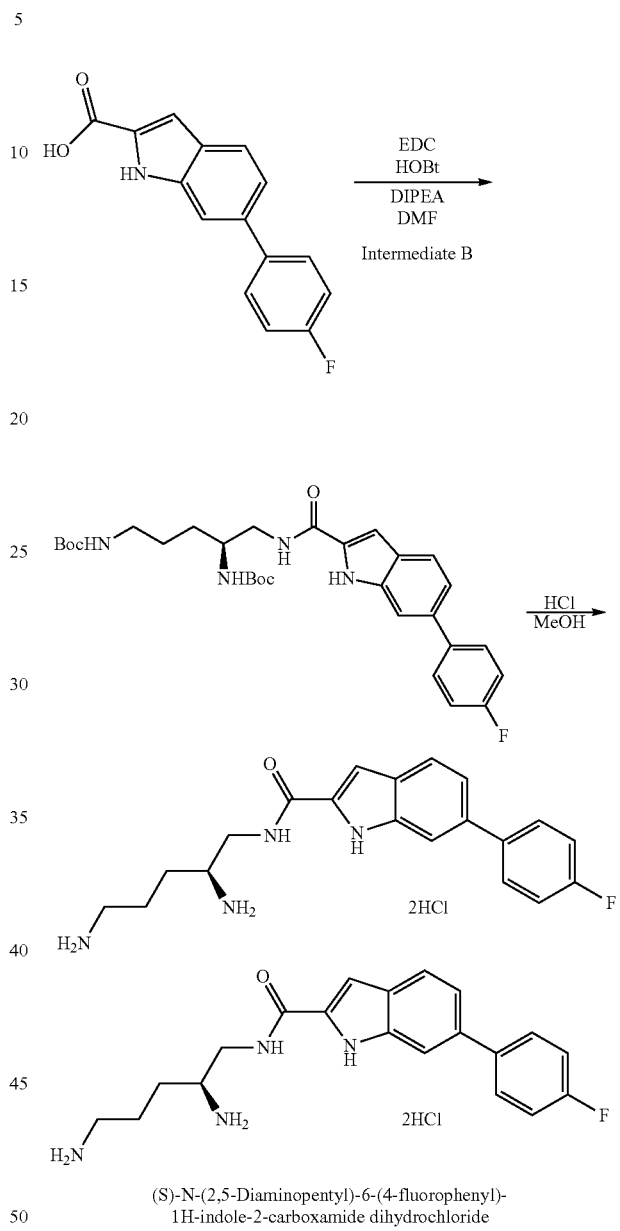

(S)-N-(2,5-Diaminopentyl)-6-(4-fluorophenyl)-1H-indole-2-carboxamide dihydrochloride To a solution of di-tert-butyl (5-(6-(4-fluorophenyl)-1H-indole-2-carboxamido)pentane-1,4-diyl)(S)-dicarbamate (25 mg, 0.045 mmol) in MeOH (10 mL) was added HCl in solution (4 M in dioxane, 0.2 mL). It was stirred at room temperature overnight and solvent was removed under reduced pressure. The residue was triturated with EtOAc and the precipitate was collected as an off-white powder (15 mg, 70% yield). $^1$H NMR (300 MHz, CD$_3$OD) δ 7.69 (d, J=8.4 Hz, 1H), 7.67 (m, 1H), 7.66 (m, 2H), 7.34 (dd, J=1.8, 8.4 Hz, 1H), 7.21 (s, 1H), 7.16 (t, J=8.7 Hz, 2H), 3.76 (m, 1H), 3.62 (m, 1H), 3.50 (m, 1H), 3.02 (m, 2H), 1.87 (m, 4H). MS (ESI+): 355.20 [M+H]$^+$ for C$_{20}$H$_{23}$FN$_4$O.

The requisite intermediate was prepared as shown in the following paragraph.

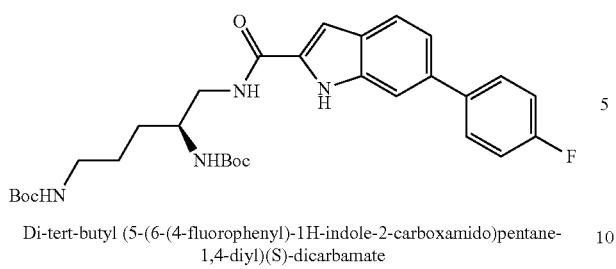

Di-tert-butyl (5-(6-(4-fluorophenyl)-1H-indole-2-carboxamido)pentane-1,4-diyl)(S)-dicarbamate To a solution of 6-(4-fluorophenyl)-1H-indole-2-carboxylic acid (60 mg, 0.24 mmol) in anhydrous DMF (2 mL) was added DIPEA (0.09 mL, 0.5 mmol), HOBt (22 mg, 0.18 mmol) and EDC (45 mg, 0.24 mmol). The reaction mixture was stirred at room temperature and di-tert-butyl (5-aminopentane-1,4-diyl)(S)-dicarbamate (76 mg, 0.24 mmol) was added. The reaction mixture was stirred at room temperature overnight. Then it was diluted with EtOAc and washed with water and brine. The organic layer was dried over anhydrous sodium sulfate and filtered. The filtrate was concentrated under reduced pressure and the residue purified by column chromatography on silica gel (40-60% ethyl acetate/hexanes) to give the product (75 mg, 57% yield) as a white solid. $^1$H NMR (300 MHz, CD$_3$OD) δ 7.57 (m, 1H), 7.48 (m, 2H), 7.33 (m, 1H), 7.18 (d, J=8.1 Hz, 1H), 6.99 (t, J=8.1 Hz, 2H), 6.92 (s, 1H), 5.78 (br, 1H), 3.57 (m, 1H), 3.30 (m, 2H), 2.95 (m, 2H), 1.43 (m, 4H), 1.28 (s, 9H), 1.24 (s, 9H).

Example 8. Preparation of (S)—N-(2,5-diaminopentyl)-6-(4-fluorophenyl)-1-methyl-1H-indole-2-carboxamide dihydrochloride

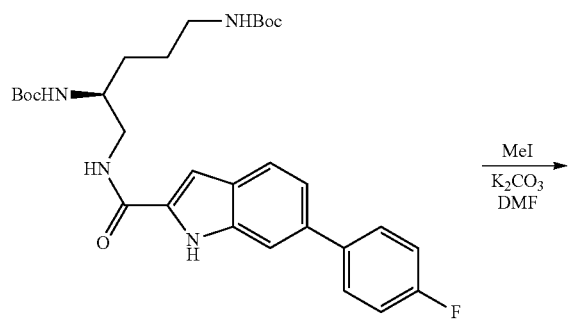

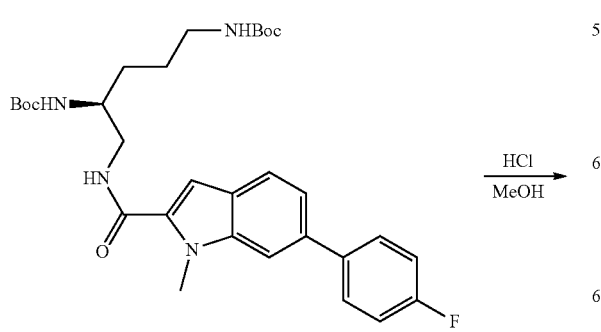

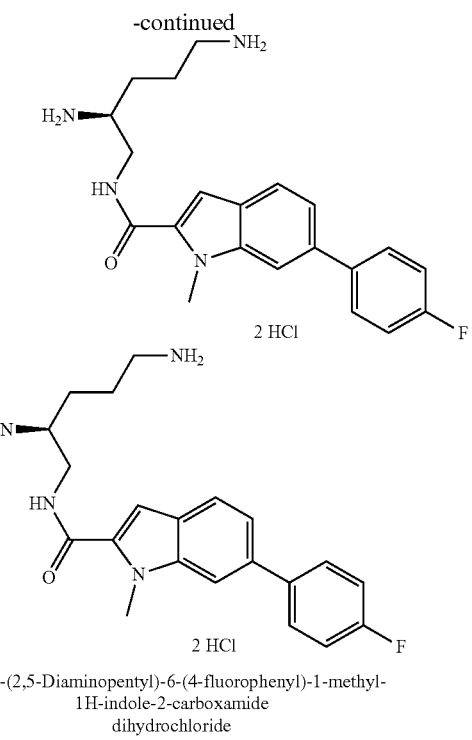

(S)-N-(2,5-Diaminopentyl)-6-(4-fluorophenyl)-1-methyl-1H-indole-2-carboxamide dihydrochloride To a solution of di-tert-butyl (5-(6-(4-fluorophenyl)-1-methyl-1H-indole-2-carboxamido)pentane-1,4-diyl)(S)-dicarbamate (20 mg, 0.045 mmol) in MeOH (2 mL) was added HCl in solution (4 M in dioxane, 0.1 mL). The reaction mixture was stirred at room temperature overnight. Solvent was removed under reduced pressure. The residue was triturated with EtOAc and the precipitate was collected as an off-white powder (12 mg, 78% yield). $^1$H NMR (300 MHz, CD$_3$OD) δ 7.72 (m, 1H), 7.67 (m, 3H), 7.38 (dd, J=1.2, 11.1 Hz, 1H), 7.22 (s, 1H), 7.19 (t, J=8.7 Hz, 2H), 4.10 (s, 3H), 3.71 (m, 1H), 3.62 (m, 1H), 3.51 (m, 1H), 3.03 (m, 2H), 2.00-1.72 (m, 4H).

The requisite intermediate was prepared as shown in the following paragraph.

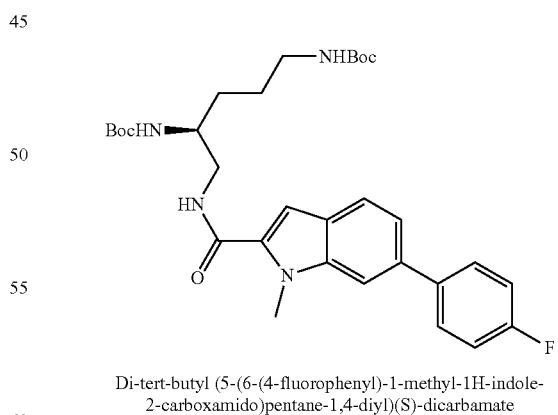

Di-tert-butyl (5-(6-(4-fluorophenyl)-1-methyl-1H-indole-2-carboxamido)pentane-1,4-diyl)(S)-dicarbamate To a solution of di-tert-butyl (5-(6-(4-fluorophenyl)-1H-indole-2-carboxamido)pentane-1,4-diyl)(S)-dicarbamate (28 mg, 0.05 mmol) and potassium carbonate (20 mg, 0.15 mmol) in anhydrous DMF (2 mL) was added MeI (57 mg, 0.4 mmol). It was heated at 55° C. for 3 hours and TLC showed no starting material left. The reaction mixture was diluted with EtOAc and washed with water and brine. The combined organic phase was dried, concentrated under reduced pressure and purified by column chromatography on silica gel chromatography to afford the desired product (22 mg, 77% yield) as a white powder. $^1$H NMR (300 MHz, CDCl$_3$) δ 7.65 (m, 1H), 7.62 (m, 2H), 7.49 (s, 1H), 7.33 (d, J=11.1 Hz, 1H), 7.17 (m, 2H), 6.93 (s, 1H), 4.79 (br, 1H), 4.64 (br, 1H), 4.09 (s, 3H), 3.83 (m, 1H), 3.49 (m, 2H), 3.16 (m, 2H), 1.62 (m, 4H), 1.43 (s, 18H).

Example 9. Preparation of (S)—N-(2,5-diaminopentyl)-1-(4-fluorobenzyl)-6-(4-fluorophenyl)-1H-indole-2-carboxamide dihydrochloride

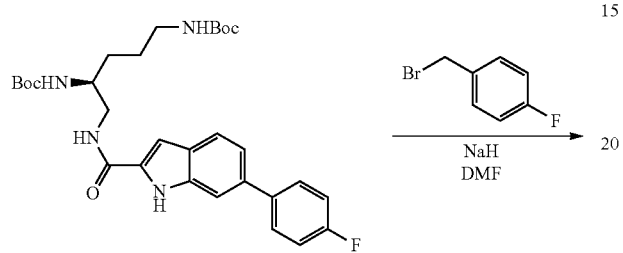

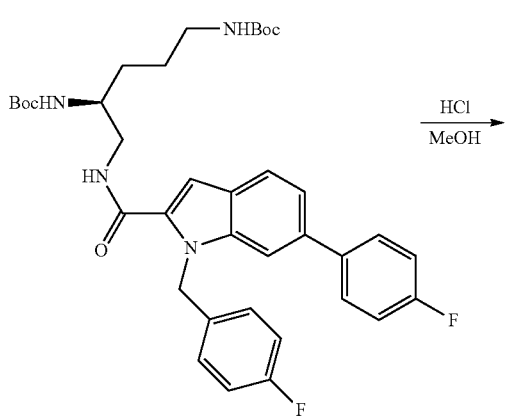

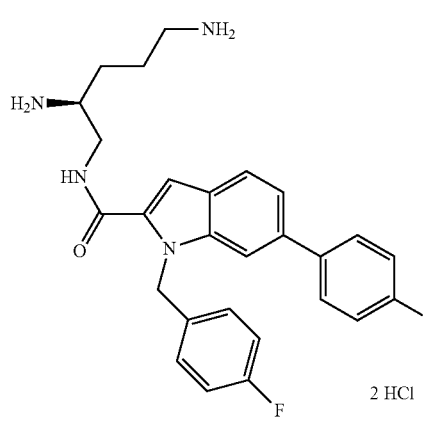

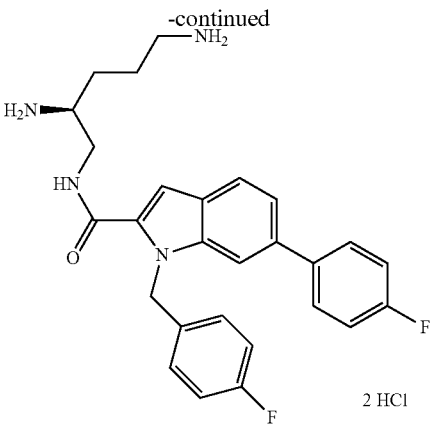

(S)-N-(2,5-Diaminopentyl)-1-(4-fluorobenzyl)-6-(4-fluorophenyl)-1H-indole-2-carboxamide dihydrochloride To a solution of di-tert-butyl (5-(1-(4-fluorobenzyl)-6-(4-fluorophenyl)-1H-indole-2-carboxamido)pentane-1,4-diyl)(S)-dicarbamate (15 mg, 0.0 mmol) in MeOH (3 mL) was added HCl in solution (4 M in dioxane, 0.1 mL). It was stirred at room temperature overnight and solvent was removed under reduced pressure. The residue was triturated with EtOAc and the precipitate was collected as an off-white powder (9.5 mg, 76% yield). $^1$H NMR (300 MHz, CD$_3$OD) δ 7.72 (d, J=8.1 Hz, 1H), 7.60 (m, 2H), 7.58 (s, 1H), 7.39 (dd, J=1.2, 11.1 Hz, 1H), 7.32 (s, 1H), 7.15 (m, 4H), 6.98 (m, 2H), 5.91 (s, 2H), 3.66 (m, 1H), 3.59 (m, 1H), 3.45 (m, 1H), 2.98 (m, 2H), 1.84 (m, 2H), 1.73 (m, 2H). MS (ESI+): 463.25 [M+H]$^+$ for C$_{27}$H$_{28}$F$_2$N$_4$O.

The requisite intermediate was prepared as shown in the following paragraph.

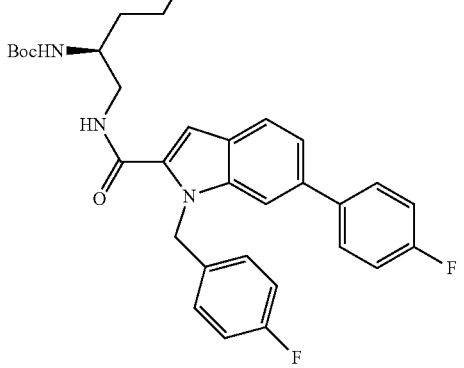

Di-tert-butyl (5-(1-(4-fluorobenzyl-6-(4-fluorophenyl)-1H-indole-2-carboxamido)pentane-1,4-diyl)(S)-dicarbamate To a solution of di-tert-butyl (5-(6-(4-fluorophenyl)-1H-indole-2-carboxamido)pentane-1,4-diyl)(S)-dicarbamate (20 mg, 0.036 mmol) and 1-(bromomethyl)-4-fluorobenzene (10 mg, 0.053 mmol) in anhydrous DMF (2 mL) was added NaH (60%, 2 mg, 0.05 mmol) at 0° C. The reaction mixture was stirred at room temperature and TLC showed a new spot formed. The reaction mixture was diluted with EtOAc and washed with NH$_4$Cl solution and brine. The combined organic phase was dried, concentrated under reduced pressure and purified by column chromatography on silica gel chromatography to afford the desired product (19 mg, 80% yield) as a white powder. ¹H NMR (300 MHz, CDCl₃) δ 8.71 (br, 1H), 7.68 (d, J=8.1 Hz, 1H), 7.54 (m, 2H), 7.42 (s, 1H), 7.33 (dd, J=1.2, 11.1 Hz, 1H), 7.10 (m, 4H), 7.02 (s, 1H), 6.93 (m, 2H), 5.83 (m, 2H), 4.72 (br, 1H), 4.59 (br, 1H), 3.80 (br, 1H), 3.45 (m, 2H), 3.14 (m, 2H), 1.60 (m, 4H), 1.43 (m, 18H).

Example 10. Preparation of N-((2S)-2,5-diamino-6-methylheptyl)-5-(4-fluorophenyl)-1H-indole-2-carboxamide dihydrochloride

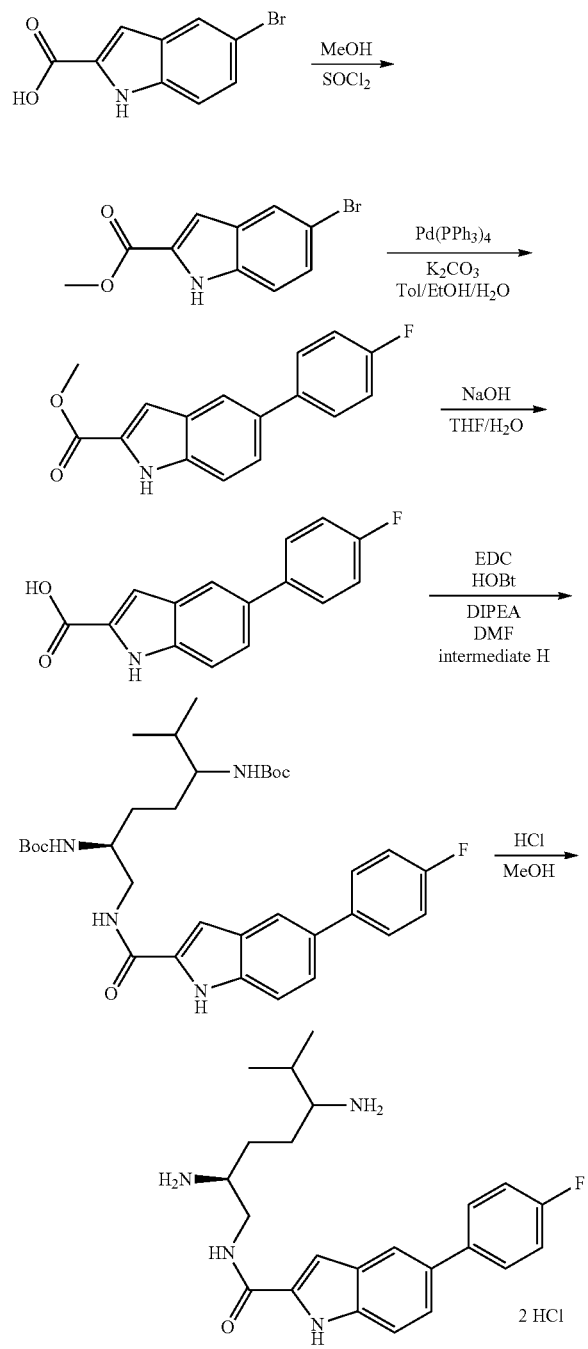

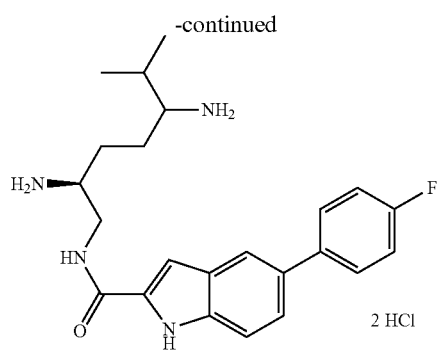

N-((2S)-2,5-Diamino-6-methylheptyl)-5-(4-fluorophenyl)-1H-indole-2-carboxamide dihydrochloride To a solution of di-tert-butyl ((2S)-1-(6-(4-fluorophenyl)-1H-indole-2-carboxamido)-6-methylheptane-2,5-diyl)dicarbamate (14 mg, 0.05 mmol) in MeOH (2 mL) and dioxane (2 mL) was added HCl in dioxane (4M, 0.1 mL, 0.4 mmol). The reaction mixture was stirred at room temperature overnight. TLC showed no starting material left. It was concentrated under reduced pressure and triturated with EtOAc to afford the desired product (10 mg, 86% yield) as off-white solid. ¹H NMR (300 MHz, CD₃OD) δ 8.77 (br, 1H), 7.82 (s, 1H), 7.62 (m, 2H), 7.50 (m, 2H), 7.28 (d, J=6.3 Hz, 1H), 7.15 (t, J=8.1 Hz, 2H), 3.70 (m, 2H), 3.49 (m, 1H), 3.12 (m, 1H), 2.10-1.80 (m, 4H), 1.05 (t, J=5.1 Hz, 6H). MS (ESI+): 397.20 [M+H]⁺ for C₂₃H₂₉FN₄O.

The requisite intermediates were prepared as shown in the following paragraphs.

Step 1)

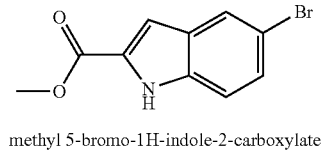

methyl 5-bromo-1H-indole-2-carboxylate

To a suspension of 5-bromo-1H-indole-2-carboxylic acid (1.5 g, 6.3 mmol) in MeOH (50 mL) was added SOCl₂ (0.91 mL, 12.6 mmol) very slowly. The mixture was heated under reflux until TLC showed no starting material left. Solvent was removed under reduced pressure and the crude product was collected as a brown powder (1.5 g, 95% yield) after drying and used without purification. ¹H NMR (300 MHz, CDCl₃) δ 8.88 (br, 1H), 7.84 (s, 1H), 7.59 (dd, J=1.8, 8.7 Hz, 1H), 7.31 (dd, J=1.8, 8.7 Hz), 7.19 (s, 1H), 3.96 (s, 3H).

Step 2)

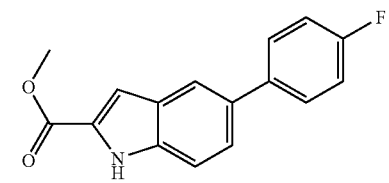

Methyl 5-(4-fluorophenyl)-1H-indole-2-carboxylate

The mixture of methyl 5-bromo-1H-indole-2-carboxylate (700 mg, 2.76 mmol), (4-fluorophenyl)boronic acid (770 mg, 5.5 mmol) in a mixture of toluene, ethanol and sat. NaHCO₃ solution (18/2/2 mL) was degassed and Pd(PPh₃)₄ (110 mg, 0.1 mmol) was added. The mixture was heated at 100° C. overnight and it was extracted with EtOAc and washed with brine and concentrated under reduced pressure. Then it was purified by column chromatography on silica gel (10-30% ethyl acetate/hexanes) to give the desired product (550 mg, 78% yield) as an off-white powder. $^1$H NMR (300 MHz, CDCl₃) δ 7.84 (s, 1H), 7.58 (m, 2H), 7.49 (m, 1H), 7.32 (m, 2H), 7.14 (m, 2H), 3.96 (s, 3H).

Step 3)

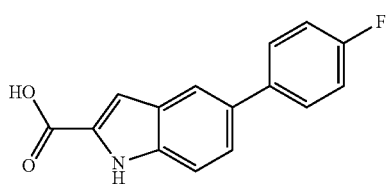

5-(4-fluorophenyl)-1H-indole-2-carboxylic acid

To a solution of methyl 5-(4-fluorophenyl)-1H-indole-2-carboxylate (0.4 g, 1.5 mmol) in THF was added NaOH solution (2 M, 5 mL). It was heated at room temperature until no starting material left. THF was removed under reduced pressure and the residue was acidified with HCl solution. The precipitate was filtered and washed with water. It was dried to provide the product as off-white powder (325 mg, 85% yield) which was used for next step reaction without further purification. MS (ESI–): 509.00 [2M–H]⁻ for C₁₅H₁₀FNO₂.

Step 4)

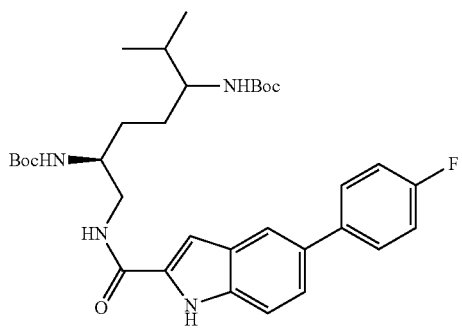

Di-tert-butyl ((2S)-1-(5-(4-fluorophenyl)-1H-indole-2-carboxamido)-6-methylheptane-2,5-diyl)dicarbamate To a solution of 5-(4-fluorophenyl)-1H-indole-2-carboxylic acid (13 mg, 0.05 mmol) in dry DMF (0.5 mL) was added DIPEA (0.008 mL, 0.05 mmol), HOBt (8 mg, 0.05 mmol) and EDC (12 mg, 0.06 mmol). The reaction mixture was stirred at room temperature and di-tert-butyl ((2S)-1-amino-6-methylheptane-2,5-diyl)dicarbamate (intermediate H) (18 mg, 0.05 mmol) was added. The reaction mixture was stirred at room temperature overnight. Then it was diluted with EtOAc and washed with water and then brine. The organic layer was dried over anhydrous sodium sulfate and filtered. The filtrate was concentrated under reduced pressure and purified by column chromatography on silica gel with 30-40% ethyl acetate in hexanes to give the desired product (17 mg, 57% yield) as a white solid. $^1$H NMR (300 MHz, CDCl₃) δ 7.82 (s, 1H), 7.49 (m, 2H), 7.40 (s, 2H), 7.04 (m, 3H), 5.73 (br, 1H), 5.55 (br, 1H), 4.90 (br, 1H), 3.60 (m, 2H), 3.35 (m, 2H), 1.59 (m, 5H), 1.31 (m, 18H), 0.80 (t, J=4.5 Hz, 6H).

Example 11. Preparation of (S)—N-(2,5-diaminopentyl)-6-(3,4-difluorophenyl)-1H-indole-2-carboxamide dihydrochloride

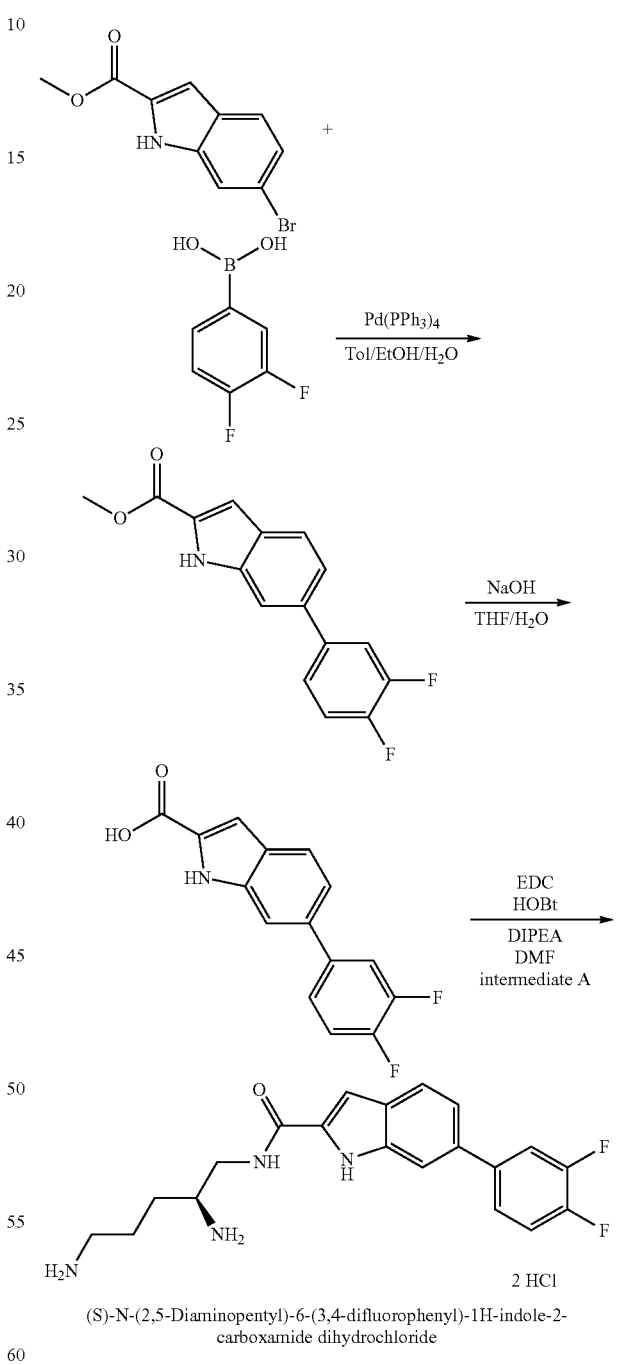

(S)-N-(2,5-Diaminopentyl)-6-(3,4-difluorophenyl)-1H-indole-2-carboxamide dihydrochloride To a solution of dibenzyl (5-(6-(3,4-difluorophenyl)-1H-indole-2-carboxamido)pentane-1,4-diyl)(S)-dicarbamate (32 mg, 0.05 mmol) in MeOH (5 mL) was added Pd/C (10%, 10 mg). The reaction mixture was stirred under H₂ overnight. The reaction mixture was filtered through a Celite pad and washed with methanol, then concentrated under reduced pressure. To the residue was added HCl in solution (4 M in dioxane, 0.05 mL). The solution was stirred at room temperature and solvent was removed under reduced pressure. The residue was triturated with EtOAc and the precipitate was collected as an off-white powder (15 mg, 67% yield). $^1$H NMR (300 MHz, CD$_3$OD) δ 8.78 (br, 1H), 7.69 (m, 2H), 7.57 (m, 1H), 7.45 (m, 1H), 7.35 (m, 2H), 7.23 (s, 1H), 3.72 (m, 1H), 3.65 (m, 1H), 3.49 (m, 1H), 3.06 (m, 2H), 2.00-1.65 (m, 4H). MS (ESI+): 373.15 [M+H]$^+$ for C$_{20}$H$_{22}$F$_2$N$_4$O.

The requisite intermediates were prepared as shown in the following paragraphs.

Step 1)

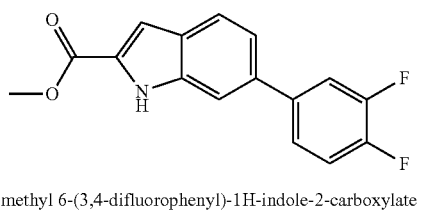 [SMILES: COC(=O)c1cc2ccc(-c3ccc(F)c(F)c3)cc2[nH]1]

methyl 6-(3,4-difluorophenyl)-1H-indole-2-carboxylate

The mixture of methyl 6-bromo-1H-indole-2-carboxylate (254 mg, 1 mmol), (3,4-difluorophenyl)boronic acid (316 mg, 2 mmol) in a mixture of toluene, ethanol and sat. NaHCO$_3$ solution (10/4/4 mL) was degassed and Pd(PPh$_3$)$_4$ (100 mg, 0.09 mmol) was added. The mixture was heated at 100° C. overnight. The cooled reaction mixture was extracted with EtOAc and washed with brine and concentrated under reduced pressure. The residue was purified by column chromatography on silica gel (10-25% ethyl acetate/hexanes) to give the desired product (140 mg, 50% yield) as an off-white powder. $^1$H NMR (300 MHz, CDCl$_3$) δ 8.89 (br, 1H), 7.73 (d, J=8.4 Hz, 1H), 7.54 (s, 1H), 7.42 (m, 2H), 7.35 (m, 3H), 3.96 (s, 3H). MS (ESI-): 286.00 [M-H]$^-$ for C$_{16}$H$_{11}$F$_2$NO$_2$.

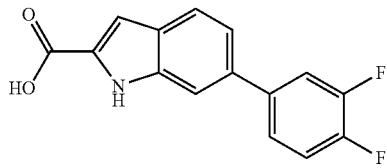

6-(3,4-Difluorophenyl)-1H-indole-2-carboxylic acid

Step 2)

To a solution of methyl 6-(3,4-difluorophenyl)-1H-indole-2-carboxylate (144 mg, 0.5 mmol) in THF (10 mL) was added NaOH solution (2 M, 2.5 mL). The reaction mixture was heated at 50° C. until no starting material left. THF was removed under reduced pressure and the residue was acidified with HCl. The precipitate was filtered and washed with water. It was dried to provide the product as an off-white powder (112 mg, 82% yield) and used for next step reaction without further purification. $^1$H NMR (300 MHz, DMSO-d$_3$) δ 11.14 (br, 1H), 7.66 (m, 2H), 7.57 (s, 1H), 7.47 (m, 2H), 7.28 (dd, J=1.5, 8.4 Hz, 1H), 6.63 (s, 1H). MS (ESI-): 272.00 [M-H]$^-$ for C$_{15}$H$_9$F$_2$NO$_2$.

Step 3)

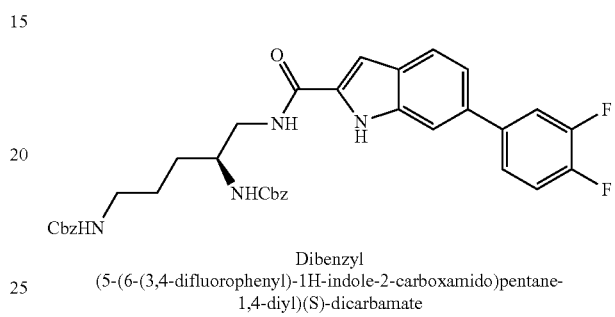

Dibenzyl (5-(6-(3,4-difluorophenyl)-1H-indole-2-carboxamido)pentane-1,4-diyl)(S)-dicarbamate To a solution of 6-(3,4-difluorophenyl)-1H-indole-2-carboxylic acid (27 mg, 0.1 mmol) in dry DMF (1 mL) was added DIPEA (0.04 mL, 0.2 mmol), HOBt (15 mg, 0.1 mmol) and EDC (19 mg, 0.1 mmol). The reaction mixture was stirred at room temperature and dibenzyl (5-aminopentane-1,4-diyl)-(S)-dicarbamate (intermediate A) (39 mg, 0.1 mmol) was added. The reaction mixture was stirred at room temperature overnight. It was diluted with EtOAc and washed with water and then brine. The organic layer was dried over anhydrous sodium sulfate and filtered. The filtrate was concentrated under reduced pressure and purified by column chromatography on silica gel to give the desired product (32 mg, 49% yield) as a white solid. $^1$H NMR (300 MHz, CDCl$_3$) δ 9.16 (br, 1H), 7.71 (m, 2H), 7.55 (m, 1H), 7.47 (m, 1H), 7.35 (m, 2H), 7.27 (m, 10H), 6.89 (m, 1H), 5.09 (m, 4H), 4.91 (m, 1H), 3.88 (br, 1H), 3.55 (m, 2H), 3.24 (m, 2H), 1.63 (m, 4H). MS (ESI+): 663.20 [M+Na]$^+$ for C$_{36}$H$_{34}$F$_2$N$_4$O$_5$.

Example 12. Preparation of (S)-6-(4-(tert-butyl)phenyl)-N-(2,5-diaminopentyl)-1H-indole-2-carboxamide dihydrochloride

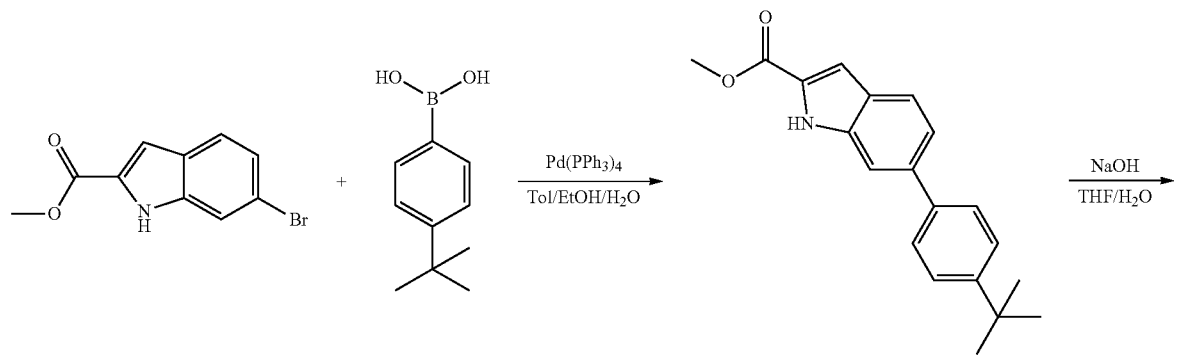

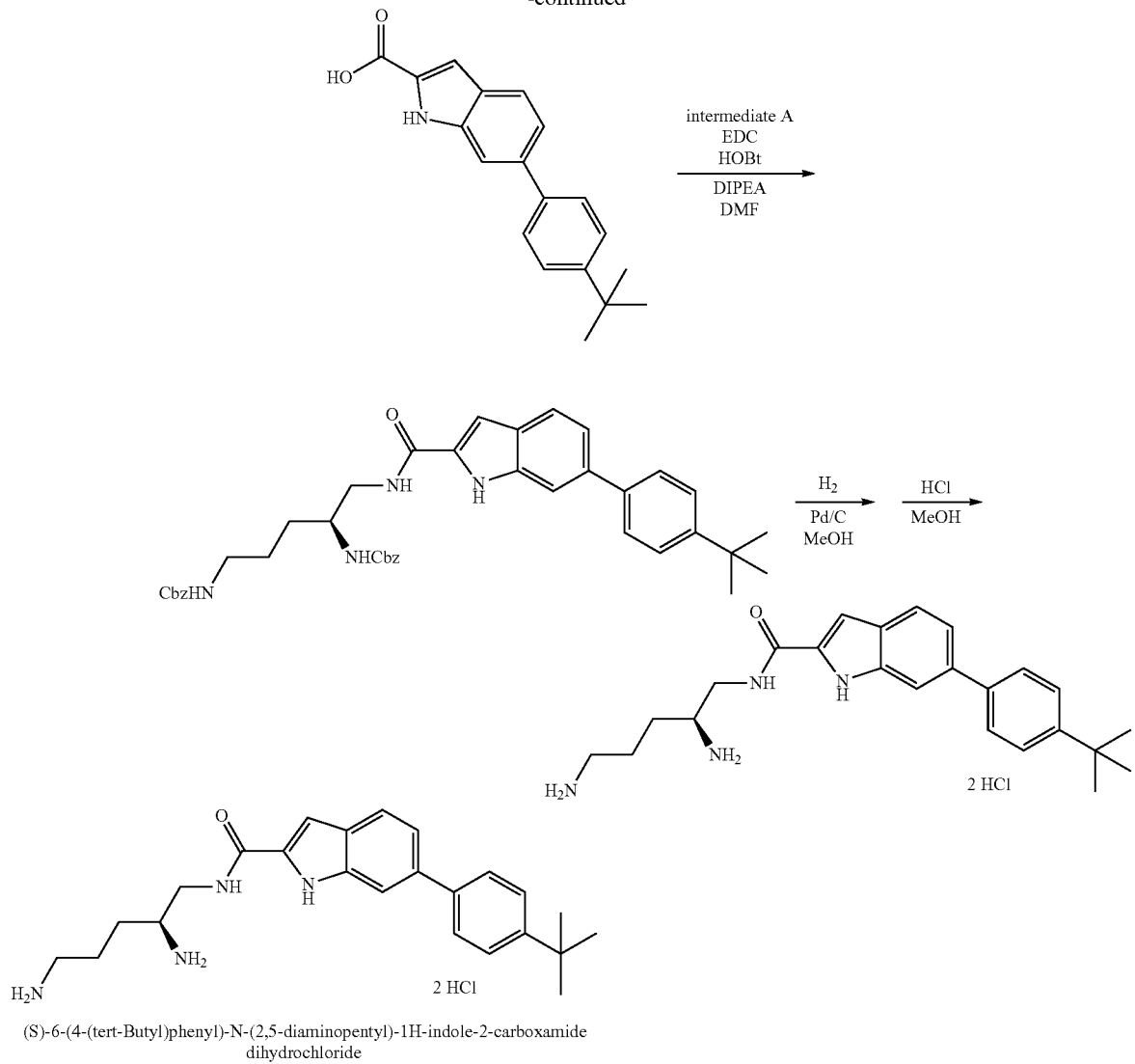

(S)-6-(4-(tert-Butyl)phenyl)-N-(2,5-diaminopentyl)-1H-indole-2-carboxamide dihydrochloride To a solution of dibenzyl (5-(6-(4-(tert-butyl)phenyl)-1H-indole-2-carboxamido)pentane-1,4-diyl)(S)-dicarbamate (44 mg, 0.066 mmol) in MeOH (5 mL) was added Pd/C (10%, 15 mg). The reaction mixture was stirred under $H_2$ overnight. It was filtered through a Celite pad and washed with methanol, then concentrated under reduced pressure and HCl in solution (4 M in dioxane, 0.1 mL) was added. The solution was stirred at room temperature and solvent was removed under reduced pressure. The residue was triturated with EtOAc and the precipitate was collected as an off-white powder (26 mg, 85% yield). $^1$H NMR (300 MHz, $CD_3OD$) δ 7.68 (s, 1H), 7.67 (m, 1H), 7.58 (d, J=8.4 Hz, 2H), 7.45 (d, J=8.4 Hz, 2H), 7.37 (d, J=8.4 Hz, 1H), 7.24 (s, 1H), 3.75 (m, 1H), 3.64 (m, 1H), 3.50 (m, 1H), 3.01 (m, 2H), 1.87 (m, 4H), 1.36 (s, 9H). MS (ESI+): 393.20 [M+H]$^+$ for $C_{24}H_{32}N_4O$.

The requisite intermediates were prepared as shown in the following paragraphs.

Step 1)

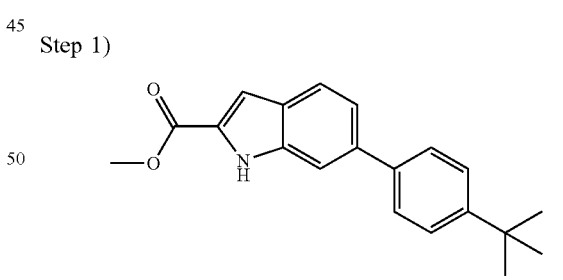

Methyl 6-(4-(tert-butyl)phenyl)-1H-indole-2-carboxylate

The mixture of methyl 6-bromo-1H-indole-2-carboxylate (254 mg, 1 mmol), (4-(tert-butyl)phenyl)boronic acid (356 mg, 2 mmol) in a mixture of toluene, ethanol and sat. $NaHCO_3$ solution (10/4/4 mL) was degassed and Pd(PPh$_3$)$_4$ (100 mg, 0.09 mmol) was added. The mixture was heated at 100° C. overnight and it was extracted with EtOAc and washed with brine and the organic layer concentrated under reduced pressure. Then it was purified by column chromatography on silica gel using 10-30% ethyl acetate in hexanes to give the product (220 mg, 72% yield) as an off-white powder. $^1$H NMR (300 MHz, CDCl$_3$) δ 8.63 (br, 1H), 7.73

(d, J=8.4 Hz, 1H), 7.59 (m, 2H), 7.50 (s, 1H), 7.47 (d, J=9 Hz, 1H), 7.42 (dd, J=1.5, 8.4 Hz, 1H), 7.24 (m, 2H), 3.95 (s, 3H), 1.37 (s, 9H).

MS (ESI−): 306.10 [M−H]− for $C_{20}H_{21}NO_2$.

Step 2)

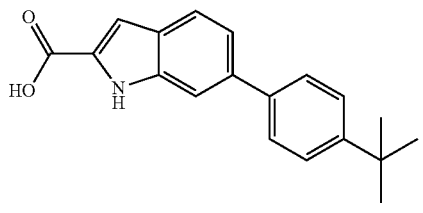

6-(4-(tert-butyl)phenyl)-1H-indole-2-carboxylic acid

To a solution of methyl 6-(4-(tert-butyl)phenyl)-1H-indole-2-carboxylate (220 mg, 0.72 mmol) in THF (10 mL) was added NaOH solution (2 M, 3 mL). The reaction mixture was heated at 50° C. until no starting material left. THF was removed under reduced pressure and the residue was acidified with HCl. The precipitate was filtered and washed with water. It was dried to provide the product as an off-white powder (200 mg, 95% yield) and used for next step reaction without further purification. $^1$H NMR (300 MHz, DMSO-$d_6$) δ 11.21 (br, 1H), 7.58 (m, 2H), 7.56 (m, 2H), 7.44 (m, 2H), 7.24 (d, J=8.4 Hz, 1H), 6.72 (s, 1H), 1.30 (s, 9H). MS (ESI−): 292.10 [M−H]− for $C_{19}H_{19}NO_2$.

Step 3)

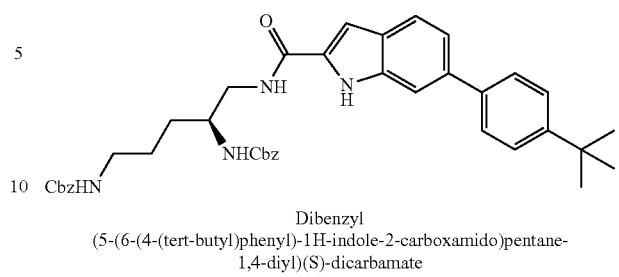

Dibenzyl (5-(6-(4-(tert-butyl)phenyl)-1H-indole-2-carboxamido)pentane-1,4-diyl)(S)-dicarbamate To a solution of 6-(4-(tert-butyl)phenyl)-1H-indole-2-carboxylic acid (29 mg, 0.1 mmol) in dry DMF (1 mL) was added DIPEA (0.04 mL, 0.2 mmol), HOBt (15 mg, 0.1 mmol) and EDC (19 mg, 0.1 mmol). The reaction mixture was stirred at room temperature and dibenzyl (5-aminopentane-1,4-diyl)-(S)-dicarbamate (intermediate A) (39 mg, 0.1 mmol) was added. The reaction mixture was stirred at room temperature overnight. It was diluted with EtOAc and washed with water and brine. The organic layer was dried over anhydrous sodium sulfate and filtered. The filtrate was concentrated under reduced pressure and purified by column chromatography on silica gel to give the desired product (46 mg, 69% yield) as a white solid. $^1$H NMR (300 MHz, CDCl$_3$) δ 9.05 (br, 1H), 7.60 (m, 1H), 7.59 (d, J=9 Hz, 2H), 7.48 (d, J=9 Hz, 2H), 7.33 (m, 2H), 7.26 (m, 10H), 6.89 (m, 1H), 5.09 (m, 4H), 4.91 (m, 1H), 3.88 (br, 1H), 3.55 (m, 2H), 3.23 (m, 2H), 1.63 (m, 4H). MS (ESI+): 661.20 [M+H]+ for $C_{40}H_{44}N_4O_5$.

Example 13. Preparation of (S)—N-(2,5-diaminopentyl)-6-(4-methoxyphenyl)-1H-indole-2-carboxamide dihydrochloride

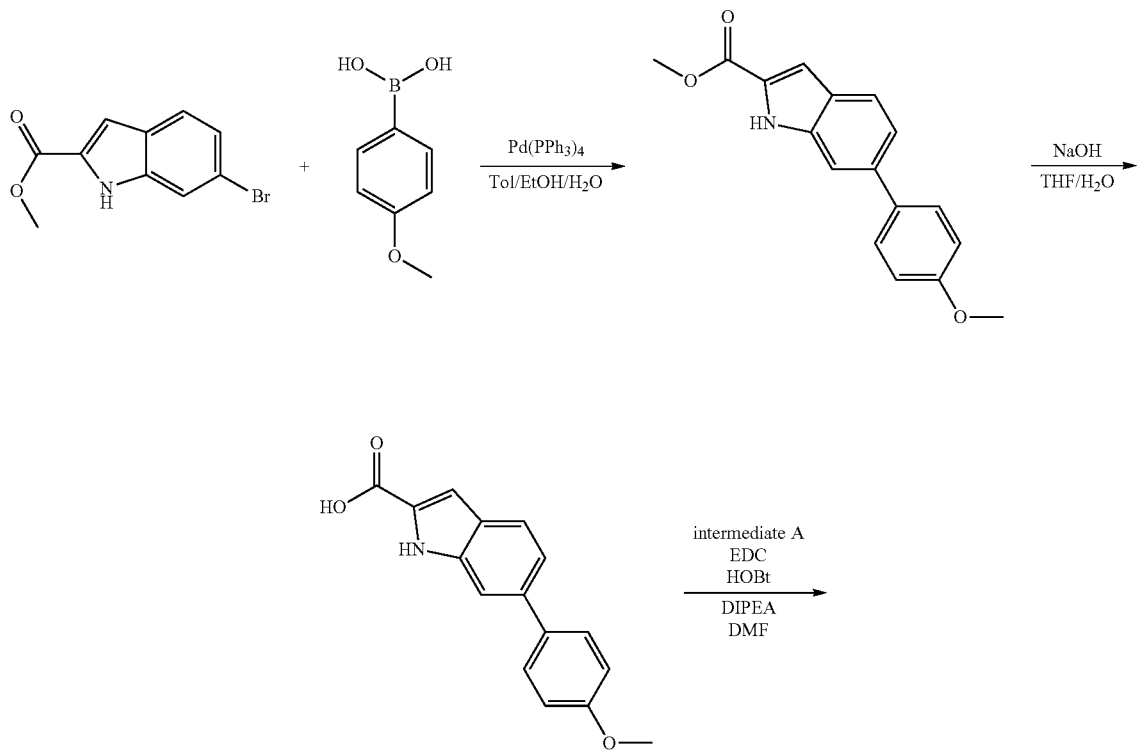

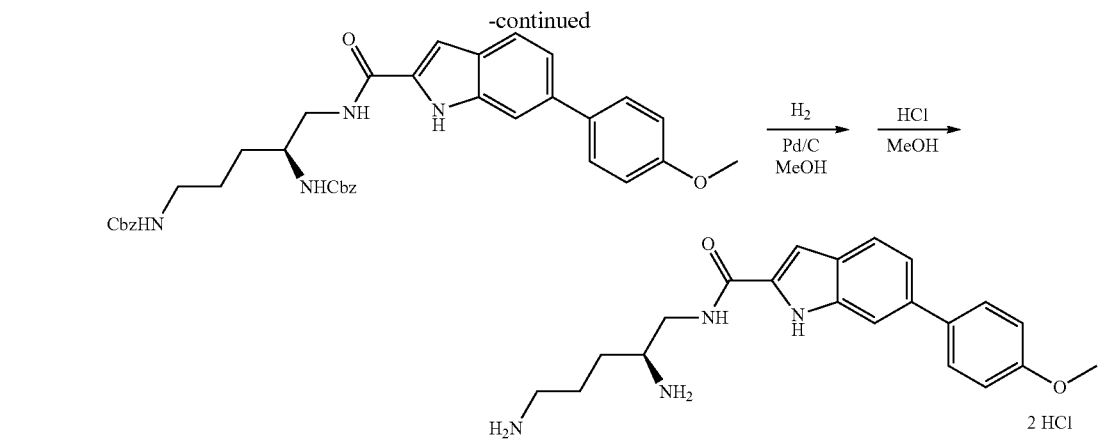

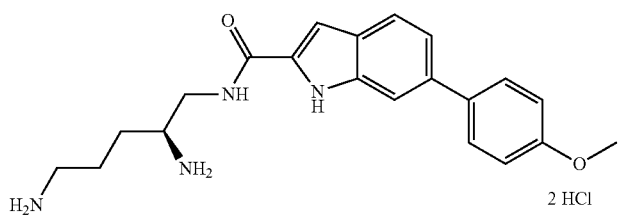

(S)-N-(2,5-Diaminopentyl)-6-(4-methoxyphenyl)-1H-indole-2-carboxamide dihydrochloride To a solution of dibenzyl (5-(6-(4-methoxyphenyl)-1H-indole-2-carboxamido)pentane-1,4-diyl)(S)-dicarbamate (42 mg, 0.066 mmol) in MeOH (5 mL) was added Pd/C (10%, 20 mg). The reaction mixture was stirred under H₂ overnight. It was filtered through a Celite pad and washed with methanol, then concentrated under reduced pressure and HCl in solution (4 M in dioxane, 0.1 mL) was added. The solution was stirred at room temperature and solvent was removed under reduced pressure. The residue was triturated with EtOAc and the precipitate was collected as an off-white powder (26 mg, 89% yield). $^1$H NMR (300 MHz, CD$_3$OD) δ 7.65 (d, J=8.4 Hz, 1H), 7.68 (s, 1H), 7.58 (m, 2H), 7.35 (m, 1H), 7.19 (s, 1H), 7.00 (t, J=8.4 Hz, 2H), 3.83 (s, 3H), 3.73 (m, 1H), 3.60 (m, 1H), 3.49 (m, 1H), 3.02 (m, 2H), 1.87 (m, 4H). MS (ESI+): 367.20 [M+H]$^+$ for C$_{21}$H$_{26}$N$_4$O$_2$.

The requisite intermediates were prepared as shown in the following paragraphs.

Step 1)

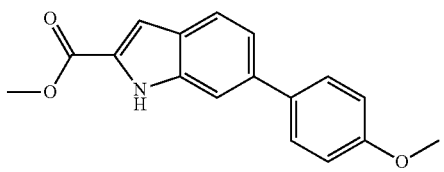

Methyl 6-(4-methoxyphenyl)-1H-indole-2-carboxylate

The mixture of methyl 6-bromo-1H-indole-2-carboxylate (254 mg, 1 mmol), (4-methoxyphenyl)boronic acid (303 mg, 2 mmol) in a mixture of toluene, ethanol and sat. NaHCO$_3$ solution (10/4/4 mL) was degassed and Pd(PPh$_3$)$_4$ (100 mg, 0.09 mmol) was added. The reaction mixture was heated at 100° C. overnight and extracted with EtOAc, then washed with brine and concentrated under reduced pressure. The crude product was purified by column chromatography on silica gel using 10-30% ethyl acetate in hexanes to give the desired product (140 mg, 50% yield) as an off-white powder. $^1$H NMR (300 MHz, CDCl$_3$) δ 8.83 (br, 1H), 7.72 (d, J=8.1 Hz, 1H), 7.56 (m, 3H), 7.38 (d, J=8.1 Hz, 1H), 7.17 (s, 1H), 7.01 (m, 2H), 3.95 (s, 3H), 3.86 (s, 3H). MS (ESI−): 280.05 [M−H]$^-$ for C$_{18}$H$_{17}$NO$_3$.

Step 2)

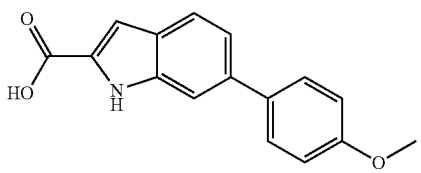

6-(4-Methoxyphenyl)-1H-indole-2-carboxylic acid

To a solution of methyl 6-(4-methoxyphenyl)-1H-indole-2-carboxylate (141 mg, 0.5 mmol) in THF (10 mL) was added NaOH solution (2 M, 3 mL). It was stirred at room temperature until no starting material left. THF was removed under reduced pressure and the residue was acidified with HCl solution. The precipitate was filtered and washed with water. It was dried to provide the product as an off-white powder (126 mg, 94% yield) which was used for next step reaction without further purification. $^1$H NMR (300 MHz, DMSO-d$_6$) δ 11.12 (br, 1H), 7.53 (m, 4H), 7.22 (d, J=8.1 Hz, 1H), 7.00 (m, 2H), 6.74 (s, 1H), 3.78 (s, 3H). MS (ESI−): 266.00 [M−H]$^-$ for C$_{17}$H$_{15}$NO$_3$.

Step 3)

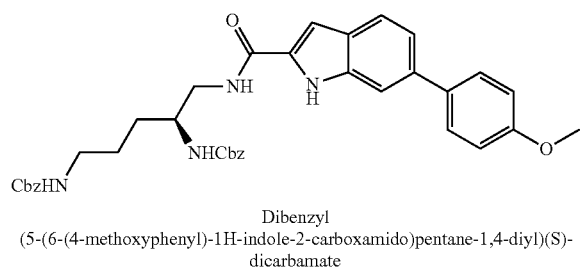 [SMILES: COc1ccc(-c2ccc3cc(C(=O)NC[C@H](CCCNC(=O)OCc4ccccc4)NC(=O)OCc4ccccc4)[nH]c3c2)cc1]

Dibenzyl (5-(6-(4-methoxyphenyl)-1H-indole-2-carboxamido)pentane-1,4-diyl)(S)-dicarbamate To a solution of 6-(4-methoxyphenyl)-1H-indole-2-carboxylic acid (27 mg, 0.1 mmol) in dry DMF (1 mL) was added DIPEA (0.04 mL, 0.2 mmol), HOBt (15 mg, 0.1 mmol) and EDC (19 mg, 0.1 mmol). The reaction mixture was stirred at room temperature and dibenzyl (5-aminopentane-1,4-diyl)-(S)-dicarbamate (intermediate A) (39 mg, 0.1 mmol) was added. The reaction mixture was stirred at room temperature overnight. It was diluted with EtOAc and washed with water and then brine. The organic layer was dried over anhydrous sodium sulfate and filtered. The filtrate was concentrated under reduced pressure and purified by column chromatography on silica gel to give the product (43 mg, 68% yield) as a white solid. $^1$H NMR (300 MHz, CDCl$_3$) δ 9.05 (br, 1H), 7.68 (m, 1H), 7.58 (d, J=6 Hz, 2H), 7.35 (m, 2H), 7.27 (m, 10H), 6.99 (d, J=6 Hz, 2H), 6.88 (m, 1H), 5.09 (m, 4H), 4.89 (m, 1H), 3.87 (s, 3H), 3.35 (m, 2H), 3.24 (m, 2H), 1.64 (m, 4H). MS (ESI+): 657.25 [M+Na]$^+$ for C$_{37}$H$_{38}$N$_4$O$_6$.

Example 14. Preparation of (R)—N-(2,5-diaminopentyl)-6-(pyridin-4-yl)-1H-indole-2-carboxamide dihydrochloride

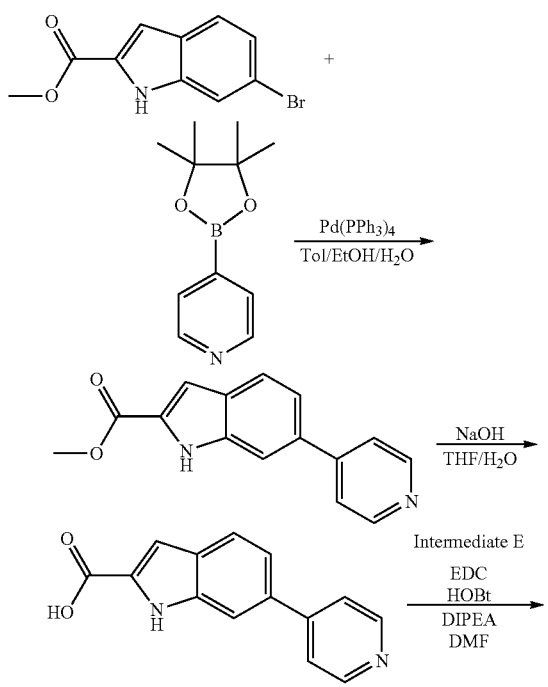

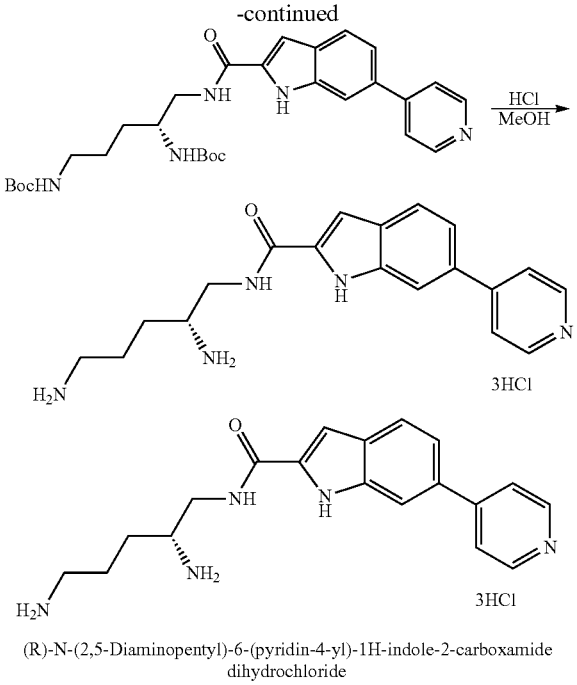

(R)-N-(2,5-Diaminopentyl)-6-(pyridin-4-yl)-1H-indole-2-carboxamide dihydrochloride To a solution of di-tert-butyl (5-(6-(pyridin-4-yl)-1H-indole-2-carboxamido)pentane-1,4-diyl)(R)-dicarbamate (18 mg, 0.05 mmol) in MeOH (3 mL) was added HCl in dioxane (4 M, 0.15 mL, 0.6 mmol). The reaction mixture was stirred at room temperature overnight. TLC showed no starting material left. The reaction mixture was concentrated under reduced pressure and triturated with EtOAc to afford the product (10 mg, 67% yield) as a pale brown solid. $^1$H NMR (300 MHz, CD$_3$OD) δ 8.60 (d, J=6.9 Hz, 2H), 8.23 (d, J=6.9 Hz, 2H), 8.01 (s, 1H), 7.82 (d, J=8.4 Hz, 1H), 7.58 (d, J=8.4 Hz, 1H), 7.13 (s, 1H), 3.66 (m, 1H), 3.53 (m, 1H), 3.48 (m, 1H), 2.94 (m, 2H), 1.80-1.55 (m, 4H).

The requisite intermediates were prepared as shown in the following paragraphs.

Step 1)

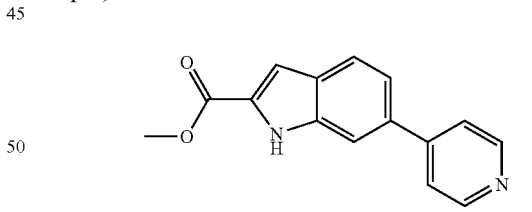

Methyl 6-(pyridin-4-yl)-1H-indole-2-carboxylate

The mixture of methyl 6-bromo-1H-indole-2-carboxylate (254 mg, 1 mmol), 4-Pyridineboronic acid pinacol ester (205 mg, 1 mmol) in a mixture of toluene, ethanol and sat. NaHCO$_3$ solution (10/4/4 mL) was degassed and Pd(PPh$_3$)$_4$ (100 mg, 0.09 mmol) was added. The reaction mixture was heated at 100° C. overnight and extracted with EtOAc, then washed with brine and concentrated under reduced pressure. The crude product was purified by column chromatography on silica gel to give the desired product (91 mg, 36% yield) as an off-white powder. MS (ESI+): 253.10 [M+H]$^+$ for C$_{15}$H$_{12}$N$_2$O$_2$.

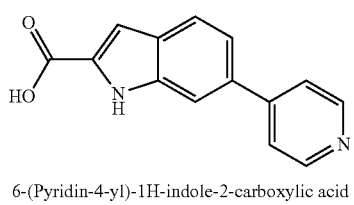 [SMILES: O=C(O)c1cc2ccc(-c3ccncc3)cc2[nH]1]

6-(Pyridin-4-yl)-1H-indole-2-carboxylic acid

Step 2)

To a solution of methyl 6-(pyridin-4-yl)-1H-indole-2-carboxylate (90 mg, 0.36 mmol) in THF (10 mL) was added NaOH solution (2 M, 3 mL). It was stirred at room temperature until no starting material left. THF was removed under reduced pressure and the residue was acidified with ammonium chloride solution. The precipitate was filtered and washed with water. It was dried to provide the product as an off-white powder (50 mg, 58% yield) which was used for next step reaction without further purification. $^1$H NMR (300 MHz, DMSO-$d_6$) δ 12.04 (br, 1H), 8.67 (m, 2H), 7.82 (m, 2H), 7.82 (m, 1H), 754 (m, 2H), 7.14 (s, 1H).

Step 3)

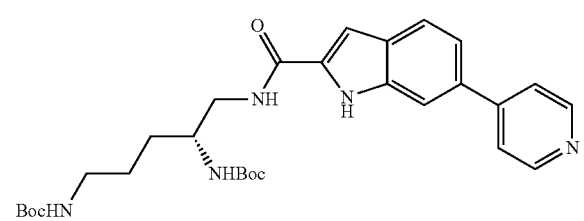

Di-tert-butyl
(5-(6-(pyridin-4-yl)-1H-indole-2-carboxamido)pentane-1,4-diyl)(R)-dicarbamate To a solution of 6-(pyridin-4-yl)-1H-indole-2-carboxylic acid (38 mg, 0.16 mmol) in dry DMF (1 mL) was added DIPEA (0.06 mL, 0.32 mmol), HOBt (17 mg, 0.12 mmol) and EDC (33 mg, 0.16 mmol). The reaction mixture was stirred at room temperature and di-tert-butyl (5-aminopentane-1,4-diyl)(R)-dicarbamate (intermediate E) (55 mg, 0.16 mmol) was added. The reaction mixture was stirred at room temperature overnight. It was diluted with EtOAc and washed with water and brine. The organic layer was dried over anhydrous sodium sulfate and filtered. The filtrate was concentrated under reduced pressure and purified by column chromatography on silica gel to give the desired product (19 mg, 20% yield) as a pale brown powder. $^1$H NMR (300 MHz, CDCl$_3$) δ 8.66 (dd, J=1.8, 4.5 Hz, 2H), 7.75 (d, J=8.1 Hz, 1H), 7.69 (s, 1H), 7.57 (dd, J=1.8, 4.5 Hz, 2H), 7.43 (dd, J=1.8, 8.1 Hz, 1H), 6.95 (s, 1H), 4.78 (br, 1H), 4.61 (br, 1H), 3.83 (m, 1H), 3.53 (m, 2H), 3.16 (m, 2H), 1.63 (m, 4H), 1.44 (s, 9H), 1.43 (s, 9H).

Example 15. Preparation of (R)—N-(2,5-diaminopentyl)-6-(4-hydroxyphenyl)-1H-indole-2-carboxamide dihydrochloride

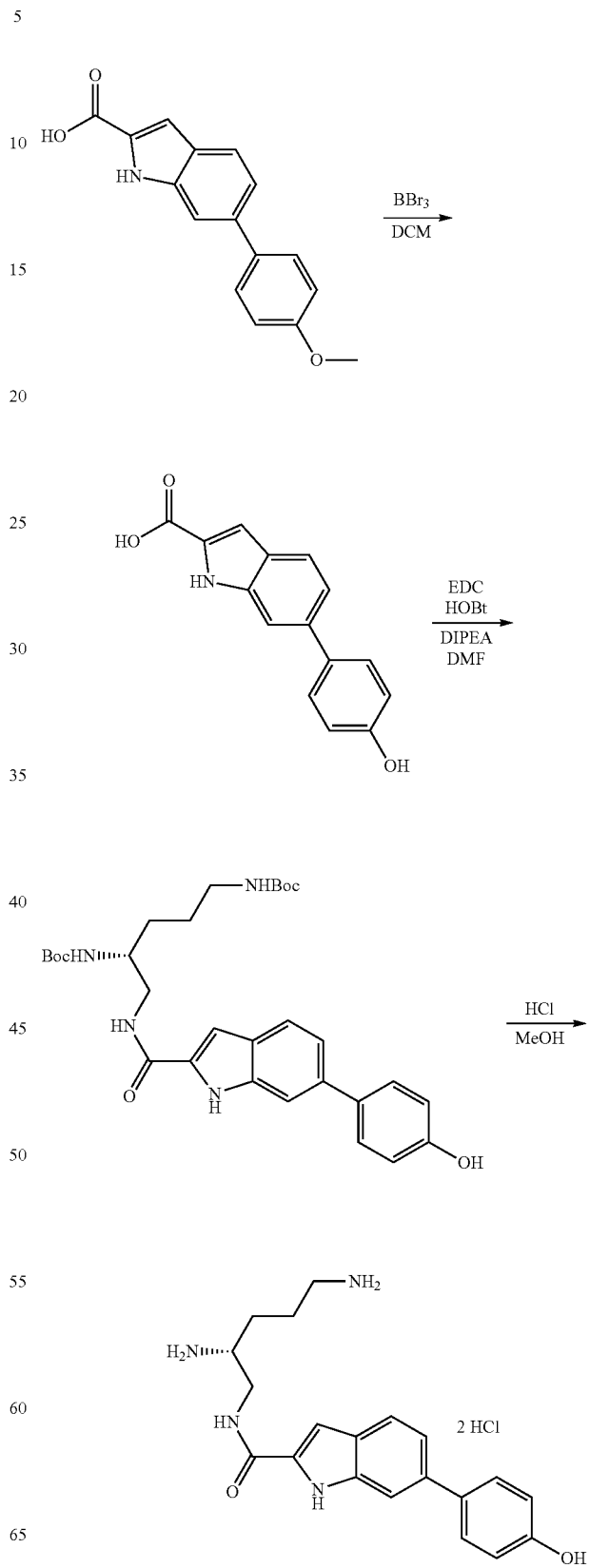

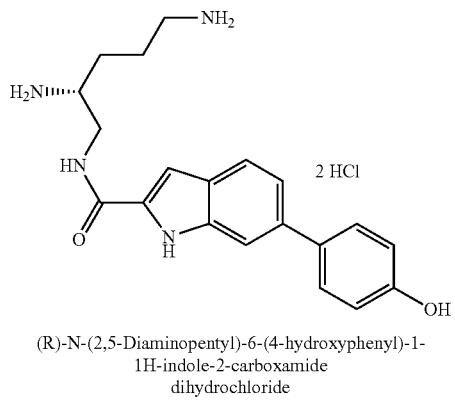

(R)-N-(2,5-Diaminopentyl)-6-(4-hydroxyphenyl)-1-
1H-indole-2-carboxamide
dihydrochloride To a solution of di-tert-butyl (5-(6-(4-hydroxyphenyl)-1H-indole-2-carboxamido)pentane-1,4-diyl)(R)-dicarbamate (36 mg, 0.065 mmol) in MeOH (3 mL) was added HCl in dioxane (4M, 0.1 mL, 0.4 mmol). The reaction mixture was stirred at room temperature overnight. TLC showed no starting material left. It was concentrated under reduced pressure and triturated with EtOAc to afford the product (24 mg, 89% yield) as a pale brown solid. $^1$H NMR (300 MHz, D$_2$O) δ 7.87 (d, J=8.1 Hz, 1H), 7.80 (s, 1H), 7.72 (d, J=8.1 Hz, 2H), 7.55 (m, 1H), 7.26 (s, 1H), 7.17 (d, J=8.1 Hz, 2H), 3.77 (m, 1H), 3.70 (m, 1H), 3.60 (m, 1H), 3.00 (m, 2H), 1.89 (m, 4H). MS (ESI+): 353.20 [M+H]$^+$ for C$_{20}$H$_{24}$N$_4$O$_2$.

The requisite intermediates were prepared as shown in the following paragraphs.

Step 1)

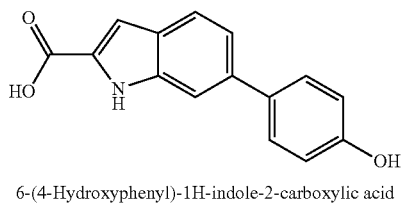 [SMILES: O=C(O)c1cc2ccc(-c3ccc(O)cc3)cc2[nH]1]

6-(4-Hydroxyphenyl)-1H-indole-2-carboxylic acid

To a solution of methyl 6-(4-methoxyphenyl)-1H-indole-2-carboxylate (0.11 g, 0.4 mmol) in methylene chloride (5 mL) was added BBr$_3$ (1.0 M in methylene chloride, 1.2 mL, 1.2 mmol) dropwise in an ice-water bath. The reaction mixture was stirred at room temperature and monitored by TLC. Once the reaction was finished, it was poured into ice and extracted with EtOAc. The combined organic phase was washed with brine and dried over anhydrous Na$_2$SO$_4$. The product was collected after removing the solvent as a pale brown powder (85 mg, 80% yield). $^1$H NMR (300 MHz, DMSO-d$_6$) δ 9.48 (br, 1H), 7.64 (d, J=8.4 Hz, 1H), 7.52 (s, 1H), 7.45 (d, J=8.4 Hz, 2H), 7.28 (dd, J=1.5, 8.4 Hz, 1H), 7.06 (s, 1H), 6.84 (d, J=8.4 Hz, 2H).

Step 2)

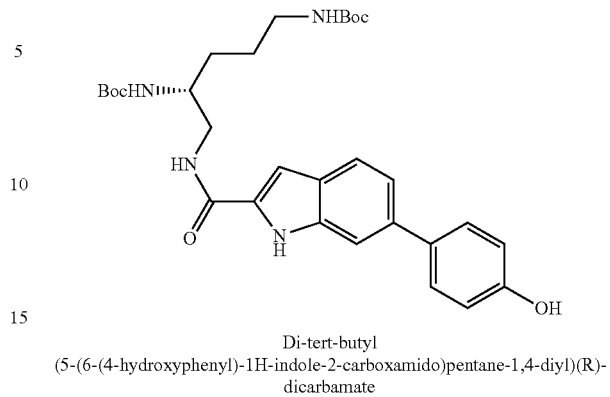

Di-tert-butyl
(5-(6-(4-hydroxyphenyl)-1H-indole-2-carboxamido)pentane-1,4-diyl)(R)-dicarbamate To a solution of 6-(4-hydroxyphenyl)-1H-indole-2-carboxylic acid (51 mg, 0.2 mmol) in dry DMF (1 mL) was added DIPEA (0.07 mL, 0.4 mmol), HOBt (28 mg, 0.17 mmol) and EDC (39 mg, 0.2 mmol). The reaction mixture was stirred at room temperature and di-tert-butyl (5-aminopentane-1,4-diyl)(R)-dicarbamate (63 mg, 0.2 mmol) was added. The reaction mixture was stirred at room temperature overnight. It was diluted with EtOAc and washed with water and then brine. The organic layer was dried over anhydrous sodium sulfate and filtered. The filtrate was concentrated under reduced pressure and the residue purified by column chromatography on silica gel to give the product (36 mg, 33% yield) as an off-white powder. $^1$H NMR (300 MHz, CD$_3$OD) δ 10.02 (br, 1H), 7.80 (s, 1H), 7.53 (m, 1H), 7.41 (m, 2H), 7.26 (m, 1H), 6.93 (s, 1H), 6.81 (m, 2H), 5.60 (br, 1H), 5.38 (br, 1H), 3.62 (m, 1H), 3.35 (m, 2H), 3.00 (m, 2H), 1.45 (m, 4H), 1.31 (s, 9H), 1.27 (s, 9H).

Example 16. Preparation of (R)-6-(4-chlorophenyl)-N-(2,5-diaminopentyl)-1H-indole-2-carboxamide dihydrochloride

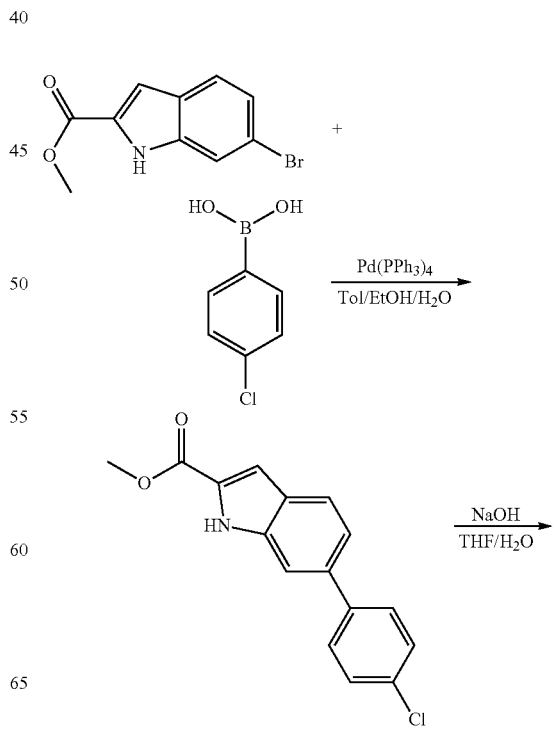

-continued

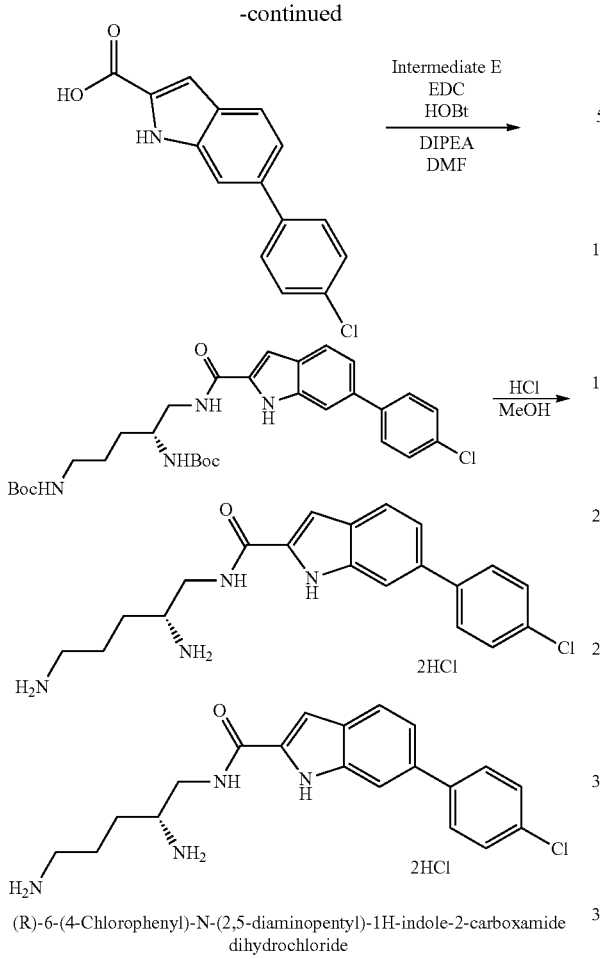

(R)-6-(4-Chlorophenyl)-N-(2,5-diaminopentyl)-1H-indole-2-carboxamide dihydrochloride To a solution of di-tert-butyl (5-(6-(4-chlorophenyl)-1H-indole-2-carboxamido)pentane-1,4-diyl)(R)-dicarbamate (80 mg, 0.14 mmol) in MeOH (10 mL) was added HCl in dioxane (4M, 0.4 mL, 2 mmol). The reaction mixture was stirred at room temperature overnight until TLC showed no starting material left. It was concentrated under reduced pressure and triturated with EtOAc to afford the product (45 mg, 72% yield) as a pale brown solid. $^1$H NMR (300 MHz, D$_2$O) δ 7.87 (m, 1H), 7.77 (m, 4H), 7.50 (m, 2H), 7.21 (s, 1H), 3.79 (m, 1H), 3.65 (m, 1H), 3.61 (m, 1H), 3.10 (m, 2H), 1.88 (m, 4H). MS (ESI+): 371.20 [M+H]$^+$ for C$_{20}$H$_{23}$ClN$_4$O.

The requisite intermediates were prepared as shown in the following paragraphs.

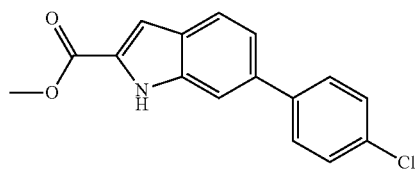

Methyl 6-(4-chlorophenyl)-1H-indole-2-carboxylate

Step 1)

The mixture of methyl 6-bromo-1H-indole-2-carboxylate (508 mg, 2 mmol), (4-chlorophenyl)boronic acid (313 mg, 2 mmol) in a mixture of toluene, ethanol and sat. NaHCO$_3$ solution (10/4/4 mL) was degassed and Pd(PPh$_3$)$_4$ (100 mg, 0.09 mmol) was added. The mixture was heated at 100° C. overnight and it was extracted with EtOAc and washed with brine and concentrated under reduced pressure. The residue was purified by silica gel column chromatography using 20-50% ethyl acetate in hexanes to give the desired product (330 mg, 58% yield) as an off-white powder. $^1$H NMR (300 MHz, CDCl$_3$) δ 8.34 (br, 1H), 7.34 (d, J=8.1 Hz, 1H), 7.57 (m, 3H), 7.44 (s, 1H), 7.37 (d, J=6.9 Hz, 1H), 7.25 (m, 2H), 3.96 (s, 3H).

Step 2)

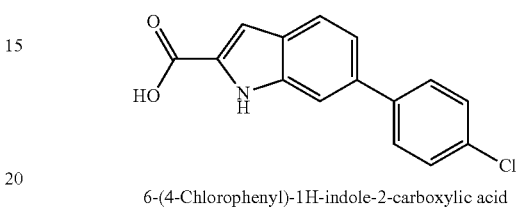

6-(4-Chlorophenyl)-1H-indole-2-carboxylic acid

To a solution of methyl 6-(4-chlorophenyl)-1H-indole-2-carboxylate (315 mg, 1.1 mmol) in THF (10 mL) was added NaOH solution (2 M, 5 mL). It was heated at 50° C. until no starting material left. THF was removed under reduced pressure and the residue was acidified with HCl solution. The precipitate was filtered and washed with water. It was dried to provide the product as an off-white powder (290 mg, 97% yield) which was used for next step reaction without further purification. $^1$H NMR (300 MHz, DMSO-d$_3$) δ 11.29 (br, 1H), 7.62 (m, 5H), 7.47 (d, J=8.4 Hz, 1H), 7.28 (d, 8.4 Hz, 1H), 6.74 (s, 1H). MS (ESI−): 541.15 [2M−H]$^-$ for C$_{15}$H$_{10}$ClNO$_2$.

Step 3)

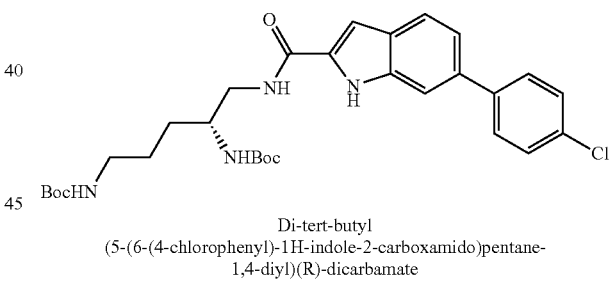

Di-tert-butyl (5-(6-(4-chlorophenyl)-1H-indole-2-carboxamido)pentane-1,4-diyl)(R)-dicarbamate To a solution of 6-(4-chlorophenyl)-1H-indole-2-carboxylic acid (54 mg, 0.2 mmol) in dry DMF (1 mL) was added DIPEA (0.07 mL, 0.4 mmol), HOBt (19 mg, 0.12 mmol) and EDC (46 mg, 0.24 mmol). The reaction mixture was stirred at room temperature and di-tert-butyl (5-aminopentane-1,4-diyl)(R)-dicarbamate (intermediate E) (64 mg, 0.2 mmol) was added. The reaction mixture was stirred at room temperature overnight then diluted with EtOAc and washed with water and brine. The organic layer was dried over anhydrous sodium sulfate and filtered. The filtrate was concentrated under reduced pressure and the residue purified by column chromatography on silica gel using 30-50% EtOAc in hexanes to give the desired product (85 mg, 74% yield) as a pale yellow powder. $^1$H NMR (300 MHz, CDCl$_3$) δ 9.87 (br, 1H), 7.64 (m, 1H), 7.53 (m, 2H), 7.39 (m, 2H), 7.36 (dd, J=1.2, 8.1 Hz, 1H), 6.96 (s, 1H), 6.41 (br, 1H), 4.98 (br, 1H), 4.71 (br, 1H), 3.83 (m, 1H), 3.50 (m, 2H), 3.13 (m, 2H), 1.60 (m, 4H), 1.46 (s, 9H), 1.43 (s, 9H).

Example 17. Preparation of (R)-6-(4-cyanophenyl)-N-(2,5-diaminopentyl)-1H-indole-2-carboxamide dihydrochloride

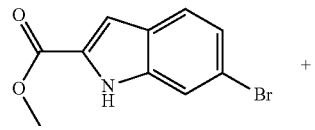

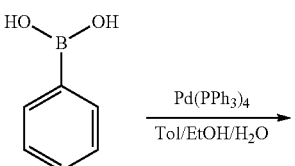

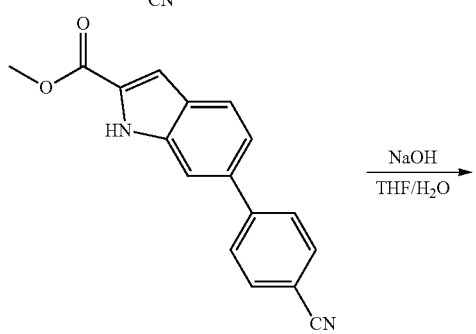

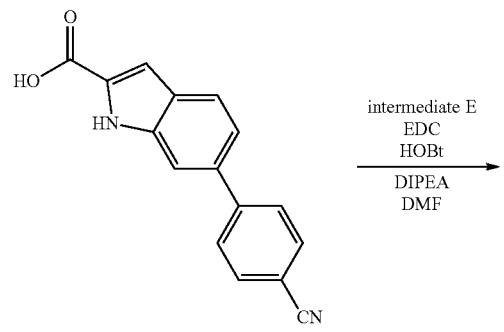

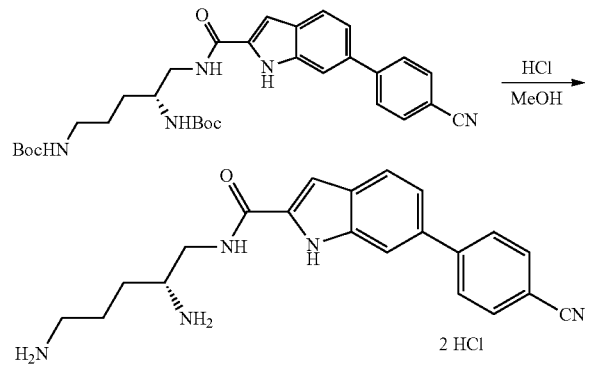

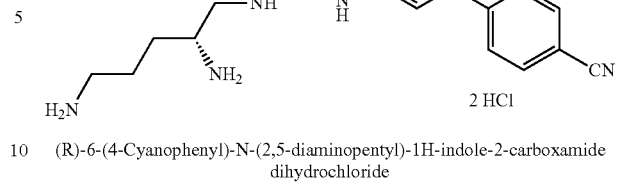

(R)-6-(4-Cyanophenyl)-N-(2,5-diaminopentyl)-1H-indole-2-carboxamide dihydrochloride To a solution of di-tert-butyl (5-(6-(4-cyanophenyl)-1H-indole-2-carboxamido)pentane-1,4-diyl)(R)-dicarbamate (50 mg, 0.09 mmol) in MeOH (8 mL) was added HCl in dioxane (4M, 0.4 mL, 1.6 mmol). The reaction mixture was stirred at room temperature overnight until TLC showed no starting material left. It was concentrated under reduced pressure and triturated with EtOAc to afford the product (22 mg, 57% yield) as a pale brown solid. $^1$H NMR (300 MHz, D$_2$O) δ 7.79 (d, J=8.7 Hz, 1H), 7.69 (s, 1H), 7.65 (d, J=8.7 Hz, 2H), 7.48 (m, 2H), 7.44 (m, 1H), 7.15 (s, 1H), 3.73 (m, 1H), 3.65 (m, 1H), 3.59 (m, 1H), 3.07 (m, 2H), 1.86 (m, 4H). MS (ESI+): 362.25 [M+H]$^+$ for C$_{21}$H$_{23}$N$_5$O.

The requisite intermediates were prepared as shown in the following paragraphs.

Step 1)

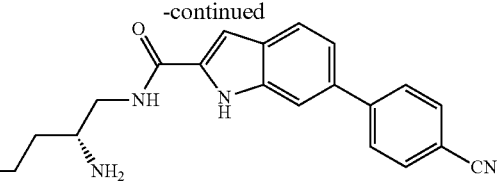

Methyl 6-(4-cyanophenyl)-1H-indole-2-carboxylate

The mixture of methyl 6-bromo-1H-indole-2-carboxylate (508 mg, 2 mmol), (4-cyanophenyl)boronic acid (290 mg, 2 mmol) in a mixture of toluene, ethanol and sat. NaHCO$_3$ solution (10/4/4 mL) was degassed and Pd(PPh$_3$)$_4$ (100 mg, 0.09 mmol) was added. The mixture was heated at 100° C. overnight and it was extracted with EtOAc and washed with brine and concentrated under reduced pressure. The residue was purified by column chromatography on silica gel using 20-60% ethyl acetate in hexanes to give the product (180 mg, 33% yield) as a pale brown powder. $^1$H NMR (300 MHz, CDCl$_3$) δ 8.96 (br, 1H), 7.79 (d, J=8.1 Hz, 1H), 7.74 (m, 5H), 7.62 (s, 1H), 7.40 (d, J=8.1 Hz, 1H), 3.97 (s, 3H).

Step 2)

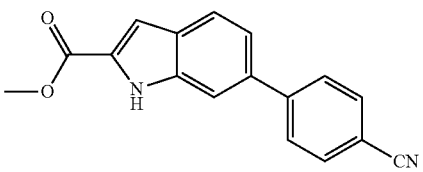

6-(4-Cyanophenyl)-1H-indole-2-carboxylic acid

To a solution of methyl 6-(4-cyanophenyl)-1H-indole-2-carboxylate (175 mg, 0.63 mmol) in THF (10 mL) was added NaOH solution (2 M, 5 mL). It was heated at 50° C. until no starting material left. THF was removed under reduced pressure and the residue was acidified with HCl solution. The precipitate was filtered and washed with water. It was dried to provide the product as an off-white powder (160 mg, 96% yield) which was used for next step reaction without further purification. $^1$H NMR (300 MHz, DMSO-$d_6$) δ 11.20 (br, 1H), 7.84 (q, J=8.1 Hz, 4H), 7.66 (s, 1H), 7.61 (d, J=8.7 Hz, 1H), 7.31 (dd, J=1.8, 8.7 Hz, 1H), 6.65 (s, 1H). MS (ESI–): 261.10 [M–H]$^-$ for $C_{16}H_{10}N_2O_2$.

Step 3)

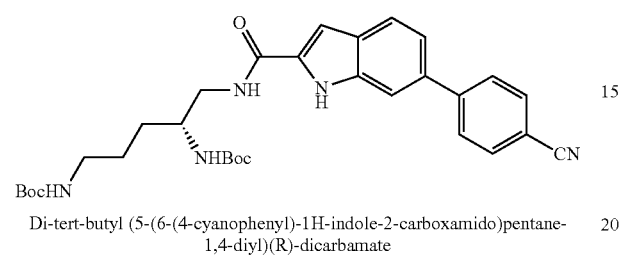

Di-tert-butyl (5-(6-(4-cyanophenyl)-1H-indole-2-carboxamido)pentane-1,4-diyl)(R)-dicarbamate To a solution of 6-(4-cyanophenyl)-1H-indole-2-carboxylic acid (52 mg, 0.2 mmol) in dry DMF (1 mL) was added DIPEA (0.07 mL, 0.4 mmol), HOBt (19 mg, 0.12 mmol) and EDC (46 mg, 0.24 mmol). The reaction mixture was stirred at room temperature and di-tert-butyl (5-aminopentane-1,4-diyl)(R)-dicarbamate (intermediate E) (64 mg, 0.2 mmol) was added. The reaction mixture was stirred at room temperature overnight. It was diluted with EtOAc and washed with water and brine. The organic layer was dried over anhydrous sodium sulfate and filtered. The filtrate was concentrated under reduced pressure and the residue purified by column chromatography on silica gel using 40-45% EtOAc in hexanes to give the product (55 mg, 49% yield) as a pale yellow powder. $^1$H NMR (300 MHz, CDCl$_3$) δ 9.23 (br, 1H), 7.74 (m, 4H), 7.63 (s, 1H), 7.41 (m, 1H), 7.39 (dd, J=1.2, 9.9 Hz, 1H), 6.96 (s, 1H), 4.75 (br, 1H), 4.61 (br, 1H), 3.84 (m, 1H), 3.53 (m, 2H), 3.16 (m, 2H), 1.64 (m, 4H), 1.45 (s, 9H), 1.43 (s, 9H).

Example 18. Preparation of (S)—N-(2,5-diaminopentyl)-4-(4-fluorophenyl)-1H-indole-2-carboxamide dihydrochloride

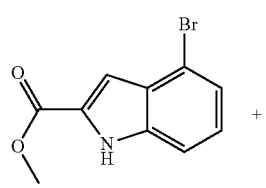

+

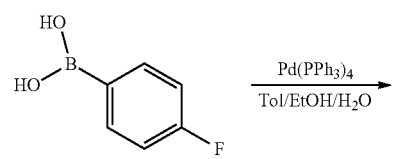

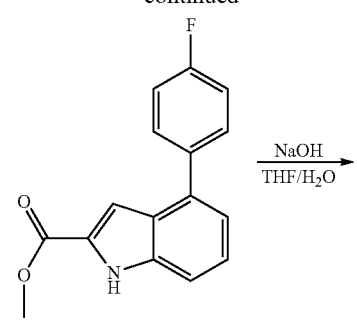

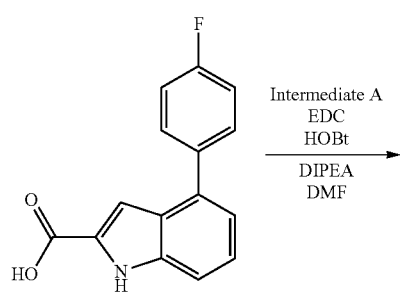

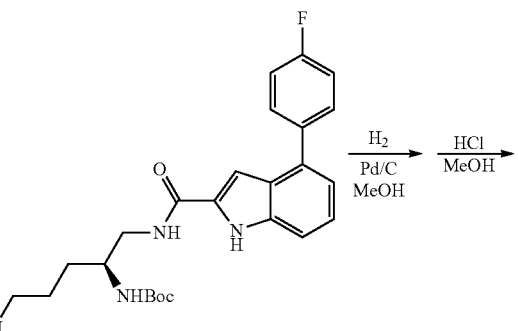

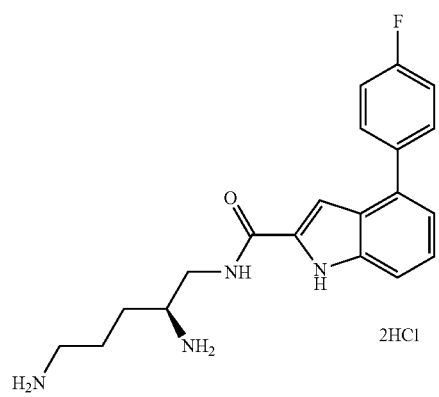

177

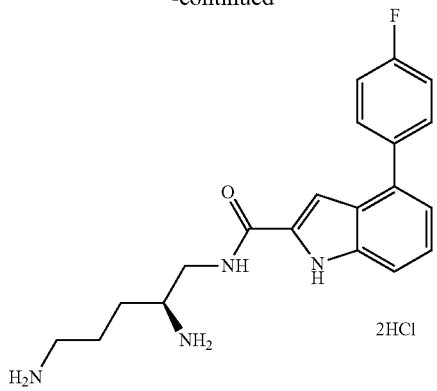

(S)-N-(2,5-Diaminopentyl)-4-(4-fluorophenyl)-1H-indole-2-carboxamide dihydrochloride To a solution of dibenzyl (5-(4-(4-fluorophenyl)-1H-indole-2-carboxamido)pentane-1,4-diyl)(S)-dicarbamate (90 mg, 0.14 mmol) in MeOH (5 mL) and EtOAc (2 mL) was added Pd/C (10%, 20 mg). The reaction mixture was stirred under $H_2$ overnight. It was filtered through a Celite pad and washed with methanol, then concentrated under reduced pressure and HCl in solution (4 M in dioxane, 0.1 mL) was added. The solution was stirred at room temperature and solvent was removed under reduced pressure. The residue was triturated with EtOAc and the precipitate was collected as an off-white powder (52 mg, 85% yield). $^1$H NMR (300 MHz, $D_2O$) δ 7.73 (m, 2H), 7.57 (m, 1H), 7.45 (m, 1H), 7.32 (m, 4H), 3.73 (m, 1H), 3.66 (m, 1H), 3.59 (m, 1H), 3.06 (m, 2H), 1.86 (m, 4H). MS (ESI+): 355.20 [M+H]$^+$ for $C_{20}H_{23}FN_4O$.

The requisite intermediates were prepared as shown in the following paragraphs.

Step 1)

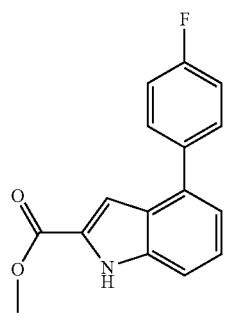

Methyl 4-(4-fluorophenyl)-1H-indole-2-carboxylate

The mixture of methyl 4-bromo-1H-indole-2-carboxylate (508 mg, 2 mmol), (4-fluorophenyl)boronic acid (420 mg, 3 mmol) in a mixture of toluene, ethanol and sat. $NaHCO_3$ solution (10/4/4 mL) was degassed and Pd(PPh$_3$)$_4$ (100 mg, 0.09 mmol) was added. The reaction mixture was heated at 100° C. overnight and extracted with EtOAc, then washed with brine and concentrated under reduced pressure. The crude product was purified by column chromatography on silica gel to give the desired product (330 mg, 61% yield) as an off-white powder. $^1$H NMR (300 MHz, CDCl$_3$) δ 8.93 (br, 1H), 7.63 (m, 2H), 7.39 (m, 2H), 7.39 (s, 1H), 7.19 (m, 3H), 3.94 (s, 3H).

178

Step 2)

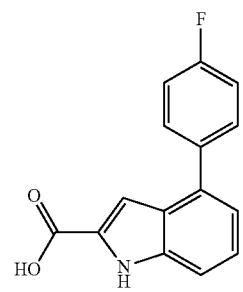

4-(4-Fluorophenyl)-1H-indole-2-carboxylic acid

To a solution of methyl 4-(4-fluorophenyl)-1H-indole-2-carboxylate (310 mg, 1.15 mmol) in THF (10 mL) was added NaOH solution (2 M, 5 mL). The reaction mixture was stirred at room temperature until no starting material left. THF was removed under reduced pressure and the residue was acidified with HCl solution. The precipitate was filtered and washed with water. It was dried to provide the desired product as an off-white powder (220 mg, 75% yield) which was used for next step reaction without further purification. $^1$H NMR (300 MHz, DMSO-d$_6$) δ 7.69 (m, 2H), 7.40 (d, J=8.1 Hz, 1H), 7.32 (t, J=9.0 Hz, 2H), 7.21 (t, J=7.2 Hz, 1H), 7.07 (d, J=7.2 Hz, 1H), 6.92 (s, 1H). MS (ESI−): 254.05 [M−H]$^-$ for $C_{15}H_{10}FNO_2$.

Step 3)

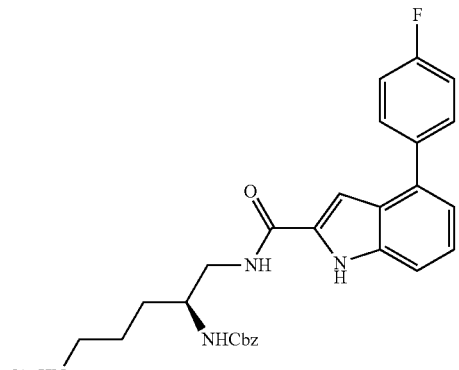

Dibenzyl (5-(4-(4-fluorophenyl)-1H-indole-2-carboxamido)pentane-1,4-diyl)(S)-dicarbamate To a solution of 4-(4-fluorophenyl)-1H-indole-2-carboxylic acid (52 mg, 0.2 mmol) in dry DMF (1.5 mL) was added DIPEA (0.07 mL, 0.4 mmol), HOBt (18 mg, 0.12 mmol) and EDC (46 mg, 0.24 mmol). The reaction mixture was stirred at room temperature and dibenzyl (5-aminopentane-1,4-diyl)-(S)-dicarbamate (intermediate A) (77 mg, 0.2 mmol) was added. The reaction mixture was stirred at room temperature overnight. It was diluted with EtOAc and washed with water and brine. The organic layer was dried over anhydrous sodium sulfate and filtered. The filtrate was concentrated under reduced pressure and purified by column chromatography on silica gel using 30-40% EtOAc in hexanes to give the desired product (100 mg, 80% yield) as an off-white powder. $^1$H NMR (300 MHz, CDCl$_3$) δ 10.00 (br, 1H), 7.62 (m, 2H), 7.29 (m, 10H), 7.17 (m, 6H), 5.52 (br, 1H), 5.02 (m, 4H), 3.82 (m, 1H), 3.48 (m, 2H), 3.15 (m, 2H), 1.54 (m, 4H). MS (ESI+): 645.35 [M+Na]+ for $C_{36}H_{35}FN_4O_5$.

Example 19. Preparation of (S)—N-(2,5-diaminopentyl)-7-(4-fluorophenyl)-1H-indole-2-carboxamide dihydrochloride

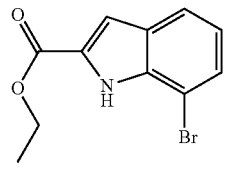

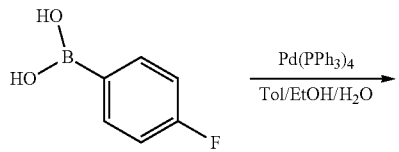

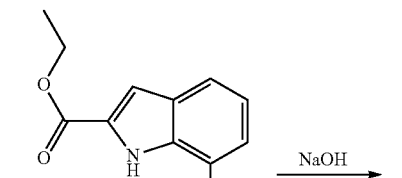

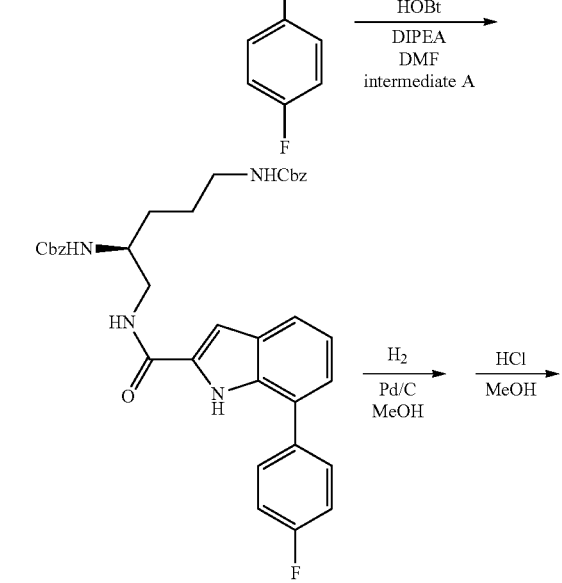

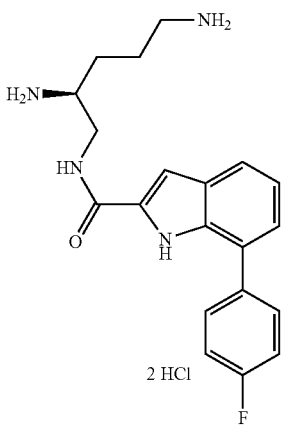

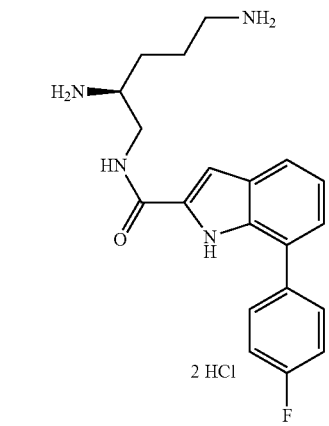

(S)-N-(2,5-Diaminopentyl)-7-(4-fluorophenyl)-1H-indole-2-carboxamide dihydrochloride To a solution of dibenzyl (5-(7-(4-fluorophenyl)-1H-indole-2-carboxamido)pentane-1,4-diyl)(S)-dicarbamate (44 mg, 0.07 mmol) in MeOH (5 mL) and EtOAc (2 mL) was added Pd/C (10%, 20 mg). The reaction mixture was stirred under H$_2$ overnight. It was filtered through a Celite pad and washed with methanol, then concentrated under reduced pressure and HCl in solution (4 M in dioxane, 0.1 mL) was added. The mixture was stirred at room temperature. The solvent removed under reduced pressure. The residue was triturated with EtOAc and the precipitate was collected as an off-white powder (17 mg, 56% yield). $^1$H NMR (300 MHz, CD$_3$OD) δ 7.66 (t, J=8.1 Hz, 2H), 7.33 (s, 1H), 7.25 (m, 5H), 3.71 (m, 1H), 3.63 (m, 1H), 3.48 (m, 1H), 3.00 (m, 2H), 1.86 (m, 4H). MS (ESI+): 355.20 [M+H]+ for $C_{20}H_{23}FN_4O$.

The requisite intermediates were prepared as shown in the following paragraphs.

Step 1)

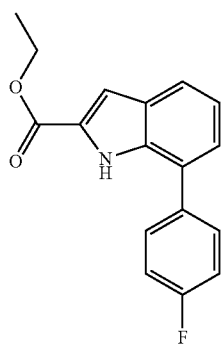

Methyl 7-(4-fluorophenyl)-1H-indole-2-carboxylate

The mixture of ethyl 7-bromo-1H-indole-2-carboxylate (536 mg, 2 mmol), (4-fluorophenyl)boronic acid (420 mg, 3 mmol) in a mixture of toluene, ethanol and sat. NaHCO$_3$ solution (10/4/4 mL) was degassed and Pd(PPh$_3$)$_4$ (100 mg, 0.09 mmol) was added. The reaction mixture was heated at 100° C. overnight and extracted with EtOAc, then washed with brine and concentrated under reduced pressure. The crude product was purified by column chromatography on silica gel to give the desired product (320 mg, 57% yield) as an off-white powder. $^1$H NMR (300 MHz, CDCl$_3$) δ 8.89 (br, 1H), 7.69 (d, J=8.4 Hz, 1H), 7.60 (m, 1H), 7.58 (m, 1H), 7.23 (m, 5H), 4.40 (q, J=6.9 Hz, 2H), 1.41 (t, J=6.9 Hz, 3H).

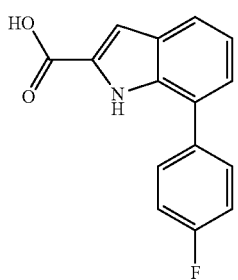

7-(4-Fluorophenyl)-1H-indole-2-carboxylic acid

Step 2)

To a solution of methyl 7-(4-fluorophenyl)-1H-indole-2-carboxylate (270 mg, 0.95 mmol) in THF (10 mL) was added NaOH solution (2 M, 5 mL). It was stirred at room temperature until no starting material left. It was concentrated under reduced pressure under reduced pressure and the residue was acidified with HCl solution. The precipitate was filtered and washed with water. It was dried to provide the product as an off-white powder (110 mg, 45% yield) which was used for next step reaction without further purification. MS (ESI-): 254.05 [M-H]$^-$ for C$_{15}$H$_{10}$FNO$_2$.

Step 3)

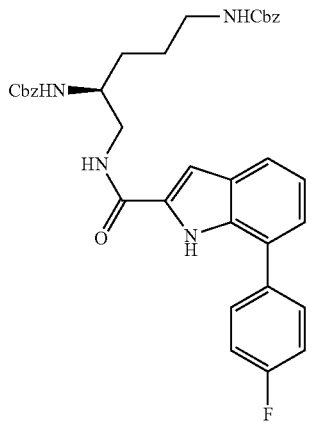

Dibenzyl (5-(7-(4-fluorophenyl)-1H-indole-2-carboxamido)pentane-1,4-diyl)(S)-dicarbamate To a solution of 7-(4-fluorophenyl)-1H-indole-2-carboxylic acid (51 mg, 0.2 mmol) in dry DMF (1.5 mL) was added DIPEA (0.07 mL, 0.4 mmol), HOBt (18 mg, 0.12 mmol) and EDC (46 mg, 0.24 mmol). The reaction mixture was stirred at room temperature and dibenzyl (5-aminopentane-1,4-diyl)-(S)-dicarbamate (intermediate A) (77 mg, 0.2 mmol) was added. The reaction mixture was stirred at room temperature overnight. The reaction mixture was diluted with EtOAc and washed with water and then brine. The organic layer was dried over anhydrous sodium sulfate and filtered. The filtrate was concentrated under reduced pressure and the residue purified by column chromatography on silica gel using 30-40% EtOAc in hexanes to give the product (55 mg, 44% yield) as an off-white powder. $^1$H NMR (300 MHz, CDCl$_3$) δ 9.26 (br, 1H), 7.59 (m, 1H), 7.50 (m, 2H), 7.40 (m, 1H), 7.26 (m, 1H), 7.21 (m, 10H), 7.17 (m, 2H), 6.99 (m, 1H), 5.52 (br, 1H), 5.04 (m, 4H), 3.84 (m, 1H), 3.47 (m, 2H), 3.17 (m, 2H), 1.46 (m, 4H). MS (ESI+): 645.30 [M+Na]$^+$ for C$_{36}$H$_{35}$FN$_4$O$_5$.

Example 20. Preparation of (R)-5-(6-(4-fluorophenyl)-1H-indole-2-carboxamido)pentane-1,4-diaminium chloride

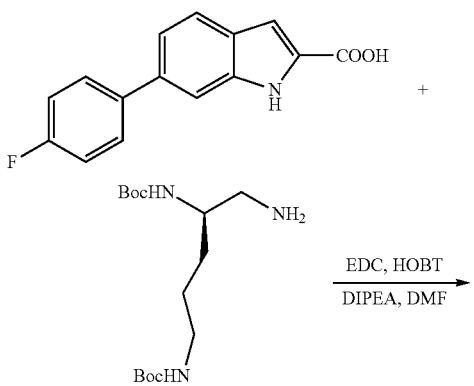

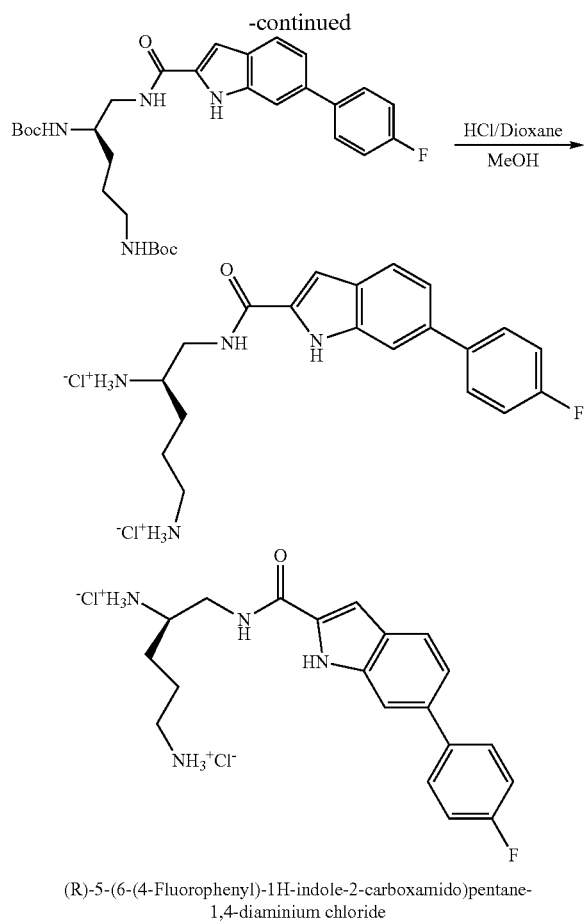

(R)-5-(6-(4-Fluorophenyl)-1H-indole-2-carboxamido)pentane-1,4-diaminium chloride To a solution of di-tert-butyl (5-(6-(4-fluorophenyl)-1H-indole-2-carboxamido)pentane-1,4-diyl)(R)-dicarbamate (134 mg, 0.24 mmol) (intermediate E) in MeOH (3 mL) was added 0.5 mL 4N HCl in dioxane. The reaction was stirred at room temperature overnight. The reaction mixture was concentrated under reduced pressure and the residue triturated with EtOAc to afford the desired product (83 mg, 81% yield) as a white solid. $^1$H NMR (300 MHz, DMSO-$d_6$) δ 11.77 (s, 1H), 8.99-8.97 (m, 1H), 8.29 (s, 3H), 8.02 (s, 3H), 7.68-7.61 (m, 4H), 7.34-7.25 (m, 4H), 3.55-3.46 (m, 2H), 3.33 (m, 1H), 2.80-2.72 (m, 2H), 1.70-1.58 (m, 4H).

The requisite intermediate was prepared as shown in the following paragraph.

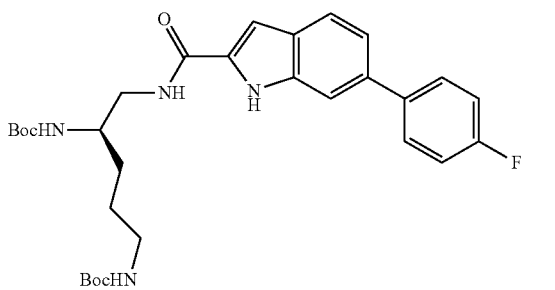

Di-tert-butyl (5-(6-(4-fluorophenyl)-1H-indole-2-carboxamido)pentane-1,4-diyl)(R)-dicarbamate To 6-(4-fluorophenyl)-1H-indole-2-carboxylic acid (77 mg, 0.31 mmol) in DMF (3 mL) was added DIPEA (0.104 mL, 0.62 mmol), HOBT (25 mg, 0.18 mmol), EDC (70 mg, 0.36 mmol). The reaction mixture was stirred at room temperature for 5 minutes. Di-tert-butyl (5-aminopentane-1,4-diyl)(R)-dicarbamate (intermediate E) (95 mg, 0.31 mmol) was added and the reaction was stirred at room temperature overnight. The reaction mixture was then diluted with EtOAc and washed with 15% LiCl and brine. The organic layer was dried over sodium sulfate and filtered. Filtrate was then concentrated under reduced pressure and purified using an ISCO column chromatography on silica gel (0-100% ethyl acetate/hexanes) to give the product (134 mg, 78% yield) as a white solid. $^1$H NMR (300 MHz, CDCl$_3$) δ 9.41 (s, 1H), 7.70-7.56 (m, 4H), 7.39-7.32 (m, 2H), 7.15-7.10 (m, 2H), 6.94 (s, 1H), 4.83-4.64 (m, 2H), 3.83 (m, 1H), 3.52 (m, 2H), 3.16-3.14 (m, 2H), 1.62-1.56 (m, 4H), 1.45-1.42 (m, 18H).

Example 21. Preparation of (S)-4-(6-(4-fluorophenyl)-1H-indole-2-carboxamido)butane-1,3-diaminium chloride

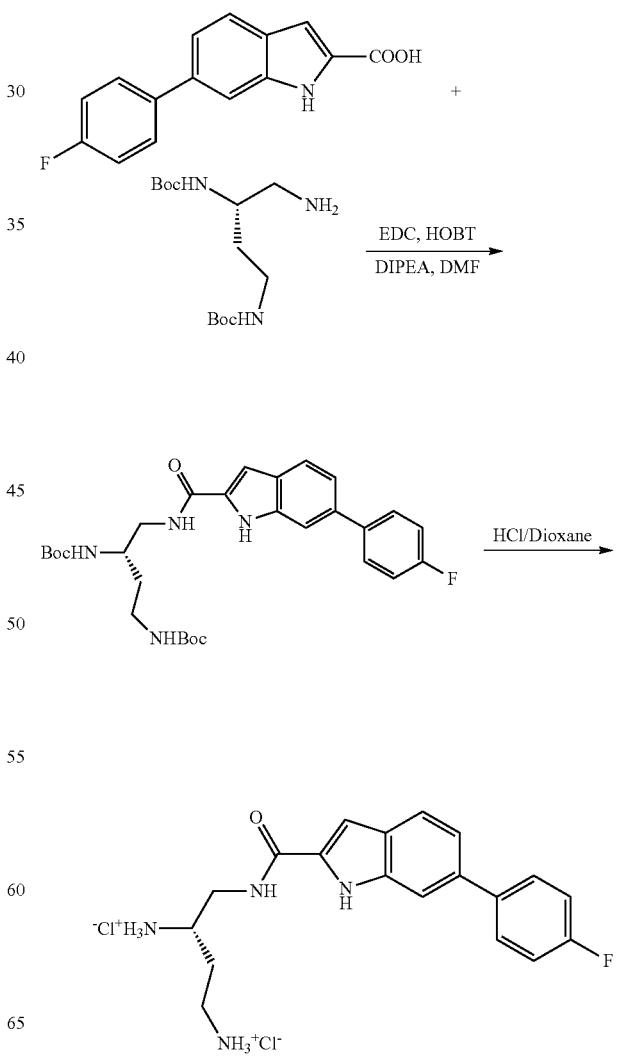

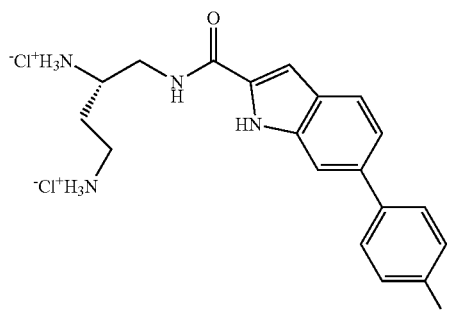

(S)-4-(6-(4-Fluorophenyl)-1H-indole-2-carboxamido)butane-1,3-diaminium chloride

To a solution of di-tert-butyl (4-(6-(4-fluorophenyl)-1H-indole-2-carboxamido)butane-1,3-diyl)(S)-dicarbamate (65 mg, 0.12 mmol) in MeOH (1 mL) was added 0.3 mL 4N HCl in dioxane. The reaction was stirred at room temperature overnight. The residue was concentrated under reduced pressure and triturated with EtOAc to afford the desired product (41 mg, 83% yield) as a white solid. $^1$H NMR (300 MHz, DMSO-$d_6$) δ 11.79 (s, 1H), 9.09-0.08 (m, 1H), 8.50 (s, 3H), 8.18 (s, 3H), 7.70-7.61 (m, 4H), 7.38-7.25 (m, 4H), 3.61-3.49 (m, 3H), 2.99 (m, 2H), 1.97 (m, 2H).

The requisite intermediate was prepared as shown in the following paragraph.

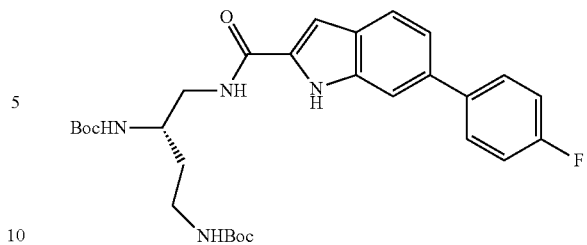

Di-tert-butyl (4-(6-(4-fluorophenyl)-1H-indole-2-carboxamido)butane-1,3-diyl)(S)-dicarbamate To 6-(4-fluorophenyl)-1H-indole-2-carboxylic acid (81 mg, 0.32 mmol) in DMF (3 mL) was added DIPEA (0.111 mL, 0.64 mmol), HOBT (26 mg, 0.20 mmol), EDC (74 mg, 0.39 mmol). The reaction mixture was stirred at room temperature for 5 minutes. Di-tert-butyl (4-aminobutane-1,3-diyl)(S)-dicarbamate (Intermediate G) (96 mg, 0.32 mmol) was added and the reaction was stirred at room temperature overnight. The reaction mixture was then diluted with EtOAc and washed with 15% LiCl and brine. The organic layer was dried over sodium sulfate and filtered. Filtrate was then concentrated under reduced pressure and purified using an ISCO column chromatography on silica gel (0-100% ethyl acetate/hexanes) to give the product (65 mg, 38% yield) as a white solid. $^1$H NMR (300 MHz, CDCl$_3$) δ 11.65 (s, 1H), 8.41 (s, 1H), 7.69-7.59 (m, 4H), 7.32-7.25 (m, 4H), 7.11 (s, 1H), 6.76-6.67 (m, 2H), 3.64 (m, 1H), 3.13-2.85 (m, 4H), 1.59 (m, 2H).

Example 22. Preparation of N-(((2S,4R)-4-(aminomethyl)pyrrolidin-2-yl)methyl)-6-(4-fluorophenyl)-1H-indole-2-carboxamide dihydrochloride

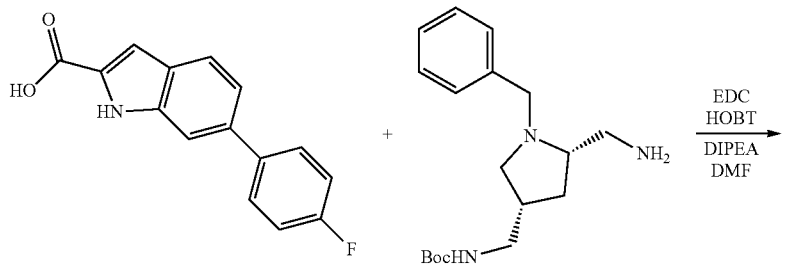

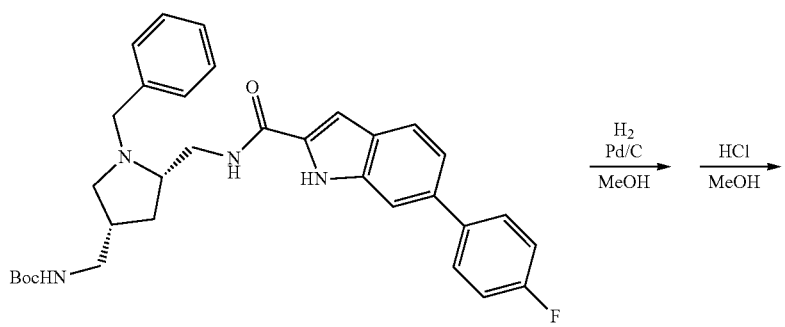

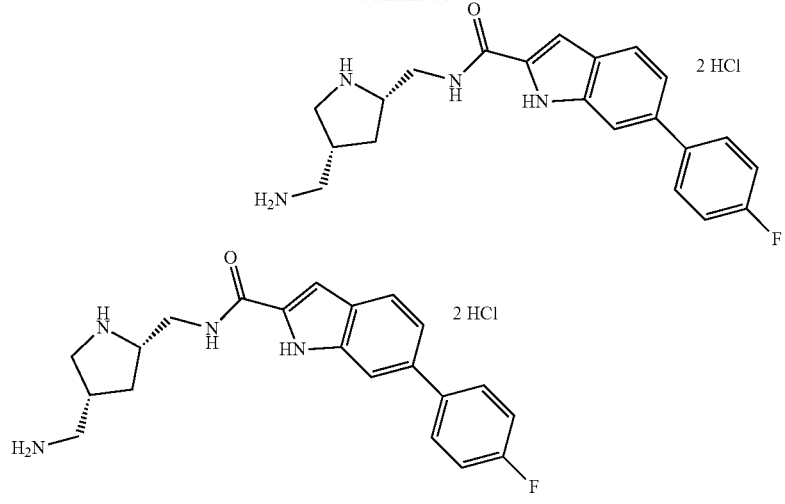

N-(((2S,4R)-4-(Aminomethyl)pyrrolidin-2-yl)methyl)-6-
(4-fluorophenyl)-1H-indole-2-
carboxamide dihydrochloride To a solution of tert-butyl (((3R,5S)-1-benzyl-5-((6-(4-fluorophenyl)-1H-indole-2-carboxamido)methyl)pyrrolidin-3-yl)methyl)carbamate (16 mg, 0.03 mmol) in methanol (10 mL) was added Pd/C (10%, 20 mg). It was stirred under H$_2$ overnight. The solid was filtered off through a Celite pad and the filtrate was concentrated under reduced pressure under reduced pressure to give a residue. The residue was dissolved in MeOH (1 mL) was added HCl solution in dioxane (4 M, 0.1 mL) and it was stirred at room temperature overnight then concentrated under reduced pressure. The crude product was triturated with EtOAc and the white solid was collected by filtration to provide the title compound (7 mg, 55% yield in two steps). $^1$H NMR (300 MHz, CD$_3$OD) δ 7.67 (m, 5H), 7.33 (m, 1H), 7.15 (m, 3H), 4.41 (m, 1H), 3.58 (m, 3H), 2.85-3.14 (m, 4H), 2.23-2.42 (m, 2H), 1.64 (m, 1H).

The requisite intermediate was prepared as shown in the following paragraph.

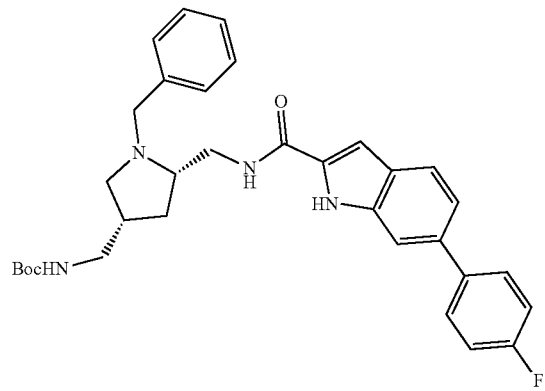

tert-Butyl (((3R,5S)-1-benyzl-5-((6-(4-fluorophenyl)-1H-indole-2-
carboxamido)methyl)pyrrolidin-3-yl)methyl)carbamate To a solution of 6-(4-fluorophenyl)-1H-indole-2-carboxylic acid (26 mg, 0.1 mmol) in dry DMF (1.0 mL) was added DIPEA (0.04 mL, 0.2 mmol), HOBt (8.1 mg, 0.06 mmol) and EDC (23 mg, 0.12 mmol). The reaction mixture was stirred at room temperature for 5 minutes and tert-butyl (((3R,5S)-5-(aminomethyl)-1-benzylpyrrolidin-3-yl)methyl)carbamate (intermediate L) (32 mg, 0.1 mmol) was added. The reaction was stirred at room temperature overnight. It was then diluted with EtOAc and washed with water and brine. The organic layer was dried over anhydrous sodium sulfate and filtered. The filtrate was concentrated under reduced pressure and purified on silica gel to give the product (20 mg, 35% yield) as a yellow solid.

$^1$H NMR (300 MHz, CDCl$_3$) δ 7.69 (d, J=8.1 Hz, 1H), 7.56-7.62 (m, 4H), 7.24-7.36 (m, 5H), 7.13 (m, 3H), 6.88 (s, 1H), 4.61 (m, 1H), 4.26 (m, 1H), 3.55 9s, 2H), 3.07 (m, 3H), 2.76 (m, 1H), 2.21 (m, 2H), 1.88 (m, 2H), 1.43 (s, 9H).

Example 23. Preparation of (S)-5-(6-(benzo[d][1,3]
dioxol-5-yl)-1H-indole-2-carboxamido) pentane-1,4-
diaminium chloride

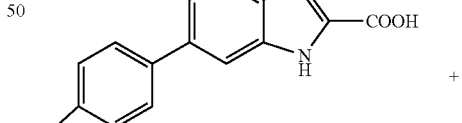

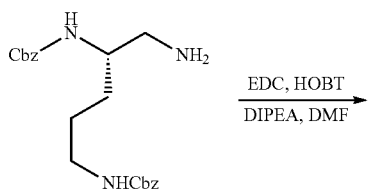

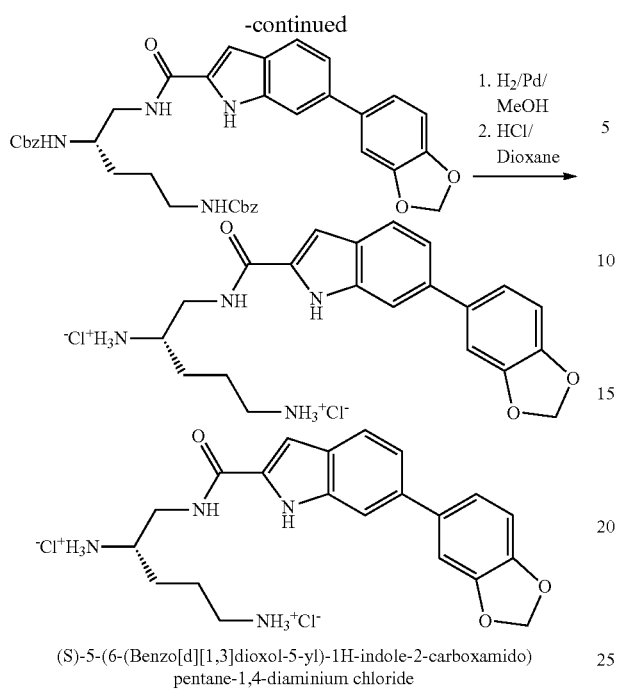

(S)-5-(6-(Benzo[d][1,3]dioxol-5-yl)-1H-indole-2-carboxamido)
pentane-1,4-diaminium chloride To a solution of dibenzyl (5-(6-(benzo[d][1,3]dioxol-5-yl)-1H-indole-2-carboxamido) pentane-1,4-diyl)(S)-dicarbamate (122 mg, 0.19 mmol) in MeOH (3 ml) was added 7 mg 10% palladium on carbon. The reaction was hydrogenated under hydrogen gas balloon at room temperature overnight. The reaction was filtered through Celite, washed with MeOH and concentrated under reduced pressure. The residue was added 0.3 ml 4N HCl in dioxane and stirred for 10 minutes. The mixture was concentrated under reduced pressure and triturated with EtOAc to afford the desired product (65 mg, 76% yield) as a yellow solid. $^1$H NMR (300 MHz, DMSO) δ 11.71 (s, 1H), 9.03 (s, 1H), 8.41 (s, 3H), 8.14 (s, 3H), 7.64-7.56 (m, 2H), 7.35-7.26 (m, 2H) 7.18-7.08 (m, 2H) 6.99-6.96 (m, 1H) 6.04 (s, 2H), 3.56 (m, 4H), 2.80 (m, 2H), 1.72 (m, 4H).

The required intermediate was prepared as follows
Step 1)

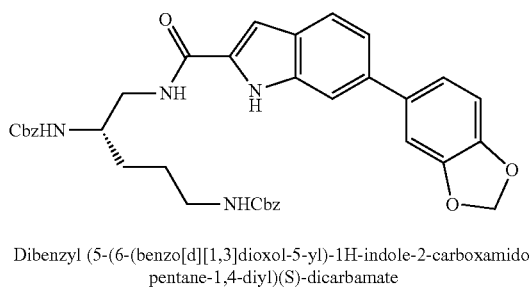

Dibenzyl (5-(6-(benzo[d][1,3]dioxol-5-yl)-1H-indole-2-carboxamido)
pentane-1,4-diyl)(S)-dicarbamate To 6-(benzo[d][1,3]dioxol-5-yl)-1H-indole-2-carboxylic acid (50 mg, 0.18 mmol) in DMF (1 ml) was added DIPEA (0.062 mL, 0.36 mmol), HOBT (15 mg, 0.11 mmol), EDC (42 mg, 0.22 mmol). The reaction mixture was stirred at room temperature for 5 minutes. Dibenzyl (5-aminopentane-1,4-diyl)(S)-dicarbamate (amine intermediate A) (70 mg, 0.18 mmol) was added and the reaction was stirred at room temperature overnight. The reaction mixture was then diluted with EtOAc and washed with 15% LiCl and brine. The organic layer was dried over sodium sulfate and filtered. The filtrate was then concentrated under reduced pressure and purified using an ISCO chromatograph with silica (0-100% ethyl acetate/hexanes) to give the desired product (61 mg, 52% yield) as a yellow solid. $^1$H NMR (300 MHz, DMSO) δ 11.58 (s, 1H), 8.43 (s, 1H), 7.64-7.54 (m, 2H), 7.29-7.09 (m, 14H) 7.00-6.97 (m, 2H) 6.99-6.96 (m, 1H) 6.04 (s, 2H), 4.99-4.96 (m, 4H) 3.69 (m, 1H), 2.96 (m, 4H), 1.47-1.40 (m, 4H).

Example 24. Preparation of (R)-5-(5-(4-fluorophenyl)-1H-indole-2-carboxamido)pentane-1,4-diaminium chloride

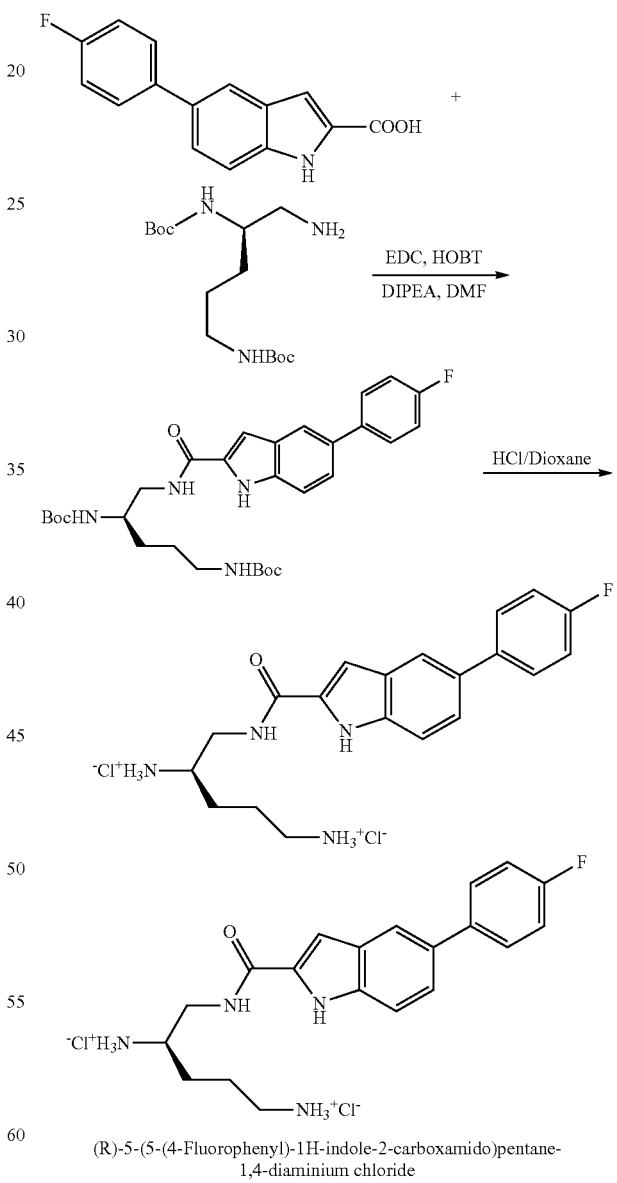

(R)-5-(5-(4-Fluorophenyl)-1H-indole-2-carboxamido)pentane-
1,4-diaminium chloride To a solution of di-tert-butyl (5-(5-(4-fluorophenyl)-1H-indole-2-carboxamido)pentane-1,4-diyl)(R)-dicarbamate (79 mg, 0.14 mmol) in MeOH (1 ml) was added 0.3 ml 4N HCl in dioxane. The reaction was stirred at room temperature overnight. The residue was concentrated under reduced pressure and triturated with EtOAc to afford the desired product (40 mg, 33% yield) as a brown solid. ¹H NMR (300 MHz, DMSO) δ 11.74 (s, 1H), 9.00 (s, 1H), 8.33 (s, 3H), 8.07 (s, 3H), 7.86 (s, 1H), 7.71-7.67 (m, 2H) 7.51-7.47 (m, 2H) 7.37-7.36 (d, 1H) 7.27-7.21 (m, 2H) 3.55-3.53 (m, 2H), 2.81-2.79 (m, 2H), 1.71-1.34 (m, 5H).

The required intermediate was prepared as follows
Step 1)

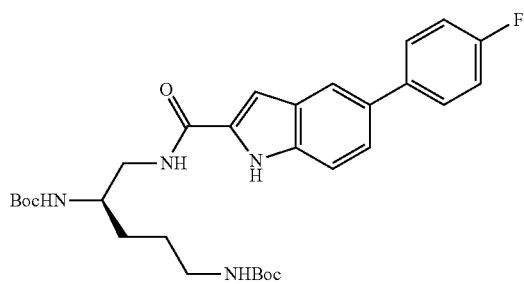

Di-tert-butyl (5-(5-(4-fluorophenyl)-1H-indole-2-carboxamido) pentane-1,4-diyl)(R)-dicarbamate To 5-(4-fluorophenyl)-1H-indole-2-carboxylic acid (127 mg, 0.50 mmol) in DMF (3 ml) was added DIPEA (0.173 mL, 1.00 mmol), TBTU (97 mg, 0.30 mmol), EDC (115 mg, 0.60 mmol). The reaction mixture was stirred at room temperature for 5 minutes. Di-tert-butyl (5-aminopentane-1,4-diyl)(R)-dicarbamate (amine intermediate E) (157 mg, 0.50 mmol) was added and the reaction was stirred at room temperature overnight. The reaction mixture was then diluted with EtOAc and washed with 15% LiCl and brine. The organic layer was dried over sodium sulfate and filtered. The filtrate was then concentrated under reduced pressure and purified using an ISCO chromatograph with silica (0-100% ethyl acetate/hexanes) to give the desired product (79 mg, 30% yield) as a white solid. ¹H NMR (300 MHz, CDCl₃) δ 9.30 (s, 1H), 7.77 (s, 1H), 7.59-7.54 (m, 2H), 7.47-7.31 (m, 3H), 7.15-7.09 (m, 2H) 6.95-6.91 (m, 1H) 4.81-4.64 (m, 2H), 3.84 (m, 1H), 3.52-3.40 (m, 2H), 3.17-3.13 (m, 2H), 1.63-1.55 (m, 4H), 1.49-1.35 (m, 18H)

Example 25. Preparation of (4S)-5-(6-(4-fluorophenyl)-1H-indole-2-carboxamido) hexane-1,4-diaminium chloride

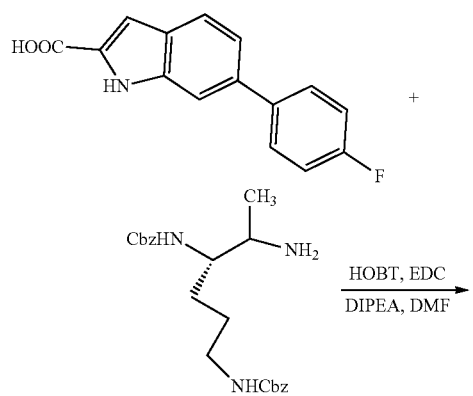

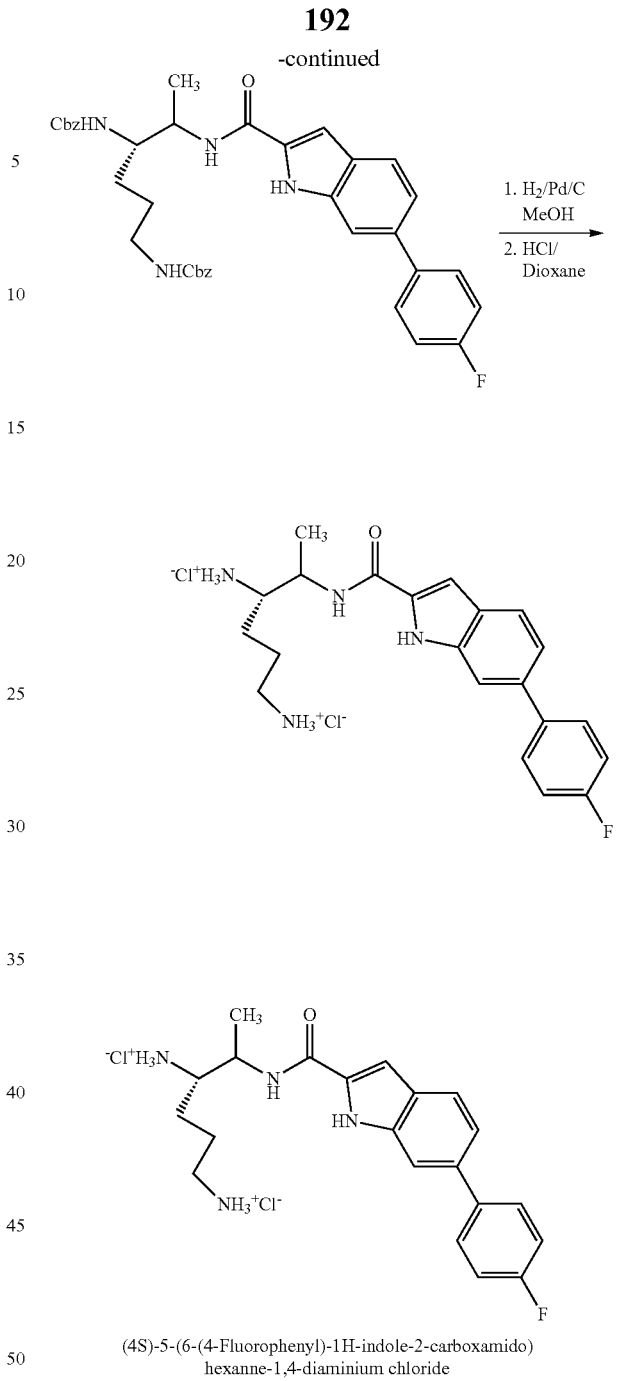

(4S)-5-(6-(4-Fluorophenyl)-1H-indole-2-carboxamido) hexanne-1,4-diaminium chloride To a solution of dibenzyl ((4S)-5-(6-(4-fluorophenyl)-1H-indole-2-carboxamido)hexane-1,4-diyl)dicarbamate (130 mg, 0.21 mmol) in MeOH (1 ml) was added 20 mg 10% palladium on carbon. The reaction was hydrogenated under hydrogen gas balloon at room temperature overnight. The reaction was filtered through celite, washed with MeOH and concentrated under reduced pressure. The residue was added 0.3 ml 4N HCl in dioxane and stirred for 10 minutes. The mixture was concentrated under reduced pressure and triturated with EtOAc to afford product (50 mg, 56% yield) as a white solid. ¹H NMR (300 MHz, DMSO) δ 11.76 (s, 1H), 8.89-8.79 (m, 1H), 8.42-8.29 (s, 3H), 8.06 (s, 3H), 7.66-7.60 (m, 4H), 7.42-7.24 (m, 4H) 4.33 (s, 1H) 3.77-3.74 (s, 1H), 2.77-2.73 (m, 2H), 1.72 (m, 4H), 1.27-1.25 (m, 3H).

The required intermediate was prepared as follows
Step 1)

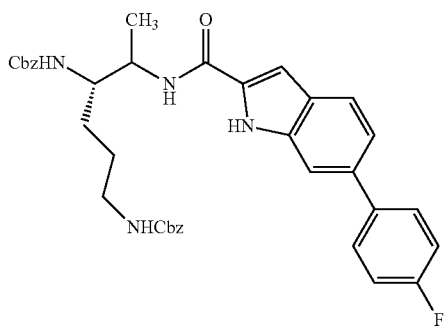

Dibenzyl ((4S)-5-(6-(4-fluorophenyl)-1H-indole-2-carboxamido)hexane-1,4-diyl)dicarbamate To 6-(4-fluorophenyl)-1H-indole-2-carboxylic acid (86 mg, 0.33 mmol) in DMF (2 ml) was added DIPEA (0.114 mL, 0.66 mmol), HOBT (27 mg, 0.20 mmol), EDC (76 mg, 0.40 mmol). The reaction mixture was stirred at room temperature for 5 minutes. Dibenzyl ((4S)-5-aminohexane-1,4-diyl)dicarbamate(amine intermediate K) (134 mg, 0.33 mmol) was added and the reaction was stirred at room temperature overnight. The reaction mixture was then diluted with EtOAc and washed with 15% LiCl and brine. The organic layer was dried over sodium sulfate and filtered. The filtrate was then concentrated under reduced pressure and purified using an ISCO chromatograph with silica (0-100% ethyl acetate/hexanes) to give the desired product (130 mg, 62% yield) as a white solid. $^1$H NMR (300 MHz, CDCl$_3$) δ 9.76-9.70 (s, 1H), 7.67-7.47 (m, 4H), 7.37-7.19 (m, 10H), 7.13-7.07 (m, 4H), 6.92 (s, 1H), 5.29-4.96 (m, 4H), 4.17-4.11 (m, 1H), 3.74-3.61 (m, 1H) 3.25-3.19 (m, 2H), 1.57-1.40 (m, 4H), 1.31-1.12 (m, 3H).

Example 26. Preparation of (4S)-1-cyclopropyl-5-(6-(4-fluorophenyl)-1H-indole-2-carboxamido)pentane-1,4-diaminium chloride

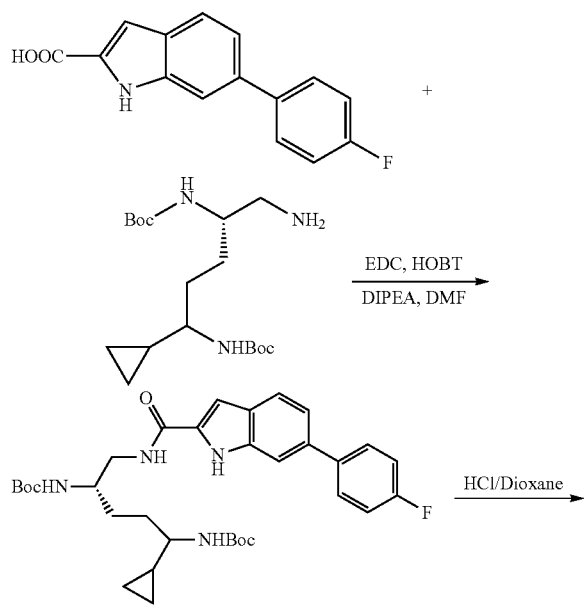

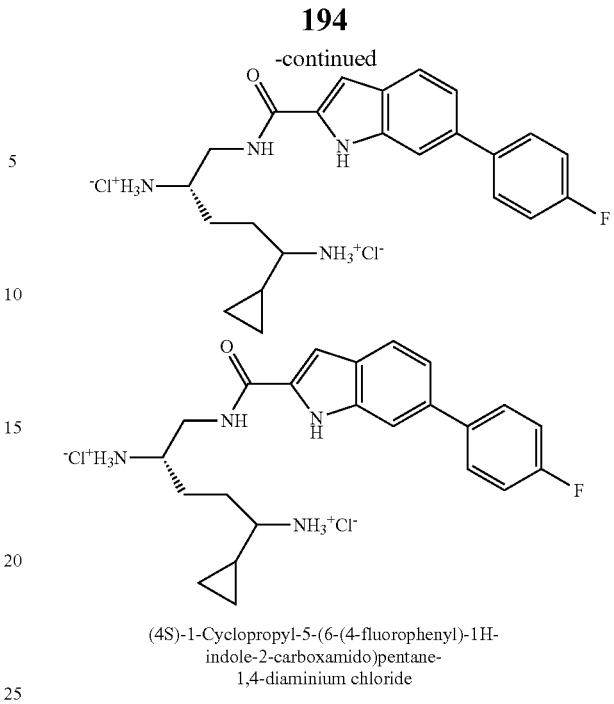

(4S)-1-Cyclopropyl-5-(6-(4-fluorophenyl)-1H-indole-2-carboxamido)pentane-1,4-diaminium chloride To a solution of di-tert-butyl ((4S)-1-cyclopropyl-5-(6-(4-fluorophenyl)-1H-indole-2-carboxamido)pentane-1,4-diyl)dicarbamate (35 mg, 0.059 mmol) in MeOH (1 ml) was added 0.3 ml 4N HCl in dioxane. The reaction was stirred at room temperature overnight. The residue was concentrated under reduced pressure and triturated with EtOAc to afford the desired product (12 mg, 44% yield) as a yellow solid. $^1$H NMR (300 MHz, DMSO) δ 11.78 (s, 1H), 9.03-9.00 (m, 1H), 8.33 (s, 3H), 8.16 (s, 3H), 7.70-7.60 (m, 4H), 7.36-7.22 (m, 4H) 3.68-3.52 (m, 3H), 2.56-2.41 (m, 1H), 1.90-1.81 (m, 4H), 0.87 (m, 1H), 0.52-0.36 (m, 4H).

The required intermediate was prepared as follows
Step 1)

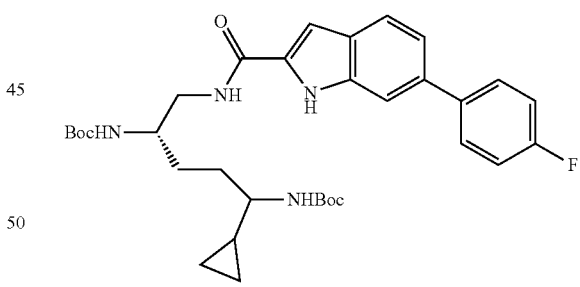

Di-tert-butyl ((4S)-1-cyclopropyl-5-(6-(4-fluorophenyl)-1H-indole-2-carboxamido)pentane-1,4-diyl)dicarbamate To 6-(4-fluorophenyl)-1H-indole-2-carboxylic acid (30 mg, 0.084 mmol) in DMF (1 ml) was added DIPEA (0.029 mL, 0.17 mmol), HOBT (7 mg, 0.051 mmol), EDC (19 mg, 0.10 mmol). The reaction mixture was stirred at room temperature for 5 minutes. Di-tert-butyl ((4S)-5-amino-1-cyclopropylpentane-1,4-diyl)dicarbamate (amine intermediate J) (34 mg, 0.084 mmol) was added and the reaction was stirred at room temperature overnight. The reaction mixture was then diluted with EtOAc and washed with 15% LiCl and brine. The organic layer was dried over sodium sulfate and filtered. The filtrate was then concentrated under reduced pressure and purified using an ISCO chromatograph with silica (0-100% ethyl acetate/hexanes) to give the desired product (35 mg, 70% yield) as a yellow solid. $^1$H NMR (300 MHz, CDCl$_3$) δ 9.55 (s, 1H), 7.68 (d, 1H), 7.61-7.57 (m, 5H), 7.34-7.32 (m, 2H), 7.19-7.05 (m, 2H) 6.98-6.95 (d, 1H) 4.55 (m, 1H), 3.56-3.33 (m, 2H), 2.92 (m, 1H), 1.67-1.50 (m, 4H), 1.49-1.15 (m, 18H), 0.76-0.71 (m, 1H), 0.51-0.22 (m, 4H).

Example 27. Preparation of (2S)-1-(6-(4-fluorophenyl)-1H-indole-2-carboxamido)hexane-2,5-diaminium chloride

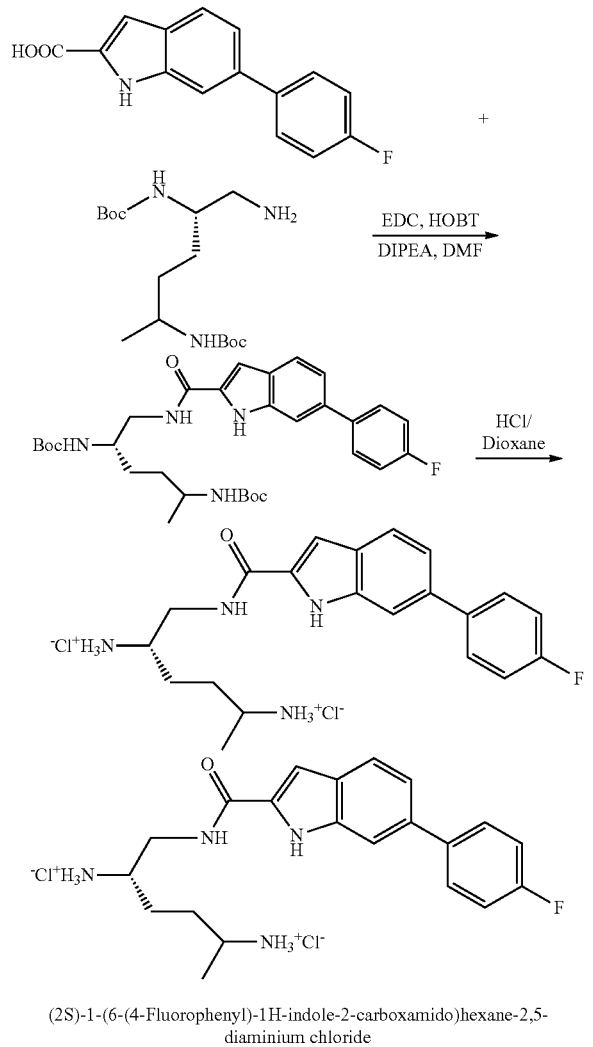

(2S)-1-(6-(4-Fluorophenyl)-1H-indole-2-carboxamido)hexane-2,5-diaminium chloride To a solution of di-tert-butyl ((2S)-1-(6-(4-fluorophenyl)-1H-indole-2-carboxamido) hexane-2,5-diyl)dicarbamate (57 mg, 0.10 mmol) in MeOH (1 ml) was added 0.3 ml 4N HCl in dioxane. The reaction was stirred at room temperature overnight. The residue was concentrated under reduced pressure and triturated with EtOAc to afford the desired product (27 mg, 62% yield) as a yellow solid. $^1$H NMR (300 MHz, DMSO) δ 11.78 (s, 1H), 9.02 (s, 1H), 8.34 (s, 3H), 8.12 (s, 3H), 7.69-7.60 (m, 4H), 7.36-7.25 (m, 4H) 3.55-3.14 (m, 4H), 1.73 (m, 4H), 1.18 (m, 3H).

The required intermediate was prepared as follows Step 1)

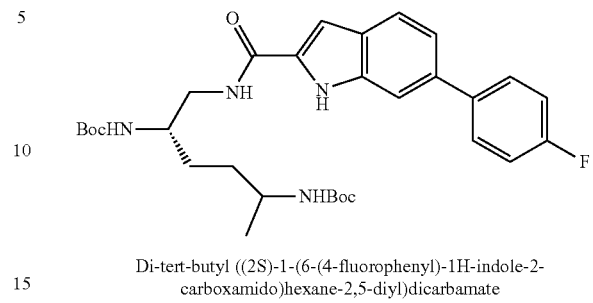

Di-tert-butyl ((2S)-1-(6-(4-fluorophenyl)-1H-indole-2-carboxamido)hexane-2,5-diyl)dicarbamate To 6-(4-fluorophenyl)-1H-indole-2-carboxylic acid (60 mg, 0.18 mmol) in DMF (2 ml) was added DIPEA (0.064 mL, 0.36 mmol), HOBT (16 mg, 0.12 mmol), EDC (42 mg, 0.22 mmol). The reaction mixture was stirred at room temperature for 5 minutes. Di-tert-butyl ((2S)-1-aminohexane-2,5-diyl)dicarbamate (amine intermediate I) (74 mg, 0.18 mmol) was added and the reaction was stirred at room temperature overnight. The reaction mixture was then diluted with EtOAc and washed with 15% LiCl and brine. The organic layer was dried over sodium sulfate and filtered. The filtrate was then concentrated under reduced pressure and the residue purified using an ISCO chromatograph with silica (0-100% ethyl acetate/hexanes) to give the desired product (57 mg, 56% yield) as a yellow solid. $^1$H NMR (300 MHz, CDCl$_3$) δ 9.94 (s, 1H), 7.67-7.56 (m, 5H), 7.54-7.30 (m, 1H) 7.23-7.03 (m, 2H) 6.99-9.97 (m, 1H), 5.11-4.94 (m, 1H), 4.44-4.41 (m, 1H), 4.08-3.52 (m, 4H), 1.43-1.28 (m, 22H), 1.26-1.08 (d, 3H).

Example 28. Preparation of N-((2S)-2,5-diamino-5-cyclo propylpentyl)-6-(4-fluorophenyl)-1H-indole-2-carboxamide hydrogen chloride salt

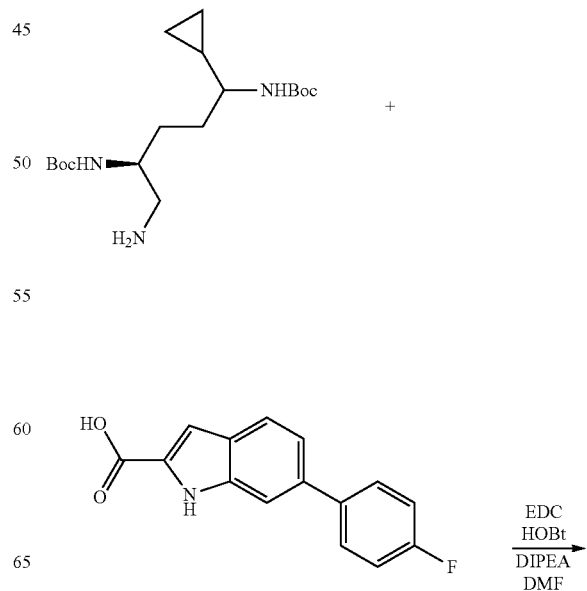

-continued

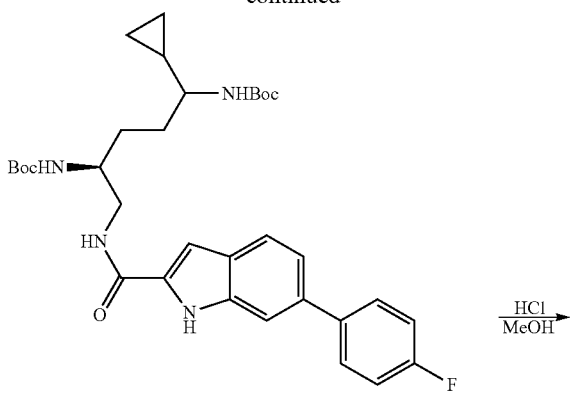

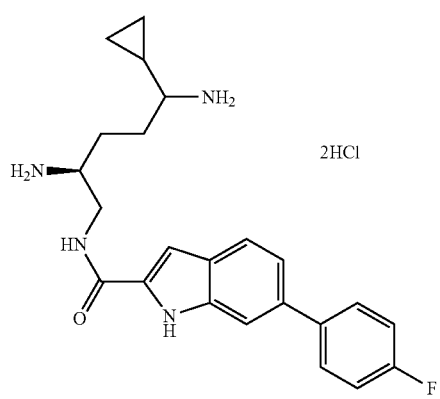

2HCl

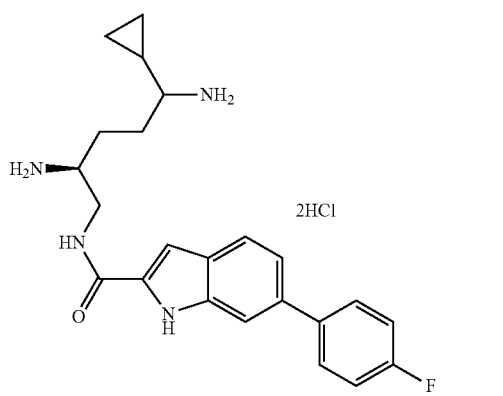

2HCl

N-((2S)-2,5-Diamino-5-cyclopropylpentyl)-6-(4-fluorophenyl)-1H-indole-2-carboxamide hydrochloride salt To a solution of di-tert-butyl ((4S)-1-cyclopropyl-5-(6-(4-fluorophenyl)-1H-indole-2-carboxamido)pentane-1,4-diyl) dicarbamate (50 mg, 0.08 mmol) in methanol (5 mL) was added HCl solution in dioxane (4 N, 0.3 mL). The reaction mixture was stirred at room temperature overnight then concentrated under reduced pressure. The crude product was triturated with EtOAc and the white solid was collected by filtration to provide the desired product (21 mg, 54% yield) as white solid. ¹H NMR (300 MHz, D₂O) δ 7.79-7.59 (m, 4H), 7.34 (m, 1H), 7.14-7.05 (m, 3H), 3.57-3.30 (m, 3H), 2.40 (m, 1H), 1.80 (m, 4H), 0.81 (m, 1H), 0.52 (m, 2H), 0.26 (m, 2H).

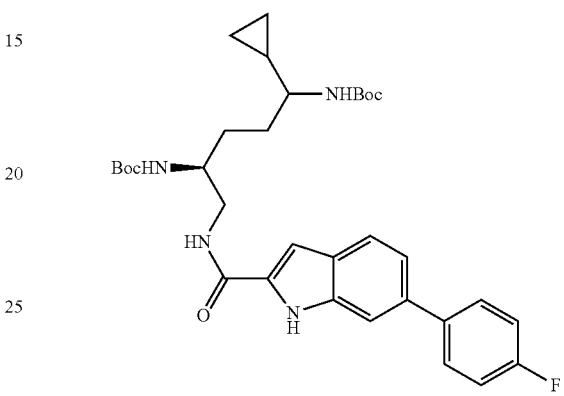

Di-tert-butyl ((4S)-1-cyclopropyl-5-(6-(4-fluorophenyl)-1H-indole-2-carboxamido)pentane-1,4-diyl)dicarbamate To a solution of 6-(4-fluorophenyl)-1H-indole-2-carboxylic acid (36 mg, 0.14 mmol) in dry DMF (2 mL) was added DIPEA (0.05 mL, 0.28 mmol), HOBt (11 mg, 0.08 mmol) and EDC (33 mg, 0.17 mmol). The reaction mixture was stirred at room temperature for 5 minutes and di-tert-butyl ((4S)-5-amino-1-cyclopropylpentane-1,4-diyl)dicarbamate (50 mg, 0.14 mmol) was added. The reaction was stirred at room temperature overnight. It was then diluted with EtOAc and washed with water and brine. The organic layer was dried over anhydrous sodium sulfate and filtered. The filtrate was concentrated under reduced pressure and purified on silica gel to give the desired product (55 mg, 66% yield) as an off white solid. ¹H NMR (300 MHz, CDCl₃) δ 9.37 (br, 1H), 7.69 (m, 1H), 7.60-7.55 (m, 3H), 7.34 (m, 1H), 7.15 (m, 2H), 6.96 (m, 1H), 4.98 (br, 1H), 4.77 (m, 1H), 4.53 (m, 1H), 3.84 (m, 1H), 3.52 (m, 2H), 3.28 (m, 1H), 2.93 (m, 1H), 1.66 (m, 5H), 1.58 (s, 9H), 1.42 (s, 9H), 0.80 (m, 1H), 0.56 (m, 2H), 0.25 (m, 2H).

Example 29. Preparation of N-(((2S,4R)-4-(aminomethyl)pyrrolidin-2-yl)methyl)-6-(4-fluorophenyl)-1H-indole-2-carboxamide hydrogen chloride salt

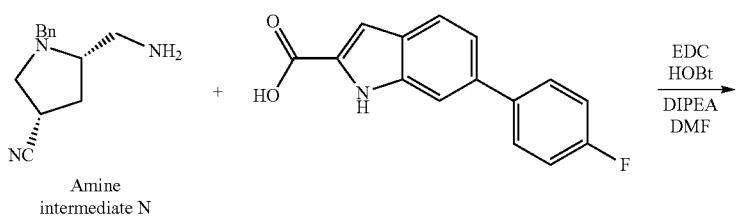

Amine intermediate N

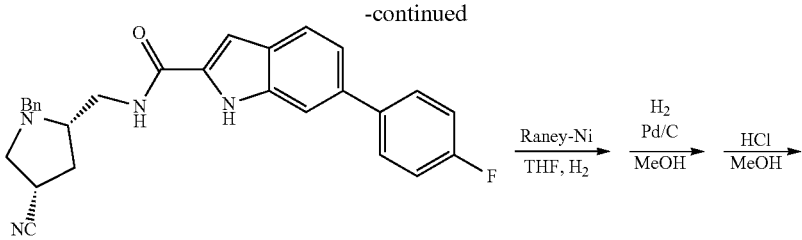

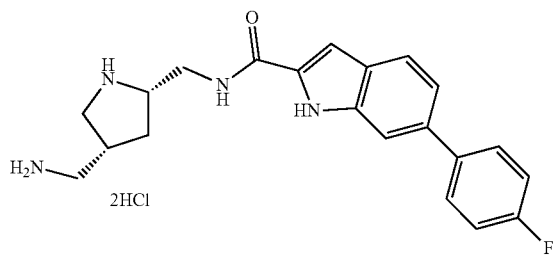

2HCl

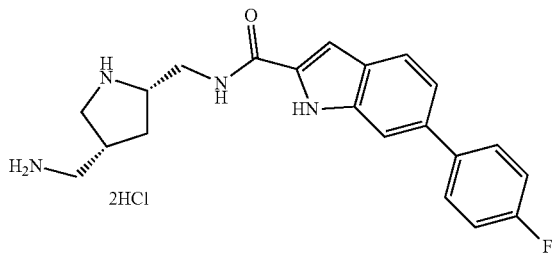

2HCl

N-(((2S,4R)-4-(Aminomethyl)pyrrolidin-2-yl)methyl)-6-(4-fluorophenyl)-1H-indole-2-carboxamide hydrogen chloride salt To a solution of N-(((2S,4S)-1-benzyl-4-cyanopyrrolidin-2-yl)methyl)-6-(4-fluorophenyl)-1H-indole-2-carboxamide (200 mg, 0.44 mmol) in THF (30 mL) was added Raney-Ni (200 mg, 50% in water) under $H_2$ (55 psi) overnight. The reaction progress was monitored by LC-MS. After the reaction was completed, the catalyst was removed by passing through a Celite plug and washed with MeOH. The filtrate was concentrated under reduced pressure to give the amine intermediate. This intermediate was dissolved in MeOH (20 mL). Pd/C (30 mg, 10% on carbon) was added then under $H_2$ (55 psi) overnight. After the reaction was completed, monitoring by LC-MS. The catalyst was removed by filtration, the filtrate was concentrated under reduced pressure to give the crude product, which was purified on an ISCO using a C18 column. Elution with water/MeOH afforded the desired product as the free base form. The free base product was dissolved in MeOH (10 mL) the added 4 N HCl in dioxane (0.5 mL). After being stirred at room temperature for 1 hour, the solvent was removed under reduced pressure and the residue was triturated with EtOAc to afforded the desired product (124 mg, 64% yield) as an off white solid. $^1$H NMR (300 MHz, $D_2O$) δ 7.59 (d, J=8.4 Hz, 1H), 7.49 (m, 3H), 7.24 (d, J=8.1 Hz, 1H), 7.03 (t, J=8.7 Hz, 2H), 6.95 (s, 1H), 3.71 (m, 1H), 3.51 (m, 2H), 3.39 (m, 1H), 3.01-2.87 (m, 3H), 2.57 (m, 1H), 2.31 (m, 1H), 1.40 (m, 1H). LC-MS 367.20 [M+H$^+$].

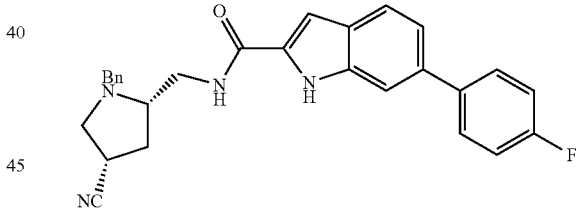

N-(((2S,4S)-1-Benzyl-4-cyanopyrrolidin-2-yl)methyl)-6-(4-fluorophenyl)-1H-indole-2-carboxamide The mixture of 6-(4-fluorophenyl)-1H-indole-2-carboxylic acid (276 mg, 1.08 mmol), (3S,5S)-5-(aminomethyl)-1-benzylpyrrolidine-3-carbonitrile (212 mg, 0.99 mmol), EDC (227 mg, 1.18 mmol), HOBt (80 mg, 0.59 mmol) in DMF (5 mL) was added DIPEA (0.35 mL, 1.97 mol). The reaction mixture was stirred at room temperature overnight. The reaction mixture was added water dropwise with stirring and the solid formed was collected by filtration. Air drying then silica gel column purification afforded the desired (270 mg, 60% yield) as a pale yellow solid. $^1$H NMR (300 MHz, CDCl$_3$) δ 9.19 (bs, 1H), 7.73 (d, J=9.0 Hz, 1H), 7.62-7.55 (m, 3H), 7.39-7.26 (m, 6H), 7.18-7.07 (m, 3H), 6.77 (m, 1H), 4.07 (d, 1H), 3.83 (m, 1H), 3.50-3.46 (m, 2H), 3.31 (d, J=9.9 Hz, 1H), 3.01 (m, 2H), 2.57 (m, 1H), 2.41 (m, 1H), 2.14 (m, 1H).

Example 30. Preparation N-(((2S,4S)-4-(aminomethyl)pyrrolidin-2-yl)methyl)-6-(4-fluorophenyl)-1H-indole-2-carboxamide hydrogen chloride salt

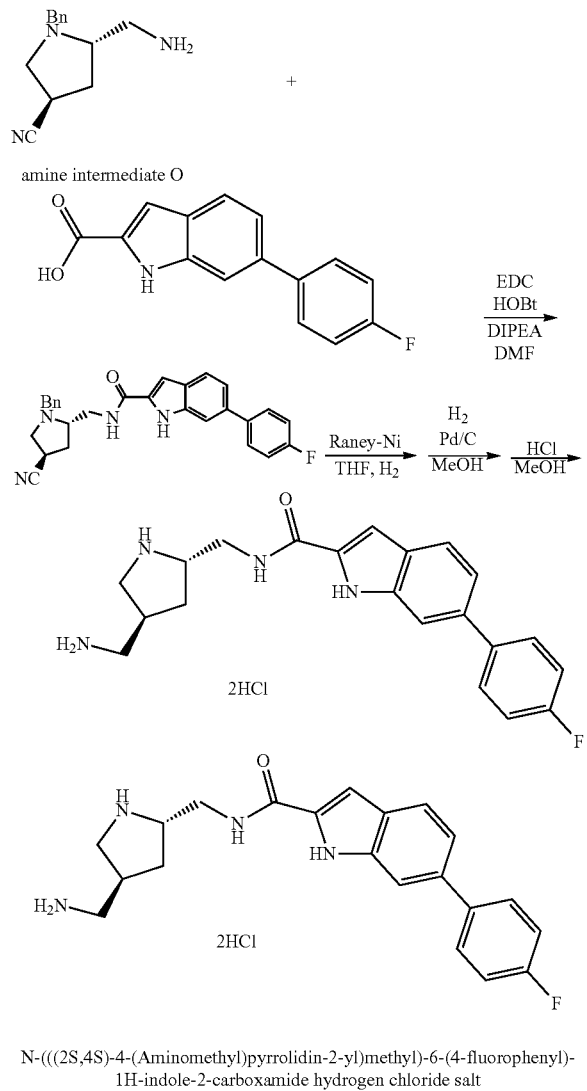

N-(((2S,4S)-4-(Aminomethyl)pyrrolidin-2-yl)methyl)-6-(4-fluorophenyl)-1H-indole-2-carboxamide hydrogen chloride salt To a solution N-(((2S,4R)-1-benzyl-4-cyanopyrrolidin-2-yl)methyl)-6-(4-fluorophenyl)-1H-indole-2-carboxamide (200 mg, 0.44 mmol) in THF (30 mL) was added Raney-Ni (200 mg, 50% in water) under $H_2$ (55 psi) overnight. The reaction progress was monitored by LC-MS. After the reaction was completed, the catalyst was removed by passing through a Celite plug and washed with MeOH. The filtrate was concentrated under reduced pressure to give the amine intermediate. This intermediate was dissolved in MeOH (20 mL). Pd/C (30 mg, 10% on carbon) was added and reaction mixture stirred under $H_2$ (55 psi) overnight. The completion of the reaction was determined by LC-MS monitoring. The catalyst was removed by filtration and the filtrate was concentrated under reduced pressure to give the crude product, which was purified on an ISCO using a C18 column. Elution with water/MeOH afforded the product as the free base form. The free base product was dissolved in MeOH (5 mL) to which was added 4 N HCl in dioxane (0.5 mL). After being stirred at room temperature for 1 hour, the solvent was removed and the residue was triturated with EtOAc to afford the desired product (135 mg, 70% yield) as an off-white solid. $^1$H NMR (300 MHz, D$_2$O) δ 7.58 (d, J=8.7 Hz, 1H), 7.50 (m, 2H), 7.23 (d, J=8.1 Hz, 1H), 7.03 (t, J=9.0 Hz, 2H), 6.94 (s, 1H), 3.78 (m, 1H), 3.48 (m, 3H), 2.95-2.82 (m, 3H), 2.61 (m, 1H), 1.99-1.86 (m, 2H). LC-MS 367.20 [M+H$^+$].

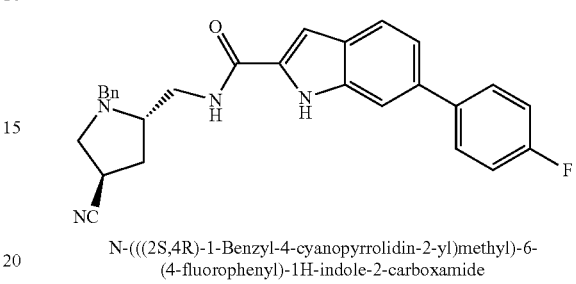

N-(((2S,4R)-1-Benzyl-4-cyanopyrrolidin-2-yl)methyl)-6-(4-fluorophenyl)-1H-indole-2-carboxamide The mixture of 6-(4-fluorophenyl)-1H-indole-2-carboxylic acid (276 mg, 1.08 mmol), (3R,5S)-5-(aminomethyl)-1-benzylpyrrolidine-3-carbonitrile (212 mg, 0.99 mmol), EDC (227 mg, 1.18 mmol), HOBt (80 mg, 0.59 mmol) in DMF (5 mL) was added DIPEA (0.35 mL, 1.97 mol). The reaction mixture was stirred at room temperature overnight. The reaction mixture was added water dropwise with stirring and the solid that formed was collected by filtration. Air drying then silica gel column purification afforded the desired product (250 mg, 56% yield) as an off-white solid. $^1$H NMR (300 MHz, CDCl$_3$) δ 9.29 (bs, 1H), 7.71 (d, J=9.0 Hz, 1H), 7.62-7.57 (m, 3H), 7.37-7.31 (m, 6H), 7.14 (t, J=8.1 Hz, 2H), 6.79 (m, 1H), 6.53 (m, 1H), 4.02 (d, J=13.5 Hz, 1H), 3.83 (m, 1H), 3.54 (d, J=13.5 Hz, 1H), 3.35 (m, 1H), 3.12 (m, 2H), 2.95 (m, 1H), 2.64 (t, 1H), 2.30 (m, 1H), 2.15 (m, 1H).

Example 31. Preparation N-(((2R,4R)-4-(aminomethyl)pyrrolidin-2-yl)methyl)-6-(4-fluorophenyl)-1H-indole-2-carboxamide hydrogen chloride salt

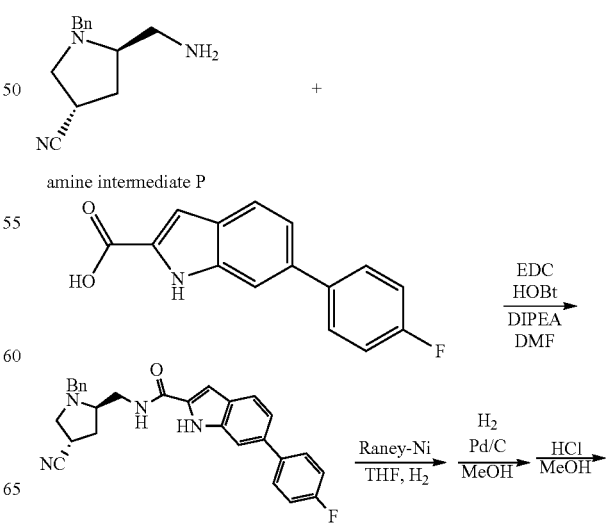

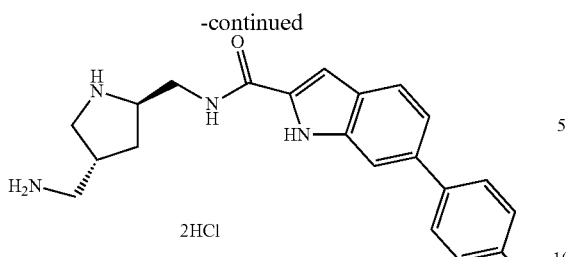

2HCl

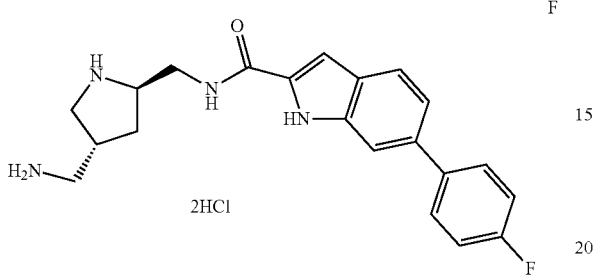

2HCl

N-(((2S,4R)-4-(Aminomethyl)pyrrolidin-2-yl)methyl)-6-(4-fluorophenyl)-1H-indole-2-carboxamide hydrogen chloride salt To a solution N-(((2R,4S)-1-benzyl-4-cyanopyrrolidin-2-yl)methyl)-6-(4-fluorophenyl)-1H-indole-2-carboxamide (120 mg, 0.27 mmol) in THF (20 mL) was added Raney-Ni (120 mg, 50% in water) under H₂ (55 psi) overnight. The reaction progress was monitored by LC-MS. After the reaction was completed, the catalyst was removed by passing through a Celite plug and washed with MeOH. The filtrate was concentrated under reduced pressure to give the amine intermediate. This intermediate was dissolved in MeOH (20 mL). Pd/C (30 mg, 10% on carbon) was added and the reaction mixture stirred under H₂ (55 psi) overnight. The completion of the reaction was determined by LC-MS monitoring. The catalyst was removed by filtration, the filtrate was concentrated under reduced pressure to give the crude product, which was purified on an ISCO using a C18 column. Elution with water/MeOH afforded the desired product as the free base form. The free base product was dissolved in MeOH (2 mL) to which was added 4 N HCl in dioxane (0.2 mL). After being stirred at room temperature for 1 hour, the solvent was removed and the residue was triturated with EtOAc to afford the desired product (42 mg, 36% yield) as a beige solid. ¹H NMR (300 MHz, D₂O) δ 7.50 (d, J=8.4 Hz, 1H), 7.43-7.36 (m, 3H), 7.14 (d, J=8.1 Hz, 1H), 6.97 (t, J=8.7 Hz, 2H), 6.86 (s, 1H), 3.81 (m, 1H), 3.49 (m, 3H), 2.96-2.86 (m, 3H), 2.63 (m, 1H), 1.98-1.85 (m, 2H). LC-MS 367.20 [M+H⁺].

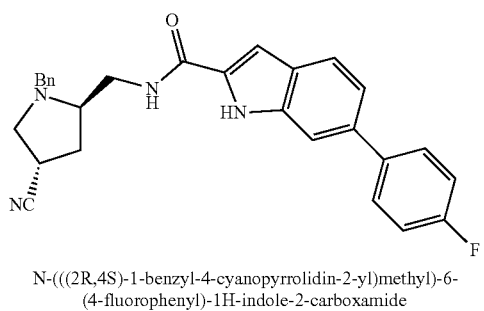 [SMILES: N#C[C@H]1C[C@H](CNC(=O)c2cc3ccc(-c4ccc(F)cc4)cc3[nH]2)N(Cc2ccccc2)C1]

N-(((2R,4S)-1-benzyl-4-cyanopyrrolidin-2-yl)methyl)-6-(4-fluorophenyl)-1H-indole-2-carboxamide The mixture of 6-(4-fluorophenyl)-1H-indole-2-carboxylic acid (140 mg, 0.54 mmol), (3S,5R)-5-(aminomethyl)-1-benzylpyrrolidine-3-carbonitrile (110 mg, 0.51 mmol), EDC (120 mg, 0.61 mmol), HOBt (41 mg, 0.31 mmol) in DMF (5 mL) was added DIPEA (0.19 mL, 1.02 mol). The reaction mixture was stirred at room temperature overnight. The reaction mixture was added water dropwise with stirring and the solid that formed was collected by filtration. Air drying then silica gel column purification afforded the desired product (150 mg, 65% yield) as a light yellow solid. ¹H NMR (300 MHz, CDCl₃) δ 9.22 (bs, 1H), 7.71 (d, J=9.0 Hz, 1H), 7.62-7.57 (m, 3H), 7.37-7.31 (m, 6H), 7.14 (t, J=8.1 Hz, 2H), 6.79 (m, 1H), 6.53 (m, 1H), 4.02 (d, J=13.5 Hz, 1H), 3.83 (m, 1H), 3.54 (d, J=13.5 Hz, 1H), 3.35 (m, 1H), 3.10 (m, 2H), 2.95 (m, 1H), 2.65 (t, 1H), 2.30 (m, 1H), 2.15 (m, 1H).

Example 32. Preparation N-(((2R,4S)-4-(aminomethyl)pyrrolidin-2-yl)methyl)-6-(4-fluorophenyl)-1H-indole-2-carboxamide hydrogen chloride salt

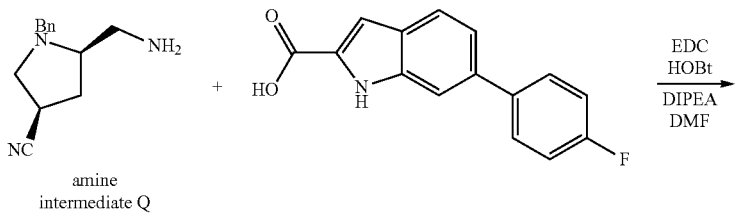

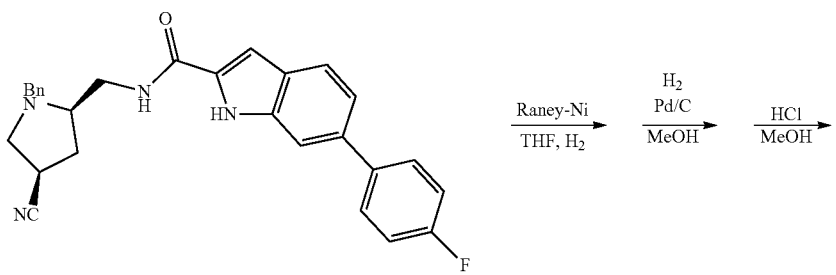

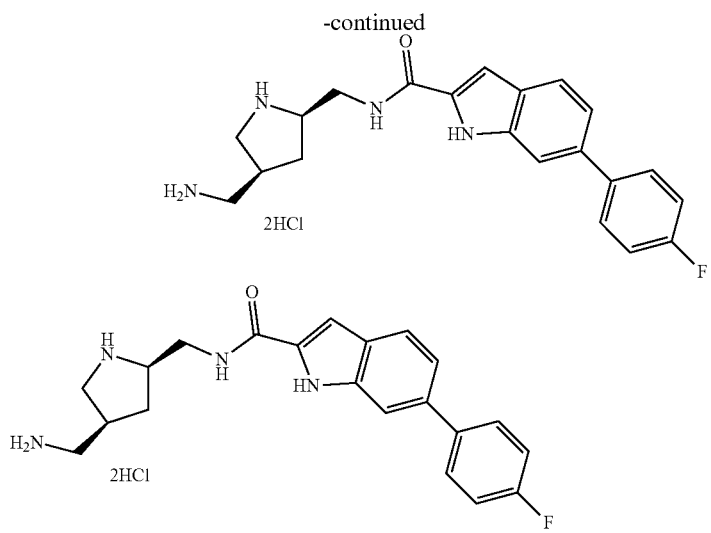

N-(((2S,4R)-4-(Aminomethyl)pyrrolidin-2-yl)methyl)-6-(4-fluorophenyl)-1H-indole-2-carboxamide hydrogen chloride salt To a solution N-(((2R,4R)-1-benzyl-4-cyanopyrrolidin-2-yl)methyl)-6-(4-fluorophenyl)-1H-indole-2-carboxamide (114 mg, 0.25 mmol) in THF (30 mL) was added Raney-Ni (110 mg, 50% in water) under $H_2$ (55 psi) overnight. The reaction progress was monitored by LC-MS. After the reaction was completed, the catalyst was removed by passing through a Celite plug and washed with MeOH. The filtrate was concentrated under reduced pressure to give the amine intermediate. This intermediate was dissolved in MeOH (20 mL). Pd/C (30 mg, 10% on carbon) was added then under $H_2$ (55 psi) overnight. The reaction progress was monitored by LC-MS. After the reaction was completed, the catalyst was removed by filtration and the filtrate was concentrated under reduced pressure to give the crude product, which was purified on an ISCO using a C18 column. Elution with water/MeOH afforded the desired product in free base form. The free base product was dissolved in MeOH (2 mL) to which was added 4 N HCl in dioxane (0.2 mL). After being stirred at room temperature for 1 hour, the solvent was removed and the residue was triturated with EtOAc to afford the desired product (32 mg, 29% yield) as a yellow solid. $^1$H NMR (300 MHz, $D_2O$) δ 7.59 (d, J=8.4 Hz, 1H), 7.52 (m, 3H), 7.25 (d, J=8.1 Hz, 1H), 7.03 (t, J=8.7 Hz, 2H), 6.96 (s, 1H), 3.76 (m, 1H), 3.52 (m, 2H), 3.44 (m, 1H), 3.01-2.92 (m, 3H), 2.58 (m, 1H), 2.31 (m, 1H), 1.44 (m, 1H). LC-MS 367.20 [M+H$^+$].

N-(((2R,4R)-1-Benzyl-4-cyanopyrrolidin-2-yl)methyl)-6-(4-fluorophenyl)-1H-indole-2-carboxamide The mixture of 6-(4-fluorophenyl)-1H-indole-2-carboxylic acid (140 mg, 0.54 mmol), (3R,5R)-5-(aminomethyl)-1-benzylpyrrolidine-3-carbonitrile (110 mg, 0.51 mmol), EDC (120 mg, 0.61 mmol), HOBt (41 mg, 0.31 mmol) in DMF (5 mL) was added DIPEA (0.19 mL, 1.02 mol). The reaction mixture was stirred at room temperature overnight. The reaction mixture was added water dropwise with stirring and the solid formed was collected by filtration. Air drying then silica gel column purification afforded the desired product (131 mg, 57% yield) as a pale yellow solid. $^1$H NMR (300 MHz, CDCl$_3$) δ 9.79 (bs, 1H), 7.72 (d, J=9.0 Hz, 1H), 7.60-7.55 (m, 3H), 7.37-7.26 (m, 6H), 7.14-7.08 (m, 3H), 6.87 (m, 1H), 4.07 (d, 1H), 3.89-3.82 (m, 1H), 3.50-3.43 (m, 2H), 3.28 (d, J=9.9 Hz, 1H), 2.97 (m, 2H), 2.55 (m, 1H), 2.39 (m, 1H), 2.12 (m, 1H).

Example 33. Preparation of N-((5-aminopiperidin-2-yl)methyl)-6-(4-fluorophenyl)-1H-indole-2-carboxamide hydrogen chloride salt

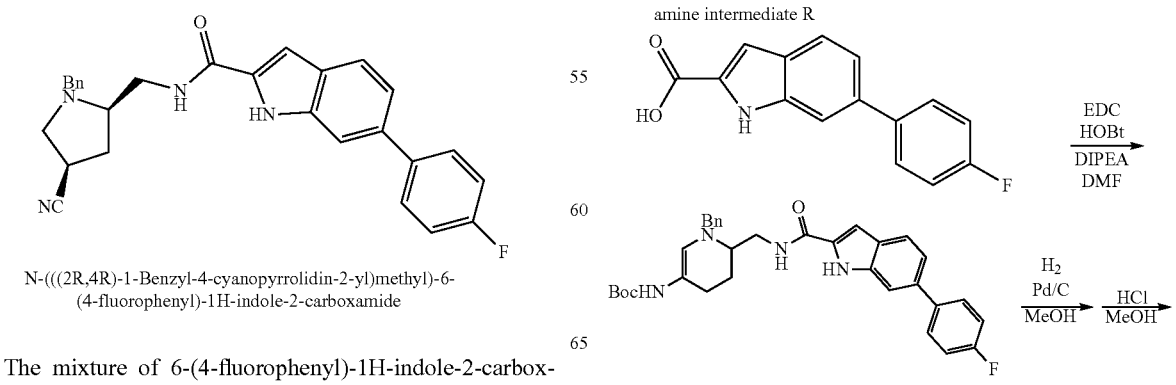

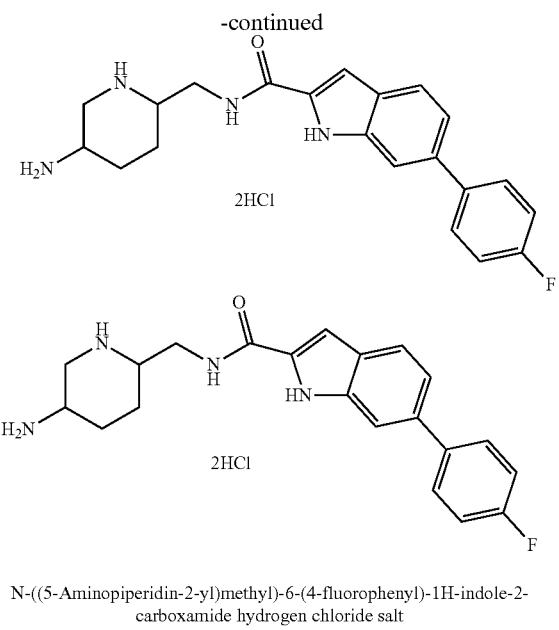

N-((5-Aminopiperidin-2-yl)methyl)-6-(4-fluorophenyl)-1H-indole-2-carboxamide hydrogen chloride salt To a solution of tert-butyl (1-benzyl-6-(((6-(4-fluorophenyl)-1H-indole-2-carboxamido)methyl)-1,4,5,6-tetrahydropyridin-3-yl)carbamate (20 mg, 0.04 mmol) in methanol (10 mL) was added Pd/C (10%, 20 mg). It was stirred under H₂ overnight. The solid was filtered off through a Celite pad and the filtrate was concentrated under reduced pressure to give a residue. The residue was dissolved in MeOH (1 mL) to which was added HCl solution in dioxane (4 N, 0.1 mL). The reaction mixture was stirred at room temperature overnight then concentrated under reduced pressure. The crude product was triturated with EtOAc and the white solid was collected by filtration to provide the title compound (7.1 mg, 44% yield in two steps). LC-MS 367.25 [M+H⁺].

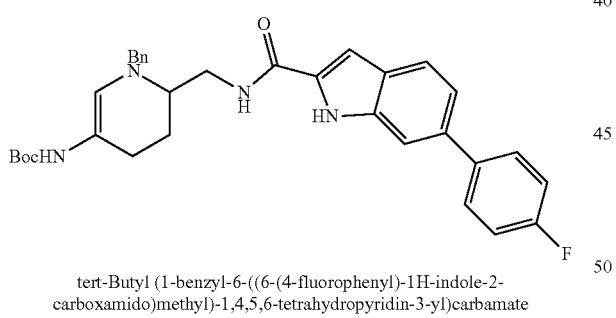

tert-Butyl (1-benzyl-6-(((6-(4-fluorophenyl)-1H-indole-2-carboxamido)methyl)-1,4,5,6-tetrahydropyridin-3-yl)carbamate To a solution of 6-(4-fluorophenyl)-1H-indole-2-carboxylic acid (14 mg, 0.06 mmol) in dry DMF (1 mL) was added DIPEA (0.01 mL, 0.10 mmol), HOBt (5 mg, 0.03 mmol) and EDC (10 mg, 0.06 mmol). The reaction mixture was stirred at room temperature for 5 minutes and tert-butyl (6-(aminomethyl)-1-benzyl-1,4,5,6-tetrahydropyridin-3-yl)carbamate (15 mg, 0.05 mmol) was added. The reaction was stirred at room temperature overnight. It was then diluted with EtOAc and washed with water and brine. The organic layer was dried over anhydrous sodium sulfate and filtered. The filtrate was concentrated under reduced pressure and purified on silica gel to give the desired product (21 mg, 80% yield) as a white solid. ¹H NMR (300 MHz, CDCl₃) 9.31 (br. s, 1H), 7.73 (d, J=8 Hz, 1H), 7.62-7.57 (m, 3H), 7.40-7.26 (m, 6H), 7.17-7.11 (m, 2H), 6.92 (br. s, 1H), 6.85 (s, 1H), 5.81 (s, 1H), 5.58 (s, 1H), 3.80-3.65 (m, 3H), 3.44-3.11 (m, 4H), 2.49-2.44 (m, 1H), 1.97 (m, 1H), 1.45 (s, 9H).

Example 34. Preparation of N-((4-aminopiperidin-2-yl)methyl)-6-(4-fluorophenyl)-1H-indole-2-carboxamide hydrogen chloride salt

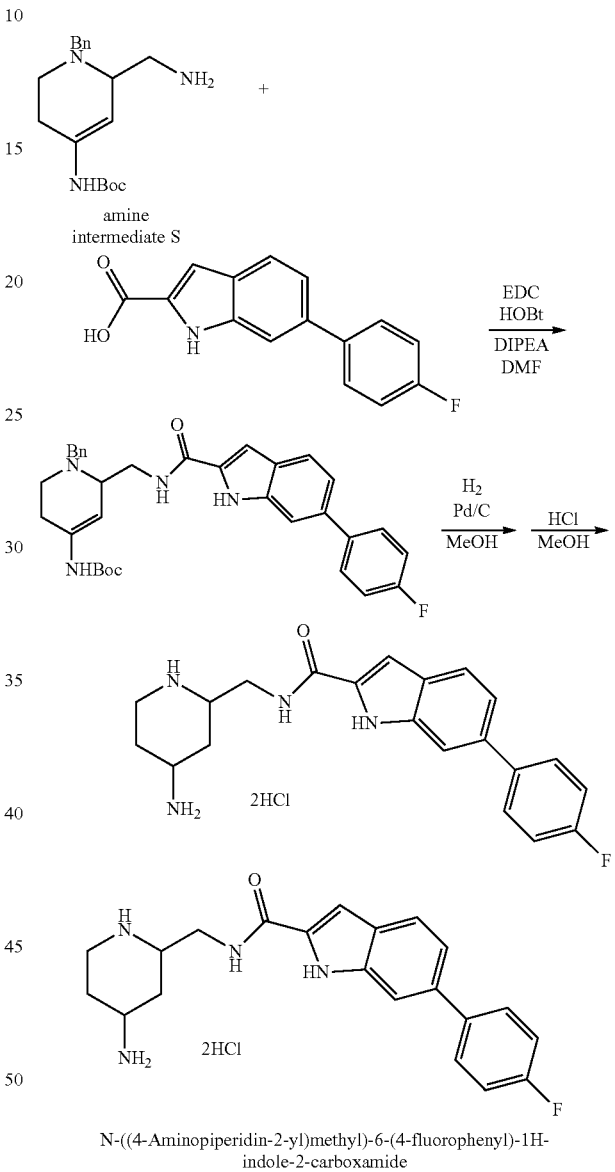

N-((4-Aminopiperidin-2-yl)methyl)-6-(4-fluorophenyl)-1H-indole-2-carboxamide

To a solution of tert-butyl (1-benzyl-6-(((6-(4-fluorophenyl)-1H-indole-2-carboxamido)methyl)-1,2,3,6-tetrahydropyridin-4-yl)carbamate (30 mg, 0.05 mmol) in methanol (10 mL) was added Pd/C (10%, 20 mg). It was stirred under H₂ overnight. The solid was filtered off through a Celite pad and the filtrate was concentrated under reduced pressure to give a residue. The residue was dissolved in MeOH (2 mL) to which was added HCl solution in dioxane (4 N, 0.1 mL). The reaction mixture was stirred at room temperature overnight then concentrated under reduced pressure. The crude product was triturated with EtOAc and the white solid was collected by filtration to provide the title compound (12 mg, 50% yield in two steps). ¹H NMR (300 MHz, MeOD) 7.70-7.64 (m, 4H), 7.34 (d, J=9 Hz, 1H), 7.19-7.14 (m, 3H), 3.71-3.47 (m, 4H), 3.29-3.18 (m, 2H), 2.39-2.24 (m, 2H), 2.00-1.76 (m, 2H). LC-MS 367.25 [M+H⁺].

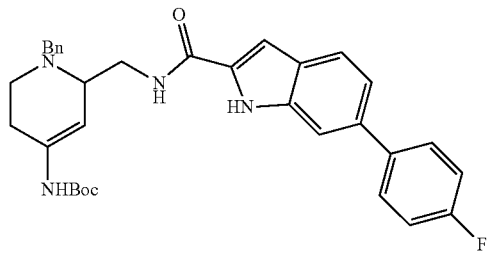

tert-Butyl (1-benzyl-6-((6-(4-fluorophenyl)-1H-indole-2-carboxamido)methyl)-1,2,3,6-tetrahydropyridin-4-yl)carbamate To a solution of 6-(4-fluorophenyl)-1H-indole-2-carboxylic acid (28 mg, 0.11 mmol) in dry DMF (1 mL) was added DIPEA (0.02 mL, 0.2 mmol), HOBt (10 mg, 0.06 mmol) and EDC (20 mg, 0.12 mmol). The reaction mixture was stirred at room temperature for 5 minutes and tert-butyl (6-(aminomethyl)-1-benzyl-1,2,3,6-tetrahydropyridin-4-yl)carbamate (30 mg, 0.10 mmol) was added. The reaction was stirred at room temperature overnight. It was then diluted with EtOAc and washed with water and brine. The organic layer was dried over anhydrous sodium sulfate and filtered. The filtrate was concentrated under reduced pressure and purified on silica gel to give the desired product (38 mg, 73% yield) as a white solid. LC-MS 555.40 [M+H⁺].

Example 35. Preparation of (S)-6-benzyl-N-(2,5-diaminopentyl)-1H-indole-2-carboxamide hydrogen chloride salt

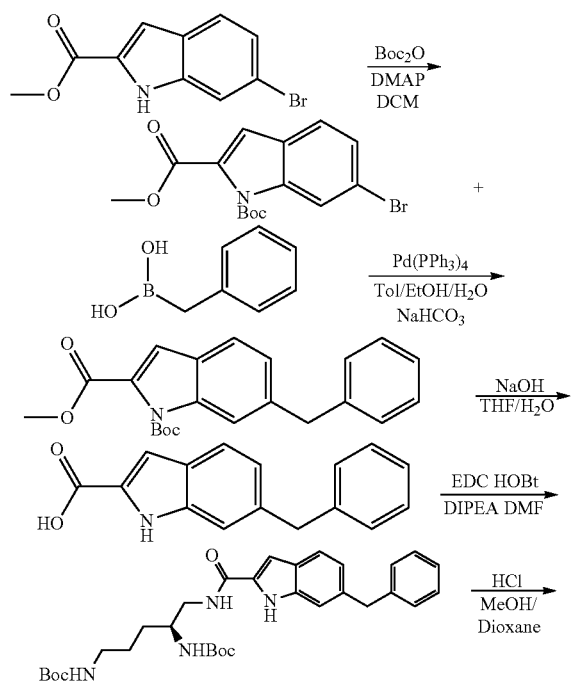

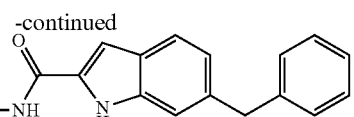

(S)-6-Benzyl-N-(2,5-diaminopentyl)-1H-indole-2-carboxamide hydrogen chloride salt To a solution of (S)-di-tert-butyl (5-(6-benzyl-1H-indole-2-carboxamido)pentane-1,4-diyl)dicarbamate (15 mg, 0.027 mmol) in MeOH (3 mL) HCl solution (4 M in dioxane, 0.1 mL, 0.4 mmol) was added. It was stirred at room temperature until no starting material left, then solvent was removed under reduced pressure. The residue was triturated with EtOAc and the precipitate was collected as an off-white powder (10 mg, 87% yield). ¹H NMR (300 MHz, D₂O) δ 7.47 (d, J=8.4 Hz, 1H), 7.22 (m, 2H), 7.20 (m, 1H), 7.18 (m, 2H), 7.10 (m, 2H), 6.89 (dd, J=8.4, 1.5 Hz, 1H), 3.99 (s, 2H), 3.63 (m, 1H), 3.57 (m, 1H), 3.42 (m, 1H), 2.95 (m, 2H), 1.80 (m, 4H). MS: Calcd for $C_{21}H_{26}N_4O$ 351.21 [M+H⁺], found 351.10 [M+H]⁺.

The requisite intermediates were prepared as follows:
Step 1)

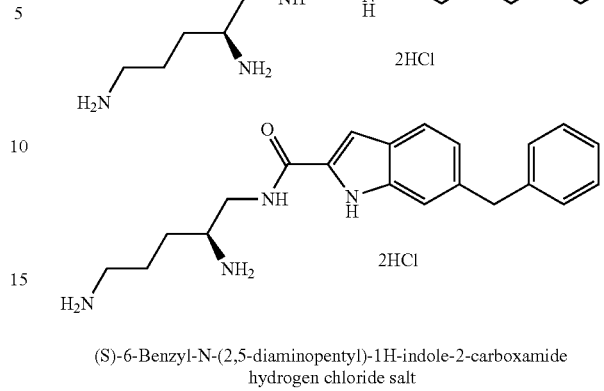

1-tert-Butyl 2-methyl 6-bromo-1H-indole-1,2-dicarboxylate

To a solution of methyl 6-bromo-1H-indole-2-carboxylate (1.07 g, 4.2 mmol) in methylene chloride (50 mL) was added Boc₂O (1.29 g, 5.9 mmol) and DMAP (100 mg, 0.8 mmol). The reaction mixture was stirred at room temperature overnight. TLC analysis showed no starting material left. The reaction mixture was extracted with EtOAc and washed with NH₄Cl solution and brine. After concentration, it was recrystallized to give white crystal (1.13 g, 76%).
Step 2)

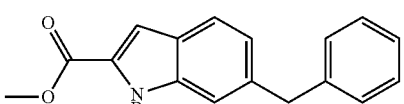

1-tert-Butyl 2-methyl 6-benzyl-1H-indole-1,2-dicarboxylate

The mixture of 1-tert-butyl 2-methyl 6-bromo-1H-indole-1,2-dicarboxylate (0.315 g, 1 mmol), benzylboronic acid (0.25 g, 1.2 mmol) in a mixture of toluene, ethanol and sat. NaHCO₃ solution (20/5/5 mL) was degassed and Pd(dppf)Cl₂ (60 mg, 0.13 mmol) was added. The reaction mixture was heated at 100° C. overnight. The cooled reaction mixture was extracted with EtOAc and washed with brine and concentrated under reduced pressure. The residue was purified by column chromatography on silica gel (10-30% ethyl acetate/hexanes) to give the desired product (0.16 g, 44% yield) as an off-white powder. $^1$H NMR (300 MHz, CDCl$_3$) δ 8.09 (d, J=8.4 Hz, 1H), 7.61 (d, J=8.4 Hz, 1H), 7.42 (t, J=8.4 Hz, 1H), 7.30-7.15 (m, 6H), 7.09 (s, 1H), 3.92 (s, 2H), 1.63 (s, 9H).

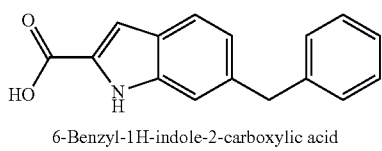 [SMILES: O=C(O)c1cc2ccc(Cc3ccccc3)cc2[nH]1]

6-Benzyl-1H-indole-2-carboxylic acid

Step 3)

To a solution of 1-tert-butyl 2-methyl 6-benzyl-1H-indole-1,2-dicarboxylate (160 mg, 0.97 mmol) in THF (10 mL) was added NaOH solution (4 M, 5 mL). It was heated at 50° C. THF was removed under reduced pressure and the residue was acidified with HCl solution. The precipitate was filtered and washed with water. It was dried to provide the product as a white powder (18 mg, 16% yield) which was used for next step reaction without further purification.

MS: Calcd for C$_{16}$H$_{13}$NO$_2$ 250.09 [M–H]$^+$, found 250.10 [M–H]$^-$.

Step 4)

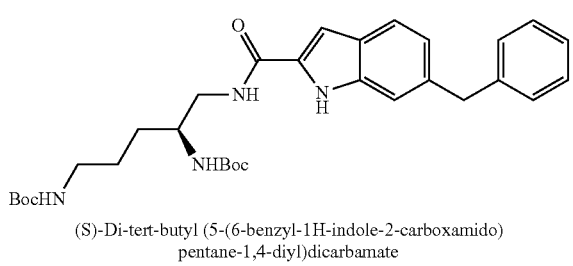 [SMILES: CC(C)(C)OC(=O)NCCC[C@@H](CNC(=O)c1cc2ccc(Cc3ccccc3)cc2[nH]1)NC(=O)OC(C)(C)C]

(S)-Di-tert-butyl (5-(6-benzyl-1H-indole-2-carboxamido)pentane-1,4-diyl)dicarbamate To a solution of 6-benzyl-1H-indole-2-carboxylic acid (18 mg, 0.072 mmol) in dry DMF (0.5 mL) was added DIPEA (0.035 mL, 0.2 mmol), HOBt (10 mg, 0.06 mmol) and EDC (23 mg, 0.12 mmol). The reaction mixture was stirred at room temperature and di-tert-butyl (5-aminopentane-1,4-diyl)(S)-dicarbamate (intermediate B) (32 mg, 0.1 mmol) was added. The reaction mixture was stirred at room temperature overnight. It was extracted with EtOAc and washed with water and brine. The organic layer was dried over anhydrous sodium sulfate and filtered. The filtrate was concentrated under reduced pressure and the residue purified by column chromatography on silica gel using 30-45% EtOAc in hexanes to give the desired product (19 mg, 48% yield) as a pale brown powder. $^1$H NMR (300 MHz, CDCl$_3$) δ 9.27 (br, 1H), 7.55 (t, J=8.4 Hz, 1H), 7.30-7.15 (m, 6H), 7.10 (t, J=8.4 Hz, 1H), 6.86 (s, 1H), 5.91 (br, 1H), 4.82 (br, 1H), 4.64 (br, 1H), 4.13 (s, 2H), 3.81 (m, 1H), 3.48 (m, 2H), 3.13 (m, 2H), 1.61 (m, 4H), 1.46 (s, 9H), 1.43 (s, 9H).

Example 36. Preparation of (S)-6-cyclopropyl-N-(2,5-diaminopentyl)-1H-indole-2-carboxamide hydrogen chloride salt

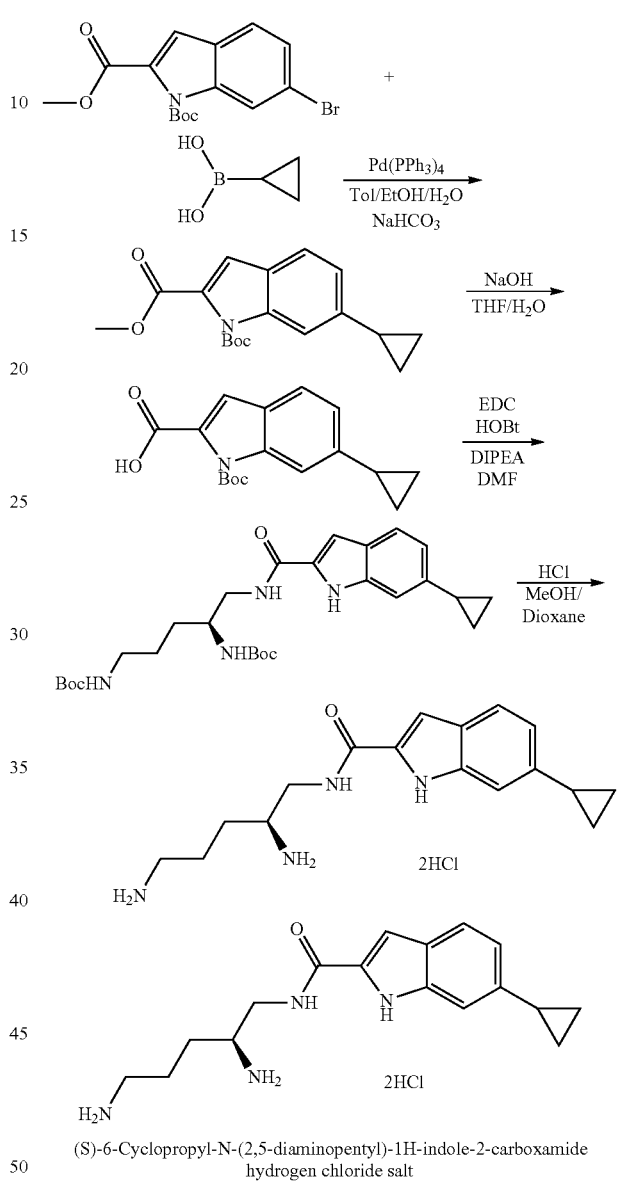

(S)-6-Cyclopropyl-N-(2,5-diaminopentyl)-1H-indole-2-carboxamide hydrogen chloride salt To a solution of (S)-di-tert-butyl (5-(6-cyclopropyl-1H-indole-2-carboxamido)pentane-1,4-diyl)dicarbamate (40 mg, 0.08 mmol) in MeOH (5 mL) was added HCl in solution (4 M in dioxane, 0.2 mL, 0.8 mmol). It was stirred at room temperature until no starting material left, then solvent was removed under reduced pressure. The residue was triturated with EtOAc and the precipitate was collected as a white powder (28 mg, 94% yield). $^1$H NMR (300 MHz, D$_2$O) δ 7.68 (d, J=8.1 Hz, 1H), 7.60 (d, J=8.1 Hz, 1H), 7.32 (s, 1H), 7.16 (s, 1H), 6.99 (d, J=8.1 Hz, 1H), 3.76 (m, 1H), 3.67 (m, 1H), 3.59 (m, 1H), 3.07 (m, 2H), 2.09 (m, 1H), 1.83 (m, 4H), 1.04 (m, 2H), 0.78 (m, 2H). MS: Calcd for C$_{23}$H$_{28}$N$_4$O 300.23 21 [M+H]$^+$, found 300.20 [M+H]$^+$.

The requisite intermediates were prepared as follows:
Step 1)

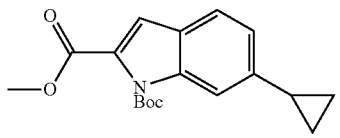

1-tert-Butyl 2-methyl 6-cyclopropyl-1H-dinole-1,2-dicarboxylate

The mixture of 1-tert-butyl 2-methyl 6-bromo-1H-indole-1,2-dicarboxylate (0.71 g, 2 mmol), cyclopropylboronic acid (0.35 g, 4 mmol) in a mixture of toluene, ethanol and sat. NaHCO₃ solution (20/6/6 mL) was degassed and Pd(dppf)Cl₂ (100 mg, 0.12 mmol) was added. The reaction mixture was heated at 105° C. overnight and it was extracted with EtOAc and washed with brine and concentrated under reduced pressure. The residue was purified by column chromatography on silica gel (0-5% ethyl acetate/hexanes) to give the desired product (0.17 g, 27% yield) as an off-white powder. $^1$H NMR (300 MHz, CDCl₃) δ 7.82 (s, 1H), 7.61 (d, J=8.4 Hz, 1H), 7.06 (s, 1H), 7.00 (d, J=8.4 Hz, 1H), 2.02 (m, 1H), 1.61 (s, 9H), 1.00 (m, 2H), 0.78 (m, 2H).

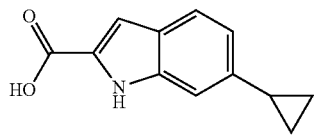

6-Cyclopropyl-1H-indole-2-carboxylic acid

Step 2)
To a solution of 1-tert-butyl 2-methyl 6-cyclopropyl-1H-indole-1,2-dicarboxylate (420 mg, 0.97 mmol) in THF (10 mL) was added NaOH solution (4 M, 5 mL). The reaction mixture was heated at 50° C. THF was removed under reduced pressure and the residue was acidified with HCl solution. The precipitate was filtered and washed with water. It was purified with ISCO C18 column chromatography using 15-30% MeOH in water as eluents to provide the product as a white powder (100 mg, 37% yield) which was used for the next reaction step without further purification. MS: Calcd for C₁₂H₁₁NO₂ 200.09 [M−H]⁻, found 200.10 [M−H]⁻.
Step 3)

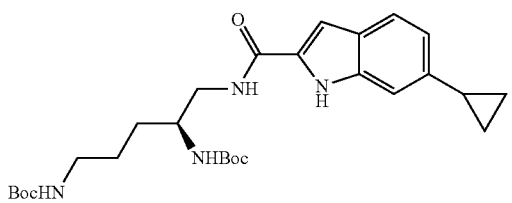

(S)-Di-tert-butyl (5-(6-cyclorpopyl-1H-indole-2-carboxamido)pentane-1,4-diyl)dicarbamate To a solution of 6-benzyl-1H-indole-2-carboxylic acid (18 mg, 0.072 mmol) in dry DMF (0.5 mL) was added DIPEA (0.035 mL, 0.2 mmol), HOBt (10 mg, 0.06 mmol) and EDC (23 mg, 0.12 mmol). The reaction mixture was stirred at room temperature and di-tert-butyl (5-aminopentane-1,4-diyl)(S)-dicarbamate (intermediate B) (32 mg, 0.1 mmol) was added. The reaction mixture was stirred at room temperature overnight. It was extracted with EtOAc and washed with water and brine. The organic layer was dried over anhydrous sodium sulfate and filtered. The filtrate was concentrated under reduced pressure and purified by column chromatography on silica gel using 30-45% EtOAc in hexanes to give the desired product (19 mg, 48% yield) as a pale brown powder. $^1$H NMR (300 MHz, CDCl₃) δ 9.26 (br, 1H), 7.49 (d, J=8.4 Hz, 1H), 7.26 (m, 1H), 7.14 (s, 1H), 6.86 (s, 1H), 4.85 (br, 1H), 4.66 (br, 1H), 4.13 (s, 2H), 3.81 (m, 1H), 3.48 (m, 2H), 3.12 (m, 2H), 2.00 (m, 1H), 1.61 (m, 4H), 1.46 (s, 9H), 1.43 (s, 9H), 0.99 (m, 2H), 0.72 (m, 2H).

Example 37. Preparation of (R)—N-(2,5-diaminopentyl)-6-(4-fluorophenyl)-4-methoxy-1H-indole-2-carboxamide hydrochloride salt

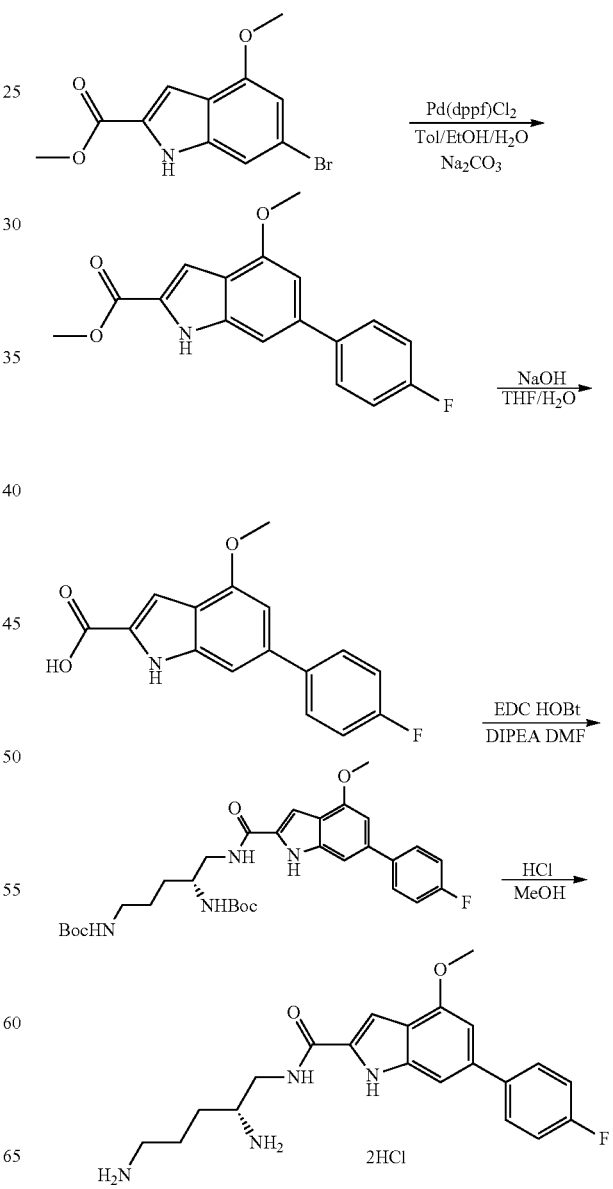

215

-continued

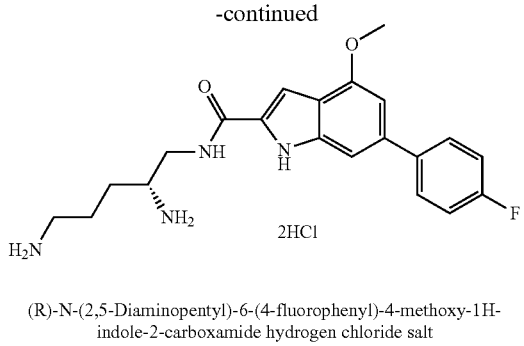

(R)-N-(2,5-Diaminopentyl)-6-(4-fluorophenyl)-4-methoxy-1H-indole-2-carboxamide hydrogen chloride salt To a solution of (R)-di-tert-butyl (5-(6-(4-fluorophenyl)-4-methoxy-1H-indole-2-carboxamido)pentane-1,4-diyl)dicarbamate (19 mg, 0.032 mmol) in MeOH (5 mL) was added HCl in solution (4 M in dioxane, 0.15 mL, 0.6 mmol). The mixture was stirred at room temperature until no starting material left, then the solvent was removed under reduced pressure. The residue was triturated with EtOAc and the precipitate was collected as a pale brown powder (13 mg, 87% yield). $^1$H NMR (300 MHz, D$_2$O) δ 7.72 (m, 2H), 7.33 (s, 1H), 7.48 (t, J=8.7 Hz, 2H), 7.17 (s, 1H), 6.87 (s, 1H), 4.05 (s, 3H), 3.72 (m, 1H), 3.65 (m, 1H), 3.61 (m, 1H), 3.09 (m, 2H), 1.86 (m, 4H). MS: Calcd for $C_{21}H_{25}FN_4O_2$ 385.20 [M+H]$^+$, found 385.20 [M+H]$^+$.

The requisite intermediates were prepared as follows:

Step 1)

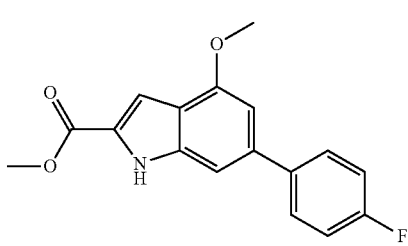

Methyl 6-(4-fluorophenyl)-4-methoxy-1H-indole-2-carboxylate

The mixture of methyl 6-bromo-4-methoxy-1H-indole-2-carboxylate (56 mg, 0.2 mmol), (4-fluorophenyl)boronic acid (56 mg, 0.4 mmol) in a mixture of toluene, ethanol and sat. NaHCO$_3$ solution (5/1/1 mL) was degassed and Pd(dppf)Cl$_2$ (30 mg, 0.037 mmol) was added. The reaction mixture was heated at 100° C. overnight. The cooled reaction mixture was extracted with EtOAc, washed with brine and concentrated under reduced pressure. The residue was purified by column chromatography on silica to give the desired product (42 mg, 70% yield) as an off-white powder. MS: Calcd for $C_{17}H_{14}FNO_3$ 300.10 [M+H]$^+$, found 300.10 [M+H]$^+$.

216

Step 2)

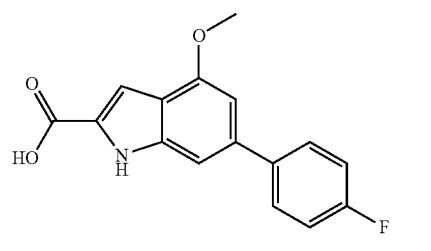

6-(4-Fluorophenyl)-4-methoxy-1H-indole-2-carboxylic acid

To a solution of methyl 6-(4-fluorophenyl)-4-methoxy-1H-indole-2-carboxylate (42 mg, 0.14 mmol) in THF (10 mL) was added NaOH solution (2 M, 5 mL). It was heated at 65° C. until no starting material left. THF was removed under reduced pressure and the residue was acidified with HCl solution. The precipitate was filtered and washed with water. It was dried to provide the product as a pale brown powder (20 mg, 50% yield) which was used for next step reaction without further purification. MS: Calcd for $C_{16}H_{12}FNO_3$ 284.08 [M−H]$^-$, found 284.00 [M−H]$^-$.

Step 3)

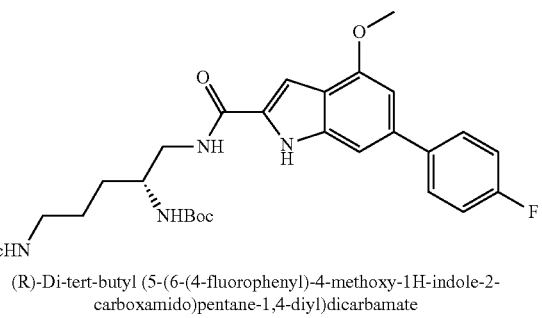

(R)-Di-tert-butyl (5-(6-(4-fluorophenyl)-4-methoxy-1H-indole-2-carboxamido)pentane-1,4-diyl)dicarbamate To a solution of 6-(4-fluorophenyl)-4-methoxy-1H-indole-2-carboxylic acid (15 mg, 0.053 mmol) in dry DMF (1 mL) was added DIPEA (0.018 mL, 0.1 mmol), HOBt (5 mg, 0.03 mmol) and EDC (12 mg, 0.06 mmol). The reaction mixture was stirred at room temperature and di-tert-butyl (5-aminopentane-1,4-diyl)(R)-dicarbamate (intermediate E) (17 mg, 0.053 mmol) was added. The reaction mixture was stirred at room temperature overnight. The reaction mixture was extracted with EtOAc and washed with water and then brine. The organic layer was dried over anhydrous sodium sulfate and filtered. The filtrate was concentrated under reduced pressure and purified by column chromatography on silica gel to give the desired product (19 mg, 61% yield) as a pale brown powder. $^1$H NMR (300 MHz, CDCl$_3$) δ 9.29 (br, 1H), 7.57 (m, 2H), 7.15 (s, 1H), 7.12 (m, 2H), 7.05 (s, 1H), 6.66 (s, 1H), 4.83 (br, 1H), 4.66 (br, 1H), 3.99 (s, 3H), 3.81 (m, 1H), 3.68 (m, 1H), 3.51 (m, 1H), 3.13 (m, 2H), 1.62 (m, 4H), 1.44 (s, 9H), 1.42 (s, 9H).

Example 38 (YY-2-124). Preparation of 6-(4-fluorophenyl)-N-methyl-N-((3S,5S)-5-(methylcarbamoyl)pyrrolidin-3-yl)-1H-indole-2-carboxamide hydrogen chloride salt

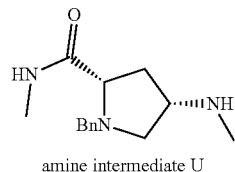

amine intermediate U

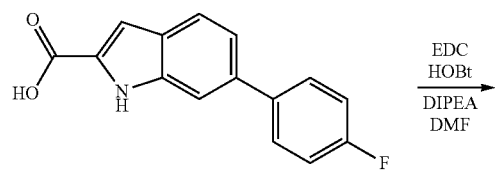

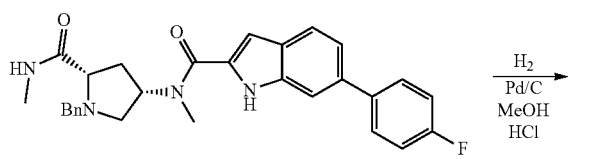

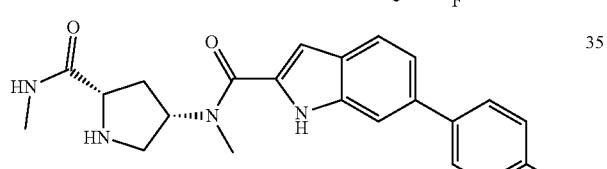

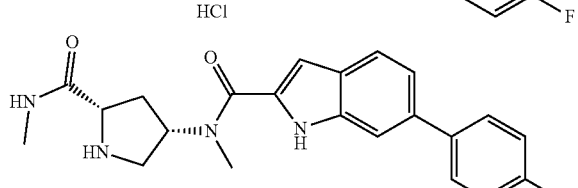

6-(4-Fluorophenyl)-N-methyl-N-((3S,5S)-5-(methylcarbamoyl)pyrrolidin-3-yl)-1H-indole-2-carboxamide To a solution of N-((3S,5S)-1-benzyl-5-(methylcarbamoyl)pyrrolidin-3-yl)-6-(4-fluorophenyl)-N-methyl-1H-indole-2-carboxamide (45 mg, 0.093 mmol) in MeOH (5 mL) was added Pd/C (10%, 25 mg). The reaction mixture was stirred under H₂ overnight. It was filtered through a Celite pad and washed with methanol, then concentrated under reduced pressure and HCl in solution (4 M in dioxane, 0.05 mL) was added. The solvent was removed under reduced pressure. The residue was triturated with EtOAc and the precipitate was collected as a pale yellow powder (25 mg, 62% yield). $^1$H NMR (300 MHz, D₂O) δ 7.86 (m, 1H), 7.78 (m, 3H), 7.52 (m, 1H), 7.29 (m, 2H), 7.09 (m, 1H), 3.73 (m, 2H), 3.37 (s, 3H), 2.85 (s, 3H), 2.42 (m, 2H), 1.42 (m, 2H). MS: Calcd for $C_{22}H_{23}FN_4O_2$ 395.18 [M+H]$^+$, found 395.25 [M+H]$^+$.

The requisite intermediates were prepared as follows:

Step 1)

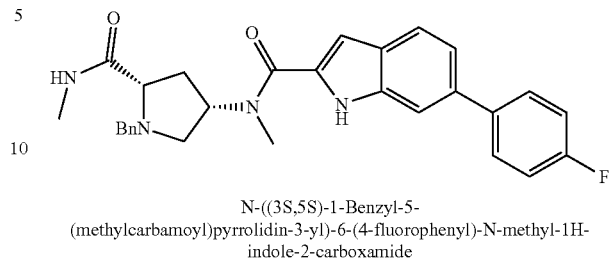

N-((3S,5S)-1-Benzyl-5-(methylcarbamoyl)pyrrolidin-3-yl)-6-(4-fluorophenyl)-N-methyl-1H-indole-2-carboxamide To a solution of 6-(4-fluorophenyl)-1H-indole-2-carboxylic acid (42 mg, 0.16 mmol) in dry DMF (1 mL) was added DIPEA (0.08 mL, 0.46 mmol), HOBt (16 mg, 0.11 mmol) and EDC (37 mg, 0.19 mmol). The reaction mixture was stirred at room temperature and (2S,4S)-1-benzyl-N-methyl-4-(methylamino)pyrrolidine-2-carboxamide (intermediate L) (40 mg, 0.16 mmol) was added. The reaction mixture was stirred at room temperature overnight. It was extracted with EtOAc and washed with water and then brine. The organic layer was dried over anhydrous sodium sulfate and filtered. The filtrate was concentrated under reduced pressure and the residue purified by column chromatography on silica gel to give the desired product (25 mg, 32% yield) as a pale brown powder. $^1$H NMR (300 MHz, CDCl₃) δ 9.33 (br, 1H), 7.69 (d, J=8.1 Hz, 1H), 7.56 (m, 2H), 7.31 (m, 6H), 7.13 (t, J=8.4 Hz, 2H), 6.98 (s, 1H), 6.79 (br, 1H), 5.37 (br, 1H), 3.97 (d, 1H), 3.36 (m, 3H), 3.30 (s, 3H), 3.08 (m, 1H), 2.95 (m, 1H), 2.87 (s, 3H), 2.76 (m, 2H). MS: Calcd for $C_{29}H_{29}FN_4O_2$ 485.23 [M+H]$^+$, found 485.30 [M+H]$^+$.

Example 39. Preparation of N-(((2S,4S)-4-((R)-2-amino-3-methylbutanamido)pyrrolidin-2-yl)methyl)-6-(4-fluorophenyl)-1H-indole-2-carboxamide hydrogen chloride salt

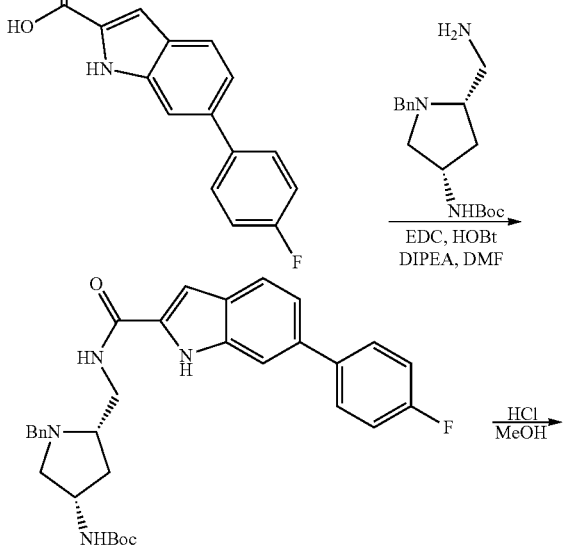

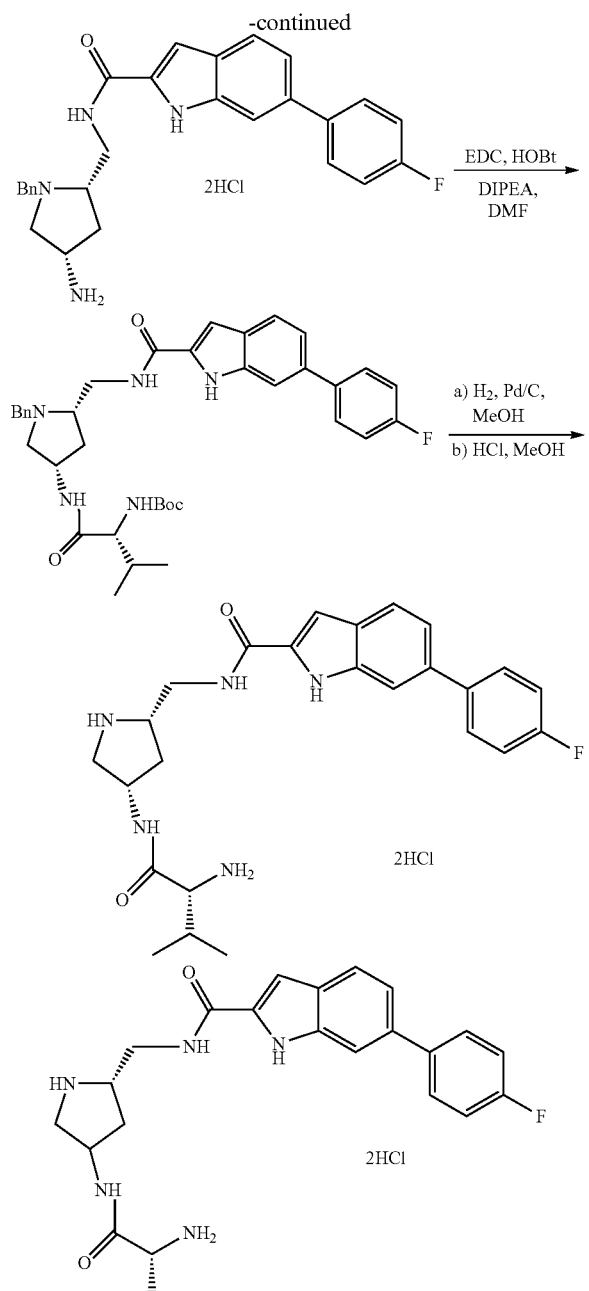

N-(((2S,4S)-4-((R)-2-Amino-3-methylbutanamido)pyrrolidin-2-yl)methyl)-6-(4-fluorophenyl)-1H-indole-2-carboxamide hydrogen chloride salt To a solution of tert-butyl ((R)-1-(((3S,5S)-1-benzyl-5-((6-(4-fluorophenyl)-1H-indole-2-carboxamido)methyl)pyrrolidin-3-yl)amino)-3-methyl-1-oxobutan-2-yl)carbamate (20 mg, 0.031 mmol) in MeOH (5 mL) was added Pd/C (10%, 20 mg). The reaction mixture was stirred under $H_2$ overnight. It was filtered through a Celite pad and washed with methanol, then concentrated under reduced pressure and HCl in solution (4 M in dioxane, 0.15 mL) was added to the residue. The solution was stirred at room temperature until no starting material left. The solvent was removed under reduced pressure. The residue was triturated with EtOAc and the precipitate was collected as an off-white powder (13 mg, 80% yield). MS: Calcd for $C_{25}H_{30}FN_5O_2$ 452.24 [M+H]$^+$, found 452.30 [M+H]$^+$.

The requisite intermediates were prepared as follows:

Step 1)

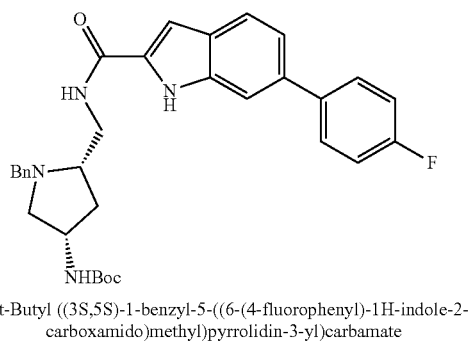

tert-Butyl ((3S,5S)-1-benzyl-5-((6-(4-fluorophenyl)-1H-indole-2-carboxamido)methyl)pyrrolidin-3-yl)carbamate To a solution of 6-(4-fluorophenyl)-1H-indole-2-carboxylic acid (123 mg, 0.5 mmol) in dry DMF (2 mL) was added DIPEA (0.17 mL, 1.0 mmol), HOBt (45 mg, 0.29 mmol) and EDC (110 mg, 0.6 mmol). The reaction mixture was stirred at room temperature and tert-butyl ((3S,5S)-5-(aminomethyl)-1-benzylpyrrolidin-3-yl)carbamate (intermediate K) (153 mg, 0.5 mmol) was added. The reaction mixture was stirred at room temperature overnight. It was extracted with EtOAc and washed with water and then brine. The organic layer was dried over anhydrous sodium sulfate and filtered. The filtrate was concentrated under reduced pressure and the residue purified by column chromatography on silica gel to give the desired product (140 mg, 52% yield) as a pale brown powder. $^1$H NMR (300 MHz, CDCl$_3$) δ 9.45 (br, 1H), 7.68 (d, J=8.1 Hz, 1H), 7.59 (m, 2H), 7.56 (s, 1H), 7.33 (m, 1H), 7.30 (m, 5H), 7.13 (t, J=8.4 Hz, 2H), 6.85 (s, 1H), 6.66 (br, 1H), 4.85 (br, 1H), 4.33 (br, 1H), 3.81 (m, 1H), 3.58 (s, 2H), 2.67 (m, 2H), 2.50 (m, 3H), 1.62 (m, 2H), 1.43 (s, 9H). MS: Calcd for $C_{32}H_{35}FN_4O_3$ 485.23 [M+H]$^+$, found 543.40 [M+H]$^+$.

Step 2)

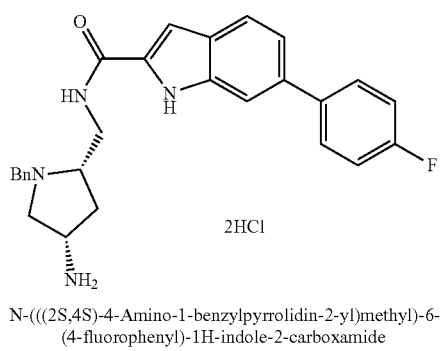 [SMILES: N[C@H]1C[C@@H](CNC(=O)c2cc3ccc(-c4ccc(F)cc4)cc3[nH]2)N(Cc2ccccc2)C1]

N-(((2S,4S)-4-Amino-1-benzylpyrrolidin-2-yl)methyl)-6-(4-fluorophenyl)-1H-indole-2-carboxamide To a solution of tert-butyl ((3S,5S)-1-benzyl-5-((6-(4-fluorophenyl)-1H-indole-2-carboxamido)methyl)pyrrolidin-3-yl)carbamate (110 mg, 0.2 mmol) in MeOH (3 mL) was added HCl in solution (4 M in dioxane, 0.1 mL, 0.4 mmol). It was stirred at room temperature until TLC analysis showed no starting material was left, then solvent was removed under reduced pressure to provide the crude product (93 mg, 90% yield).

Step 3)

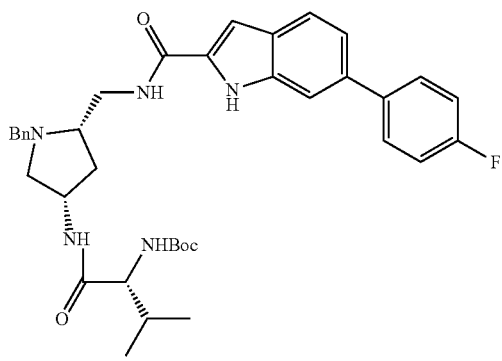

tert-Butyl ((R)-1-(((3S,5S)-1-benzyl-5-((6-(4-fluorophenyl)-1H-indole-2-carboxamido)methyl)pyrrolidin-3-yl)amino)-3-methyl-1-oxobutan-2-yl)carbamate To a solution of N-(((2S,4S)-4-amino-1-benzylpyrrolidin-2-yl)methyl)-6-(4-fluorophenyl)-1H-indole-2-carboxamide (30 mg, 0.056 mmol) in dry DMF (0.5 mL) was added DIPEA (0.035 mL, 0.2 mmol), HOBt (10 mg, 0.06 mmol) and EDC (23 mg, 0.12 mmol). The reaction mixture was stirred at room temperature and Boc-Val-OH (24 mg, 0.11 mmol) was added. The reaction mixture was stirred at room temperature overnight. It was extracted with EtOAc and washed with water and brine. The organic layer was dried over anhydrous sodium sulfate and filtered. The filtrate was concentrated under reduced pressure and purified by column chromatography on silica gel using 40-80% EtOAc in hexanes to give the desired product (22 mg, 62% yield) as a pale brown powder. MS: Calcd for $C_{37}H_{44}FN_5O_4$ 642.34 $[M+H]^+$, found 642.20 $[M+H]^+$.

Example 40. Preparation of (S)-3-bromo-N-(2,5-diaminopentyl)-5-(4-fluorophenyl)-1H-indole-2-carboxamide hydrogen chloride salt

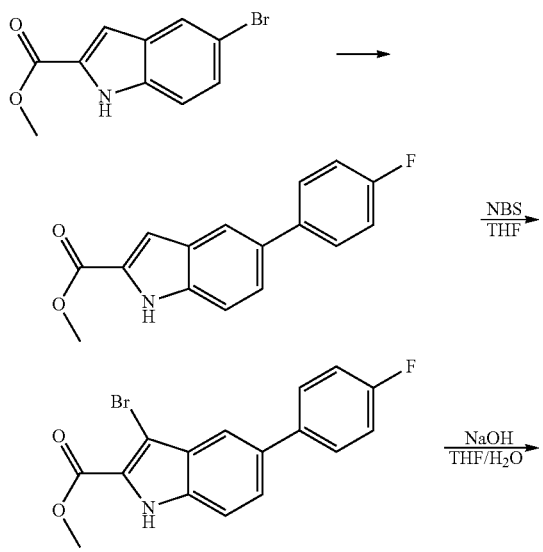

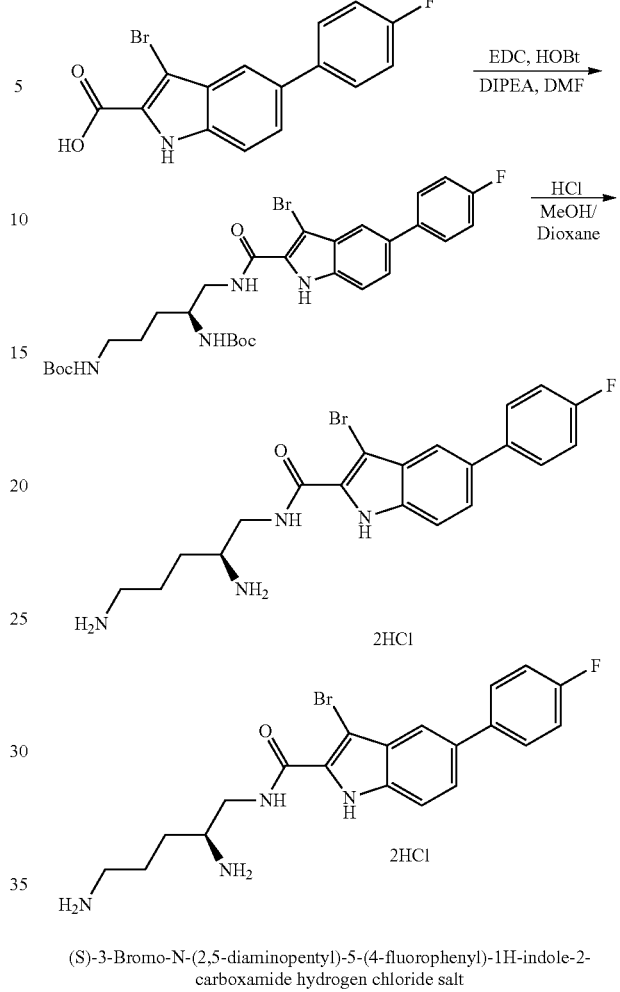

(S)-3-Bromo-N-(2,5-diaminopentyl)-5-(4-fluorophenyl)-1H-indole-2-carboxamide hydrogen chloride salt To a solution of di-tert-butyl (5-(3-bromo-6-(4-fluorophenyl)-1H-indole-2-carboxamido)pentane-1,4-diyl)(S)-dicarbamate (30 mg, 0.052 mmol) in MeOH (3 mL) HCl solution (4 M in dioxane, 0.1 mL, 0.4 mmol) was added. It was stirred at room temperature until TLC showed no starting material left, then solvent was removed under reduced pressure. The residue was triturated with EtOAc and the precipitate was collected as an off-white powder (18 mg, 69% yield). $^1$H NMR (300 MHz, $D_2O$) δ 7.80 (s, 1H), 7.67 (m, 3H), 7.62 (m, 1H), 7.22 (d, J=8.4 Hz, 2H), 3.75 (m, 1H), 3.67 (m, 1H), 3.58 (m, 1H), 3.05 (m, 2H), 1.82 (m, 4H). MS: Calcd for $C_{20}H_{22}BrFN_4O$ 433.10 and 435.10 $[M+H]^+$, found 433.15 and 435.15 $[M+H]^+$.

The requisite intermediates were prepared as follows:
Step 1)

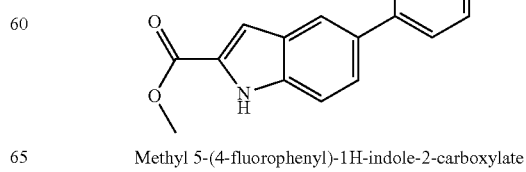

Methyl 5-(4-fluorophenyl)-1H-indole-2-carboxylate

The mixture of methyl 5-bromo-1H-indole-2-carboxylate (4.5 g, 17.7 mmol), (4-fluorophenyl)boronic acid (2.6 g, 18.6 mmol) in a mixture of toluene, ethanol and sat. NaHCO$_3$ solution (100/20/20 mL) was degassed and Pd(dppf)Cl$_2$ (300 mg, 0.37 mmol) was added. The reaction mixture was heated at 105° C. overnight and it was extracted with EtOAc and the organic layer washed with brine and concentrated under reduced pressure. The residue was purified by column chromatography on silica gel (10-30% ethyl acetate/hexanes) to give the desired product (3.5 g, 73% yield) as an off-white powder. $^1$H NMR (300 MHz, CDCl$_3$) δ 8.94 (br, 1H), 7.74 (d, J=8.4 Hz, 1H), 7.62 (m, 3H), 7.36 (d, J=8.4 Hz, 1H), 7.24 (m, 1H), 7.15 (m, 2H), 3.96 (s, 3H). MS: Calcd for C$_{16}$H$_{12}$FNO$_2$ 268.09 [M−H]$^−$ found 268.10 [M−H]$^−$.

Step 2)

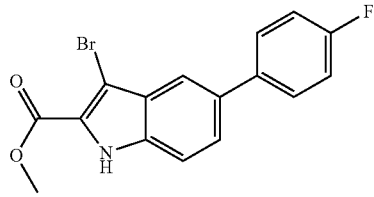

Methyl 3-bromo-5-(4-fluorophenyl)-1H-indole-2-carboxylate

To a solution of methyl 5-(4-fluorophenyl)-1H-indole-2-carboxylate (0.27 g, 1.0 mmol) in dry THF (10 mL) was added NBS (187 mg, 1.05 mmol). The reaction mixture was heated at 50° C. until TLC showed no starting material left. The reaction mixture was cooled to room temperature and concentrated under reduced pressure. The resulting precipitate was filtered off and washed with THF to give the desired product (0.34 g, 98% yield) as a white crystalline solid. It was used for next step reaction without further purification. $^1$H NMR (300 MHz, CDCl$_3$) δ 7.45 (t, J=8.4 Hz, 2H), 7.41 (m, 1H), 7.19 (dd, J=8.4, 1.5 Hz, 2H), 6.95 (t, J=8.4 Hz, 2H), 3.80 (s, 3H). MS: Calcd for C$_{16}$H$_{11}$BrFNO$_2$ 346.00 and 347.99 [M−H]$^−$, found 345.85 and 347.85 [M−H]$^−$.

Step 3)

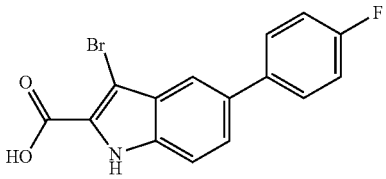

3-Bromo-5-(4-fluorophenyl)-1H-indole-2-carboxylic acid

To a solution of methyl 3-bromo-5-(4-fluorophenyl)-1H-indole-2-carboxylate (340 mg, 0.97 mmol) in THF (10 mL) was added NaOH solution (2 M, 5 mL). The reaction mixture was heated at 70° C. until no starting material was left. The THF was removed under reduced pressure and the residue was acidified with HCl solution. The precipitate was filtered and washed with water. It was dried to provide the desired product as a pale brown powder (260 mg, 79% yield) which was used for the next reaction step without further purification. MS: Calcd for C$_{15}$H$_9$BrFNO$_2$ 331.98 and 333.98 [M−H]$^−$, found 331.90 and 333.95 [M−H]$^−$.

Step 4)

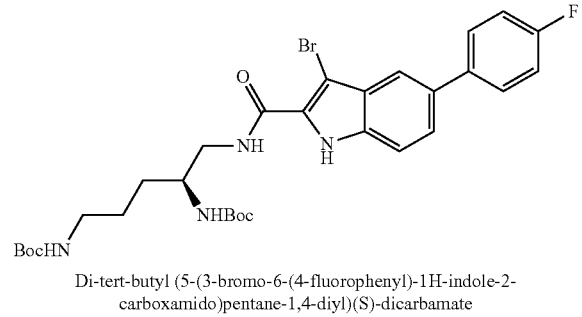 [SMILES: CC(C)(C)OC(=O)NCCC[C@@H](CNC(=O)c1[nH]c2ccc(-c3ccc(F)cc3)cc2c1Br)NC(=O)OC(C)(C)C]

Di-tert-butyl (5-(3-bromo-6-(4-fluorophenyl)-1H-indole-2-carboxamido)pentane-1,4-diyl)(S)-dicarbamate To a solution of 3-bromo-5-(4-fluorophenyl)-1H-indole-2-carboxylic acid (34 mg, 0.1 mmol) in dry DMF (1 mL) was added DIPEA (0.035 mL, 0.2 mmol), HOBt (10 mg, 0.06 mmol) and EDC (23 mg, 0.12 mmol). The reaction mixture was stirred at room temperature and di-tert-butyl (5-aminopentane-1,4-diyl)(S)-dicarbamate (intermediate B) (32 mg, 0.1 mmol) was added. The reaction mixture was stirred at room temperature overnight. It was extracted with EtOAc and washed with water and brine. The organic layer was dried over anhydrous sodium sulfate and filtered. The filtrate was concentrated under reduced pressure and purified by column chromatography on silica gel using 40-50% EtOAc in hexanes to give the desired product (37 mg, 58% yield) as a pale brown powder. $^1$H NMR (300 MHz, CDCl$_3$) δ 9.69 (br, 1H), 7.61 (m, 3H), 7.49 (m, 2H), 7.15 (t, J=8.4 Hz, 2H), 4.75 (br, 1H), 4.68 (br, 1H), 3.87 (m, 1H), 3.69 (m, 1H), 3.52 (m, 1H), 3.15 (m, 2H), 1.58 (m, 4H), 1.43 (s, 9H), 1.40 (s, 9H).

Example 41. Preparation of (S)-6-(cyclopropylethynyl)-N-(2,5-diaminopentyl)-1H-indole-2-carboxamide hydrogen chloride salt

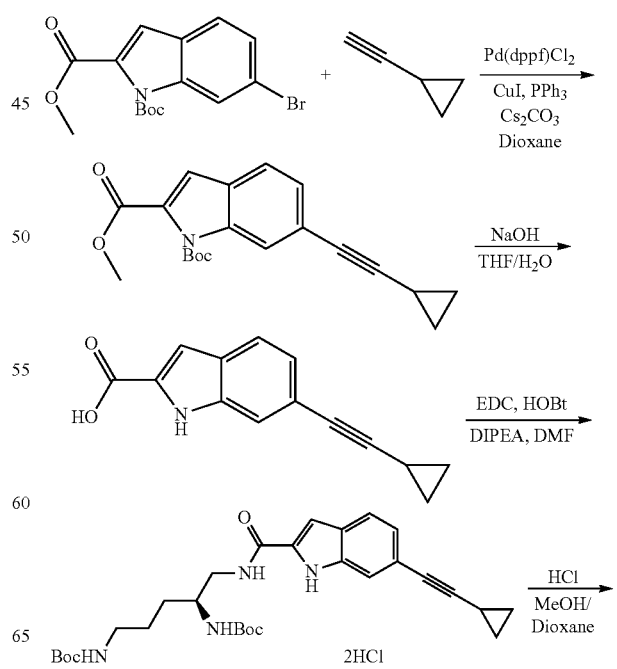

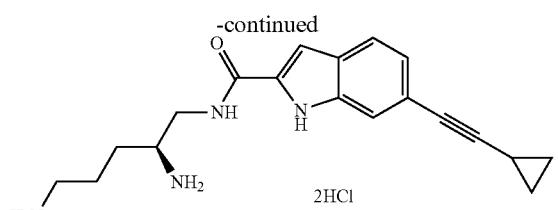

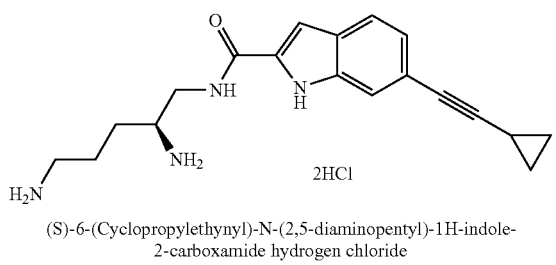

(S)-6-(Cyclopropylethynyl)-N-(2,5-diaminopentyl)-1H-indole-2-carboxamide hydrogen chloride To a solution of (S)-di-tert-butyl (5-(6-(cyclopropylethynyl)-1H-indole-2-carboxamido)pentane-1,4-diyl)dicarbamate (40 mg, 0.076 mmol) in MeOH (5 mL) was added a solution of HCl (4 M in dioxane, 0.2 mL, 0.8 mmol). The reaction mixture was stirred at room temperature until no starting material left. The solvent was then removed under reduced pressure. The residue was triturated with EtOAc and the precipitate was collected as a white powder (23 mg, 76% yield). $^1$H NMR (300 MHz, D$_2$O) δ 7.45 (d, J=8.4 Hz, 1H), 7.37 (s, 1H), 7.07 (s, 1H), 6.97 (d, J=8.4 Hz, 1H), 3.62 (m, 1H), 3.56 (m, 1H), 3.40 (m, 1H), 2.93 (m, 2H), 1.93 (m, 4H), 1.39 (m, 1H), 0.81 (m, 2H), 0.66 (m, 2H). MS: Calcd for C$_{19}$H$_{24}$N$_4$O 325.20 [M+H]$^+$, found 325.20 [M+H]$^+$.

The requisite intermediates were prepared as follows:

Step 1)

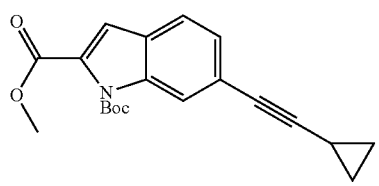

1-tert-Butyl 2-methyl 6-(cylclopropylethynyl)-1H-indole-1,2-dicarboxylate

The mixture of 1-tert-butyl 2-methyl 6-bromo-1H-indole-1,2-dicarboxylate (0.354 g, 1 mmol), ethynylcyclopropane (0.39 g, 5.9 mmol), PPh$_3$ (40 mg, 0.15 mmol), Cs$_2$CO$_3$ (0.45 g, 1.38 mmol) in dioxane was degassed and CuI (54 mg, 0.03 mmol) and Pd(dppf)Cl$_2$ (65 mg, 0.08 mmol) were added. The reaction mixture was heated at 85° C. overnight and it was extracted with EtOAc and washed with brine and concentrated under reduced pressure. The residue was purified by column chromatography on silica gel (0-15% ethyl acetate/hexanes) to give the desired product (0.29 g, 85% yield) as an off-white powder. $^1$H NMR (300 MHz, CDCl$_3$) δ 8.14 (s, 1H), 7.47 (d, J=8.4 Hz, 1H), 7.26 (d, J=8.4 Hz, 1H), 7.05 (s, 1H), 3.91 (s, 3H), 1.55 (s, 9H), 1.47 (m, 1H), 0.87 (m, 2H), 0.83 (m, 2H).

Step 2)

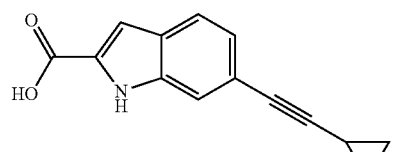

6-(Cyclopropylethynyl)-1H-indole-2-carboxylic acid

To a solution of 1-tert-butyl 2-methyl 6-(cyclopropylethynyl)-1H-indole-1,2-dicarboxylate (320 mg, 0.97 mmol) in THF (10 mL) was added NaOH solution (4 M, 5 mL). The reaction mixture was heated at 50° C. THF was removed under reduced pressure and the residue was acidified with HCl solution. The precipitate was filtered and washed with water to provide the desired product as a white powder (180 mg, 85% yield) which was used for next step reaction without further purification. MS: Calcd for C$_{14}$H$_{11}$NO$_2$ 224.08 [M−H]$^−$, found 224.05 [M−H]$^−$.

Step 3)

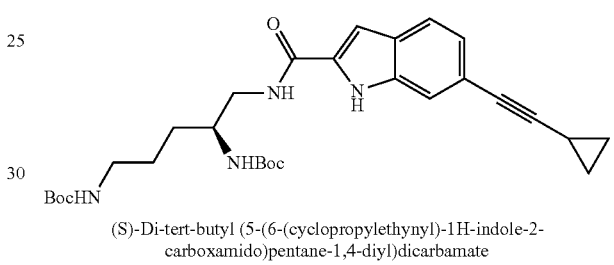

(S)-Di-tert-butyl (5-(6-(cyclopropylethynyl)-1H-indole-2-carboxamido)pentane-1,4-diyl)dicarbamate To a solution of 6-benzyl-1H-indole-2-carboxylic acid (25 mg, 0.11 mmol) in dry DMF (0.5 mL) was added DIPEA (0.035 mL, 0.2 mmol), HOBt (10 mg, 0.06 mmol) and EDC (25 mg, 0.13 mmol). The reaction mixture was stirred at room temperature and di-tert-butyl (5-aminopentane-1,4-diyl)(S)-dicarbamate (intermediate B) (35 mg, 0.11 mmol) was added. The reaction mixture was stirred at room temperature overnight. The cooled reaction mixture was extracted with EtOAc and washed with water and then brine. The organic layer was dried over anhydrous sodium sulfate and filtered. The filtrate was concentrated under reduced pressure and the residue purified by column chromatography on silica gel using 0-5% EtOAc in hexanes to give the desired product (44 mg, 76% yield) as a pale brown powder. $^1$H NMR (300 MHz, CDCl3) δ 9.24 (br, 1H), 7.52 (d, J=8.4 Hz, 1H), 7.45 (s, 1H), 7.13 (d, J=8.4 Hz, 1H), 6.87 (s, 1H), 4.80 (br, 1H), 4.64 (br, 1H), 4.13 (s, 2H), 3.80 (m, 1H), 3.49 (m, 2H), 3.13 (m, 2H), 1.61 (m, 4H), 1.49 (m, 1H), 1.43 (s, 9H), 1.39 (s, 9H), 0.84 (m, 2H), 0.82 (m, 2H).

Example 42. Preparation of N-(((2S,4S)-4-(aminomethyl)pyrrolidin-2-yl)methyl)-6-(2-cyclopropylethyl)-1H-indole-2-carboxamide hydrogen chloride salt

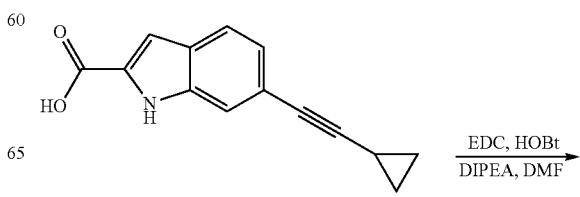

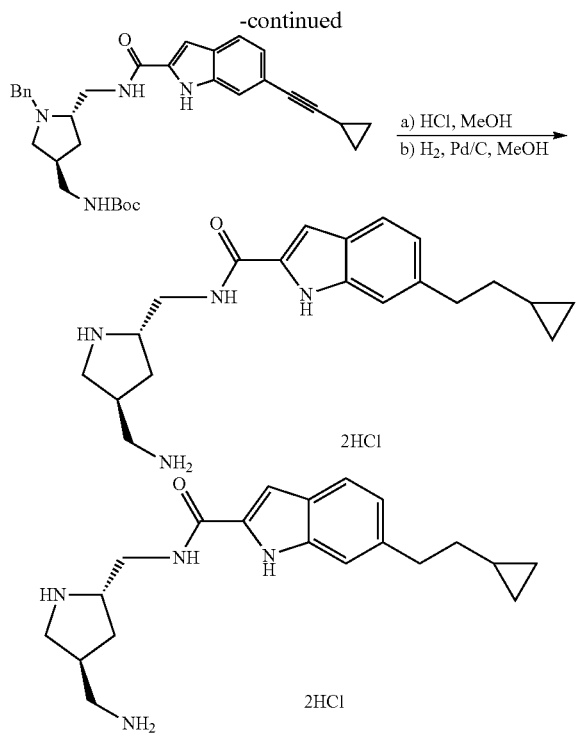

N-(((2S,4S)-4-(Aminomethyl)pyrrolidin-2-yl)methyl)-6-(2-cyclopropylethyl)-1H-indole-2-carboxamide hydrogen chloride salt To a solution of tert-butyl (((3S,5S)-1-benzyl-5-((6-(cyclopropylethynyl)-1H-indole-2-carboxamido)methyl)pyrrolidin-3-yl)methyl)carbamate (40 mg, 0.076 mmol) in MeOH (5 mL) was added a solution of HCl (4 M in dioxane, 0.1 mL, 0.4 mmol). After no starting material left, to the reaction mixture was added Pd/C (10%, 20 mg). The reaction mixture was then stirred under $H_2$ overnight. It was filtered through a Celite pad and washed with methanol, then concentrated under reduced pressure to provide the desired product as an off-white powder (23 mg, 73% yield). MS: Calcd for $C_{20}H_{28}N_4O$ 341.23 $[M+H]^+$, found 341.25 $[M+H]^+$.

The requisite intermediates were prepared as follows:

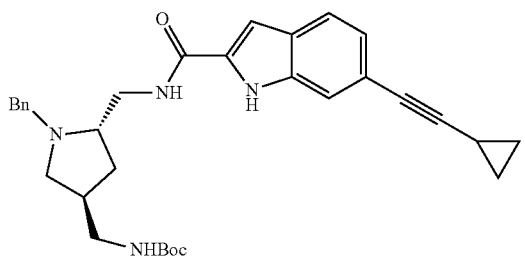

tert-Butyl (((3S,5S)-1-benzyl-5-((6-(cyclopropylethynyl)-1H-indole-2-carboxamido)methyl)pyrrolidin-3-yl)methyl)carbamate To a solution of 6-(cyclopropylethynyl)-1H-indole-2-carboxylic acid (45 mg, 0.2 mmol) in dry DMF (1 mL) was added DIPEA (0.07 mL, 0.4 mmol), HOBt (20 mg, 0.12 mmol) and EDC (46 mg, 0.24 mmol). The reaction mixture was stirred at room temperature and tert-butyl (((3S,5S)-5-(aminomethyl)-1-benzylpyrrolidin-3-yl)methyl)carbamate (intermediate M) (40 mg, 0.12 mmol) was added. The reaction mixture was stirred at room temperature overnight. It was extracted with EtOAc and washed with water and then brine. The organic layer was dried over anhydrous sodium sulfate and filtered. The filtrate was concentrated under reduced pressure and purified by column chromatography on silica gel using 0-50% EtOAc in hexanes to give the product (43 mg, 65% yield) as a pale brown powder. $^1$H NMR (300 MHz, CDCl$_3$) δ 9.53 (br, 1H), 7.54 (d, J=8.4 Hz, 1H), 7.47 (s, 1H), 7.27 (m, 5H), 7.14 (d, J=8.4 Hz, 1H), 6.98 (s, 1H), 4.83 (br, 1H), 4.01 (m, 1H), 3.64 (m, 2H), 3.25 (m, 1H), 3.04 (m, 1H), 2.82 (m, 1H), 2.75 (m, 1H), 2.36 (m, 1H), 2.15 (m, 2H), 1.73 (m, 2H), 1.52 (m, 1H), 1.42 (s, 9H), 1.39 (s, 9H), 0.87 (m, 2H), 0.82 (m, 2H). MS: Calcd for $C_{32}H_{38}N_4O_3$ 527.29 $[M+H]^+$, found 527.35 $[M+H]^+$.

Example 43. Preparation of (S)-3-methyl-N-(2,5-diaminopentyl)-5-(4-fluorophenyl)-1H-indole-2-carboxamide hydrogen chloride salt

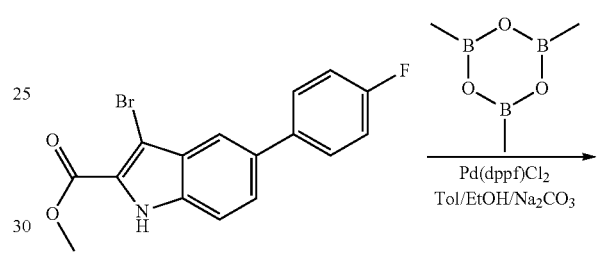

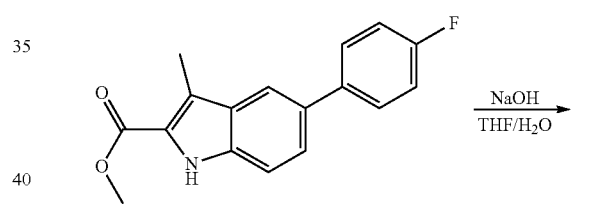

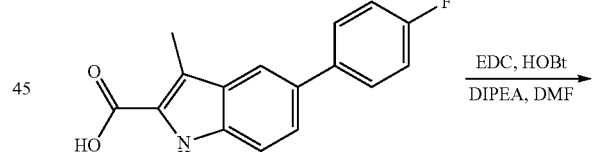

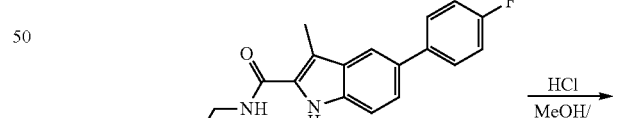

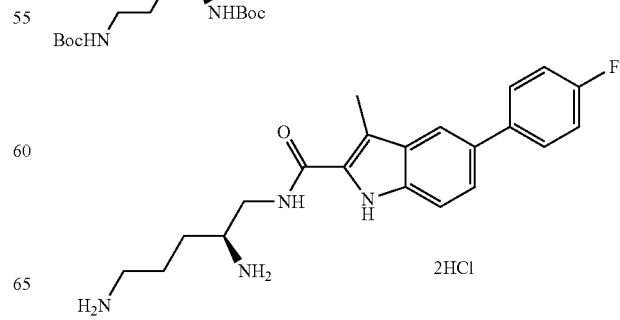

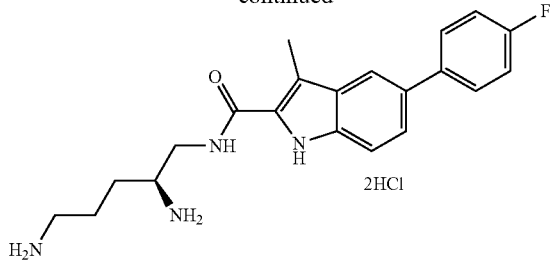

(S)-3-Methyl-N-(2,5-diaminopentyl)-5-(4-fluorophenyl)-1H-indole-2-carboxamide hydrogen chloride salt To a solution of (S)-di-tert-butyl (5-(5-(4-fluorophenyl)-3-methyl-1H-indole-2-carboxamido)pentane-1,4-diyl)dicarbamate (26 mg, 0.045 mmol) in MeOH (3 mL) was added HCl in solution (4 M in dioxane, 0.15 mL, 0.6 mmol). The reaction mixture was stirred at room temperature until LC-MS showed no starting material left, then solvent was removed under reduced pressure. The residue was triturated with EtOAc and the precipitate was collected as an off-white powder (15 mg, 74% yield). $^1$H NMR (300 MHz, D$_2$O) δ 7.73 (m, 3H), 7.63 (s, 1H), 7.41 (m, 1H), 7.24 (m, 2H), 3.70 (m, 1H), 3.62 (m, 1H), 3.56 (m, 1H), 3.07 (m, 2H), 2.57 (s, 3H), 1.86 (m, 4H). MS: Calcd for C$_{21}$H$_{25}$FN$_4$O 369.20 [M+H]$^+$, found 369.20 [M+H]$^+$.

The requisite intermediates were prepared as follows:
Step 1)

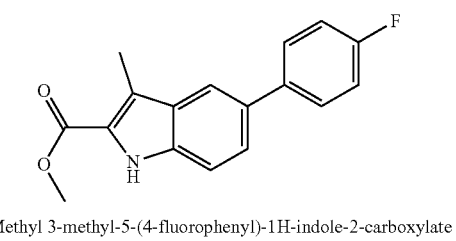

Methyl 3-methyl-5-(4-fluorophenyl)-1H-indole-2-carboxylate

The mixture of methyl 3-bromo-5-(4-fluorophenyl)-1H-indole-2-carboxylate (310 mg, 0.9 mmol), trimethylboroxine (0.45 mL, 50% w/w, 1.8 mmol) in a mixture of toluene, ethanol and sat. Na$_2$CO$_3$ solution (10/3/3 mL) was degassed and Pd(dppf)Cl$_2$ (60 mg, 0.07 mmol) was added. The reaction mixture was heated at 105° C. overnight and the cooled reaction mixture was extracted with EtOAc and washed with brine and concentrated under reduced pressure. The residue was purified by column chromatography on silica to give the desired product (86 mg, 34% yield) as an off-white powder. MS: Calcd for C$_{17}$H$_{14}$FNO$_2$ 282.10 [M−H]$^-$, found 282.15 [M−H]$^-$.
Step 2)

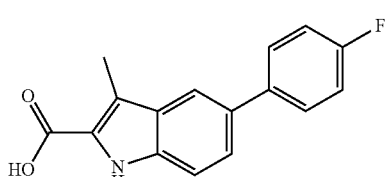

3-Methyl-5-(4-fluorophenyl)-1H-indole-2-carboxylic acid

To a solution of methyl 3-methyl-5-(4-fluorophenyl)-1H-indole-2-carboxylate (86 mg, 0.3 mmol) in THF (5 mL) was added NaOH solution (2 M, 5 mL). The reaction mixture was heated at 60° C. until no starting material left. THF was removed under reduced pressure and the residue was acidified with HCl solution. The precipitate was filtered and washed with water. It was dried to provide the product as a pale brown powder (60 mg, 73% yield) which was used for next step reaction without further purification. MS: Calcd for C$_{16}$H$_{12}$FNO$_2$ 268.09 [M−H]$^-$, found 268.00 [M−H]$^-$.
Step 3)

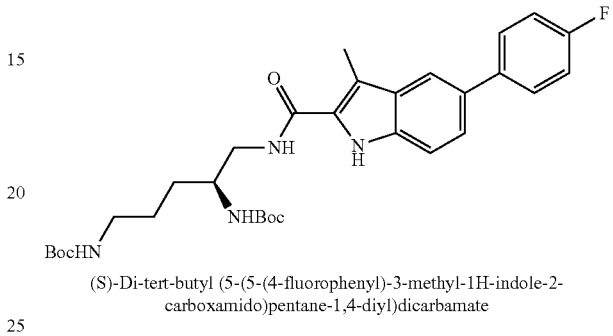

(S)-Di-tert-butyl (5-(5-(4-fluorophenyl)-3-methyl-1H-indole-2-carboxamido)pentane-1,4-diyl)dicarbamate To a solution of 3-methyl-5-(4-fluorophenyl)-1H-indole-2-carboxylic acid (25 mg, 0.09 mmol) in dry DMF (1 mL) was added DIPEA (0.035 mL, 0.2 mmol), HOBt (9 mg, 0.06 mmol) and EDC (24 mg, 0.12 mmol). The reaction mixture was stirred at room temperature and di-tert-butyl (5-aminopentane-1,4-diyl)(S)-dicarbamate (intermediate B) (30 mg, 0.09 mmol) was added. The reaction mixture was stirred at room temperature overnight. It was extracted with EtOAc and washed with water and brine. The organic layer was dried over anhydrous sodium sulfate and filtered. The filtrate was concentrated under reduced pressure and purified by column chromatography on silica gel using 50-60% EtOAc in hexanes to give the product (29 mg, 57% yield) as a pale brown powder. MS: Calcd for C$_{31}$H$_{41}$FN$_4$O$_5$ 569.31 [M+H]$^+$, found 569.30 [M+H]$^+$.

Example 44. Preparation of N-(((2S,4R)-4-(aminomethyl)pyrrolidin-2-yl)methyl)-5-(4-fluorophenyl)-3-methyl-1H-indole-2-carboxamide hydrogen chloride salt

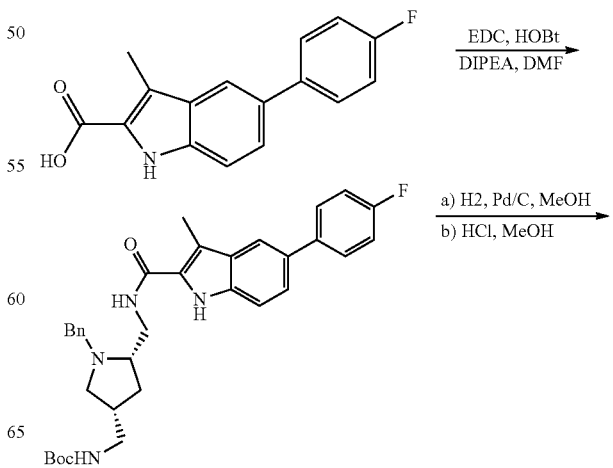

-continued

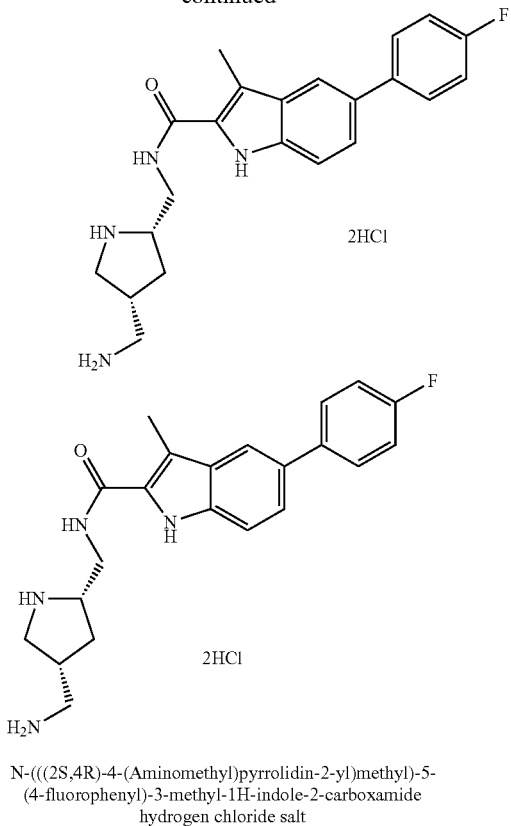

N-(((2S,4R)-4-(Aminomethyl)pyrrolidin-2-yl)methyl)-5-(4-fluorophenyl)-3-methyl-1H-indole-2-carboxamide hydrogen chloride salt To a solution of tert-butyl (((3R,5S)-1-benzyl-5-((5-(4-fluorophenyl)-3-methyl-1H-indole-2-carboxamido)methyl)pyrrolidin-3-yl)methyl)carbamate (30 mg, 0.053 mmol) in MeOH (5 mL) was added Pd/C (10%, 20 mg). The reaction mixture was stirred under $H_2$ overnight. It was filtered through a Celite pad and washed with methanol, then concentrated under reduced pressure and HCl in solution (4 M in dioxane, 0.1 mL) was added. The solution was stirred at room temperature until no starting material left. The solvent was removed under reduced pressure. The residue was triturated with EtOAc and the precipitate was collected as an off-white powder (16 mg, 67% yield). MS: Calcd for $C_{22}H_{25}FN_4O$ 381.20 $[M+H]^+$, found 381.20 $[M+H]^+$.

The requisite intermediates were prepared as follows:

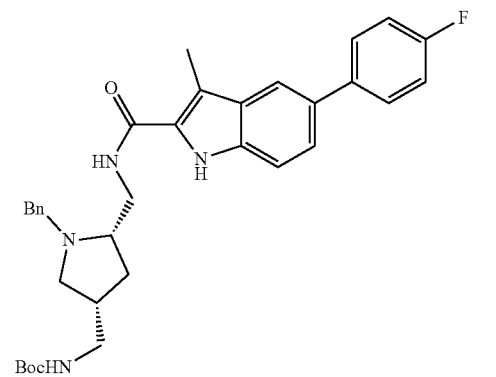

tert-Butyl (((3R,5S)-1-benzyl-5-((5-(4-fluorophenyl)-3-methyl-1H-indole-2-carboxamido)methyl)pyrrolidin-3-yl)methyl)carbamate To a solution of 3-methyl-5-(4-fluorophenyl)-1H-indole-2-carboxylic acid (30 mg, 0.11 mmol) in dry DMF (1 mL) was added DIPEA (0.043 mL, 0.25 mmol), HOBt (12 mg, 0.09 mmol) and EDC (29 mg, 0.15 mmol). The reaction mixture was stirred at room temperature and tert-butyl (((3R,5S)-5-(aminomethyl)-1-benzylpyrrolidin-3-yl)methyl)carbamate (intermediate L) (35 mg, 0.11 mmol) was added. The reaction mixture was stirred at room temperature overnight. The reaction mixture was extracted with EtOAc and washed with water and then brine. The organic layer was dried over anhydrous sodium sulfate and filtered. The filtrate was concentrated under reduced pressure and purified by column chromatography on silica gel to give the product 34 mg, 54% yield) as a pale brown powder. $^1$H NMR (300 MHz, CDCl$_3$) δ 9.14 (br, 1H), 7.74 (s, 1H), 7.58 (m, 2H), 7.43 (d, J=8.4 Hz, 1H), 7.33 (m, 1H), 7.24 (m, 5H), 7.20 (m, 1H), 7.13 (t, J=8.1 Hz, 2H), 6.17 (br, 1H), 4.55 (br, 1H), 4.28 (br, 1H), 3.55 (m, 2H), 3.16 (m, 1H), 3.06 (m, 2H), 2.74 (m, 1H), 2.58 (s, 3H), 2.11 (m, 2H), 1.89 (m, 2H), 1.56 (m, 2H), 1.43 (s, 9H). MS: Calcd for $C_{34}H_{39}FN_4O_3$, 571.30$[M+H]^+$, found 571.30 $[M+H]^+$.

Example 45 (YY-3-90). Preparation of (S)—N-(2,5-diaminopentyl)-6-(4-fluorophenyl)-3-methyl-1H-indole-2-carboxamide hydrogen chloride salt

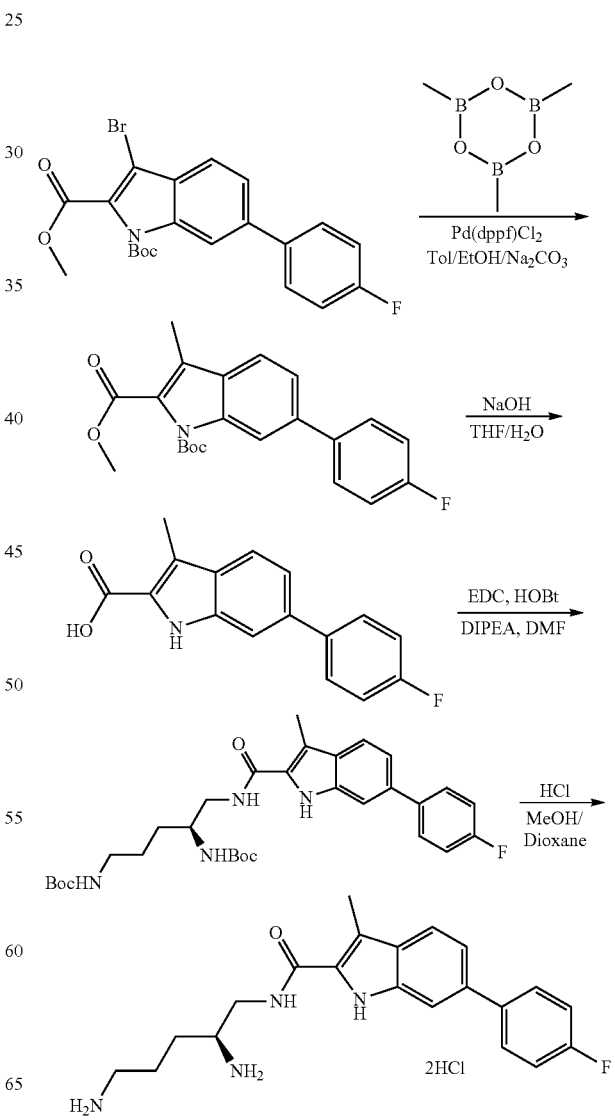

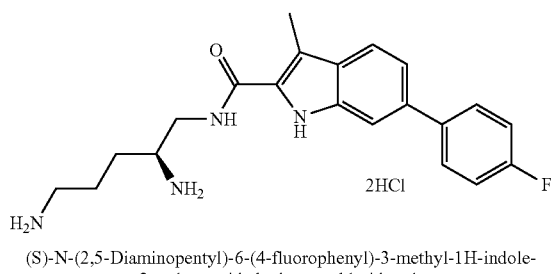

(S)-N-(2,5-Diaminopentyl)-6-(4-fluorophenyl)-3-methyl-1H-indole-2-carboxamide hydrogen chloride salt To a solution of (S)-di-tert-butyl (5-(6-(4-fluorophenyl)-3-methyl-1H-indole-2-carboxamido)pentane-1,4-diyl)dicarbamate (40 mg, 0.07 mmol) in MeOH (4 mL) was added a solution of HCl (4 M in dioxane, 0.2 mL, 0.8 mmol). The reaction mixture was stirred at room temperature until LC-MS analysis showed no starting material left, then the solvent was removed under reduced pressure. The residue was triturated with EtOAc and the precipitate was collected as a brown powder (26 mg, 84% yield). $^1$H NMR (300 MHz, D$_2$O) δ 7.71 (m, 3H), 7.65 (s, 1H), 7.22 (m, 2H), 3.73 (m, 1H), 3.64 (m, 1H), 3.59 (m, 1H), 3.06 (m, 2H), 2.49 (s, 3H), 1.83 (m, 4H). MS: Calcd for C$_{21}$H$_{25}$FN$_4$O 369.20 [M+H]$^+$, found 369.25 [M+H]$^+$.

The requisite intermediates were prepared as follows:

Step 1)

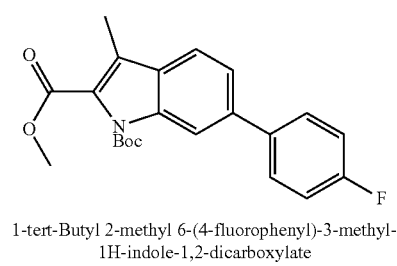 [SMILES: COC(=O)c1c(C)c2ccc(-c3ccc(F)cc3)cc2n1C(=O)OC(C)(C)C]

1-tert-Butyl 2-methyl 6-(4-fluorophenyl)-3-methyl-1H-indole-1,2-dicarboxylate

The mixture of methyl 1-tert-butyl 2-methyl 3-bromo-6-(4-fluorophenyl)-1H-indole-1,2-dicarboxylate (850 mg, 1.9 mmol), trimethylboroxine (1 mL, 50% w/w, 4 mmol) in a mixture of toluene, ethanol and sat. Na$_2$CO$_3$ solution (20/6/6 mL) was degassed and Pd(dppf)Cl$_2$ (130 mg, 0.15 mmol) was added. The reaction mixture was heated at 105° C. overnight and the cooled reaction mixture extracted with EtOAc and washed with brine and concentrated under reduced pressure. The residue was purified by column chromatography on silica to give the desired product (185 mg, 25% yield) as an off-white powder. $^1$H NMR (300 MHz, CDCl$_3$) δ 8.30 (s, 1H), 7.61 (m, 3H), 7.47 (d, J=8.4 Hz, 1H), 7.14 (t, J=8.1 Hz, 2H), 3.95 (s, 3H), 2.51 (s, 3H), 1.49 (s, 9H).

Step 2)

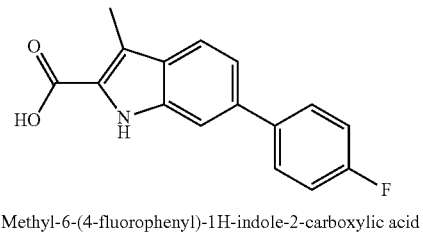

3-Methyl-6-(4-fluorophenyl)-1H-indole-2-carboxylic acid

To a solution of methyl 3-methyl-6-(4-fluorophenyl)-1H-indole-2-carboxylate (180 mg, 0.3 mmol) in THF (5 mL) was added NaOH solution (4 M, 5 mL). The reaction mixture was heated at 90° C. until no starting material left. THF was removed under reduced pressure and the residue was acidified with HCl solution. The precipitate was filtered and washed with water. It was dried to provide the product as a pale brown powder (106 mg, 84% yield) which was used for next step reaction without further purification. MS: Calcd for C$_{16}$H$_{12}$FNO$_2$ 268.09 [M–H]$^-$, found 268.00 [M–H]$^-$.

Step 3)

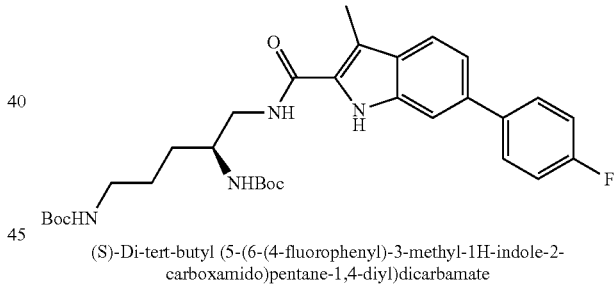

(S)-Di-tert-butyl (5-(6-(4-fluorophenyl)-3-methyl-1H-indole-2-carboxamido)pentane-1,4-diyl)dicarbamate To a solution of 3-methyl-6-(4-fluorophenyl)-1H-indole-2-carboxylic acid (54 mg, 0.2 mmol) in dry DMF (1 mL) was added DIPEA (0.07 mL, 0.4 mmol), HOBt (18 mg, 0.12 mmol) and EDC (48 mg, 0.24 mmol). The reaction mixture was stirred at room temperature and di-tert-butyl (5-aminopentane-1,4-diyl)(S)-dicarbamate (intermediate B) (64 mg, 0.2 mmol) was added. The reaction mixture was stirred at room temperature overnight. It was extracted with EtOAc and washed with water and then brine. The organic layer was dried over anhydrous sodium sulfate and filtered. The filtrate was concentrated under reduced pressure and purified by column chromatography on silica gel to give the product 42 mg, 37% yield) as a pale brown powder. $^1$H NMR (300 MHz, CDCl$_3$) δ 9.05 (br, 1H), 7.67 (d, J=8.4 Hz, 1H), 7.60 (m, 2H), 7.50 (s, 1H), 7.33 (d, J=8.4 Hz, 1H), 7.13 (t, J=8.1 Hz, 2H), 4.73 (br, 1H), 4.64 (br, 1H), 3.84 (m, 1H), 3.58 (m, 1H), 3.13 (m, 2H), 2.06 (s, 3H), 1.62 (m, 4H), 1.44 (s, 9H), 1.42 (s, 9H). MS: Calcd for C$_{31}$H$_{41}$FN$_4$O$_5$ 569.31 [M+H]$^+$, found 569.30 [M+H]$^+$.

Example 46. Preparation of N-(((2S,4R)-4-(aminomethyl)pyrrolidin-2-yl)methyl)-6-(4-fluorophenyl)-3-methyl-1H-indole-2-carboxamide hydrogen chloride salt

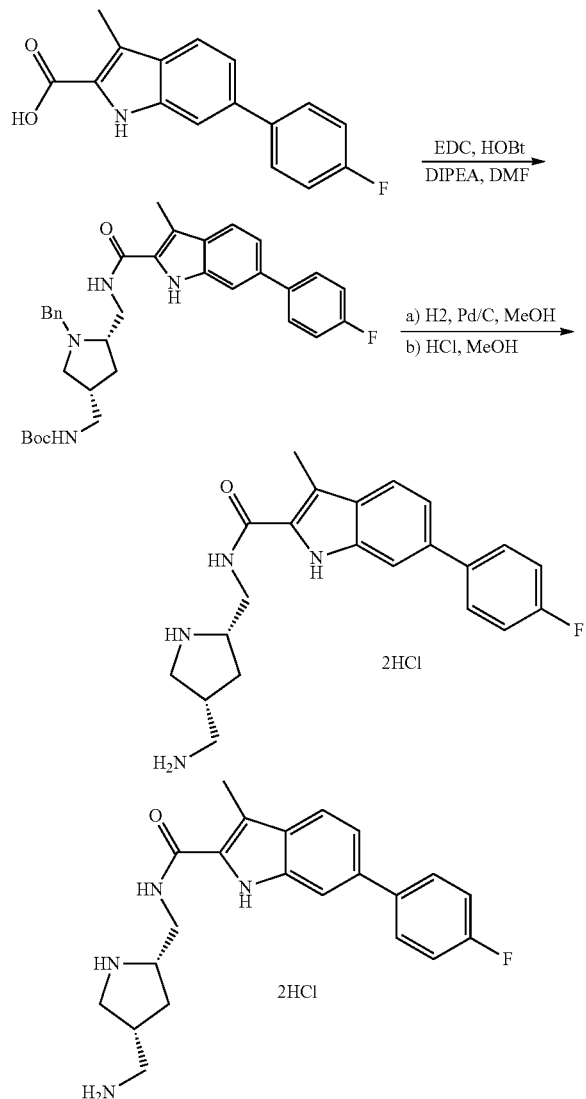

N-(((2S,4R)-4-(Aminomethyl)pyrrolidin-2-yl)methyl)-6-(4-fluorophenyl)-3-methyl-1H-indole-2-carboxamide hydrogen chloride salt To a solution of tert-butyl (((3R,5S)-1-benzyl-5-((6-(4-fluorophenyl)-3-methyl-1H-indole-2-carboxamido)methyl)pyrrolidin-3-yl)methyl)carbamate (30 mg, 0.053 mmol) in MeOH (5 mL) was added Pd/C (10%, 20 mg). The reaction mixture was stirred under $H_2$ overnight. It was filtered through a Celite pad and washed with methanol, then concentrated under reduced pressure and HCl solution (4 M in dioxane, 0.1 mL) was added. The solution was stirred at room temperature until no starting material left. The solvent was removed under reduced pressure. The residue was triturated with EtOAc and the precipitate was collected as an off-white powder (17 mg, 71% yield). MS: Calcd for $C_{22}H_{25}FN_4O$ 381.20 [M+H]$^+$, found 381.25 [M+H]$^+$.

The requisite intermediates were prepared as follows:

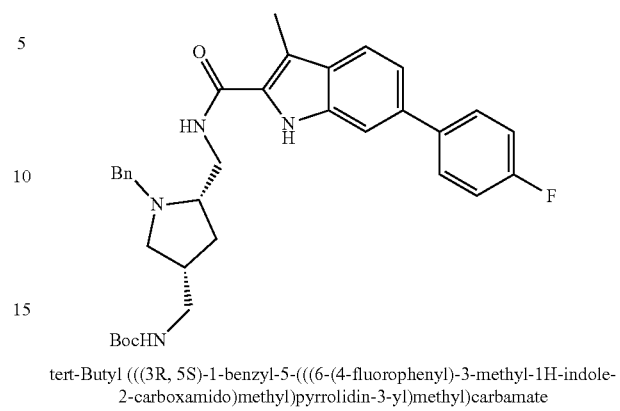

tert-Butyl (((3R, 5S)-1-benzyl-5-(((6-(4-fluorophenyl)-3-methyl-1H-indole-2-carboxamido)methyl)pyrrolidin-3-yl)methyl)carbamate To a solution of 3-methyl-6-(4-fluorophenyl)-1H-indole-2-carboxylic acid (30 mg, 0.11 mmol) in dry DMF (1 mL) was added DIPEA (0.043 mL, 0.25 mmol), HOBt (12 mg, 0.09 mmol) and EDC (29 mg, 0.15 mmol). The reaction mixture was stirred at room temperature and tert-butyl (((3R,5S)-5-(aminomethyl)-1-benzylpyrrolidin-3-yl)methyl)carbamate (intermediate L) (31 mg, 0.1 mmol) was added. The reaction mixture was stirred at room temperature overnight. It was extracted with EtOAc and washed with water and brine. The organic layer was dried over anhydrous sodium sulfate and filtered. The filtrate was concentrated under reduced pressure and purified by column chromatography on silica gel to give the product 32 mg, 56% yield) as a pale brown powder. $^1$H NMR (300 MHz, CDCl$_3$) δ 9.20 (br, 1H), 7.66 (d, J=8.4 Hz, 1H), 7.60 (m, 2H), 7.51 (s, 1H), 7.35 (m, 5H), 7.33 (d, J=8.4 Hz, 1H), 7.13 (t, J=8.1 Hz, 2H), 6.13 (br, 1H), 4.58 (br, 1H), 4.28 (br, 1H), 3.57 (m, 2H), 3.16 (m, 1H), 3.08 (m, 2H), 2.77 (m, 1H), 2.49 (s, 3H), 2.11 (m, 2H), 1.91 (m, 2H), 1.50 (m, 2H), 1.44 (s, 9H). MS: Calcd for $C_{34}H_{39}FN_4O_3$, 571.30[M+H]$^+$, found 571.40 [M+H]$^+$.

Example 47. Preparation of (S)—N-(2,5-diaminopentyl)-3-fluoro-6-(4-fluorophenyl)-1H-indole-2-carboxamide hydrogen chloride salt

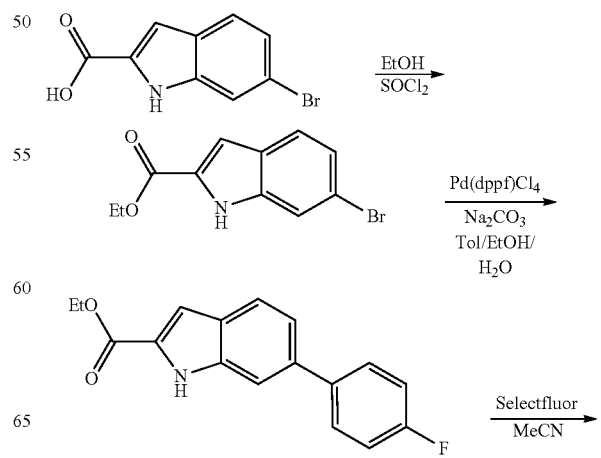

237

-continued

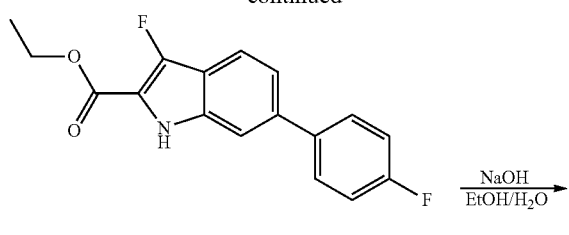

NaOH
EtOH/H₂O →

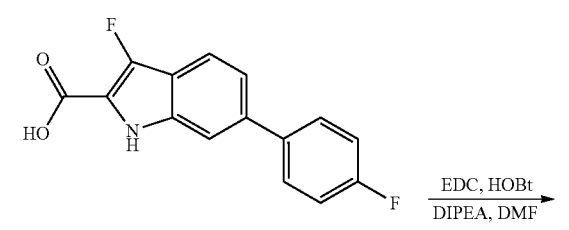

EDC, HOBt
DIPEA, DMF →

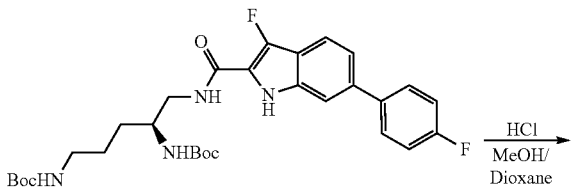

HCl
MeOH/
Dioxane →

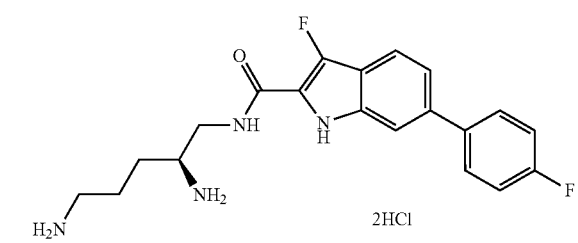

2HCl

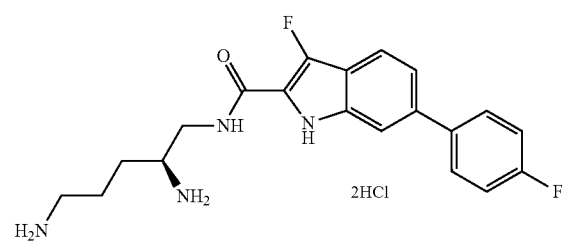

2HCl (S)-N-(2,5-Diaminopentyl)-3-fluoro-6-(4-fluorophenyl)-1H-indole-2-carboxamide hydrogen chloride salt To a solution of (S)-di-tert-butyl (5-(3-fluoro-6-(4-fluorophenyl)-1H-indole-2-carboxamido)pentane-1,4-diyl)dicarbamate (15 mg, 0.026 mmol) in MeOH (2 mL) was added HCl in dioxane (4M, 0.1 mL, 0.4 mmol). The reaction mixture was stirred at room temperature overnight. TLC analysis of the reaction mixture showed no starting material was left. The reaction mixture was concentrated under reduced pressure and triturated with EtOAc to afford the desired product (8 mg, 69% yield) as an off-white solid. $^1$H NMR (300 MHz, CD₃OD) δ 7.71 (m, 3H), 7.60 (s, 1H), 7.44 (d, J=8.4 Hz, 1H), 7.22 (m, 2H), 3.72 (m, 1H), 3.64 (m, 1H), 3.59 (m, 1H), 3.05 (m, 2H), 1.83 (m, 4H). Calcd for C₂₀H₂₂F₂N₄O 373.18 [M+H]⁺, found 373.25 [M+H]⁺.

238

The requisite intermediates were prepared as follows:
Step 1)

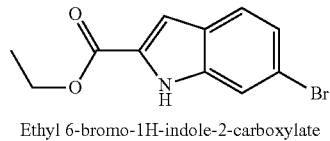

Ethyl 6-bromo-1H-indole-2-carboxylate

To a suspension of 6-bromo-1H-indole-2-carboxylic acid (5.0 g, 20.8 mmol) in MeOH (100 mL) was added SOCl₂ (2.26 mL, 31 mmol) very slowly. The mixture was heated under reflux until TLC analysis showed no starting material was left. Solvent was removed under reduced pressure and the crude product was collected as a brown powder (5.52 g, 99% yield) after drying. It was used for next step reaction without purification. MS: Calcd for C₁₁H₁₁BrNO₂ 265.99 and 267.99 [M−H⁻], found 265.95 and 267.95 [M−H⁻].

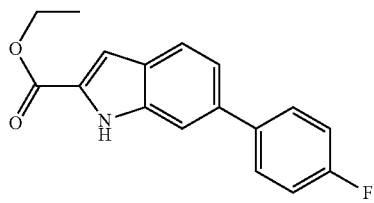

Ethyl 6-(4-fluorophenyl)-1H-indole-2-carboxylate

Step 2)
The mixture of methyl 6-bromo-1H-indole-2-carboxylate (3.60 g, 13.40 mmol), (4-fluorophenyl)boronic acid (2.82 g, 20.14 mmol) in a mixture of toluene, ethanol and sat. Na₂CO₃ solution (60/15/15 mL) was degassed and Pd(dppf)Cl₂ (250 mg, 0.31 mmol) was added. The reaction mixture was heated at 110° C. overnight. The cooled reaction mixture was extracted with EtOAc and washed with brine and concentrated under reduced pressure. The residue was purified by column chromatography on silica gel (10-30% ethyl acetate/hexanes) to give the desired product (2.85 g, 75% yield) as an off-white powder. MS: Calcd for C₁₇H₁₄FNO₂ 284.10 [M+H]⁺, found 284.10 [M+H]⁺.

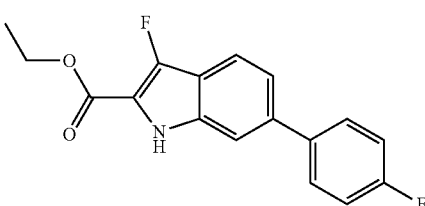

Ethyl 3-fluoro-6-(4-fluorophenyl)-1H-indole-2-carboxylate

Step 3)
To a solution of ethyl 6-(4-fluorophenyl)-1H-indole-2-carboxylate (269 mg, 1 mmol) in acetonitrile was added Selectfluor (354 mg, 1 mmol) at 0° C. Then it was stirred at 0° C. and allowed to warm to room temperature. It was concentrated under reduced pressure and purified using silica gel column chromatography to give the desired product as a white powder (50 mg, 17% yield). $^1$H NMR (300 MHz, CDCl₃) δ 8.38 (br, 1H), 7.75 (d, J=8.4 Hz, 1H), 7.71

(m, 2H), 7.46 (s, 1H), 7.37 (d, J=8.4 Hz, 1H), 7.17 (m, 2H), 4.42 (q, J=7.8 Hz, 2H), 1.43 (t, J=7.8 Hz, 3H).

Step 4)

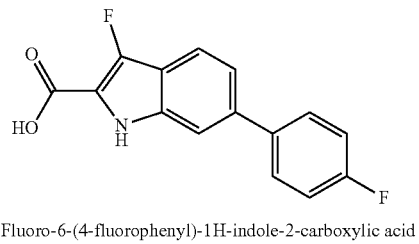

3-Fluoro-6-(4-fluorophenyl)-1H-indole-2-carboxylic acid

To a solution of ethyl 3-fluoro-6-(4-fluorophenyl)-1H-indole-2-carboxylate (0.48 g, 0.16 mmol) in EtOH (5 mL) was added NaOH solution (2 M, 5 mL). The reaction mixture was stirred at room temperature until no starting material left. EtOH was removed under reduced pressure and the residue was acidified with 1 N HCl solution. The precipitate was filtered and washed with water. It was purified on ISCO using a C18 column with MeOH and water as eluents to provide the product as an off-white powder (30 mg, 69% yield). $^1$H NMR (300 MHz, DMSO-d$_6$) δ 11.00 (br, 1H), 7.56 (d, J=8.4 Hz, 1H), 7.52 (m, 2H), 7.45 (s, 1H), 7.21 (d, J=8.4 Hz, 1H), 7.04 (m, 2H).

Step 5)

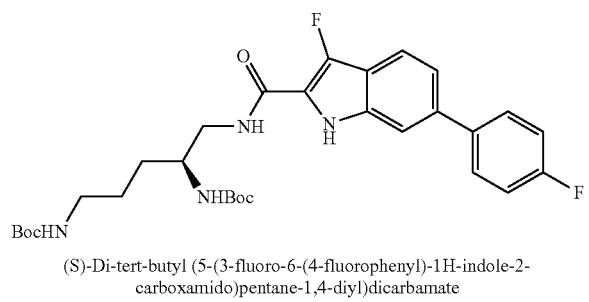 [SMILES: CC(C)(C)OC(=O)NCCC[C@@H](CNC(=O)c1[nH]c2cc(-c3ccc(F)cc3)ccc2c1F)NC(=O)OC(C)(C)C]

(S)-Di-tert-butyl (5-(3-fluoro-6-(4-fluorophenyl)-1H-indole-2-carboxamido)pentane-1,4-diyl)dicarbamate To a solution of 3-fluoro-6-(4-fluorophenyl)-1H-indole-2-carboxylic acid (14 mg, 0.05 mmol) in dry DMF (0.5 mL) was added DIPEA (0.018 mL, 0.1 mmol), HOBt (8 mg, 0.05 mmol) and EDC (12 mg, 0.06 mmol). The reaction mixture was stirred at room temperature and (S)-di-tert-butyl (5-aminopentane-1,4-diyl)dicarbamate (Intermediate B) (18 mg, 0.05 mmol) was added. The reaction mixture was stirred at room temperature overnight. The reaction mixture was then diluted with EtOAc and washed with water and then brine. The organic layer was dried over anhydrous sodium sulfate and filtered. The filtrate was concentrated under reduced pressure and purified by column chromatography on silica gel with 30-40% ethyl acetate in hexanes to give the product (16 mg, 56% yield) as a white solid. MS: Calcd for $C_{30}H_{38}F_2N_4O_5$ 573.28 [M+H]$^+$, found 573.40 [M+H]$^+$.

Example 48. Preparation of N-(((2S,4R)-4-(aminomethyl)pyrrolidin-2-yl)methyl)-3-fluoro-6-(4-fluorophenyl)-1H-indole-2-carboxamide hydrogen chloride salt

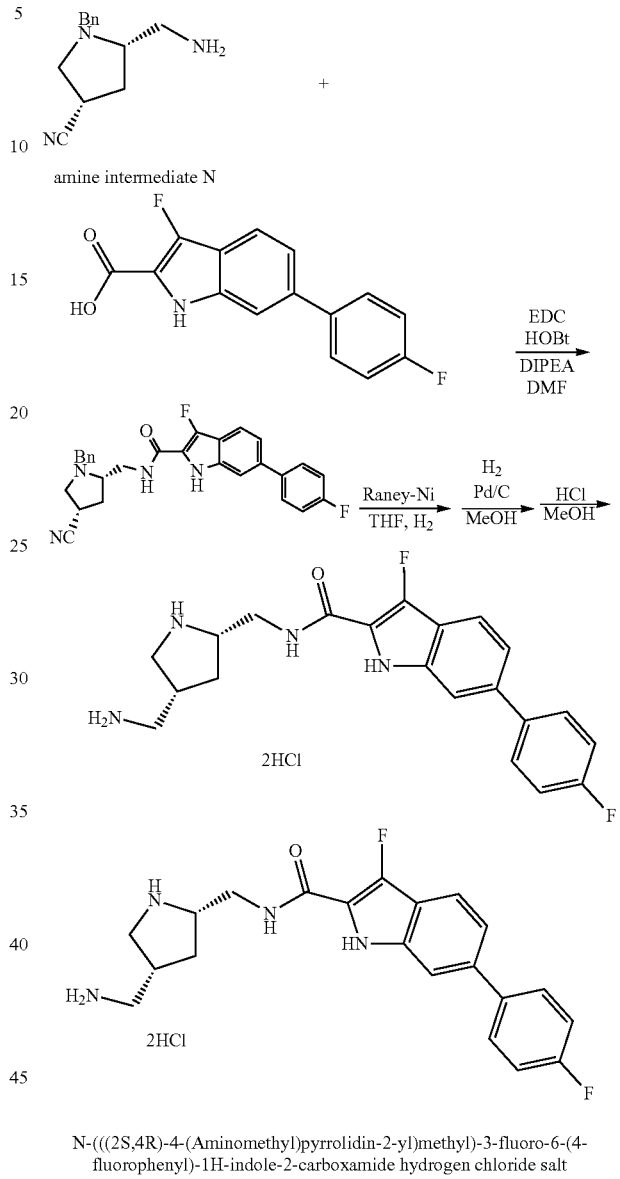

N-(((2S,4R)-4-(Aminomethyl)pyrrolidin-2-yl)methyl)-3-fluoro-6-(4-fluorophenyl)-1H-indole-2-carboxamide hydrogen chloride salt To a solution of N-(((2S,4S)-1-benzyl-4-cyanopyrrolidin-2-yl)methyl)-3-fluoro-6-(4-fluorophenyl)-1H-indole-2-carboxamide (110 mg, 0.23 mmol) in THF (20 mL) was added Raney-Ni (110 mg, 50% in water) under H$_2$ (55 psi) overnight. The reaction progress was monitored by LC-MS. After the reaction was completed, the catalyst was removed by passing through a Celite plug and washed with MeOH. The filtrate was concentrated under reduced pressure to give the amine intermediate. This intermediate was dissolved in MeOH (20 mL). Pd/C (30 mg, 10% on carbon) was added then under H$_2$ (55 psi) overnight. After the reaction was completed as indicated by monitoring by LC-MS, the catalyst was removed by filtration. The filtrate was concentrated under reduced pressure to give the crude product, which was purified on an ISCO using a C18 column. Elution with water/MeOH afforded the desired product as the free base form. The free base product was dissolved in MeOH (2 mL) the added 4 N HCl in dioxane (0.2 mL). After being stirred at room temperature for 1 hour, the solvent was removed and the residue was triturated with EtOAc to afford the desired product (36 mg, 34% yield) as beige solid. $^1$H NMR (300 MHz, D$_2$O) δ 7.54 (d, J=8.1 Hz, 1H), 7.47 (m, 2H), 7.28 (m, 1H), 7.18 (m, 2H), 6.98 (s, 1H), 3.76 (m, 1H), 3.51 (m, 2H), 3.43 (m, 1H), 3.01-2.93 (m, 3H), 2.60 (m, 1H), 2.32 (m, 1H), 1.43 (m, 1H). LC-MS 385.20 [M+H$^+$].

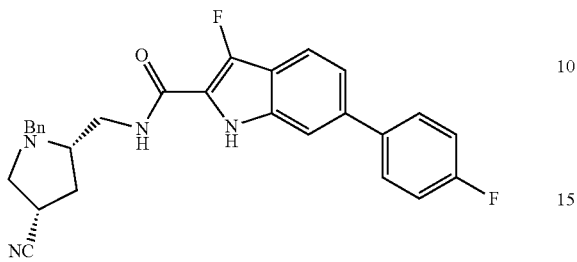

N-(((2S, 4S)-1-Benzyl-4-cyanopyrrolidin-2-yl)methyl)-3-fluoro-6-(4-fluorophenyl)-1H-indole-2-carboxamide The mixture of 3-fluoro-6-(4-fluorophenyl)-1H-indole-2-carboxylic acid (210 mg, 0.77 mmol), (3S,5S)-5-(aminomethyl)-1-benzylpyrrolidine-3-carbonitrile (166 mg, 0.77 mmol), EDC (176 mg, 0.92 mmol), HOBt (62 mg, 0.46 mmol) in DMF (5 mL) was added DIPEA (0.28 mL, 1.54 mol). The reaction mixture was stirred at room temperature overnight. The reaction mixture was added water dropwise with stirring and the solid formed was collected by filtration. Air drying and purification by silica gel column chromatography afforded the desired product (150 mg, 41% yield) as a pale yellow solid. LC-MS 471.20 [M+H$^+$].

Example 49. Preparation of (S)—N-(2,5-diaminopentyl)-6-(4-fluorophenoxy)-1H-indole-2-carboxamide hydrogen chloride salt

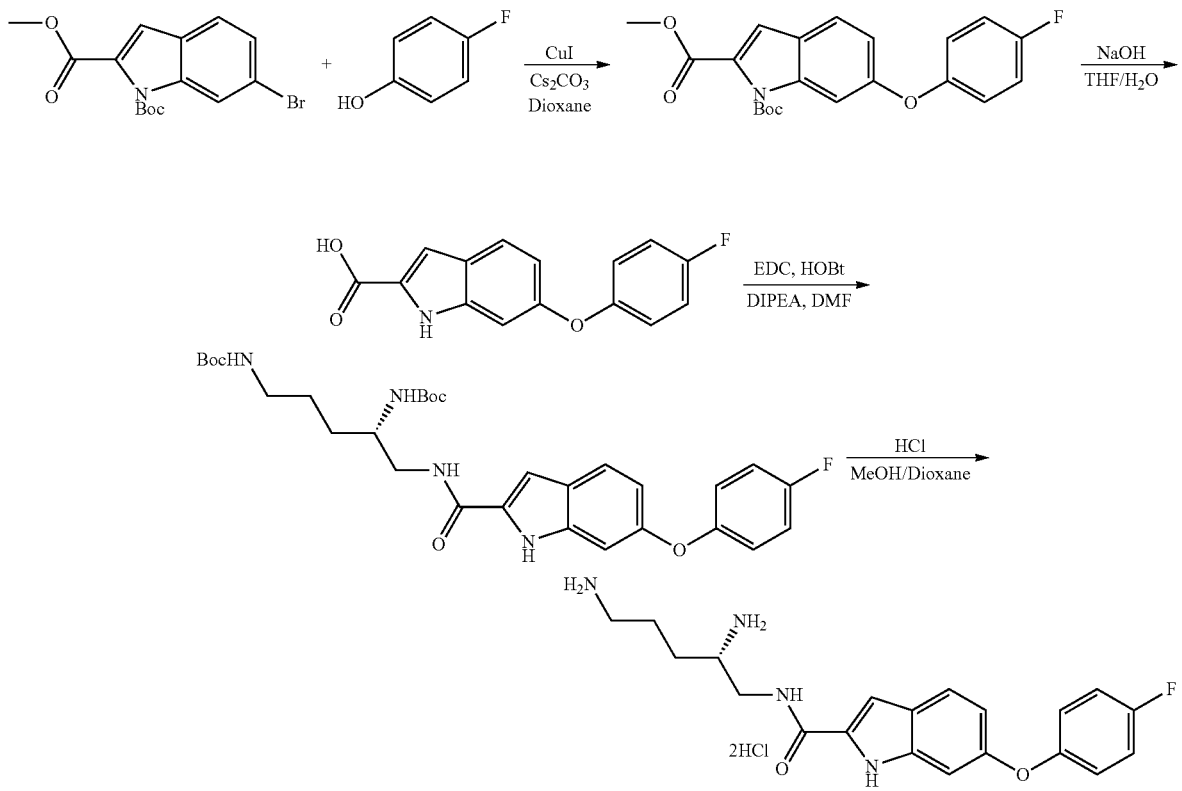

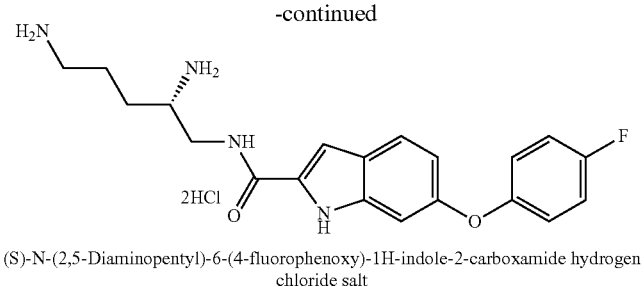

(S)-N-(2,5-Diaminopentyl)-6-(4-fluorophenoxy)-1H-indole-2-carboxamide hydrogen chloride salt To a solution of (S)-di-tert-butyl (5-(6-(4-fluorophenoxy)-1H-indole-2-carboxamido)pentane-1,4-diyl)dicarbamate (35 mg, 0.06 mmol) in MeOH (4 mL) was added HCl in dioxane (4 M in dioxane, 0.2 mL, 0.8 mmol). The reaction mixture was stirred at room temperature until LC-MS showed no starting material left, the solvent was then removed under reduced pressure. The residue was triturated with EtOAc and the precipitate was collected as a brown powder (19 mg, 70% yield). $^1$H NMR (300 MHz, D$_2$O) δ 7.73 (d, J=8.1 Hz, 1H), 7.17 (s, 1H), 7.15 (m, 2H), 7.00 (m, 3H), 6.95 (d, J=8.1 Hz, 1H), 3.73 (m, 1H), 3.64 (m, 1H), 3.59 (m, 1H), 3.05 (m, 2H), 1.84 (m, 4H). MS: Calcd for C$_{20}$H$_{23}$FN$_4$O$_2$ 371.18 [M+H]$^+$, found 371.25 [M+H]$^+$.

The requisite intermediates were prepared as follows:

Step 11

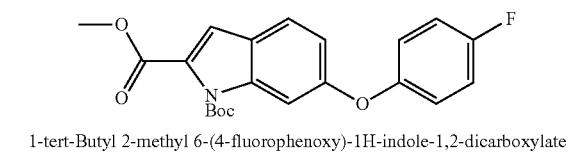 [SMILES: COC(=O)c1cc2ccc(Oc3ccc(F)cc3)cc2n1C(=O)OC(C)(C)C]

1-tert-Butyl 2-methyl 6-(4-fluorophenoxy)-1H-indole-1,2-dicarboxylate

The mixture of 1-tert-butyl 2-methyl 6-bromo-1H-indole-1,2-dicarboxylate (71 mg, 0.2 mmol), 4-fluorophenol (34 mg, 0.3 mmol) Cs$_2$CO$_3$ (100 mg, 0.3 mmol) and 2-(dimethylamino)acetic acid HCl salt (9 mg, 0.006 mmol) in dioxane was degassed and CuI (8 mg, 0.04 mmol) was then added. The reaction mixture was heated at 100° C. overnight and it was diluted with EtOAc and purified by column chromatography on silica gel to give the desired product (35 mg, 45% yield) as an off-white powder. $^1$H NMR (300 MHz, CDCl$_3$) δ 7.62 (d, J=8.4 Hz, 1H), 7.27 (m, 1H), 7.22-7.15 (m, 3H), 7.02 (m, 2H), 6.91 (s, 1H), 3.94 (s, 2H), 1.56 (s, 9H).

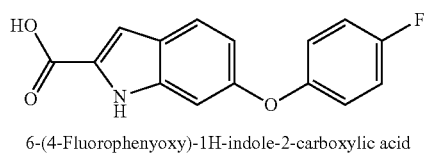 [SMILES: O=C(O)c1cc2ccc(Oc3ccc(F)cc3)cc2[nH]1]

6-(4-Fluorophenyoxy)-1H-indole-2-carboxylic acid

Step 2)

To a solution of 1-tert-butyl 2-methyl 6-(4-fluorophenoxy)-1H-indole-1,2-dicarboxylate (34 mg, 0.12 mmol) in ethanol (3 mL) was added NaOH solution (2 M, 3 mL). The reaction mixture was stirred at room temperature. After the reaction was complete, the solvent was removed under reduced pressure and the residue was acidified with HCl solution. The precipitate was filtered and washed with water. It was dried to provide the desired product as a white powder (25 mg, 77% yield) which was used for next step reaction without further purification. MS: Calcd for C$_{15}$H$_{10}$FNO$_3$ 270.06 [M−H]$^−$, found 270.10 [M−H]$^−$.

Step 3)

(S)-Di-tert-butyl (5-(6-(4-fluorophenoxy)-1H-indole-2-carboxamido)pentane-1,4-diyl)dicarbamate To a solution of 6-(4-fluorophenoxy)-1H-indole-2-carboxylic acid (25 mg, 0.09 mmol) in dry DMF (0.5 mL) was added DIPEA (0.035 mL, 0.2 mmol), HOBt (10 mg, 0.06 mmol) and EDC (23 mg, 0.12 mmol). The reaction mixture was stirred at room temperature and di-tert-butyl (5-aminopentane-1,4-diyl)(S)-dicarbamate (intermediate B) (30 mg, 0.09 mmol) was added. The reaction mixture was stirred at room temperature overnight. It was then extracted with EtOAc and washed with water and then brine. The organic layer was dried over anhydrous sodium sulfate and filtered. The filtrate was concentrated and purified by silica gel column chromatography using 30-45% EtOAc in hexanes to give the desired product (36 mg, 68% yield) as a pale brown powder. $^1$H NMR (300 MHz, CDCl$_3$) δ 9.07 (br, 1H), 7.57 (d, J=8.4 Hz, 1H), 7.30-7.15 (m, 4H), 6.94 (s, 1H), 6.88 (d, J=8.4 Hz, 2H), 4.77 (br, 1H), 4.62 (br, 1H), 4.13 (s, 2H), 3.80 (m, 1H), 3.50 (m, 2H), 3.15 (m, 2H), 1.61 (m, 4H), 1.47 (s, 9H), 1.41 (s, 9H).

Example 50. (S)—N-(1-(4-aminocyclohexyl)pyrrolidin-3-yl)-6-(4-fluorophenyl)-1H-indole-2-carboxamide hydrogen chloride salt

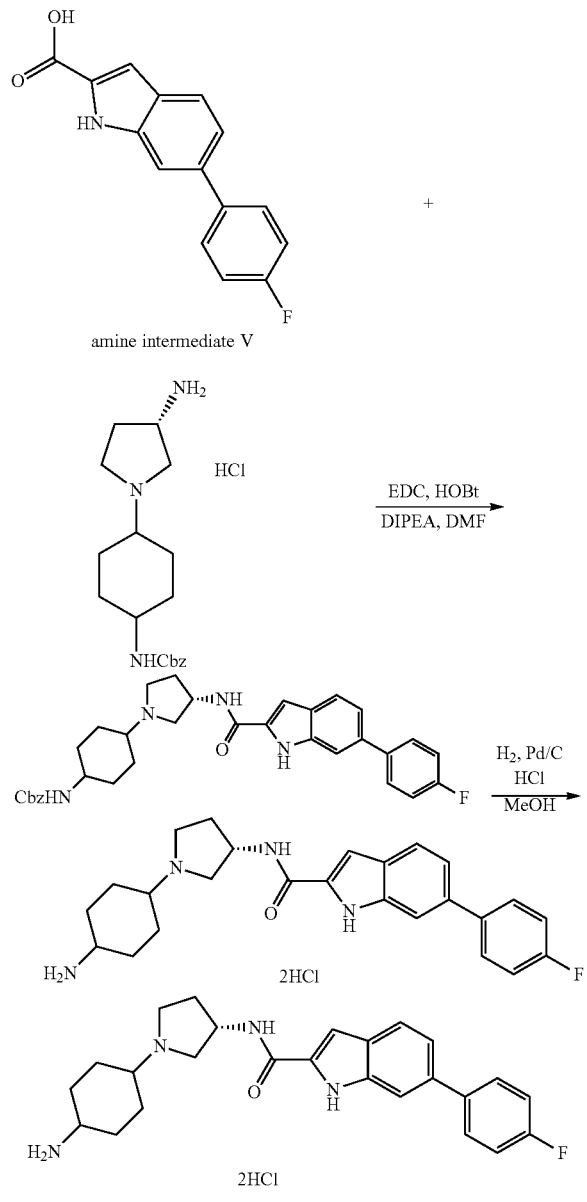

(S)-N-(1-(4-Aminocyclohexyl)pyrrolidin-3-yl)-6-(4-fluorophenyl)-1H-indole-2-carboxamide hydrogen chloride salt To a solution of (S)-benzyl (4-(3-(6-(4-fluorophenyl)-1H-indole-2-carboxamido)pyrrolidin-1-yl)cyclohexyl)carbamate (25 mg, 0.06 mmol) in MeOH (5 mL) was added Pd/C (10%, 15 mg). The reaction mixture was stirred under H$_2$ overnight. It was then filtered through a Celite pad and washed with methanol, then concentrated under reduced pressure and HCl in dioxane (4 M, 0.05 mL) was added. The solvent was removed under reduced pressure. The residue was triturated with EtOAc and the precipitate was collected as an off-white powder (16 mg, 72% yield). $^1$H NMR (300 MHz, D$_2$O) δ 7.76 (d, J=8.4 Hz, 1H), 7.55 (s, 1H), 7.51 (m, 2H), 7.43 (d, J=8.4 Hz, 1H), 7.20 (m, 2H), 7.14 (s, 1H), 3.67 (m, 2H), 3.58 (m, 1H), 3.51 (m, 2H), 3.27 (m, 2H), 2.28 (m, 4H), 2.17 (m, 2H), 1.53 (m, 4H). MS: Calcd for C$_{25}$H$_{29}$FN$_4$O 421.23 [M+H]$^+$, found 421.30 [M+H]$^+$.

The requisite intermediates were prepared as follows:

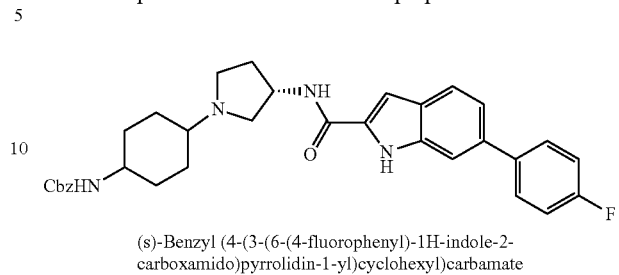

(s)-Benzyl (4-(3-(6-(4-fluorophenyl)-1H-indole-2-carboxamido)pyrrolidin-1-yl)cyclohexyl)carbamate To a solution of 6-(4-fluorophenyl)-1H-indole-2-carboxylic acid (30 mg, 0.12 mmol) in dry DMF (0.5 mL) was added DIPEA (0.10 mL, 0.6 mmol), HOBt (15 mg, 0.1 mmol) and EDC (30 mg, 0.15 mmol). The reaction mixture was stirred at room temperature and (S)-benzyl (4-(3-aminopyrrolidin-1-yl)cyclohexyl)carbamate hydrogen chloride salt (Intermediate V) (50 mg, 0.12 mmol) was added. The reaction mixture was stirred at room temperature overnight. The reaction mixture was diluted with EtOAc and washed with water and then brine. The organic layer was dried over anhydrous sodium sulfate and filtered. The filtrate was concentrated under reduced pressure and purified by column chromatography on silica gel to give the desired product (16 mg, 59% yield) as a white solid. MS: Calcd for C$_{33}$H$_{35}$FN$_4$O$_3$ 555.27 [M+H]$^+$, found 555.40 [M+H]$^+$.

The following compounds were prepared according to the procedure described above.

Example 51

(S)—N-(2,5-diaminopentyl)-6-phenyl-1H-indole-2-carboxamide hydrogen chloride salt was prepared using similar methods as used for the preparation of Example 7

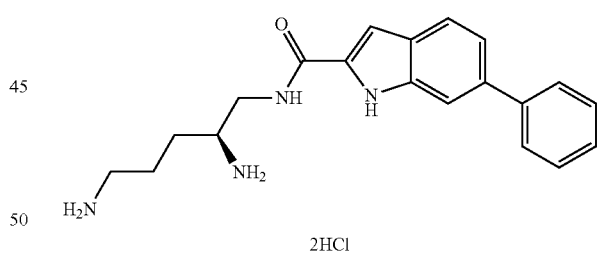

$^1$H NMR (300 MHz, D$_2$O) δ 7.86 (m, 4H), 7.60 (m, 2H), 7.48 (m, 2H), 7.23 (s, 1H), 3.77 (m, 1H), 3.68 (m, 1H), 3.63 (m, 1H), 3.09 (m, 2H), 1.87 (m, 4H).
$^{13}$C NMR (75 MHz, D$_2$O) δ 164.22, 140.84, 137.28, 137.22, 130.17, 128.98, 127.27, 126.96, 126.52, 122.50, 120.11, 109.97, 104.89, 51.66, 40.83, 39.09, 27.12, 23.03. MS: Calcd for C$_{20}$H$_{24}$N$_4$O 337.21[M+H]$^+$, found 337.20 [M+H]$^+$.

Example 52

(S)—N-(2,5-diaminopentyl)-6-(p-tolyl)-1H-indole-2-carboxamide hydrogen chloride salt was prepared using similar methods as used for the preparation of Example 7.

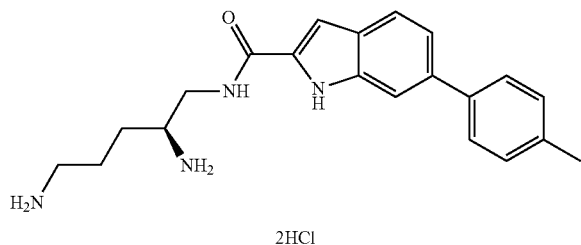 [SMILES: Cc1ccc(-c2ccc3cc(C(=O)NC[C@@H](N)CCCN)[nH]c3c2)cc1]

¹H NMR (300 MHz, D₂O) δ 7.90 (m, 2H), 7.71 (m, 2H), 7.52 (m, 2H), 7.13 (m, 1H), 7.06 (m, 1H), 3.61-3.42 (m, 3H), 3.04 (m, 2H), 2.73 (s, 3H), 1.79 (m, 4H). MS: Calcd for $C_{21}H_{26}N_4O$ 351.21 [M+H]⁺, found 351.20 [M+H]⁺.

Example 53

(S)—N-(2,5-diaminopentyl)-6-(4-fluoro-3-methoxyphenyl)-1H-indole-2-carboxamide hydrogen chloride salt was prepared using similar methods as used for the preparation of Example 7.

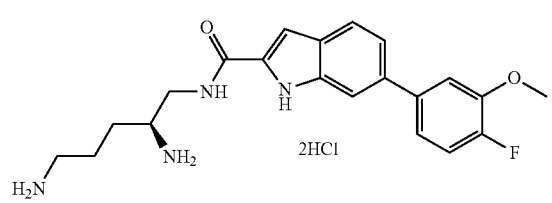 [SMILES: COc1cc(-c2ccc3cc(C(=O)NC[C@@H](N)CCCN)[nH]c3c2)ccc1F]

¹H NMR (300 MHz, D₂O) δ 7.66 (d, J=8.4 Hz, 1H), 7.45 (s, 1H), 7.29 (d, J=8.4 Hz, 1H), 7.09 (m, 3H), 7.05 (s, 1H), 3.85 (s, 3H), 3.72 (m, 1H), 3.68 (m, 1H), 3.55 (m, 1H), 3.02 (m, 2H), 1.82 (m, 4H). MS: Calcd for $C_{21}H_{25}FN_4O_2$ 385.20 [M+H]⁺, found 385.25 [M+H]⁺.

Example 54

(S)—N-(2,5-diaminopentyl)-6-(4-fluoro-2-chlorophenyl)-1H-indole-2-carboxamide hydrogen chloride salt was prepared using similar methods as used for the preparation of Example 7.

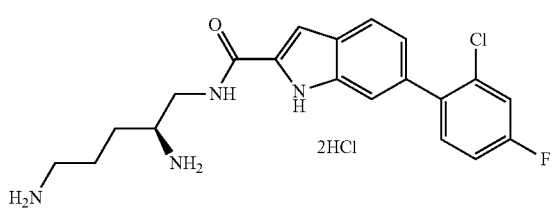

¹H NMR (300 MHz, D₂O) δ 7.74 (d, J=8.4 Hz, 1H), 7.52 (s, 1H), 7.36 (m, 2H), 7.29 (d, J=8.4 Hz, 1H), 7.18 (m, 1H), 7.17 (s, 1H), 7.09 (m, 1H), 3.73 (m, 1H), 3.63 (m, 1H), 3.58 (m, 1H), 3.03 (m, 2H), 1.81 (m, 4H). MS: Calcd for $C_{20}H_{22}ClFN_4O$ 389.15 [M+H]⁺, found 389.20 [M+H]⁺.

Example 55

(S)—N-(2,5-diaminopentyl)-6-(3-fluorophenyl)-1H-indole-2-carboxamide hydrogen chloride salt was prepared using similar methods as used for the preparation of Example 7.

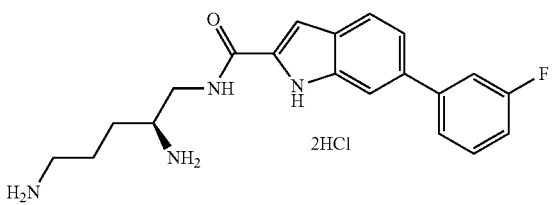 [SMILES: NCCC[C@H](N)CNC(=O)c1cc2ccc(-c3cccc(F)c3)cc2[nH]1]

¹H NMR (300 MHz, D₂O) δ 7.79 (m, 1H), 7.79 (s, 1H), 7.58-7.41 (m, 4H), 7.18 (s, 1H), 7.12 (m, 1H), 3.73 (m, 1H), 3.68 (m, 1H), 3.53 (m, 1H), 3.02 (m, 2H), 1.82 (m, 4H).
MS: Calcd for $C_{20}H_{23}FN_4O$ 355.19 [M+H]⁺, found 355.25 [M+H]⁺.

Example 56

(S)—N-(2,5-diaminopentyl)-6-(2,4-difluorophenyl)-1H-indole-2-carboxamide hydrogen chloride salt was prepared using similar methods as used for the preparation of Example 7.

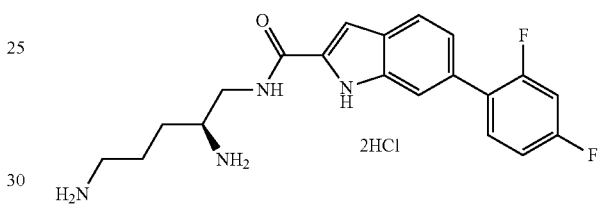

¹H NMR (300 MHz, D₂O) δ 7.81 (d, J=8.4 Hz, 1H), 7.69 (s, 1H), 7.56 (m, 2H), 7.35 (d, J=8.4 Hz, 1H), 7.30 (m, 1H), 7.20 (s, 1H), 7.07 (m, 2H), 3.77 (m, 1H), 3.65 (m, 1H), 3.57 (m, 1H), 3.04 (m, 2H), 1.82 (m, 4H). MS: Calcd for $C_{20}H_{22}F_2N_4O$ 373.18 [M+H]⁺, found 373.25 [M+H]⁺.

Example 57

(S)—N-(2,5-diaminopentyl)-6-(4-fluoro-3-chlorophenyl)-1H-indole-2-carboxamide hydrogen chloride salt was prepared using similar methods as used for the preparation of Example 7.

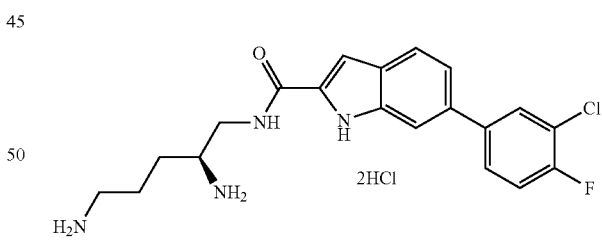

¹H NMR (300 MHz, D₂O) δ 7.79 (d, J=8.4 Hz, 1H), 7.57 (s, 1H), 7.48-7.32 (m, 2H), 7.24 (d, J=8.4 Hz, 1H), 7.20 (s, 1H), 7.16 (m, 1H), 3.74 (m, 1H), 3.65 (m, 1H), 3.59 (m, 1H), 3.04 (m, 2H), 1.83 (m, 4H). MS: Calcd for $C_{14}H_{19}BrN_4O$ 339.07 and 341.07 [M+H]⁺, found 339.10 and 341.10 [M+H]⁺.

Example 58

(S)-6-bromo-N-(2,5-diaminopentyl)-1H-indole-2-carboxamide hydrogen chloride salt was prepared using similar methods as used for the preparation of Example 7 without Suzuki coupling.

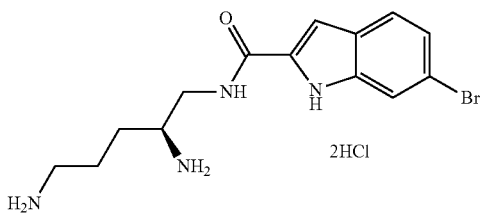 [SMILES: NCCC[C@H](N)CNC(=O)c1cc2ccc(Br)cc2[nH]1]

$^1$H NMR (300 MHz, D$_2$O) δ 7.70 (s, 1H), 7.59 (d, J=8.4 Hz, 1H), 7.26 (d, J=8.4 Hz, 1H), 7.11 (s, 1H), 3.74 (m, 1H), 3.64 (m, 1H), 3.56 (m, 1H), 3.01 (m, 2H), 1.80 (m, 4H).
MS: Calcd for C$_{14}$H$_{19}$BrN$_4$O 339.07 and 341.07 [M+H]$^+$, found 339.10 and 341.10 [M+H]$^+$.

Example 59

N-(3-aminocyclohexyl)-6-(4-fluorophenyl)-1H-indole-2-carboxamide hydrogen chloride salt was prepared using similar methods as used for the preparation of Example 50 using appropriately protected amine component (Intermediate W).

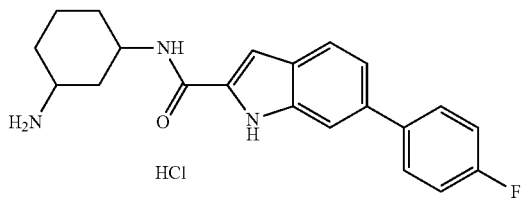 [SMILES: NC1CCCC(NC(=O)c2cc3ccc(-c4ccc(F)cc4)cc3[nH]2)C1 ; Cl]

$^1$H NMR (300 MHz, D$_2$O) δ 7.75 (d, J=8.4 Hz, 1H), 7.71 (s, 1H), 7.69 (m, 2H), 7.43 (d, J=8.4 Hz, 1H), 7.21 (s, 1H), 7.03 (m, 2H), 3.71 (m, 1H), 3.35 (m, 1H), 1.93 (m, 4H), 1.75 (m, 2H), 1.43 (m, 2H). MS: Calcd for C$_{21}$H$_{22}$FN$_3$O 352.17 [M+H]$^+$, found 352.25 [M+H]$^+$.

Example 60

(S)-6-(4-fluorophenyl)-N-(1-(piperidin-4-yl)pyrrolidin-3-yl)-1H-indole-2-carboxamide hydrogen chloride salt was prepared using similar methods as used for the preparation of Example 50 using appropriately protected amine component (Intermediate Z3).

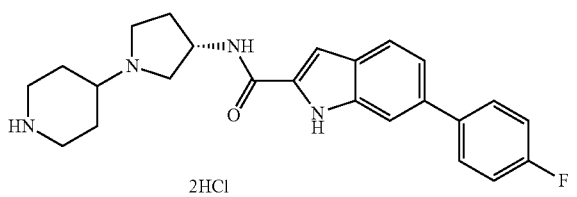 [SMILES: O=C(N[C@H]1CCN(C2CCNCC2)C1)c1cc2ccc(-c3ccc(F)cc3)cc2[nH]1]

MS: Calcd for C$_{24}$H$_{27}$FN$_4$O 407.22 [M+H]$^+$, found 407.25 [M+H]$^+$.

Example 61

N-(2-aminoethyl)-6-(4-fluorophenyl)-N-(piperidin-4-yl)-1H-indole-2-carboxamide hydrogen chloride salt was prepared using similar methods as used for the preparation of Example 50 using appropriately protected amine component (Intermediate X).

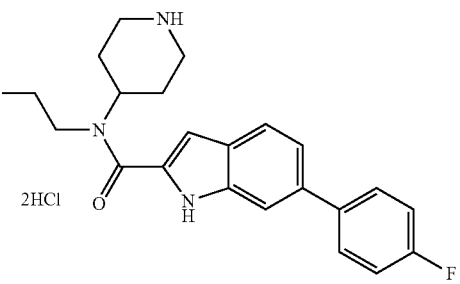

$^1$H NMR (300 MHz, D$_2$O) δ 7.78 (d, J=8.4 Hz, 1H), 7.72 (s, 1H), 7.69 (m, 2H), 7.44 (d, J=8.4 Hz, 1H), 7.21 (m, 2H), 6.92 (s, 1H), 3.79 (m, 2H), 3.53 (m, 3H), 3.26 (m, 2H), 3.07 (m, 2H), 2.16 (m, 4H). MS: Calcd for C$_{22}$H$_{25}$FN$_4$O 381.20 [M+H]$^+$, found 381.20 [M+H]$^+$.

Example 62

N-(2-((4-aminocyclohexyl)amino)ethyl)-6-(4-fluorophenyl)-1H-indole-2-carboxamide hydrogen chloride salt was prepared using similar methods as used for the preparation of Example 50 using appropriately protected amine component (Intermediate Y).

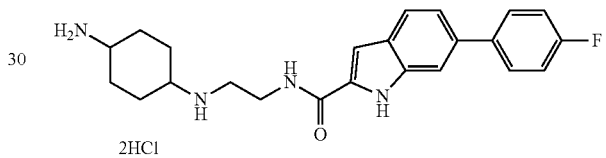

$^1$H NMR (300 MHz, D$_2$O) δ 7.69 (d, J=8.4 Hz, 1H), 7.61 (m, 2H), 7.56 (s, 1H), 7.34 (d, J=8.4 Hz, 1H), 7.17 (m, 2H), 7.03 (s, 1H), 3.64 (m, 2H), 3.27 (m, 2H), 3.20 (m, 2H), 2.22 (m, 2H), 2.17 (m, 2H), 1.51 (m, 4H). MS: Calcd for C$_{23}$H$_{27}$FN$_4$O 395.22 [M+H]$^+$, found 395.30 [M+H]$^+$.

Example 63

6-(4-fluorophenyl)-N-(2-(piperidin-4-ylamino)ethyl)-1H-indole-2-carboxamide hydrogen chloride salt was prepared using similar methods as used for the preparation of Example 50 using appropriately protected amine component (Intermediate Z).

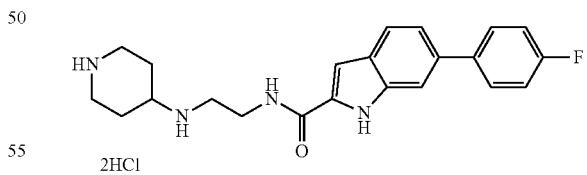

$^1$H NMR (300 MHz, D$_2$O) δ 7.61 (d, J=8.4 Hz, 1H), 7.52 (m, 2H), 7.45 (s, 1H), 7.25 (d, J=8.4 Hz, 1H), 7.10 (m, 2H), 6.97 (s, 1H), 3.62 (m, 2H), 3.59 (m, 1H), 3.27 (m, 2H), 3.06 (m, 2H), 2.35 (m, 2H), 1.85 (m, 2H). MS: Calcd for C$_{22}$H$_{25}$FN$_4$O 381.20 [M+H]$^+$, found 381.25 [M+H]$^+$.

Example 64

6-(4-fluorophenyl)-N-(2-(pyrrolidin-3-ylamino)ethyl)-1H-indole-2-carboxamide hydrogen chloride salt was prepared using similar methods as used for the preparation of Example 50 using appropriately protected amine component (Intermediate Z1).

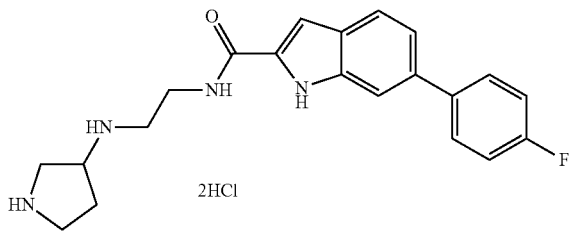 [SMILES: O=C(NCCNC1CCNC1)c1cc2ccc(-c3ccc(F)cc3)cc2[nH]1]

$^1$H NMR (300 MHz, D$_2$O) δ 7.72 (d, J=8.4 Hz, 1H), 7.62 (m, 2H), 7.59 (s, 1H), 7.35 (d, J=8.4 Hz, 1H), 7.17 (m, 2H), 7.05 (s, 1H), 3.83 (m, 1H), 3.71 (m, 2H), 3.53 (m, 1H), 3.45 (m, 3H), 3.36 (m, 2H), 2.59 (m, 1H), 2.22 (m, 1H). MS: Calcd for C$_{21}$H$_{23}$FN$_4$O 367.19 [M+H]$^+$, found 367.20 [M+H]$^+$.

Example 65

N-(2-(3-aminocyclohexyl)amino)ethyl)-6-(4-fluorophenyl)-1H-indole-2-carboxamide hydrogen chloride salt was prepared using similar methods as used for the preparation of Example 50 using appropriately protected amine component (Intermediate Z2).

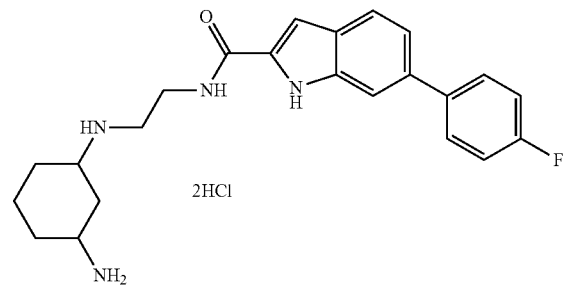 [SMILES: NC1CCCC(NCCNC(=O)c2cc3ccc(-c4ccc(F)cc4)cc3[nH]2)C1]

$^1$H NMR (300 MHz, D$_2$O) δ 7.74 (d, J=8.4 Hz, 1H), 7.64 (m, 3H), 7.39 (d, J=8.4 Hz, 1H), 7.19 (m, 2H), 7.08 (s, 1H), 3.68 (m, 2H), 3.32 (m, 4H), 2.43 (m, 1H), 2.35 (m, 1H), 2.21 (m, 1H), 2.04 (m, 1H), 1.70 (m, 2H), 1.35 (m, 2H). MS: Calcd for C$_{23}$H$_{27}$FN$_4$O 395.22 [M+H]$^+$, found 395.30.

Example 66. Description of General Test Methods

Intrinsic MIC Assays

MIC assays were conducted in accordance with Clinical and Laboratory Standards Institute (CLSI) guidelines for broth microdilution. A 96-well plate containing cation-adjusted Mueller-Hinton (CAMH broth with 2-fold serial dilution of compounds was inoculated with log-phase bacterial at 5×10$^5$ CFU/mL. The final volume in each well was 100 μL. Each compound was tested in duplicate. The microtiter plates were incubated in an aerobic environment for 18 hours at 37° C. Then the bacterial growth was tested by reading the plate with a Veramex plate reader (Molecular Devices, Inc.) at 600 nm. The MIC was defined as the lowest compound concentration that inhibited 90% of bacteria growth.

The intrinsic MIC of the experimental EPIs was tested with the method described. The 2-fold serial dilution begins with 100 μg/mL of tested compound in the first column of the 96-well plates. The following Gram-negative bacterial strains were included in these assays:
Escherichia coli ATCC 25922
Klebsiella pneumoniae ATCC 13883 and ATCC 10031
Pseudomonas aeruginosa ATCC 27853.
Acinetobacter baumannii ATCC 19606

Bacterial EPI Assays
Tier 1 Testing

The EPI assay for the purposes of these studies represents a MIC assay in which the MIC of the antibiotic against the bacteria is tested in the presence of an experimental efflux pump inhibitor (EPI). The highest concentration of the EPI present in the assay typically is ½ of the intrinsic MIC of the compound. If the intrinsic MIC of the EPI is greater than 100 μg/mL, the EPI assay was tested with 50 μg/mL. Using serial dilutions of the EPI, its enhancement of antibiotic activity was then evaluated. The relative EPI activity was decided by comparing the MIC of the antibiotic in the presence of the EPI compound with the intrinsic MIC of the antibiotic alone. For the evaluation of the efficacy of an EPI against bacteria that were pre-exposed to an antibiotic, the inoculum of bacteria that used was developed from a bacterial culture isolated as a single colony following exposure at ½ the MIIC of the antibiotic (so as to induce efflux pump expression), was to be used in combination with the EPI.

Example 67. Standard EPI Assays

The impact of Example 6 on the MIC values of two test antibiotics (levofloxacin and cefepime) against P. aeruginosa ATCC 27853 were evaluated using our standard EPI assay. Both levofloxacin and cefepime are known substrates of efflux pumps in P. aeruginosa, and are thus well-suited to be test antibiotics to assay for EPI activity.

In our standard EPI assay, the MIC of the test antibiotic is determined in the absence and presence of sub-inhibitory concentrations of the EPI. Initially, the sub-inhibitory concentration used was ½×MIC of the EPI. As the intrinsic MIC of Example 6 against P. aeruginosa ATCC 27853 is 25 μg/mL, we used 12.5 μg/mL (½×MIC) of the Example 6 or lower in the standard EPI assay. The MIC of levofloxacin against P. aeruginosa ATCC 27853 in the absence of EPI is 1 μg/mL. In the presence of 6.25 μg/mL of the Example 6, the MIC of levofloxacin was markedly reduced to 0.063 μg/mL, a 32-fold reduction relative to the MIC of levofloxacin in the absence of EPI (1 μg/mL). When cefepime was used as the test antibiotic, the MIC of cefepime decreased by 2-fold, from 2 μg/mL in the absence of EPI to 1.0 μg/mL in the presence of 12.5 μg/mL of the Example 6. Similar methodology was employed to examine the synergy with Escherichia coli ATCC 25922 in the presence of varied concentrations of these EPIs using clarithromycin as the antibiotic.

Tier 2 Testing

A second tier of in vitro evaluation was performed for those compounds that exhibited EPI activity wherein bacteria were pre-exposed to the antibiotic at ½ of its MIC. This novel method of assessment provided a better prediction of those compounds that did demonstrate synergy with an antibiotic in vitro to demonstrate similar efficacy in vivo in mouse models of infection. These "Pre-exposure Bacterial EPI Assays" proved to be very effective method for prioritizing the selection of compounds for further assessment in vivo.

Example 68. Pre-Exposure Bacterial EPI Assays

For the Pre-exposure EPI assay, P. aeruginosa ATCC 27853 bacteria used in the assay were first grown in CAMH at 37° C. overnight in the presence of ½×MIC of the test antibiotic (cefepime or levofloxacin). The principle underlying this pre-exposure is that exposure of the bacteria to sub-inhibitory concentrations of the test antibiotic will induce expression of efflux pumps, if any, and may represent the scenario in vivo more accurately.

The MIC of cefepime against *P. aeruginosa* bacteria that have been pre-exposed to cefepime was determined to be 16 µg/mL, 8-fold higher than the MIC of cefepime against unexposed *P. aeruginosa* (1 µg/mL). The impact of Example 20 on the MIC of cefepime against pre-exposed bacteria was then assayed in a manner similar to the standard EPI assay described above, with the exception that pre-exposed bacteria were used to inoculate the 96-well plates. The MIC of cefepime against cefepime-exposed *P. aeruginosa* reduced from 16 µg/mL to 0.5 µg/mL in the presence of 6.25 µg/mL of the Example 20, a 8-fold reduction. This result indicates that Example 20 is able to inhibit the pump induced in bacteria that have been pre-exposed to cefepime.

Thus by using the Pre-exposure EPI assay, information regarding the ability of an EPI to inhibit efflux pumps induced upon exposure to different antibiotics can be gleaned. This information is valuable in directing in vivo experiments and predicting the efficacy of a particular EPI-antibiotic pair.

Example 69. Fluorescent-Based Cellular Assay for Efflux Inhibition

The impact of potential EPI compounds on the activity of efflux pumps was also evaluated with a fluorescence-based cellular assay that measures the efflux of Hoechst 33342, a known substrate of Gram-negative bacterial efflux pumps. When bound to intracellular bacterial DNA, Hoechst 33342 fluoresces brightly, while the unbound fluorophore outside the bacterial cell exhibits little or no fluorescence. Thus, the efflux of Hoechst 33342 from inside to outside the bacterial cell is associated with a substantive decrease in fluorescence.

Bacterial cells were harvested from overnight cultures by centrifugation, and the cell pellet was washed with phosphate-buffered containing 1 mM $MgCl_2$ (PBSM). After washing the cells, the cell pellets were resuspended in PBSM to achieve a final OD at 600 nm of 0.6 to 0.9. The ATP required for efflux pump function was then depleted by addition of carbonyl cyanide 3-chlorophenylhydrazone (CCCP) to a final concentration in the range of 3 to 10 µM. Hoechst 33342 was then added to a final concentration of 10 and the cells were incubated aerobically at 37° C. for 0.5 to 18 hours. The bacterial suspension (200 µL) was added to wells of a black, flat-bottom 96-well plate containing test EPI compounds at concentrations of ranging from 1.6 to 25 µg/mL or an equivalent volume of the vehicle (DMSO) alone. A plate vortexer was used to mix the bacterial cells with the test EPI compounds, and the plates are pre-incubated at 37° C. for 5 minutes. After the pre-incubation, Hoechst 33342 efflux was initiated by addition of glucose to a final concentration of 10 to 50 mM. A SpectraMax® 2 fluorescent plate reader (Molecular Devices, Inc., Sunnyvale, CA) was used to monitor the fluorescence of each well at 37° C. once per minute for 20 to 60 minutes. The excitation and emission wavelengths were set at 355 and 460 nm, respectively. *E. coli* ATCC 25922, *K. pneumoniae* ATCC 13883, *P. aeruginosa* ATCC 27853 and *Acinetobacter baumannii* ATCC 19606 were used as model Gram-negative bacterial strains in this assay.

A general method for the in vivo assessment of bacterial EPIs is complicated by the fact that that both the antibiotic and the EPI need to be present for synergy to be achieved. A general method was discovered that has proven to be effective in establishing the relative efficacy of bacterial EPIs in a mouse septicemia model. The bacterial EPI is administered initially intravenously to mice with septicemia, followed 5 minutes later by the intravenous administration or oral administration of the antibiotic. A second administration of the EPI is then administered subcutaneously after an additional 5 minutes to act as a booster, followed by the final administration of the antibiotic either intravenously or orally after the second administration of the EPI. In many instances, this regiment has proved effective in demonstrating synergy and allowing survival of the infected mice. In a few instances, a second regiment of both EPI and antibiotic as administered on day 1 was required after 24 hours to affect cures.

Example 70. Methods of Assessment of In Vivo Efficacy of Efflux Pump Inhibitors Determination of the in vivo efficacy of bacterial efflux pump inhibitors (EPIs) can be efficiently determined using a mouse septicemia model of infection. The systemic infection is initiated by a 500 ul intraperitoneal injection of an inoculum containing bacteria (such as *P. aeruginosa* [ATCC 27853]) at a concentration of approximately $5\times10^5$ cells in 5% mucin in Swiss Webster female mice. The experimental groups (4-6 infected mice each) consist of both positive and negative controls, as well as infected mice treated with antibiotic alone or EPI alone, as well as the EPI administered in combination with the antibiotic. Five mutes post-infection an EPI is administered iv with an antibiotic such as cefepime (250 ul of a 10 mg/ml solution) being administered 10 minutes post-infection. A second dose of the EPI is then administered sc 20 minutes post-infection, with cefepime again being administered (250 ul of a 10 mg/ml solution) 25 minutes post-infection. Mice treated with cefepime alone were injected with an iv dose (250 ul of a 10 mg/ml solution) b.i.d. at 10 and 25 minutes post-infection. Mice treated with EPI alone were treated iv 5 minutes post infection and sc 20 minutes post-infection. Additional experimental groups consisting of 4-6 infected mice were untreated or treated with vehicle alone at the appropriate time points. If required, this regiment would be repeated 24 hours post-infection on day 2 of the assay.

| Experiment | EPI | % Survival (24 hr) Vehicle Controls | % Survival* (72 hr) Antibiotic Only | % Survival* (72 hr) Antibiotic + EPI |
|---|---|---|---|---|
| #512 | Example 6 | 0% | 25% | 100% |

*cefepime, 10 mg/ml b.i.d.; 250 ul; Example 6; 3.0 mg/ml b.i.d.

Example 71

The following can illustrate representative pharmaceutical dosage forms, containing a compound of formula I ('Compound X') or a pharmaceutically acceptable salt thereof, for therapeutic or prophylactic use in humans. The tablets can optionally comprise an enteric coating.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
|---|---|
| Compound X = | 20 |
| Oleic acid | 10 |
| Trichloromonofluoromethane | 5,000 |
| Dichlorodifluoromethane | 10,000 |
| Dichlorotetrafluoroethane | 5,000 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

The invention claimed is:

1. A compound of formula I:

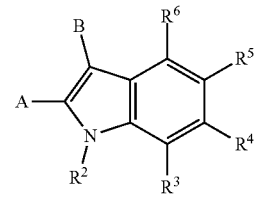

wherein:
A is —C(=O)N($R^{a1}$)—$R^1$, —($C_1$-$C_3$)alkyl-C(=O)N($R^{a1}$)$R^1$, —($C_1$-$C_3$)alkyl-O—$R^1$, or —O—$R^1$, and B is hydrogen, halogen, or ($C_1$-$C_4$)alkyl;

each $R^1$ is independently:
(a) ($C_2$-$C_8$)alkyl substituted with two or more —$NR^{b2}R^{c2}$ and wherein ($C_2$-$C_8$)alkyl is optionally substituted independently with one or more halo, ($C_1$-$C_4$)alkyl or ($C_3$-$C_7$)carbocyclyl; or
(b) pyrrolidinyl-($CH_2$), ($C_3$-$C_7$)carbocyclyl-$NR^e$—($C_1$-$C_4$)alkyl- or 4-7 membered monocyclic heterocyclyl-$NR^e$—($C_1$-$C_4$)alkyl- wherein each ($C_3$-$C_7$)carbocyclyl-$NR^e$—($C_1$-$C_4$)alkyl- is independently substituted with one or more $Z^1$ or $Z^2$, and wherein each pyrrolidinyl-($CH_2$)— or 4-7 membered monocyclic heterocyclyl-$NR^e$—($C_1$-$C_4$)alkyl- is independently substituted with one or more $Z^1$ or $Z^2$, and wherein any pyrrolidinyl-($CH_2$), ($C_3$-$C_7$)carbocyclyl $NR^e$—($C_1$-$C_4$)alkyl- or 4-7 membered monocyclic heterocyclyl-$NR^e$—($C_1$-$C_4$)alkyl-of $R^1$ is independently optionally substituted with one or more halo, ($C_1$-$C_4$)alkyl, ($C_3$-$C_7$)carbocyclyl, —C(=O)$NH_2$, —C(=O)NH($C_1$-$C_4$)alkyl, —C(=O)N(($C_1$-$C_4$)alkyl)$_2$, —NHC(=O)($C_1$-$C_4$)alkyl-$NH_2$, or 3-7 membered monocyclic heterocyclyl wherein ($C_1$-$C_4$)alkyl, ($C_3$-$C_7$)carbocyclyl or 3-7 membered monocyclic heterocyclyl is optionally substituted with one or more halogen, ($C_1$-$C_4$)alkyl, —$NH_2$, —NH($C_1$-$C_4$)alkyl or —N(($C_1$-$C_4$)alkyl)$_2$;

$R^2$ is hydrogen or ($C_1$-$C_4$)alkyl;

$R^3$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, aryl, or heteroaryl wherein the aryl or heteroaryl is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy;

$R^4$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, aryl, heteroaryl, aryl($C_1$-$C_4$)alkyl-, heteroaryl($C_1$-$C_4$)alkyl-, ($C_3$-$C_7$)carbocyclyl($C_1$-$C_4$)alkyl-, ($C_3$-$C_7$)carbocyclyl($C_2$-$C_4$)alkynyl-, phenoxy or heteroaryloxy, wherein the aryl, heteroaryl, aryl($C_1$-$C_4$)alkyl-, heteroaryl($C_1$-$C_4$)alkyl-, ($C_3$-$C_7$)carbocyclyl($C_1$-$C_4$)alkyl-, ($C_3$-$C_7$)carbocyclyl($C_2$-$C_4$)alkynyl-, phenoxy or heteroaryloxy, is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, ($C_1$-$C_4$)haloalkoxy, methylenedioxy (—$OCH_2O$—), and ($C_3$-$C_7$)carbocyclyl;

R⁵ is hydrogen, halo, $(C_1-C_4)$alkyl, $(C_1-C_4)$haloalkyl, $(C_1-C_4)$alkoxy, $(C_1-C_4)$haloalkoxy, aryl, heteroaryl, aryl$(C_1-C_4)$alkyl-, heteroaryl$(C_1-C_4)$alkyl-, $(C_3-C_7)$carbocyclyl$(C_1-C_4)$alkyl-, $(C_3-C_7)$carbocyclyl$(C_2-C_4)$alkynyl-, phenoxy or heteroaryloxy, wherein the aryl, heteroaryl, aryl$(C_1-C_4)$alkyl-, heteroaryl$(C_1-C_4)$alkyl-, $(C_3-C_7)$carbocyclyl$(C_1-C_4)$alkyl-, $(C_3-C_7)$carbocyclyl$(C_2-C_4)$alkynyl-, phenoxy or heteroaryloxy, is optionally substituted with one or more groups independently selected from the group consisting of halo, —OH, —NO₂, —CN, $(C_1-C_4)$alkyl, $(C_1-C_4)$haloalkyl, $(C_1-C_4)$alkoxy, $(C_1-C_4)$haloalkoxy, methylenedioxy (—OCH₂O—), and $(C_3-C_7)$carbocyclyl;

R⁶ is hydrogen, halo, $(C_1-C_4)$alkyl, $(C_1-C_4)$haloalkyl, $(C_1-C_4)$alkoxy, $(C_1-C_4)$haloalkoxy, aryl, or heteroaryl wherein the aryl or heteroaryl is optionally substituted with one or more groups independently selected from the group consisting of halo, —OH, —NO₂, —CN, $(C_1-C_4)$alkyl, $(C_1-C_4)$haloalkyl, $(C_1-C_4)$alkoxy, and $(C_1-C_4)$haloalkoxy;

each $Z^1$ is independently selected from the group consisting of —NR$^{b3}$R$^{c3}$, —NHNH₂, —C(=NR$^{a3}$)(NR$^{b3}$R$^{c3}$), —NR$^{a3}$C(=NR$^{a3}$)(R$^{d3}$), and —NR$^{a3}$C(=NR$^{a3}$)(NR$^{b3}$R$^{c3}$);

each $Z^2$ is independently —(C₁-C₆)alkyl substituted with one or more $Z^1$ and optionally substituted with one or more $Z^3$;

each $Z^3$ is independently halo or $(C_3-C_7)$carbocyclyl;

each R$^{a1}$ is independently hydrogen, $(C_1-C_4)$alkyl, $(C_3-C_7)$carbocyclyl or 3-7 membered monocyclic heterocyclyl optionally substituted with one or more halogen or $(C_1-C_4)$alkyl;

each R$^{b2}$ and R$^{c2}$ is independently hydrogen, $(C_1-C_4)$alkyl or $(C_3-C_7)$carbocyclyl;

each R$^{a3}$ is independently hydrogen, $(C_1-C_4)$alkyl or $(C_3-C_7)$carbocyclyl;

each R$^{b3}$ is hydrogen;

each R$^{c3}$ is independently hydrogen, $(C_1-C_4)$alkyl, or $(C_3-C_7)$carbocyclyl;

R$^{d3}$ is $(C_1-C_4)$alkyl or $(C_3-C_7)$carbocyclyl; and each R$^e$ is independently hydrogen, $(C_1-C_4)$alkyl or $(C_3-C_7)$carbocyclyl;

or a salt thereof; and wherein any carbocyclyl is saturated or partially unsaturated.

2. The compound or salt of claim 1, wherein A is —C(=O)N(R$^{a1}$)—R¹ or —(C₁-C₃)alkyl-C(=O)N(R$^{a1}$)R¹, and B is hydrogen, halogen, or $(C_1-C_4)$alkyl.

3. A compound of formula Ia:

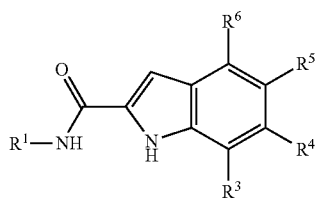

Ia wherein:
R¹ is:
(a) $(C_2-C_8)$alkyl substituted with two or more —NR$^{b2}$R$^{c2}$ and wherein $(C_2-C_8)$alkyl is optionally substituted independently with one or more halo, $(C_1-C_4)$alkyl or $(C_3-C_7)$carbocyclyl; or (b) pyrrolidinyl-$(C_1-C_4)$alkyl-, $(C_3-C_7)$carbocyclyl-NR$^e$—$(C_1-C_4)$alkyl- or 4-7 membered monocyclic heterocyclyl-NR$^e$—$(C_1-C_4)$alkyl- wherein each $(C_3-C_7)$carbocyclyl-NR$^e$—$(C_1-C_4)$alkyl- is independently substituted with one or more $Z^1$ or $Z^2$, and wherein each pyrrolidinyl-$(C_1-C_4)$alkyl- or 4-7 membered monocyclic heterocyclyl-NR$^e$—$(C_1-C_4)$alkyl- is independently substituted with one or more $Z^1$ or $Z^2$, and wherein any pyrrolidinyl-$(C_1-C_4)$alkyl-, $(C_3-C_7)$carbocyclyl NR$^e$—$(C_1-C_4)$alkyl- or 4-7 membered monocyclic heterocyclyl-NR$^e$—$(C_1-C_4)$alkyl- of R¹ is independently optionally substituted with one or more halo, $(C_1-C_4)$alkyl, $(C_3-C_7)$carbocyclyl, —C(=O)NH₂, —C(=O)NH$(C_1-C_4)$alkyl, —C(=O)N$((C_1-C_4)$alkyl)₂, —NHC(=O)$(C_1-C_4)$alkyl-NH₂, or 3-7 membered monocyclic heterocyclyl wherein $(C_1-C_4)$alkyl, $(C_3-C_7)$carbocyclyl or 3-7 membered monocyclic heterocyclyl is optionally substituted with one or more halogen, $(C_1-C_4)$alkyl, —NH₂, —NH$(C_1-C_4)$alkyl or —N$((C_1-C_4)$alkyl)₂;

R³ is hydrogen, halo, $(C_1-C_4)$alkyl, $(C_1-C_4)$haloalkyl, $(C_1-C_4)$alkoxy, $(C_1-C_4)$haloalkoxy, aryl, or heteroaryl wherein the aryl or heteroaryl is optionally substituted with one or more groups independently selected from the group consisting of halo, —OH, —NO₂, —CN, $(C_1-C_4)$alkyl, $(C_1-C_4)$haloalkyl, $(C_1-C_4)$alkoxy, and $(C_1-C_4)$haloalkoxy;

R⁴ is hydrogen, halo, $(C_1-C_4)$alkyl, $(C_1-C_4)$haloalkyl, $(C_1-C_4)$alkoxy, $(C_1-C_4)$haloalkoxy, aryl, heteroaryl, aryl$(C_1-C_4)$alkyl-, heteroaryl$(C_1-C_4)$alkyl-, $(C_3-C_7)$carbocyclyl$(C_1-C_4)$alkyl-, $(C_3-C_7)$carbocyclyl$(C_2-C_4)$alkynyl-, phenoxy or heteroaryloxy, wherein the aryl, heteroaryl, aryl$(C_1-C_4)$alkyl-, heteroaryl$(C_1-C_4)$alkyl-, $(C_3-C_7)$carbocyclyl$(C_1-C_4)$alkyl-, $(C_3-C_7)$carbocyclyl$(C_2-C_4)$alkynyl-, phenoxy or heteroaryloxy, is optionally substituted with one or more groups independently selected from the group consisting of halo, —OH, —NO₂, —CN, $(C_1-C_4)$alkyl, $(C_1-C_4)$haloalkyl, $(C_1-C_4)$alkoxy, $(C_1-C_4)$haloalkoxy, methylenedioxy (—OCH₂O—), and $(C_3-C_7)$carbocyclyl;

R⁵ is hydrogen, halo, $(C_1-C_4)$alkyl, $(C_1-C_4)$haloalkyl, $(C_1-C_4)$alkoxy, $(C_1-C_4)$haloalkoxy, aryl, heteroaryl, aryl$(C_1-C_4)$alkyl-, heteroaryl$(C_1-C_4)$alkyl-, $(C_3-C_7)$carbocyclyl$(C_1-C_4)$alkyl-, $(C_3-C_7)$carbocyclyl$(C_2-C_4)$alkynyl-, phenoxy or heteroaryloxy, wherein the aryl, heteroaryl, aryl$(C_1-C_4)$alkyl-, heteroaryl$(C_1-C_4)$alkyl-, $(C_3-C_7)$carbocyclyl$(C_1-C_4)$alkyl-, $(C_3-C_7)$carbocyclyl$(C_2-C_4)$alkynyl-, phenoxy or heteroaryloxy, is optionally substituted with one or more groups independently selected from the group consisting of halo, —OH, —NO₂, —CN, $(C_1-C_4)$alkyl, $(C_1-C_4)$haloalkyl, $(C_1-C_4)$alkoxy, $(C_1-C_4)$haloalkoxy, methylenedioxy (—OCH₂O—), and $(C_3-C_7)$carbocyclyl;

R⁶ is hydrogen, halo, $(C_1-C_4)$alkyl, $(C_1-C_4)$haloalkyl, $(C_1-C_4)$alkoxy, $(C_1-C_4)$haloalkoxy, aryl, or heteroaryl wherein the aryl or heteroaryl is optionally substituted with one or more groups independently selected from the group consisting of halo, —OH, —NO₂, —CN, $(C_1-C_4)$alkyl, $(C_1-C_4)$haloalkyl, $(C_1-C_4)$alkoxy, and $(C_1-C_4)$haloalkoxy;

each $Z^1$ is independently selected from the group consisting of —NR$^{b3}$R$^{c3}$, —NHNH₂, —C(=NR$^{a3}$)(NR$^{b3}$R$^{c3}$); —NR$^{a3}$(=NR$^{a3}$)(R$^{d3}$); and —NR$^{a3}$C(=NR$^{a3}$)(NR$^{b3}$R$^{c3}$);

each $Z^2$ is independently —(C₁-C₆)alkyl substituted with one or more $Z^1$ and optionally substituted with one or more $Z^3$;

each $Z^3$ is independently halo or $(C_3\text{-}C_7)$carbocyclyl;
each $R^{b2}$ and $R^{c2}$ is independently hydrogen, $(C_1\text{-}C_4)$alkyl or $(C_3\text{-}C_7)$carbocyclyl;
each $R^{a3}$ is independently hydrogen, $(C_1\text{-}C_4)$alkyl or $(C_3\text{-}C_7)$carbocyclyl;
each $R^{b3}$ is hydrogen;
each $R^{c3}$ is independently hydrogen, $(C_1\text{-}C_4)$alkyl, or $(C_3\text{-}C_7)$carbocyclyl;
$R^{d3}$ is $(C_1\text{-}C_4)$alkyl or $(C_3\text{-}C_7)$carbocyclyl; and
each $R^e$ is independently hydrogen, $(C_1\text{-}C_4)$alkyl or $(C_3\text{-}C_7)$carbocyclyl;
or a salt thereof; and
wherein any carbocyclyl is saturated or partially unsaturated.

4. The compound or salt of claim 1, wherein $R^3$ is hydrogen, halo, $(C_1\text{-}C_4)$alkyl, $(C_1\text{-}C_4)$haloalkyl, $(C_1\text{-}C_4)$alkoxy, or $(C_1\text{-}C_4)$haloalkoxy.

5. The compound or salt of claim 1, wherein $R^3$ is hydrogen or phenyl wherein the phenyl is optionally substituted with one or more groups independently selected from the group consisting of halo, —OH, —NO$_2$, —CN, $(C_1\text{-}C_4)$alkyl, $(C_1\text{-}C_4)$haloalkyl, $(C_1\text{-}C_4)$alkoxy and $(C_1\text{-}C_4)$haloalkoxy.

6. The compound or salt of claim 1, wherein $R^4$ is hydrogen, aryl, or heteroaryl wherein the aryl or heteroaryl is optionally substituted with one or more groups independently selected from the group consisting of halo, —OH, —NO$_2$, —CN, $(C_1\text{-}C_4)$alkyl, $(C_1\text{-}C_4)$haloalkyl, $(C_1\text{-}C_4)$alkoxy, methylenedioxy (—OCH$_2$O—), and $(C_1\text{-}C_4)$haloalkoxy.

7. The compound or salt of claim 1, wherein $R^4$ is hydrogen, phenyl, or pyridinyl wherein the phenyl or pyridinyl is optionally substituted with one or more groups independently selected from the group consisting of halo, —OH, —NO$_2$, —CN, $(C_1\text{-}C_4)$alkyl, $(C_1\text{-}C_4)$haloalkyl, $(C_1\text{-}C_4)$alkoxy, methylenedioxy (—OCH$_2$O—), and $(C_1\text{-}C_4)$haloalkoxy.

8. The compound or salt of claim 1, wherein $R^5$ is hydrogen or aryl wherein the aryl is optionally substituted with one or more groups independently selected from the group consisting of halo, —OH, —NO$_2$, —CN, $(C_1\text{-}C_4)$alkyl, $(C_1\text{-}C_4)$haloalkyl, $(C_1\text{-}C_4)$alkoxy, methylenedioxy (—OCH$_2$O—), and $(C_1\text{-}C_4)$haloalkoxy.

9. The compound or salt of claim 1 wherein $R^5$ is hydrogen or phenyl wherein the phenyl is optionally substituted with one or more groups independently selected from the group consisting of halo, —OH, —NO$_2$, —CN, $(C_1\text{-}C_4)$alkyl, $(C_1\text{-}C_4)$haloalkyl, $(C_1\text{-}C_4)$alkoxy, methylenedioxy (—OCH$_2$O—), and $(C_1\text{-}C_4)$haloalkoxy.

10. The compound or salt of claim 1, wherein $R^6$ is hydrogen, halo, $(C_1\text{-}C_4)$alkyl, $(C_1\text{-}C_4)$haloalkyl, $(C_1\text{-}C_4)$alkoxy, or $(C_1\text{-}C_4)$haloalkoxy.

11. The compound or salt of claim 1, wherein $R^6$ is hydrogen or phenyl wherein the phenyl is optionally substituted with one or more groups independently selected from the group consisting of halo, —OH, —NO$_2$, —CN, $(C_1\text{-}C_4)$alkyl, $(C_1\text{-}C_4)$haloalkyl, $(C_1\text{-}C_4)$alkoxy and $(C_1\text{-}C_4)$haloalkoxy.

12. The compound or salt of claim 1, wherein $R^1$ is $(C_4\text{-}C_8)$alkyl substituted with two or more groups independently selected from —NR$^{b2}$R$^{c2}$.

13. The compound or salt of claim 1, wherein $R^1$ is pyrrolidinyl-(CH$_2$), $(C_3\text{-}C_7)$carbocyclyl-NR$^e$—(C$_1$-C$_4$)alkyl- or 4-7 membered monocyclic heterocyclyl-NR$^e$—(C$_1$-C$_4$)alkyl- wherein each $(C_3\text{-}C_7)$carbocyclyl-NR$^e$—(C$_1$-C$_4$)alkyl- is independently substituted with one or more $Z^1$ or $Z^2$, and wherein each pyrrolidinyl-(CH$_2$) or 4-7 membered monocyclic heterocyclyl-NR$^e$—(C$_1$-C$_4$)alkyl- is independently substituted with one or more $Z^1$ or $Z^2$, and wherein any pyrrolidinyl-(CH$_2$), $(C_3\text{-}C_7)$carbocyclyl NR$^e$—(C$_1$-C$_4$)alkyl- or 4-7 membered monocyclic heterocyclyl-NR$^e$—(C$_1$-C$_4$)alkyl- of $R^1$ is independently optionally substituted independently with one or more halo, $(C_1\text{-}C_4)$alkyl, $(C_3\text{-}C_7)$carbocyclyl, —C(=O)NH$_2$, —C(=O)NH(C$_1$-C$_4$)alkyl, —C(=O)N((C$_1$-C$_4$)alkyl)$_2$, —NHC(=O)(C$_1$-C$_4$)alkyl-NH$_2$, or 3-7 membered monocyclic heterocyclyl wherein $(C_1\text{-}C_4)$alkyl, $(C_3\text{-}C_7)$carbocyclyl or 3-7 membered monocyclic heterocyclyl is optionally substituted with one or more halogen, $(C_1\text{-}C_4)$alkyl, —NH$_2$, —NH(C$_1$-C$_4$)alkyl or —N((C$_1$-C$_4$)alkyl)$_2$.

14. The compound or salt of claim 1, wherein $R^1$ is a pyrrolidinyl-(CH$_2$)—, wherein the pyrrolidinyl-(CH$_2$) is substituted with one or more groups independently selected from the group consisting of Z and $(C_1\text{-}C_6)$alkyl substituted with one or more Z, wherein each Z is independently —NR$^{b3}$R$^{c3}$ and wherein the pyrrolidinyl-(CH$_2$) is optionally substituted with one or more $(C_1\text{-}C_4)$alkyl.

15. The compound or salt of claim 1, wherein $R^1$ is:

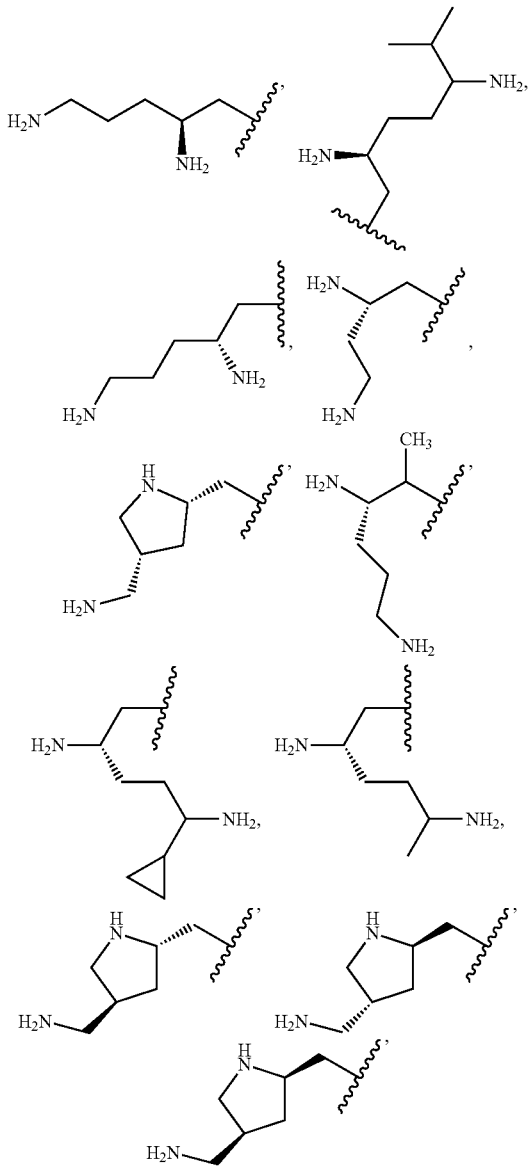

-continued
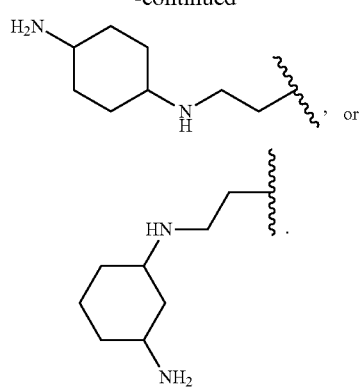, or
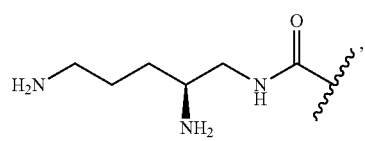.
16. The compound or salt of claim 1, wherein A is:
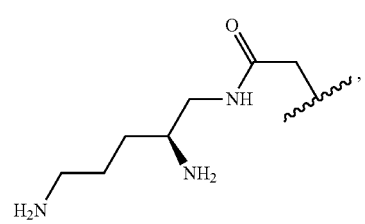,
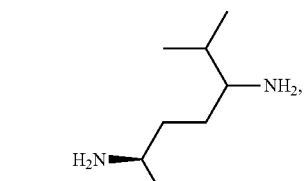,
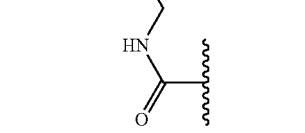,
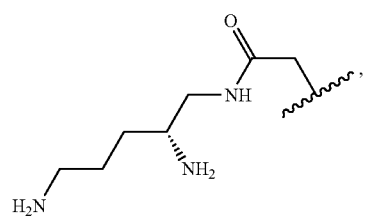,
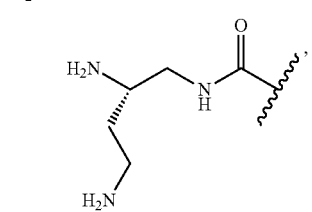,
-continued
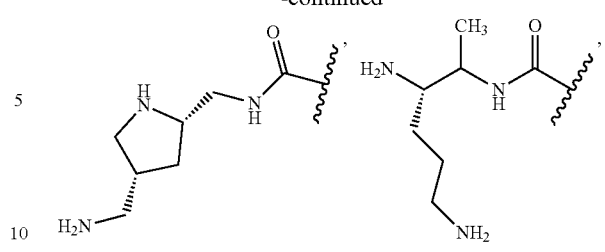,
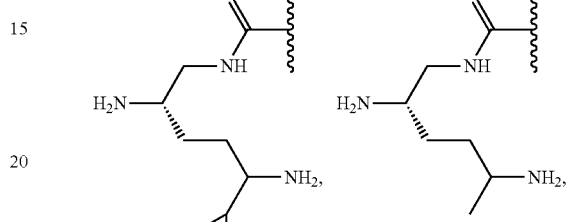,
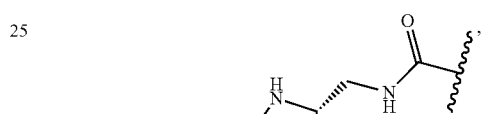,
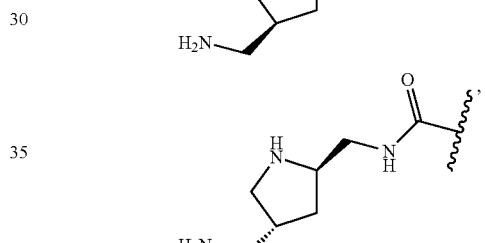,
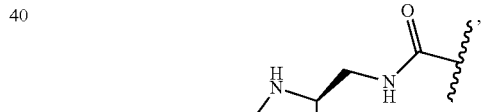,
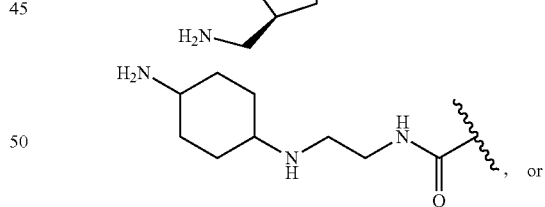, or
.

17. A compound or salt thereof that is:
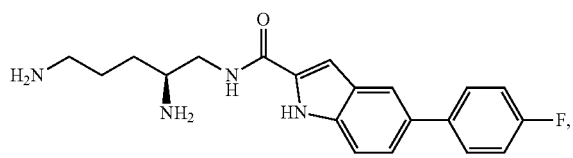
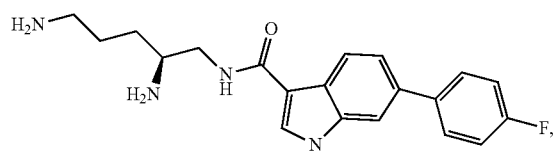
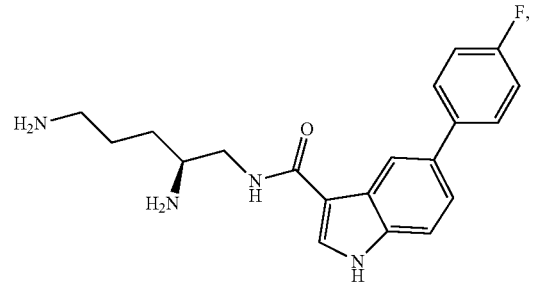
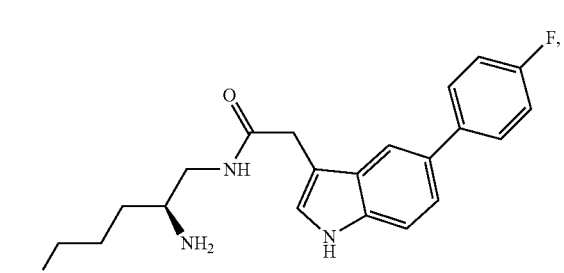
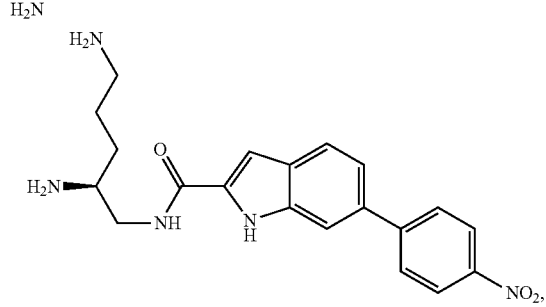
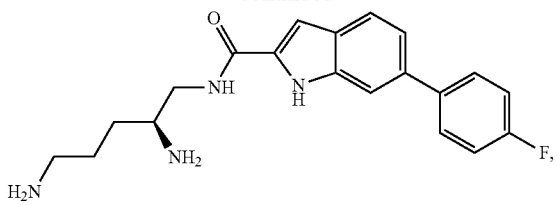
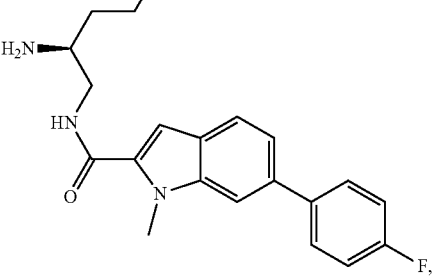
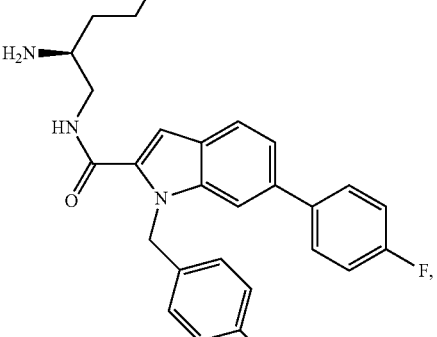

-continued
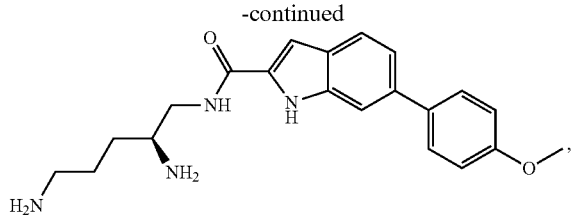
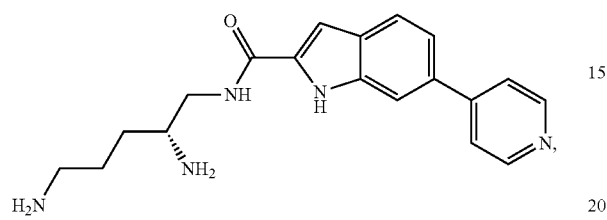
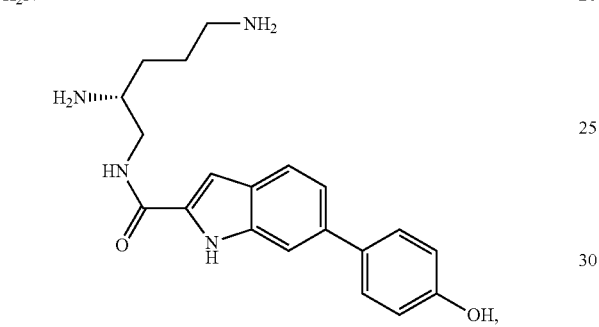
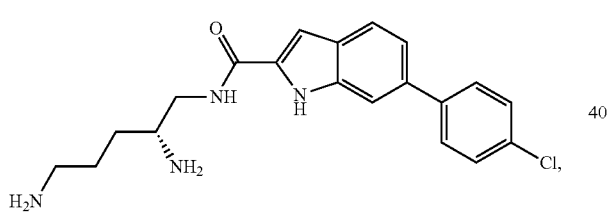
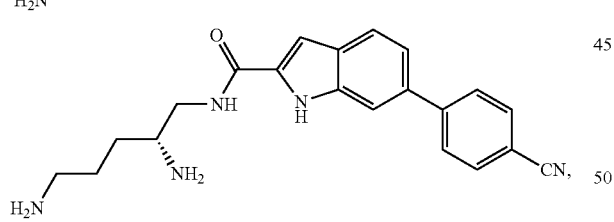
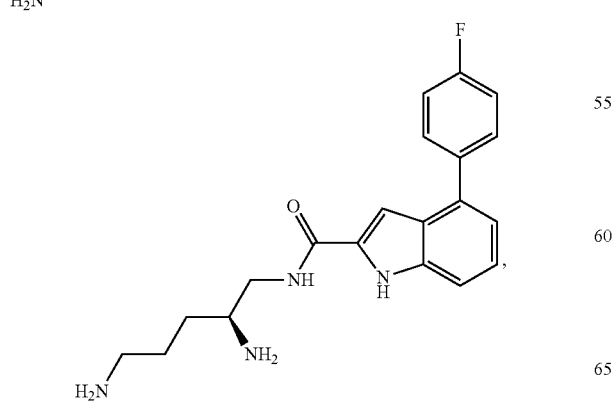
-continued
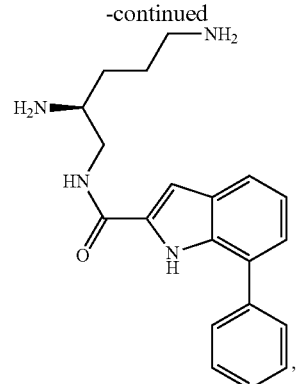
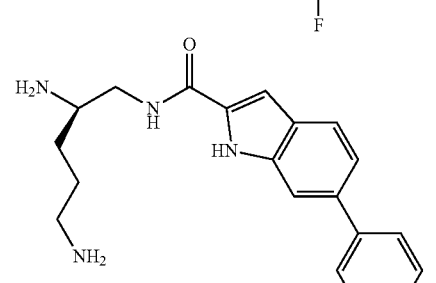
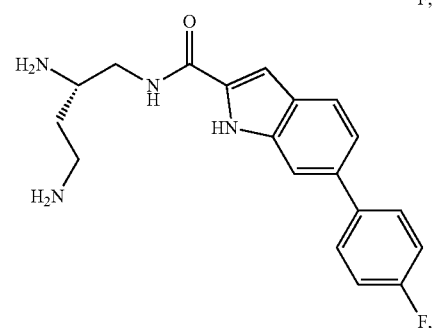
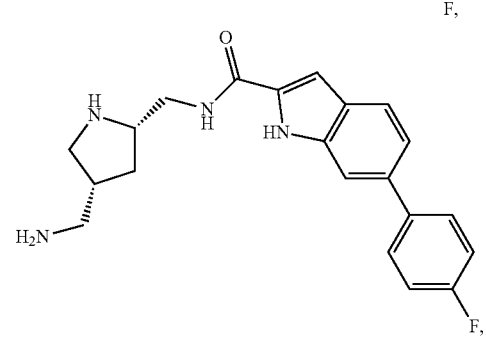
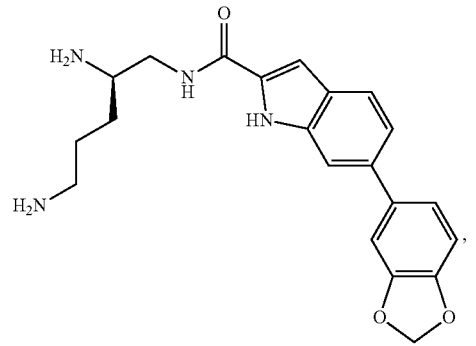

267
-continued
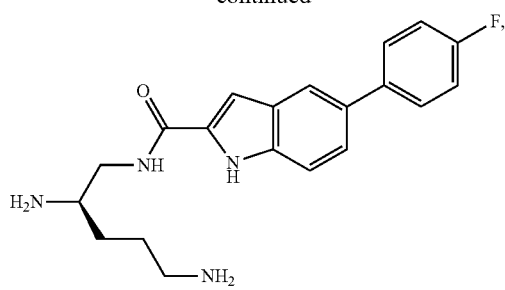
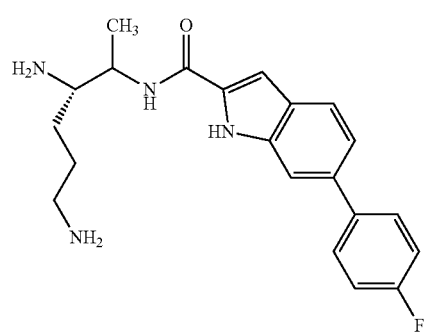
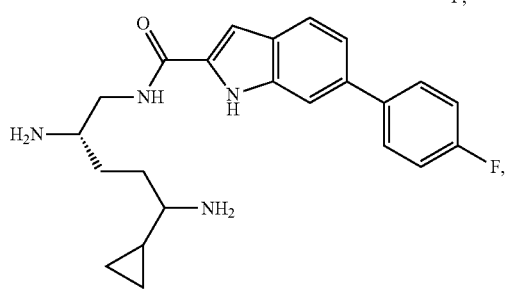
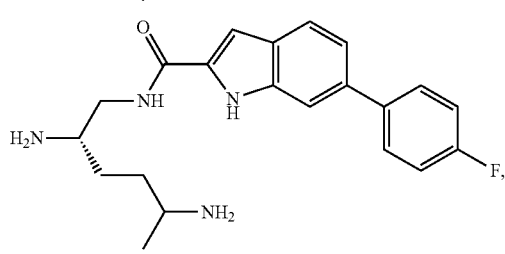
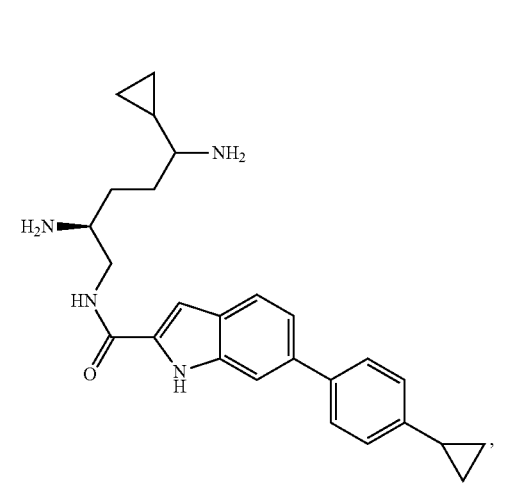
268
-continued
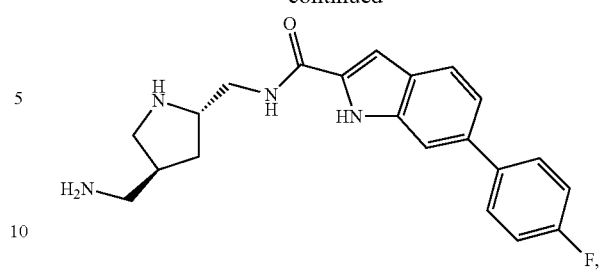
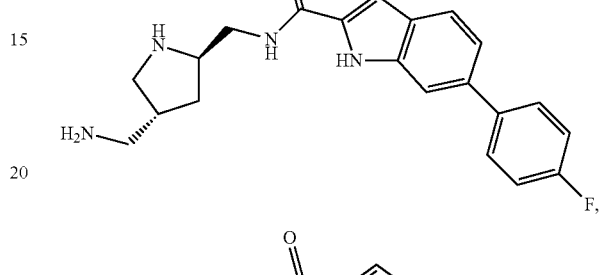
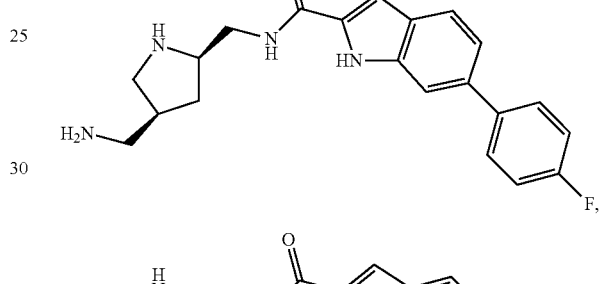
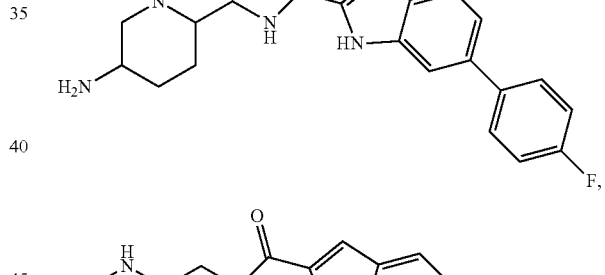
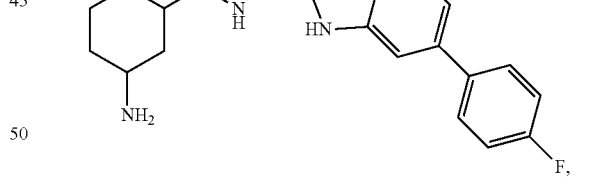
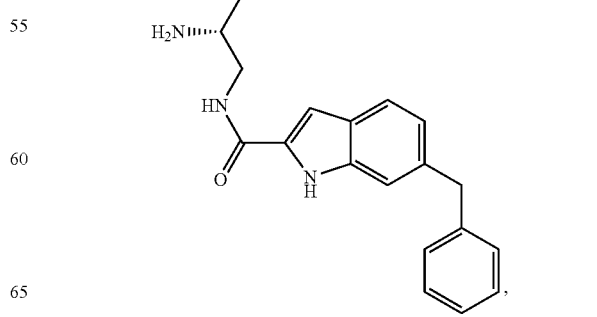

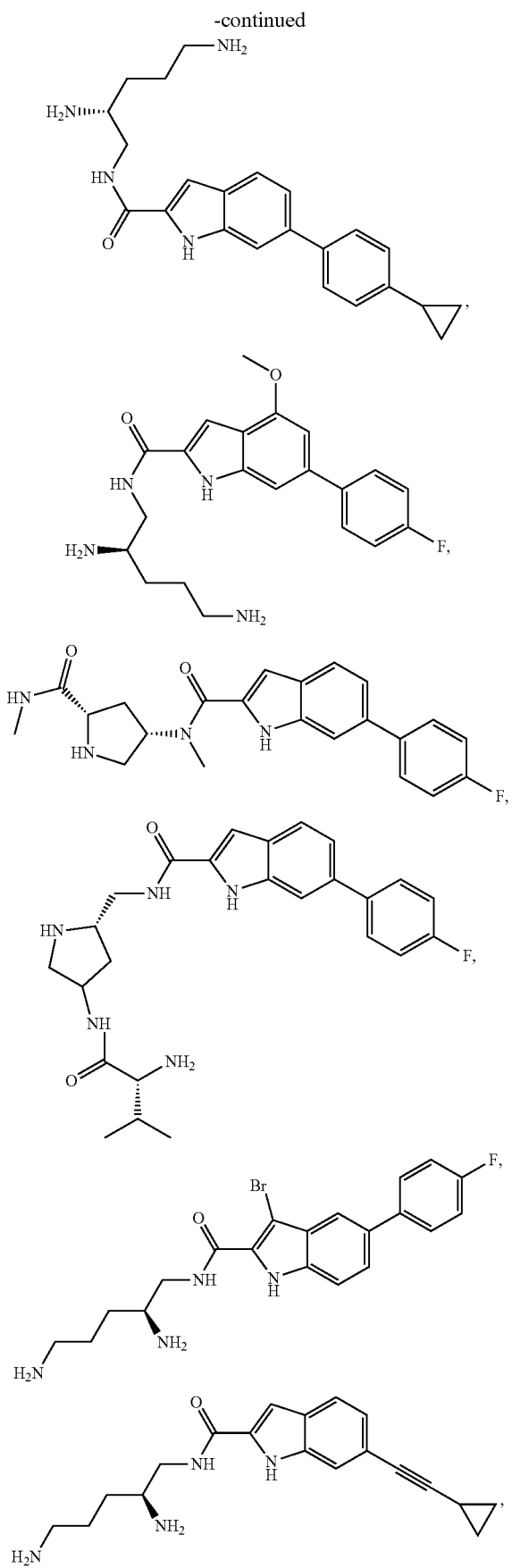

271
-continued
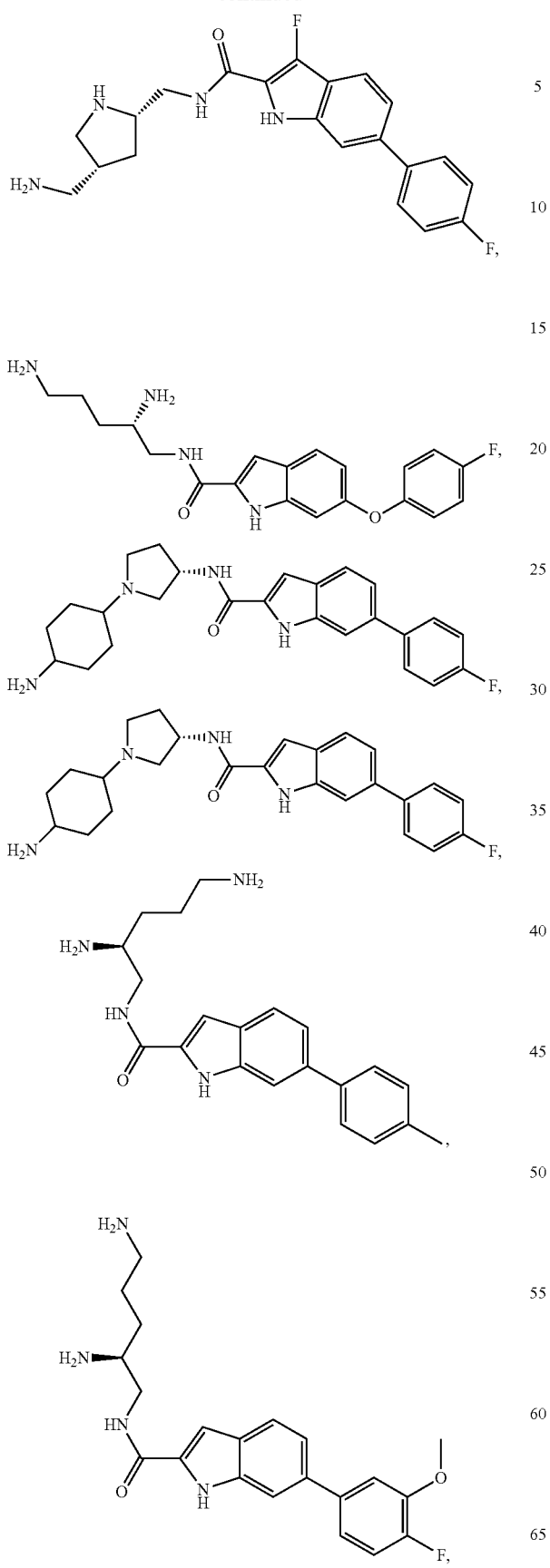
272
-continued
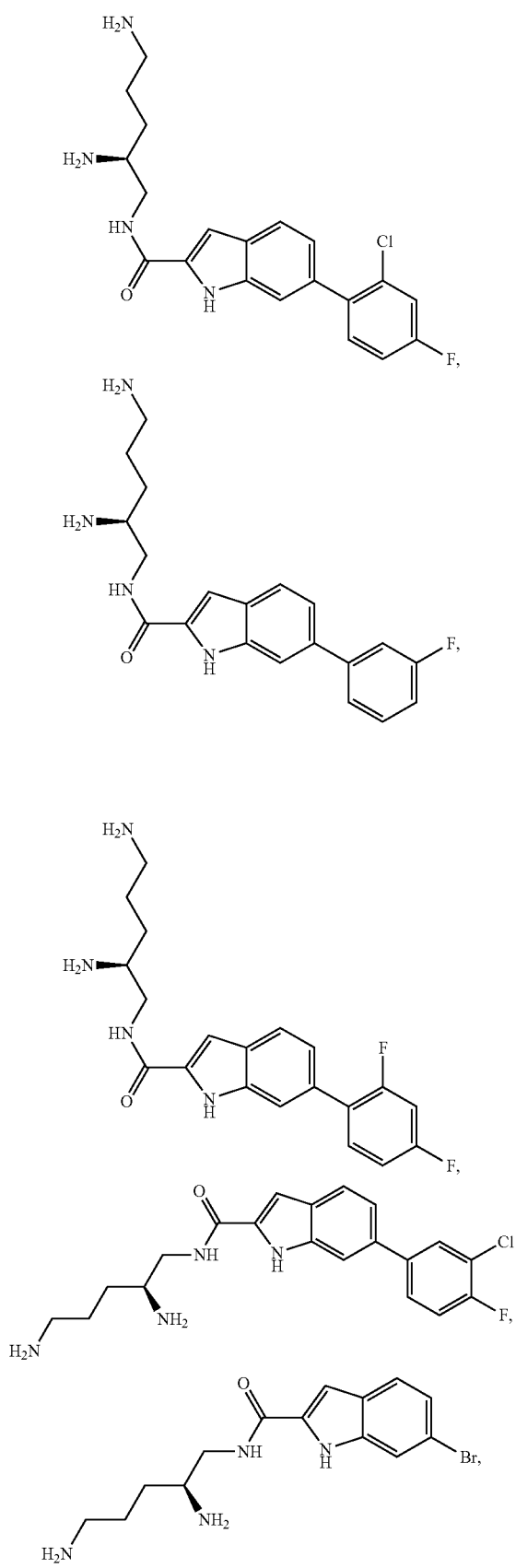

273
-continued
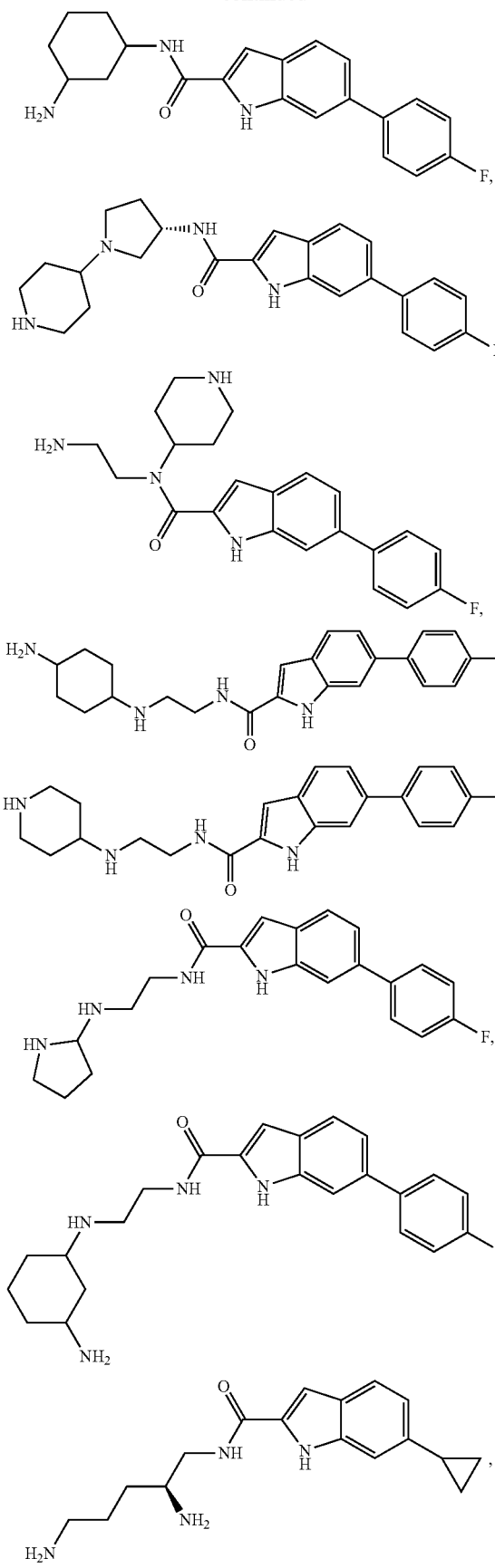
274
-continued
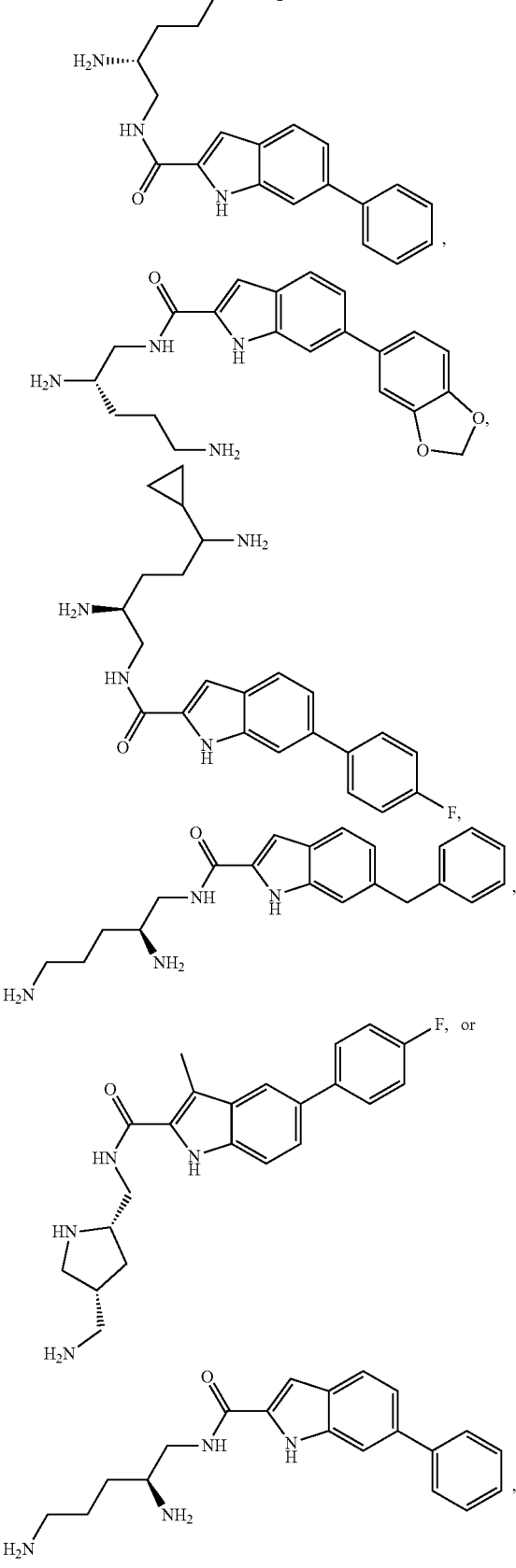
or a salt thereof.

18. A pharmaceutical composition comprising a compound as described in claim 1 or a pharmaceutically acceptable salt thereof and a pharmaceutically acceptable vehicle.

19. A pharmaceutical composition comprising a compound as described in claim 1 or a pharmaceutically acceptable salt thereof, one or more antibacterial agents and a pharmaceutically acceptable vehicle.

20. A method of inhibiting a bacterial efflux pump in an animal comprising administering to the animal a compound as described in claim 1 or a pharmaceutically acceptable salt thereof.

21. A method of treating or preventing a bacterial infection in an animal comprising co-administering to the animal a compound as described in claim 1 or a pharmaceutically acceptable salt thereof and one or more antibacterial agents.

22. A pharmaceutical composition comprising a compound as described in claim 17 or a pharmaceutically acceptable salt thereof and a pharmaceutically acceptable vehicle.

23. A pharmaceutical composition comprising a compound as described in claim 17 or a pharmaceutically acceptable salt thereof, one or more antibacterial agents and a pharmaceutically acceptable vehicle.

24. A method of inhibiting a bacterial efflux pump in an animal comprising administering to the animal a compound as described in claim 17 or a pharmaceutically acceptable salt thereof.

25. A method of treating or preventing a bacterial infection in an animal comprising co-administering to the animal a compound as described in claim 17 or a pharmaceutically acceptable salt thereof and one or more antibacterial agents.

26. The compound or salt of claim 1, wherein $R^2$ is hydrogen.

* * * * *

UNITED STATES PATENT AND TRADEMARK OFFICE
CERTIFICATE OF CORRECTION

PATENT NO. : 11,993,571 B2
APPLICATION NO. : 16/492901
DATED : May 28, 2024
INVENTOR(S) : Edmond J. LaVoie et al.

Page 1 of 2

It is certified that error appears in the above-identified patent and that said Letters Patent is hereby corrected as shown below:

In the Claims

Column 258, Line 62, Claim 3, please delete "$(NR^{b3}R^{c3})$;" and insert -- $(NR^{b3}R^{c3})$, --;

Column 258, Line 63, Claim 3, please delete "$(=NR^{a3})(R^{d3})$;" and insert -- $(=NR^{a3})(R^{d3})$, --;

Column 262, Lines 55-65, Claim 16, please delete " 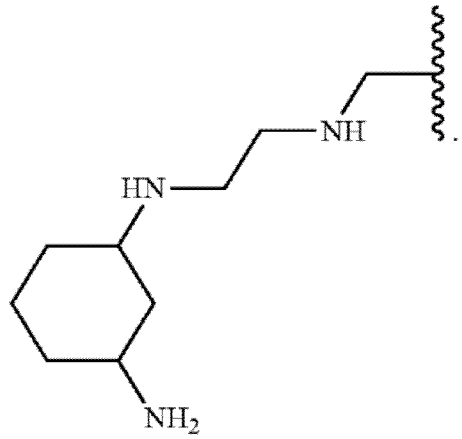 [SMILES: *CNCCNC1CCCC(N)C1] " and

Signed and Sealed this
Ninth Day of September, 2025

Coke Morgan Stewart
*Acting Director of the United States Patent and Trademark Office*

CERTIFICATE OF CORRECTION (continued)
U.S. Pat. No. 11,993,571 B2 insert -- 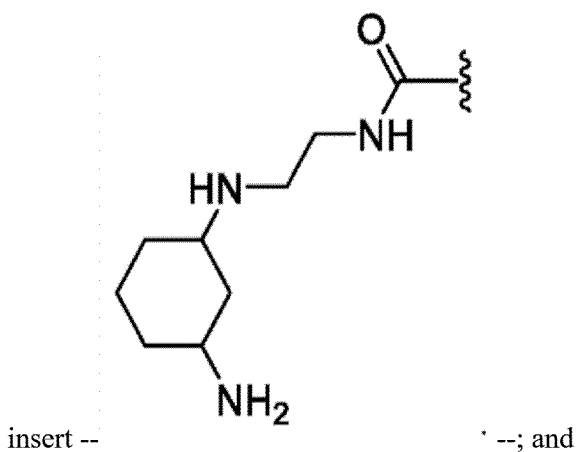 --; and

Column 273, Lines 40-45, Claim 17, please delete

" 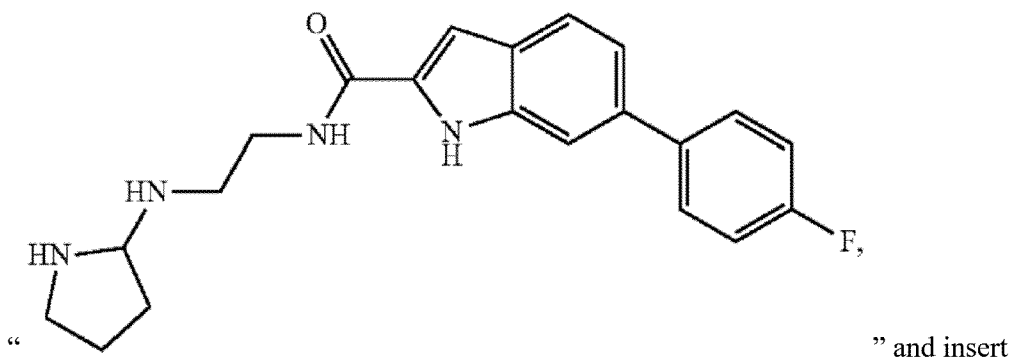 " and insert

-- 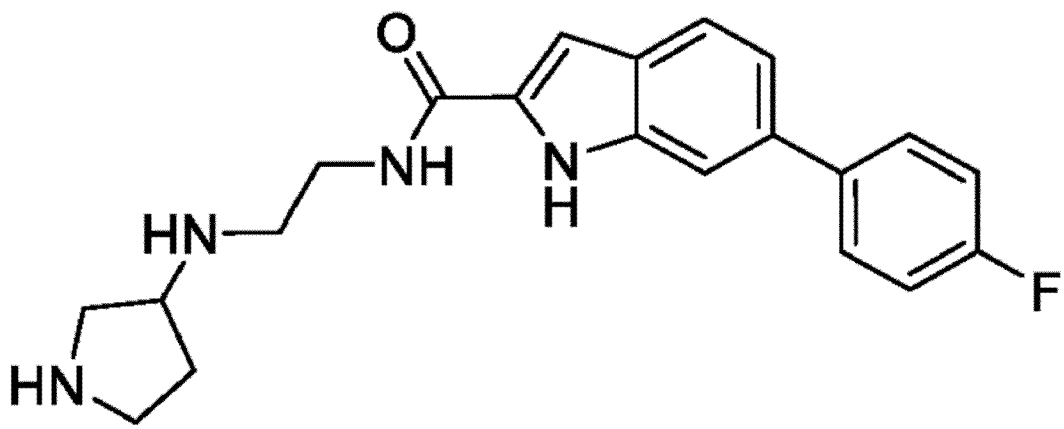 -- therefore.